(12) United States Patent
Klein et al.

(10) Patent No.: US 10,294,246 B2
(45) Date of Patent: May 21, 2019

(54) SUBSTITUTED BORONIC ACIDS AND BORONATE ESTERS AS IMMUNOPROTEASOME INHIBITORS

(71) Applicant: MERCK PATENT GMBH, Darmstadt (DE)

(72) Inventors: Markus Klein, Darmstadt (DE); Oliver Schadt, Rodenbach (DE); Philipp Haselmayer, Wiesbaden (DE); Michael Busch, Darmstadt (DE)

(73) Assignee: MERCK PATENT GMBH, Darmstadt (DE)

(*) Notice: Subject to any disclaimer, the term of this patent is extended or adjusted under 35 U.S.C. 154(b) by 0 days.

(21) Appl. No.: 15/516,424

(22) PCT Filed: Oct. 1, 2015

(86) PCT No.: PCT/EP2015/002008
§ 371 (c)(1),
(2) Date: Apr. 3, 2017

(87) PCT Pub. No.: WO2016/050359
PCT Pub. Date: Apr. 7, 2016

(65) Prior Publication Data
US 2018/0105539 A1    Apr. 19, 2018

(30) Foreign Application Priority Data
Oct. 1, 2014 (EP) .................... 14003392

(51) Int. Cl.
| | | |
|---|---|---|
| *A61K 31/69* | (2006.01) | |
| *C07F 5/02* | (2006.01) | |
| *A61P 17/06* | (2006.01) | |
| *A61P 11/06* | (2006.01) | |
| *A61P 37/06* | (2006.01) | |
| *A61P 19/02* | (2006.01) | |
| *A61P 35/02* | (2006.01) | |
| *A61P 11/00* | (2006.01) | |
| *A61P 29/00* | (2006.01) | |
| *A61P 35/00* | (2006.01) | |

(52) U.S. Cl.
CPC .............. *C07F 5/025* (2013.01); *A61K 31/69* (2013.01); *A61P 11/00* (2018.01); *A61P 11/06* (2018.01); *A61P 17/06* (2018.01); *A61P 19/02* (2018.01); *A61P 29/00* (2018.01); *A61P 35/00* (2018.01); *A61P 35/02* (2018.01); *A61P 37/06* (2018.01)

(58) Field of Classification Search
CPC .................. A61K 31/69; C07F 5/02
USPC ................................. 514/64; 568/6
See application file for complete search history.

(56) References Cited

U.S. PATENT DOCUMENTS

2018/0105538 A1    4/2018 Klein et al.

FOREIGN PATENT DOCUMENTS

| WO | WO 01/02424 | 1/2001 |
|---|---|---|
| WO | WO 2013/092979 | 6/2013 |
| WO | WO 2016/050355 | 4/2016 |
| WO | WO 2016/050356 | 4/2016 |
| WO | WO 2016/050358 | 4/2016 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Matteson, et al. Organometallics, 3(8), 1984, 1284-1288.*
Currently pending claims of U.S. Appl. No. 15/516,420, 2017.
Currently pending claims of U.S. Appl. No. 15/516,427, 2017.
Written Opinion in International Application No. PCT/EP2015/002008, dated Feb. 12, 2016, pp. 1-9.
Caselli, E. et al. "Click Chemistry in Lead Optimization of Boronic Acids as β-Lactamase Inhibitors" *Journal of Medicinal Chemistry*, Jun. 23, 2015, pp. 5445-5458, vol. 58, No. 14.
Dzhekieva, L. et al. "Interaction of Bora-Penicilloates with serine β-Lactamases and DD-Peptidases" *Biochemistry*, Oct. 10, 2014, pp. 6530-6538, vol. 53, No. 41.
Ness, S. et al. "Structure-Based Design Guides the Improved Efficacy of Deacylation Transition State Analogue Inhibitors of TEM-1 β-Lactamase" *Biochemistry*, 2000, pp. 5312-5321, vol. 39, No. 18.

* cited by examiner

*Primary Examiner* — Douglas M Willis
(74) *Attorney, Agent, or Firm* — Saliwanchik, Lloyd & Eisenschenk

(57) ABSTRACT

Compounds of formula (I) are inhibitors of LMP7 and can be employed, inter alia, for the treatment of an autoimmune disorder or hematological malignancies.

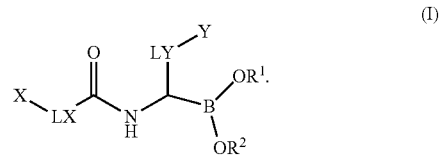

22 Claims, No Drawings

SUBSTITUTED BORONIC ACIDS AND BORONATE ESTERS AS IMMUNOPROTEASOME INHIBITORS

CROSS-REFERENCE TO RELATED APPLICATION

This application is the U.S. national stage application of International Patent Application No. PCT/EP2015/002008, filed Oct. 1, 2015.

FIELD OF THE INVENTION

The present invention relates to α-Amino boronic acid derivatives. These compounds are useful for inhibiting the activity of immunoproteasome (LMP7) and for the treatment and/or prevention of medical conditions affected by immunoproteasome activity such as inflammatory and autoimmune diseases, neurodegenerative diseases, hematological malignancies and proliferative diseases. In particular, the compounds of the present invention are selective immunoproteasome inhibitors.

BACKGROUND TO THE INVENTION

The proteasome (also known as macropain, the multicatalytic protease, and 20S protease) is a high molecular weight, multisubunit protease which has been identified in every examined species from an archaebacterium to human. The enzyme has a native molecular weight of approximately 650,000 and, as revealed by electron microscopy, a distinctive cylinder-shaped morphology (Rivett, (1989) Arch. Biochem. Biophys. 268:1-8; and Orlowski, (1990) Biochemistry 29:10289-10297). The proteasome subunits range in molecular weight from 20,000 to 35,000, and are homologous to one another but not to any other known protease.

The 20S proteasome is a 700 kDa cylindrical-shaped multicatalytic protease complex comprised of 28 subunits, classified as α- and β-type, that are arranged in 4 stacked heptameric rings. In yeast and other eukaryotes, 7 different a subunits form the outer rings and 7 different β subunits comprise the inner rings. The a subunits serve as binding sites for the 19S (PA700) and 1 IS (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome.

Cleavage of amino-terminal prosequences of β subunits during particle formation exposes amino-terminal threonine residues, which serve as the catalytic nucleophiles. The subunits responsible for catalytic activity in proteasome thus possess an amino terminal nucleophilic residue, and these subunits belong to the family of N-terminal nucleophile (Ntn) ATTY REF: 26500-0023WO1 hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed 3 subunits, higher vertebrates also possess three interferon-γ-inducible β subunits (LMP7, LMP2 and MECL1), which replace their normal counterparts, β5, β1 and β2, respectively. When all three IFN-γ-inducible subunits are present, the proteasome is referred to as an "immunoproteasome". Thus, eukaryotic cells can possess two forms of proteasomes in varying ratios.

Through the use of different peptide substrates, three major proteolytic activities have been defined for the eukaryote 20S proteasomes: chymotrypsin-like activity (CT-L), which cleaves after large hydrophobic residues; trypsin-like activity (T-L), which cleaves after basic residues; and peptidylglutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. Although both forms of the proteasome possess all five enzymatic activities, differences in the extent of the activities between the forms have been described based on specific substrates. For both forms of the proteasome, the major proteasome proteolytic activities appear to be contributed by different catalytic sites within the 20S core.

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, which cleaves proteins into short peptides through the action of its three major proteolytic activities. While having a general function in intracellular protein turnover, proteasome-mediated degradation also plays a key role in many processes such as major histocompatibility complex (MHC) class I presentation, apoptosis and cell viability, antigen processing, NF-κB activation, and transduction of pro-inflammatory signals.

Proteasome activity is high in muscle wasting diseases that involve protein breakdown such as muscular dystrophy, cancer and AIDS. Evidence also suggests a possible role for the proteasome in the processing of antigens for the class I MHC molecules (Goldberg, et al. (1992) Nature 357:375-379).

Proteasomes are involved in neurodegenerative diseases and disorders such as Amyotrophic Lateral Sclerosis (ALS), (J Biol Chem 2003, Allen S et al., Exp Neurol 2005, Puttaparthi k et al.), Sjogren's syndrome (Arthritis & Rheumatism, 2006, Egerer T et al.), systemic lupus erythematoses and lupus nephritis (SLE/LN), (Arthritis & rheuma 2011, Ichikawa et al., J Immunol, 2010, Lang V R et al., Nat Med, 2008, Neubert K et al), glomerulonephritis (J Am Soc nephrol 2011, Bontscho et al.), Rheumatoid Arthritis (Clin Exp Rheumatol, 2009, Van der Heiden J W et al.), Inflammatory bowel disease (IBD), ulcerative colitis, Crohn's diseases, (Gut 2010, Schmidt N et al., J Immunol 2010, Basler M et al., Clin Exp Immunol, 2009, Inoue S et al.), multiple sclerosis (Eur J Immunol 2008, Fissolo N et al., J Mol Med 2003, Elliott P J et al., J Neuroimmunol 2001, Hosseini et al., J Autoimmun 2000, Vanderlugt C L et al.), Amyotrophic lateral sclerosis (ALS), (Exp Neurol 2005, Puttaparthi k et al., J Biol Chem 2003, Allen S et al.), osteoarthritis (Pain 2011, Ahmed s et al., Biomed Mater Eng 2008, Etienne S et al.), Atherosclerosis (J Cardiovasc Pharmacol 2010, Feng B et al., Psoriasis (Genes & Immunity, 2007, Kramer U et al.), Myasthenia Gravis (J Immunol, 2011, Gomez A M et al.), Dermal fibrosis (Thorax 2011, Mutlu G M et al., Inflammation 2011, Koca S S et al., Faseb J 2006, Fineschi S et al.), renal fibrosis (Nephrology 2011 Sakairi T et al.), cardiac fibrosis (Biochem Pharmacol 2011, Ma y et al.,) Liver fibrosis (Am J Physiol gastrointest Liver Physiol 2006, Anan A et al.), Lung fibrosis (Faseb J 2006, Fineschi S et al et al.), Immunoglobulin A nephropathy (IGa nephropathy), (Kidney Int, 2009, Coppo R et al.), Vasculitis (J Am Soc nephrol 2011, Bontscho et al.), Transplant rejection (Nephrol Dial transplant 2011, Waiser J et al.), Hematological malignancies (Br J Haematol 2011, Singh A V et al., Curr Cancer Drug Target 2011, Chen D et al.) and asthma.

Yet, it should be noted that commercially available proteasome inhibitors inhibit both the constitutive and immunoforms of the proteasome. Even bortezomib, the FDA-approved proteasome inhibitor for the treatment of relapsed multiple myeloma patients, does not distinguish between the two forms (Altun et al., Cancer Res 65:7896, 2005). Furthermore, the use of Bortezomib is associated with a treatment-emergent, painful peripheral neuropathy (PN), this bortezomib-induced neurodegeneration in vitro occurs via a proteasome-independent mechanism and that bortezomib inhibits several nonproteasomal targets in vitro and in vivo (Clin. Cancer Res, 17(9), May 1, 2011).

In addition to conventional proteasome inhibitors, a novel approach may be to specifically target the hematological-specific immunoproteasome, thereby increasing overall effectiveness and reducing negative off-target effects. It has been shown that immunoproteasome-specific inhibitor, could display enhanced efficiency on cells from a hematologic origin (Curr Cancer Drug Targets, 11(3), March, 2011).

Thus there is a need to provide new proteasome inhibitors that are selective of one specific form of the proteasome. In particular there is a need to provide selective immunoproteasome inhibitors, which could be used as therapeutic agents for the treatment of e.g. SLE or other immune or autoimmune disorders in the context of rheumatoid arthritis. Selective immunoproteasome inhibitors are helpful in order to minimize unwanted side effects mediated by inhibition of the constitutive proteasome or other nonproteasomal targets.

WO 2013/092979 A1 describes boronic acid derivatives, which show selectivity towards the inhibition of the LMP7 activity. However, the extent of selectivity, which is achievable with the described types of compounds, is limited, particularly with respect to the split to the inhibitory activity of the constitutive proteasome.

Unspecific inhibitors of the proteasome and the immunoproteasome like Bortezomib and Carfilzomib have demonstrated their clinical value in the indication of multiple myeloma. Although this unspecific profile, hitting major components in the immunoproteasome as well as the constitutive proteasome, is regarded as beneficial in terms of target inhibition and clinical effectiveness, this unspecific profile limits the clinical applicability of these agents by inducing pronounced side effects like thrombocytopenia, neutropenia as well as peripheral neuropathy. To a certain extent, this side effect profile could be attributed to the broad inhibition of the catalytic activity, especially the combined inhibition of the ß5 subunits of the constitutive and the immunoproteasome. The approach to come up with more selective inhibitors of the immunoproteasome (and especially the ß5i subunit of the immunoproteasome), in order to reduce major side effects has been described e.g. in 2011 by Singh et al. (Br. J. Hematology 152(2): 155-163) for PR-924, a 100 fold selective inhibitor of the LMP7 subunit of the immunoproteasome. The authors demonstrated the presence of high expression levels of the immunoproteasome in multiple myeloma. The authors also described the effect of a selective inhibitor of the LMP7 subunit on the induction of cell death in MM cell lines as well as CD138+ MM primary patient cells without decreasing the viability of control PBMC's of healthy volunteers which can be regarded as a conceptual proof. Besides the concept of a reduced side effect profile for selective ß5i inhibitors other groups demonstrated the efficacy of selective ß5i inhibition on the viability of Bortezomib resistant cell lines underlining the value and potential perspective for the application of selective LMP7 inhibitors for hematological malignancies (D. Niewerth et al./Biochemical Pharmacology 89 (2014) 43-51).

Surprisingly, it was found that amino boronic acid derivatives according to this invention also inhibit LMP7. These compounds show very good properties in terms of their use in the treatment and/or prevention of medical conditions affected by immunoproteasome activity. In particular the compounds of the present invention are able to inhibit the activity of the immunoproteasome (LMP7) providing a significant split to the inhibitory activity of the constitutive proteasome. Besides this, the structural assembly of the compounds allows a simple and straightforward fine-tuning of the compound properties. Further important advantages are their good results regarding plasma-protein binding, CYP inhibition, PK profile and oral bioavailability.

SUMMARY OF THE INVENTION

Compounds of the present invention are inhibitors of the immunoproteasome subunit LMP7. They show significant selectivity on LMP7 over Beta5 (cP) and good properties in terms of solubility, plasma-protein binding, CYP inhibition, PK profile and oral bioavailability.

The present invention further provides compounds of formula (I)

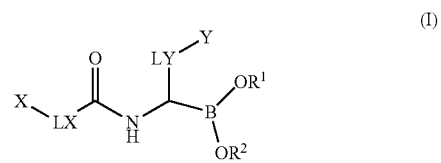

wherein

LX denotes $CH_2$, $O-(CH_2)_n$ or $S-(CH_2)_p$, wherein in each case, independently from one another, 1 to 5 H atoms may be replaced by Hal, $N_3$, $R^{3a}$, $OR^{4a}$, C3-C6-cycloalkyl, $(CH_2)_r$-A2, $(CH_2)_r$—Ar2 and/or $(CH_2)_r$-Het2, and/or one $CH_2$ group may be replaced by a C3-C6-cycloalkyl group;

LY denotes $(CH_2)_m$, wherein 1 to 5 H atoms may be replaced by Hal, $R^{3b}$ and/or $OR^{4b}$, and/or wherein 1 or 2 non-adjacent $CH_2$ groups may be replaced by O, SO and/or $SO_2$;

X denotes an aromatic 6-membered carbocycle or heterocycle, each independently from one another unsubstituted or mono-, di-, tri-, tetra- or pentasubstituted by Hal, A1, $N_3$, CN, OH, $NR^{4a}R^{4b}$, Ar1, Het1, OA1, OAr1, OHet1, COA1, COAr1, COHet1, $CONR^{4a}R^{4b}$, $NR^{4a}COR^{3a}$, $NR^{4a}SO_2R^{3a}$, $SO_2R^{3a}$, $SOR^{3a}$, $NR^{4a}COOR^{3a}$, $OCONR^{3a}R^{4a}$, $O-(CH_2)_q$-A1, $(CH_2)_r$—$SR^{3a}$, $(CH_2)_r$—$N(R^{4a})_2$ and/or $(CH_2)_r$-A2;

Y denotes $OR^{3c}$ or Cyc;

$R^1$, $R^2$ denote each, independently from one another, H or C1-C6-alkyl, or $R^1$ and $R^2$ form together a residue according to formula (CE)

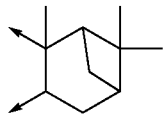

$R^{3a}$, $R^{3b}$, $R^{3c}$ denote each, independently from one another, linear or branched C1-C6-alkyl, wherein 1 to 5 H atoms may be replaced by Hal, OH and/or OAlk;

$R^{4a}$, $R^{4b}$ each, independently from one another, H or $R^{3a}$; or $R^{4a}$, $R^{4b}$ form together a C3-C6-cycloalkyl residue (in a specific embodiment $R^{4a}$, $R^{4b}$ denote each, independently from one another, H or $R^{3a}$);

A1 denotes linear or branched C1-C6-alkyl or C3-C6-cycloalkyl, each unsubstituted or mono-, di-, tri-, tetra- or pentasubstituted by Hal, CN, $R^{3a}$, $SR^{3a}$, $OR^{4a}$ and/or $(CH_2)_r$-A2, wherein 1, 2 or 3 $CH_2$ groups of C3-C6-cycloalkyl may be replaced by O, C=O, and/or N;

A2 denotes $OR^{4a}$;

Alk denotes linear or branched C1-C6-alkyl;

Ar1 denotes phenyl, which is unsubstituted, mono-, di- or trisubstituted by Hal, $NO_2$, CN, $R^{3a}$, $OR^{4a}$, $CONR^{4a}R^{4b}$, $NR^{4a}COR^{3b}$, $SO_2R^{3a}$, $SOR^{3a}$, $NR^{4a}R^{4b}$ Ar2, Het2 and/or $(CH_2)_r$-A2;

Het1 denotes saturated, unsaturated or aromatic 5- or 6-membered heterocycle having 1 to 4 N, O and/or S atoms, wherein each heterocycle may independently be unsubstituted or mono-, di-, tri-, tetra- or pentasubstituted by Hal, $NO_2$, CN, $R^{3a}$, $OR^{4a}$, $CONR^{4a}R^{4b}$, $NR^{4a}COR^{3b}SO_2R^{3a}$, $SOR^{3a}$, $NR^{4a}R^{4b}$, Ar2, Het2 and/or $(CH_2)_r$-A2;

Ar2 denotes phenyl, biphenyl or naphthyl, each independently from one another unsubstituted or mono-, di- or trisubstituted by Hal, CN, $R^{3a}$, $OR^{4a}$, $CONR^{4a}R^{4b}$, $NR^{4a}COR^{3b}$, $SO_2R^{3a}$, $SOR^{3a}$, $NR^{4a}R^{4b}$ and/or $(CH_2)_q$-A2;

Het2 denotes a saturated, unsaturated or aromatic 5- or 6-membered heterocycle having 1 to 4 N, O and/or S atoms, which is unsubstituted or mono- di- or trisubstituted by Hal, CN, $R^{3a}$, $OR^{4a}$, $CONHR^{3a}$, $NR^{3a}COR^{3b}SO_2R^{3a}$, $SOR^{3a}$, $NR^{4a}R^{4b}$ and/or $(CH_2)_q$-A2;

Cyc denotes a mono- or bicyclic, 4-, 5-, 6-, 7-, 8-, 9- or 10-membered hydrocarbon or heterocycle, each independently from one another unsubstituted or mono-, di-, tri-, tetra- or pentasubstituted by Hal, CN, $R^{3a}$, $OR^{3a}$, $CONR^{4a}R^{4b}$, $NR^{3a}COR^{3b}$, $SO_2R^{3a}$, $SOR^{3a}$, $NR^{4a}R^{4b}$, Ar2, Het2, $(CH_2)_r$—$SR^{3a}$, $(CH_2)_r$—$N(R^{4a})_2$ and/or $(CH_2)_r$-A2, wherein the monocyclic hydrocarbon system is aromatic and at least one ring of the bicyclic hydrocarbon or heterocycle is aromatic, and wherein the heterocyclic system contains 1, 2 or 3 N and/or O and/or S atoms;

n, p denote each, independently from one another, 1, 2, 3, 4, 5 or 6;

m, q, r denote each, independently from one another, 0, 1, 2, 3 or 4; Hal denotes F, Cl, Br or I;

and derivatives, prodrugs, solvates, tautomers or stereoisomers thereof, as well as the physiologically acceptable salts of each of the foregoing, including mixtures thereof in all ratios.

It is known that boronic acid derivatives such as compounds of formula (I) (and formula (PI) as described below), wherein $R^1$ and $R^2$ denote H form oligomers (Boronic Acids. Edited by Dennis G. Hall, Copyright © 2005 WILEY-VCH Verlag, GmbH & Co. KGaA, Weinheim, ISBN 3-527-30991-8). Such oligomers (in particular but not limited to dimers or trimers) of compounds of formula (I) are included within this invention. Known cyclic trimers of boronic acids have for example, the following structure:

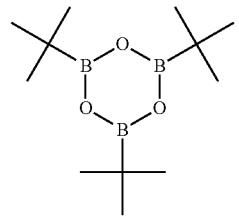 [SMILES: CC(C)(C)B1OB(C(C)(C)C)OB(C(C)(C)C)O1]

It is to be noted that the compounds of the present invention bear a stereogenic center at the carbon atom adjacent to the boronic acid residue; it has been denoted with an asterisk (*) in formula (I)* below:

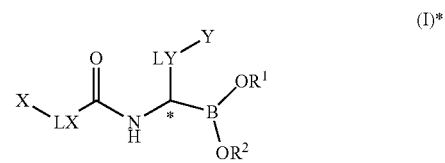

(I)*

The compounds according to formula (I) thus exhibit two different configurations at this stereogenic center, i.e. the (R)-configuration and the (S)-configuration. Hence, the compounds of the present invention may be present either enantiopure or as a racemic (1:1) mixture of the two enantiomers of formulas (R)-(Ia) and (S)-(Ia). This applies accordingly to the compounds according to formula (PI) as described below.

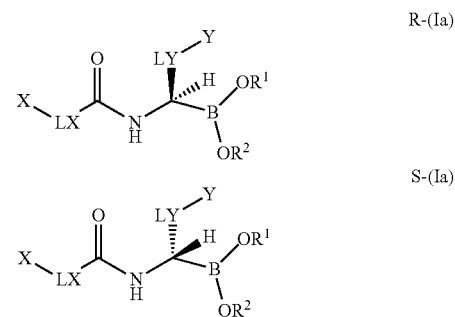

R-(Ia)

S-(Ia)

Compounds of formula (I) may also be present in a mixture in which one of the enantiomers (R)-(Ia) or (S)-(Ia) is present in an excess over the other one, e.g. 60:40, 70:30, 80:20, 90:10, 95:5 or the like. In a particular embodiment of the present invention the stereoisomer of formula (R)-(Ia) of the compound of formula (Ia) and the stereoisomer of formula (S)-(Ia) of the compound of formula (Ia) are present in a ratio of (R)-(Ia) to (S)-(Ia) of at least 90 parts of (R)-(Ia) to not more than 10 parts of (S)-(Ia), preferably of at least 95 (R)-(Ia) to not more than 5 (S)-(Ia), more preferably of at least 99 (R)-(Ia) to not more than 1 (S)-(Ia), even more preferably of at least 99.5 (R)-(Ia) to not more than 0.5 (S)-(Ia). In another particular embodiment of the present invention the stereoisomer of formula (S)-(Ia) of the compound of formula (Ia) and the stereoisomer of formula (R)-(Ia) of the compound of formula (Ia) are present in a ratio of (S)-(Ia) to (R)-(Ia) of at least 90 (S)-(Ia) to not more than 10 (R)-(Ia), preferably of at least 95 (S)-(Ia) to not more than 5 (R)-(Ia), more preferably of at least 99 (S)-(Ia) to not more than 1 (R)-(Ia), even more preferably of at least 99.5 (S)-(Ia) to not more than 0.5 (R)-(Ia). This applies accordingly to the compounds according to formula (PI) as described below.

Enriched or pure stereoisomers of formulas (R)-(Ia) and (S)-(Ia) can be obtained by usual methods known in the art and described hereinafter. A particular method for obtaining them is preparative column chromatography, such as HPLC or SFC, using chiral column material. This applies accordingly to the compounds according to formula (PI) as described below.

In a particular preferred embodiment of the present invention the stereogenic center at the carbon atom adjacent to the boronic acid residue shows an (R)-configuration. This applies accordingly to the compounds according to formula (PI) as described below The compounds according to formula (I) might also carry stereogenic centers located a carbon atoms other than at the carbon atom adjacent to the boronic acid residue. Such stereogenic centers may occur in (R)- or (S)-configuration. This applies accordingly to the compounds according to formula (PI) as described below.

Above and below, in those cases, where a chemical structure with a stereogenic center is shown and no specific stereochemistry is indicated, the structures include all possible stereoisomers.

In general, all residues of compounds described herein which occur more than once may be identical or different, i.e. are independent of one another. Above and below, the residues and parameters have the meanings indicated for formula (I), unless expressly indicated otherwise. Accordingly, the invention relates, in particular, to the compounds of formula (I) in which at least one of the said residues has one of the preferred meanings indicated below. Furthermore, all specific embodiments described below shall include derivatives, prodrugs, solvates, tautomers or stereoisomers thereof as well as the physiologically acceptable salts of each of the foregoing, including mixtures thereof in all ratios.

In case Cyc denotes a bicyclic hydrocarbon or heterocycle, wherein at least one of the two rings of is an aromatic ring, the other ring may be a saturated, unsaturated or aromatic ring. In specific embodiments the covalent linkage between Cyc and the adjacent group LY occurs via the at least one aromatic ring of Cyc. The bicyclic hydrocarbon or heterocycle is preferably 8-, 9- or 10-membered. Furthermore, in case Cyc is a monocyclic heterocycle it preferably contains 1, 2 or 3 heteroatoms selected from N, O and/or S, most preferably it contains 1 or 2 heteroatoms. In case Cyc is a bicyclic heterocycle it preferably contains 1, 2, 3 or 4 heteroatoms selected from N, O and/or S, most preferably it contains 1, 2 or 3 heteroatoms.

In case Cyc denotes a monocyclic, aromatic hydrocarbon system it is preferably phenyl, which is unsubstituted or mono-, di- or trisubstituted by Hal, CN, $R^{3a}$, $OR^{3a}$, $CONR^{4a}R^{3a}NR^{3a}COR^{3b}$, $SO_2R^{3a}$, $SOR^{3a}$, $NR^{4a}R^{3a}$, Ar2, Het2 and/or $(CH_2)_r$-A2. Particularly preferred are embodiments wherein Cyc denotes a di- or trisubstituted phenyl. In those embodiments where Cyc denotes a disubstituted phenyl, the two substituents are preferably in 2,4- or 3,4-position. And in those embodiments where Cyc denotes a trisubstituted phenyl, the three substituents are preferably in 2,3,4-position of the aromatic ring.

In case Cyc denotes a monocyclic heterocycle this heterocycle can be saturated, unsaturated or aromatic.

One embodiment of the present invention comprises compounds, wherein:

$R^1$, $R^2$ denote H or C1-C4-alkyl or $R^1$ and $R^2$ form together a residue according to formula (CE)

and

X denotes phenyl, pyridinyl, pyridazinyl, pyrimidyl, pyrazinyl or triazinyl, each independently from one another unsubstituted or mono-, di-, tri-, tetra- or pentasubstituted by Hal, $N_3$, A1, CN, OH, $NR^{4a}R^{4b}$, Ar1, Het1, OA1, OAr1, OHet1, COA1, COAr1, COHet1, $CONR^{4a}R^{4b}$, $NR^{4a}COR^{3a}$, $NR^{4a}SO_2R^{3a}$, $SO_2R^{3a}$, $SOR^{3a}$, $NR^{4a}COOR^{3a}$, $OCONR^{3a}R^{4a}$, $O$—$(CH_2)_q$-A1, $(CH_2)_r$—$SR^{3a}$, $(CH_2)_r$—$N(R^{4a})_2$ and/or $(CH_2)_r$-A2;

Y denotes Cyc;

n, p, r, q denote each, independently from one another, 1, 2, 3 or 4; and m denotes 1 or 2;

and derivatives, prodrugs, solvates, tautomers or stereoisomers thereof, as well as the physiologically acceptable salts of each of the foregoing, including mixtures thereof in all ratios.

Other specific embodiments of the invention comprise compounds according to formula (I), wherein LX denotes —$CH_2$—, —O—$CH_2$—, —O—$CH_2$—$CH_2$—, —S—$CH_2$—, —S—$CH_2$—$CH_2$— wherein in each case, independently from one another, 1 to 4 H atoms may be replaced by Hal, $R^{3a}$, $OR^{4a}$, $(CH_2)_r$-A2, Ar2 and/or Het2, or one H atom or $CH_2$ group may be replaced by cyclopropyl, cyclobutyl or cyclopentyl;

LY denotes $(CH_2)_m$, wherein 1 to 4 H atoms may be replaced by Hal, $R^{3b}OR^{4b}$;

Cyc denotes phenyl, which is unsubstituted, mono-, di- or trisubstituted by Hal, CN, $R^{3a}$, $OR^{3a}$, $CONR^{4a}R^{4b}$, $NR^{3a}COR^{3b}$, $SO_2R^{3a}$, $SOR^{3a}$, $NR^{4a}R^{4b}$, Ar2, Het2, $(CH_2)_r$—$SR^{3a}$, $(CH_2)_r$—$N(R^{4a})_2$ and/or $(CH_2)_r$-A2; wherein in case of disubstitution substituents are in 2,4-, 2,5- or 3,4-position and in case of trisubstitution substituents are in 2,3,4-position;

or 1- or 2-naphthyl, 4- or 5-indanyl, 1-, 2-, 3-, 4-, 5-, 6- or 7-indolyl, 1-, 2-, 4-, 5- or 6-azulenyl, 1- or 2-tetrahydronaphthalin 5- or 6-yl, 2- or 3-furyl, 2-, 3-, 4-, 5-, 6- or 7-benzofuryl, 2,3-dihydrobenzofuran-2- or 3-yl, 2-, 3-, 4-, 5-, 6- or 7-benzothiophenyl, methylenedioxyphenyl, benzodioxan-6- or 7-yl or 3,4-dihydro-1,5-benzodioxepin-6- or -7-yl, each independently from one another, unsubstituted, mono-, disubstituted or trisubstituted by Hal, CN, $R^{3a}$, $OR^{3a}$, $CONR^{4a}R^{4b}$, $NR^{3a}COR^{3b}$, $SO_2R^{3a}$, $SOR^{3a}$, $NR^{4a}R^{4b}$, Ar2, Het2, $(CH_2)_r$—$SR^{3a}$, $(CH_2)_r$—$N(R^{4a})_2$ and/or $(CH_2)_r$-A2;

and derivatives, prodrugs, solvates, tautomers or stereoisomers thereof, as well as the physiologically acceptable salts of each of the foregoing, including mixtures thereof in all ratios.

In particular embodiments of the invention
LX denotes —$CH_2$—, —O—$CH_2$—, —O—$CH_2$—$CH_2$—, —S—$CH_2$—, —S—$CH_2$—$CH_2$—, wherein in each case, independently from one another, 1 to 4 H atoms may be replaced by Hal, $R^{3a}$, $OR^{4a}$, $(CH_2)_r$-A2, phenyl, tolyl, ethylphenyl, fluorophenyl, chlorophenyl, bromophenyl, aminophenyl, furyl, thienyl, pyrrolyl, imidazolyl, pyrazolyl, pyrimidyl, morpholinyl and/or piperidinyl,
or
one H or $CH_2$ group may be replaced by cyclopropyl, cyclobutyl or cyclopentyl;
LY denotes $CH_2$ or $CH_2$—$CH_2$ wherein 1 to 4 H atoms may be replaced by Hal, $R^{3b}$, $OR^{4b}$;
Cyc 1- or 2-naphthyl, 2- or 3-benzofuryl, 2,3-dihydrobenzofuran-2- or 3-yl, benzothiophen-2- or 3-yl or 1-, 2-, 3-, 4-, 5-, 6- or 7-indolyl, each independently from one another, unsubstituted, mono-, disubstituted or trisubstituted by Hal, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_r$—$SR^{3a}$, $(CH_2)_r$—$N(R^{4a})_2$ and/or $(CH_2)_r$-A2;
q, r denote each, independently from one another, 1, 2 or 3.

Further embodiments of the invention comprise compounds:
$R^1$, $R^2$ denote H or C1-C4-alkyl or $R^1$ and $R^2$ form together a residue according to formula (CE);
LX denotes —$CH_2$—, —O—$CH_2$—, —O—$CH_2$—$CH_2$—, —S—$CH_2$—, —S—$CH_2$—$CH_2$—, wherein in each case, independently from one another, 1 to 4 H atoms may be replaced by Hal, $R^{3a}$, $OR^{4a}$ and/or $(CH_2)_r$-A2;
or
one H atom or $CH_2$ group may be replaced by cyclopropyl, cyclobutyl or cyclopentyl;
LY denotes —$CH_2$— or —$CH_2$—$CH_2$—;
X denotes phenyl, pyridinyl, pyridazinyl, pyrimidyl, pyrazinyl or triazinyl, each independently from one another unsubstituted or mono-, di-, tri-, tetra- or pentasubstituted by Hal, $N_3$, A1, CN, OH, $NR^{4a}R^{4b}$, Ar1, Het1, OA1, OAr1, OHet1, COA1, COAr1, COHet1, $CONR^{4a}R^{4b}$, $NR^{4a}COR^{3a}$, $NR^{4a}SO_2R^{3a}$, $SO_2R^{3a}$, $SOR^{3a}$, $NR^{4a}COOR^{3a}$, $OCONR^{3a}R^{4a}$, O—$(CH_2)_q$-A1 and/or $(CH_2)_r$-A2;
Y denotes Cyc;
$R^{3a}$, $R^{3b}$ and $R^{3c}$ denote each, independently from one another, linear or branched C1-C4-alkyl, wherein 1 to 5 H atoms may be replaced by Hal, OH and/or OAlk;
A1 denotes C1-C6-alkyl or C3-C6-cycloalkyl, each independently from each other, unsubstituted or mono- or disubstituted by Hal, CN, $R^{3a}$, $SR^{3a}$, $OR^{4a}$ and/or $(CH_2)_r$-A2, wherein 1 or 2 $CH_2$ groups of the C3-C6-cycloalcyl group may be replaced by O, C=O and/or N;
Alk denotes methyl, ethyl, n-propyl or isopropyl;
Cyc
  1- or 2-naphthyl, 2- or 3-benzofuryl, 2,3-dihydrobenzofuran-2- or 3-yl, benzothiophen-2- or 3-yl or 1-, 2-, 3-, 4-, 5-, 6- or 7-indolyl, each, independently from one another, unsubstituted, mono-, disubstituted or trisubstituted by Hal, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_r$—$SR^{3a}$, $(CH_2)_r$—$N(R^{4a})_2$ and/or $(CH_2)_r$-A2;
q, r denote each, independently from one another, 0, 1, 2, 3 or 4;

and derivatives, prodrugs, solvates, tautomers or stereoisomers thereof, as well as the physiologically acceptable salts of each of the foregoing, including mixtures thereof in all ratios.

In specific embodiments of the invention Cyc denotes unsubstituted or mono- or disubstituted 1- or 2-naphthyl or 2-, 3-benzothiophenyl, wherein the substituents are selected from a group consisting of Hal, CN, $R^{3a}$, $OR^{3a}$, $CONR^{4a}R^{4b}$, $NR^{3a}COR^{3b}$, $SO_2R^{3a}$, $SOR^{3a}$, $NR^{4a}R^{4b}$, Ar2, Het2, $(CH_2)_r$—$SR^{3a}$, $(CH_2)_r$—$N(R^{4a})_2$ and/or $(CH_2)_r$-A2 (preferably F, Cl, $CH_3$, $C_2H_5$, $CF_3$, $OCH_3$, $OCF_3$ $OC_2H_5$, $CH_2OCH_3$);
or
Cyc is a residue according to formula (Fa7) or (Fb7)

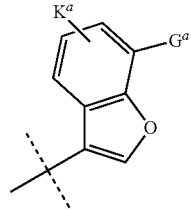

(Fa7)

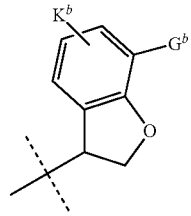

(Fb7)

wherein,
$G^a$ denotes, F, Cl, Br, CN, $R^{3a}$, $OR^{3a}$, $CONHR^{3a}$, $CONR^{3b}R^{3a}$, $CONH_2$, $NR^{3a}COR^{3b}SO_2R^{3a}$, $SOR^{3a}$, $NHR^{3a}$, $N(R^{3a})_2$, $(CH_2)_r$—$SR^{3a}$, $(CH_2)_r$—$N(R^{4a})_2$ and/or $(CH_2)_r$-A2;
$G^b$ denotes H, F, Cl, Br, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_r$—$SR^{3a}$, $(CH_2)_r$—$N(R^{4a})_2$ and/or $(CH_2)_r$-A2;
$K^a$, $K^b$ denote each, independently from one another, H, F, Cl, Br, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_r$—$SR^{3a}$, $(CH_2)_r$—$N(R^{4a})_2$ and/or $(CH_2)_r$-A2;
$R^{3a}$, $R^{3b}$ and $R^{3c}$ denote each, independently from one another, linear or branched C1-C3-alkyl, wherein 1 to 5 H atoms may be replaced by F, Cl, OH and OAlk, wherein Alk is methyl or ethyl;
r denotes 1 or 2
and derivatives, prodrugs, solvates, tautomers or stereoisomers thereof, as well as the physiologically acceptable salts of each of the foregoing, including mixtures thereof in all ratios.

The residue according to formula (Fb7) bears a stereogenic center at the carbon atom next to LY; it has been denoted with an asterisk (*) in formula (Fb7)* below:

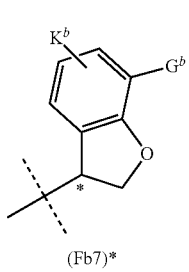

(Fb7)*

(Fb7)*

The residues according to formula (Fb7) thus exhibit two different configurations at this stereogenic center, i.e. the (R)-configuration and the (S)-configuration. Hence, the compounds of the present invention may be present either enantiopure or as a racemic (1:1) mixture of the two enantiomers of formulas (R)-(Fb7) and (S)-(Fb7).

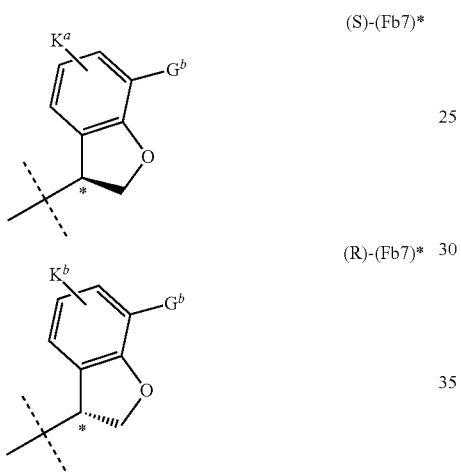

(S)-(Fb7)*

(R)-(Fb7)*

Compounds of formula (I) which include residues according to formula (Fb7) may also be present in a mixture in which one of the enantiomers (R)-(Fb) or (S)-(Fb) is present in an excess over the other one, e.g. 60:40, 70:30, 80:20, 90:10, 95:5 or the like. In a particular embodiment of the present invention the stereoisomer of formula (R)-(Fb7) of the compound of formula (Ia) and the stereoisomer of formula (S)-(Fb7) of the compound of formula (Ia) are present in a ratio of (R)-(Fb7) to (S)-(Fb7) of at least 90 parts of (R)-(Fb7) to not more than 10 parts of (S)-(Fb7), preferably of at least 95 (R)-(Fb7) to not more than 5 (S)-(Fb7), more preferably of at least 99 (R)-(Fb7) to not more than 1 (S)-(Fb7), even more preferably of at least 99.5 (R)-(Fb7) to not more than 0.5 (S)-(Fb7). In another particular embodiment of the present invention the stereoisomer of formula (S)-(Fb7) of the compound of formula (Fb7) and the stereoisomer of formula (R)-(Fb7) of the compound of formula (I) are present in a ratio of (S)-(Fb7) to (R)-(Fb7) of at least 90 (S)-(Fb7) to not more than 10 (R)-(Fb7), preferably of at least 95 (S)-(Fb7) to not more than 5 (R)-(Fb7), more preferably of at least 99 (S)-(Fb7) to not more than 1 (R)-(Fb7), even more preferably of at least 99.5 (S)-(Fb7) to not more than 0.5 (R)-(Fb7).

In a preferred embodiment of the present invention, the stereogenic center at the carbon atom in position 3 of the dihydrofuranyl residue shows an (S)-configuration. Thus, the residue is a (3S)-2,3-dihydrobenzofuran-3-yl residue (S)-(Fb7):

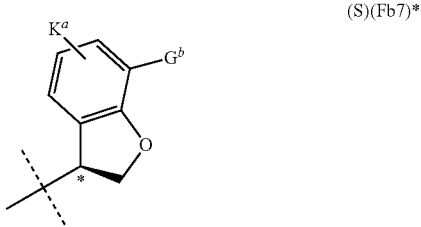

(S)(Fb7)*

Accordingly, in another very important embodiment of the invention the present invention comprises compounds according to formula (I), which include a residue according to formula (Fb7), wherein the stereogenic center at the carbon atom in position 3 of the dihydrofuranyl residue shows an (S)-configuration and the stereogenic center at the carbon atom adjacent to the boronic acid residue shows an (R)-configuration:

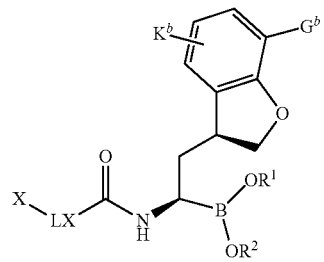

Particular embodiments of the invention comprise compounds, wherein Cyc denotes unsubstituted or mono- or disubstituted 1- or 2-naphthyl or 2-, 3-benzothiophenyl, wherein the substituents are selected from a group consisting of Hal, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_r$—$SR^{3a}$, $(CH_2)_r$—$N(R^{4a})_2$ and/or $(CH_2)_r$-A2 (preferably F, Cl, $CH_3$, $C_2H_5$, $CF_3$, $OCH_3$, $OCF_3$ $OC_2H_5$, $CH_2OCH_3$);

or

Cyc is a residue according to formula (Fa7) or (S)-(Fb7)

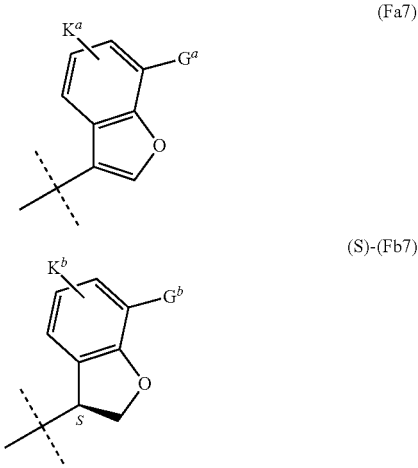

(Fa7)

(S)-(Fb7)

wherein, $G^a$ denotes F, Cl, Br, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_r$—$SR^{3a}$, $(CH_2)_r$—$N(R^{4a})_2$ and/or $(CH_2)_r$-A2;

$G^b$ denotes H, F, Cl, Br, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_r$—$SR^{3a}$, $(CH_2)_r$—$N(R^{4a})_2$ and/or $(CH_2)_r$-A2;

$K^a$, $K^b$ denote each, independently from one another, H, F, Cl, Br, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_r$—$SR^{3a}$, $(CH_2)_r$—$N(R^{4a})_2$ and/or $(CH_2)_r$-A2;

$R^{3a}$, $R^{3b}$ and $R^{3c}$ denote each, independently from one another, linear or branched C1-C3-alkyl, wherein 1 to 5 H atoms may be replaced by F, Cl, OH and OAlk, wherein Alk is methyl or ethyl;

r denotes 1 or 2 and derivatives, prodrugs, solvates, tautomers or stereoisomers thereof, as well as the physiologically acceptable salts of each of the foregoing, including mixtures thereof in all ratios.

Further specific embodiments comprise compounds, wherein Cyc denotes unsubstituted or mono- or disubstituted 1- or 2-naphthyl, wherein the substituents are each, independently from one another, selected from a group consisting of F, Cl, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$ or $N(C_2H_5)_2$; (preferably F, Cl, $CH_3$, $C_2H_5$, $CF_3$, $OCH_3$, $OCF_3$ $OC_2H_5$, $CH_2OCH_3$)

or

Cyc is a residue according to formula (Fa7), (Fb7) or (S)-(Fb7), wherein $G^a$ denotes F, Cl, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$ or $N(C_2H_5)_2$;

$G^b$ denotes H, F, Cl, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$ or $N(C_2H_5)_2$;

$K^a$, $K^b$ denote each, independently from one another, H, F, Cl, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$ or $N(C_2H_5)_2$;

and derivatives, prodrugs, solvates, tautomers or stereoisomers thereof, as well as the physiologically acceptable salts of each of the foregoing, including mixtures thereof in all ratios.

A particular embodiment of the present invention comprises compounds, wherein the stereogenic center at the carbon atom adjacent to the boronic acid residue shows an (R)-configuration

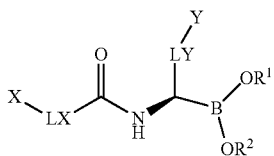

wherein

LX denotes $CH_2$—, —$CH_2$—$CH_2$—, —$CH_2$—O—, —$CH_2$—$CH_2$—$CH_2$—, —$CH_2$—$OCH_2$—$CH_2$—$CH_2$—, —$CH_2$—$CH_2$—O—$CH_2$—, wherein 1 to 4 H atoms may be replaced by F or Cl and/or 1 or 2 H atoms may be replaced by OH, methyl, ethyl, isopropyl, $CF_3$, $CF_2CF_3$, $OCH_3$, $OCH_2CH_3$, O—$CH_2$—$CH_2$—OH, O—$CH_2$—$CH_2$—$OCH_3$; or wherein 1 H atom or $CH_2$ group may be replaced by cyclopropyl; and LY denotes —$CH_2$— or —$CH_2$—$CH_2$— wherein 1 to 4 H atoms may be replaced by F or Cl and/or 1 or 2 H atoms may be replaced by OH, methyl, ethyl, isopropyl, $CF_3$, $CF_2CF_3$, $OCH_3$, $OCH_2CH_3$, O—$CH_2$—$CH_2$—OH and/or O—$CH_2$—$CH_2$—$OCH_3$; and X phenyl, pyridinyl, pyridazinyl, pyrazinyl or triazinyl, each independently from one another unsubstituted or mono-, di-, tri-, tetra- or pentasubstituted by Hal, $N_3$, A1, CN, OH, $NR^{4a}R^{4b}$, Ar1, Het1, OA1, OAr1, OHet1, COA1, COAr1, COHet1, $CONR^{4a}R^{4b}NR^{4a}COR^{3a}$, $NR^{4a}SO_2R^{3a}$, $SO_2R^{3a}$, $SOR^{3a}$, $NR^{4a}COOR^{3a}$, $OCONR^{3a}R^{4a}$, O—$(CH_2)_q$-A1 and/or $(CH_2)_r$-A2;

Y denotes Cyc; and $R^1$, $R^2$ denote each, independently from one another H or C1-C4-alkyl, or $R^1$ and $R^2$ form together a residue according to formula (CE) as described above; and $R^{3a}$, $R^{3b}$ and $R^{3c}$ denote each, independently from one another, linear or branched C1-C3-alkyl, wherein 1 to 5 H atoms may be replaced by F, Cl, OH and OAlk, wherein Alk is methyl or ethyl; and A1 denotes ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl or 1-ethyl-2-methylpropyl, each unsubstituted or mono-, di-, tri- or tetrasubstituted by Hal, CN, $R^{3a}$, $SR^{3a}$, $OR^{3a}$, Ar1, Het1, and/or $(CH_2)_r$-A2; and Ar1 denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxy-phenyl, o-, m- or p-ethoxyphenyl, o-, m- or p-(N,N-dimethylamino)phenyl, o-, m- or p-(N-ethylamino) phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonyl)phenyl, o-, m- or p-methylsulfanylphenyl, o-, m- or p-cyanophenyl, o-, m- or p-(3-oxomorpholin-4-yl)-phenyl, o-, m- or p-(piperidinyl) phenyl, o-, m- or p-(morpholin-4-yl)phenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl; and Het1 denotes 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3- thiadiazol-4- or -5-yl, 3- or 4-pyridazinyl or pyrazinyl, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl or 1-, 2- or 3-piperazinyl; each, independently from one another, unsubstituted or mono- or disubstituted by F, Cl, $CH_3$, $C_2H_5$, $CF_3$, $OCH_3$, $OC_2H_5$, $COCF_3$, $SCH_3$, $SC_2H_5$, $N(CH_3)_2$, $NHCH_3$, $CH_2N(CH_3)_2$ and/or $N(C_2H_5)_2$; and Cyc unsubstituted or mono- or disubstituted 1- or 2-naphthyl, wherein the substituents are selected from a group consisting of Hal, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_r$—$SR^{3a}$, $(CH_2)_r$—$N(R^{4a})_2$ and/or $(CH_2)_r$-A2 (preferably F, Cl, $CH_3$, $C_2H_5$, $CF_3$, $OCH_3$, $OCF_3$ $OC_2H_5$, $CH_2OCH_3$);

or residue according to formula (Fa7), (Fb7) or (S)-(Fb7), wherein $G^a$ denotes F, Cl, Br, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_r$—$SR^{3a}$, $(CH_2)_r$—$N(R^{4a})_2$ and/or $(CH_2)_r$-A2;

$G^b$ denotes H, F, Cl, Br, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_r$—$SR^{3a}$, $(CH_2)_r$—$N(R^{4a})_2$ and/or $(CH_2)_r$-A2;

$K^a$, $K^b$ denote each, independently from one another, H, F, Cl, Br, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_r$—$SR^{3a}$, $(CH_2)_r$—$N(R^{4a})_2$ and/or $(CH_2)_r$-A2;

A2 denotes OH, $OCH_3$, $OCH_2CH_3$, $OCF_3$, O—$CH_2$—$CH_2$—OH or O—$CH_2$—$CH_2$—$OCH_3$;

r denotes 1, 2, 3 or 4; and and derivatives, prodrugs, solvates, tautomers or stereoisomers thereof, as well as the physiologically acceptable salts of each of the foregoing, including mixtures thereof in all ratios.

In another particular embodiment of the invention, the boronic acid residue shows an (R)-configuration

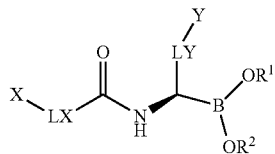

wherein

LX denotes —$CH_2$—, —$CH_2$—$CH_2$—, —$CH_2$—$CH_2$—$CH_2$—, —$CH_2$—$CH_2$—$CH_2$—$CH_2$—, —$CH_2$—$CH_2$—O—$CH_2$—, wherein 1 to 4 H atoms may be replaced by F or Cl and/or 1 or 2 H atoms may be replaced by OH, methyl, ethyl, isopropyl, $CF_3$, $CF_2CF_3$, $OCH_3$, $OCH_2CH_3$, O—$CH_2$—$CH_2$—OH, O—$CH_2$—$CH_2$—$OCH_3$; or wherein 1 H atom or $CH_2$ group may be replaced by cyclopropyl; and LY denotes —$CH_2$— or —$CH_2$—$CH_2$— wherein 1 to 4 H atoms may be replaced by F or Cl and/or 1 or 2 H atoms may be replaced by OH, methyl, ethyl, isopropyl, $CF_3$, $CF_2CF_3$, $OCH_3$, $OCH_2CH_3$, O—$CH_2$—$CH_2$—OH and/or O—$CH_2$—$CH_2$—$OCH_3$; and X phenyl, pyridinyl, pyridazinyl, pyrazinyl or triazinyl, each independently from one another unsubstituted or mono-, di- or trisubstituted by OH, CN, methyl, ethyl, isopropyl, $CF_3$, $CF_2CF_3$, $OCH_3$, $OCH_2CH_3$, O—$CH_2$—$CH_2$—OH, COmorpholinyl, COpiperazinyl, $CON(CH_3)_2$, $CON(C_2H_5)_2$, $CH_2$—$OCH_3$, and/or O—$CH_2$—$CH_2$—$OCH_3$;

Y denotes Cyc; and $R^1$, $R^2$ denote each, independently from one another H or C1-C4-alkyl, or $R^1$ and $R^2$ form together a residue according to formula (CE) as described above; and $R^{3a}$, $R^{3b}$ and $R^{3c}$ denote each, independently from one another, linear or branched C1-C3-alkyl, wherein 1 to 5 H atoms may be replaced by F, Cl, OH and OAlk, wherein Alk is methyl or ethyl; and A1 denotes ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl or 1-ethyl-2-methylpropyl;

Cyc denotes unsubstituted or mono- or disubstituted 1- or 2-naphthyl, wherein the substituents selected from a group consisting of Hal, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $CH_2$—Z, $CH_2$—$SR^3a$ $CH_2$—$N(R^{4a})_2$;

or a residue according to formula (Fa7) or (S)-(Fb7) $G^a$ denotes F, Cl, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$ or $N(C_2H_5)_2$;

$G^b$ denotes H, F, Cl, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$ or $N(C_2H_5)_2$;

$K^a$, $K^b$ denote each, independently from one another, H, F, Cl, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$ or $N(C_2H_5)_2$;

A2 denotes OH, $OCH_3$, $OCH_2CH_3$, $OCF_3$, O—$CH_2$—$CH_2$—OH or O—$CH_2$—$CH_2$—$OCH_3$;

r denotes 1, 2, 3 or 4; and and derivatives, prodrugs, solvates, tautomers or stereoisomers thereof, as well as the physiologically acceptable salts of each of the foregoing, including mixtures thereof in all ratios.

In specific embodiments, Cyc is unsubstituted or mono or disubstituted by Hal, $R^{3a}$ or $OR^{3a}$. In other specific embodiments Cyc is unsubstituted or mono or disubstituted by F, Cl, $CH_3$, $C_2H_5$, $C_2F_5$, $OCH_3$, $OC_2H_5$, $CF_3$, $OCF_3$, $OC_2F_5$.

The present invention further provides compounds of formula (PI):

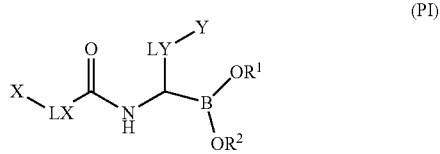

(PI)

wherein
LX denotes $CH_2$, $O-(CH_2)_n$ or $S-(CH_2)_p$, wherein in each case, independently from one another, 1 to 5 H atoms may be replaced by Hal, A1, $OR^{4a}$, $(CH_2)_r$-A2, $(CH_2)_r$-Ar2 and/or $(CH_2)_r$-Het2, and/or one $CH_2$ group of LX may be replaced by a C3-C6-cycloalkyl group;
LY denotes $(CH_2)_m$, wherein 1 to 5 H atoms may be replaced by Hal, $R^{3b}$ and/or $OR^{4b}$, and/or wherein 1 or 2 non-adjacent $CH_2$ groups may be replaced by O, SO and/or $SO_2$;
X denotes an aromatic 6-membered carbocycle or heterocycle, each independently from one another unsubstituted or mono-, di-, tri-, tetra- or pentasubstituted by Hal, A1, CN, OH, $NR^{4a}R^{4b}$, Ar1, Het1, OA1, OAr1, OHet1, COA1, COAr1, COHet1, $CONR^{4a}R^{4b}$, $NR^{4a}COR^{3a}$, $NR^{4a}SO_2R^{3a}$, $SO_2R^{3a}$, $SOR^{3a}NR^{4a}COOR^{3a}$, $OCONR^{3a}R^{4a}$, $O-(CH_2)_q$-A1 and/or $(CH_2)_r$-A2, wherein the heterocycle preferably contains 1, 2 or 3 N atoms;
Y denotes $OR^{3c}$ or Cyc;
$R^1$, $R^2$ denote each, independently from one another, H or C1-C6-alkyl, or $R^1$ and $R^2$ form together a residue according to formula (CE)

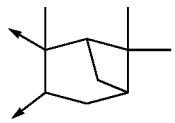

(CE)

$R^{3a}$, $R^{3b}$, $R^{3c}$ denote each, independently from one another, linear or branched C1-C6-alkyl, wherein 1 to 5 H atoms may be replaced by Hal, OH and/or OAlk;
$R^{4a}$, $R^{4b}$ denote each, independently from one another, H or $R^{3a}$;
A1 denotes linear or branched C1-C6-alkyl or C3-C6-cycloalkyl, each, independently from each other, unsubstituted or mono-, di-, tri-, tetra- or pentasubstituted by Hal, CN, $R^{3a}$, $OR^{4a}$ and/or $(CH_2)_r$-A2, wherein 1, 2 or 3 $CH_2$ groups of the C3-C6-cycloalkyl group may be replaced by O, C=O, and/or N;
A2 denotes $OR^{4a}$;
Alk denotes linear or branched C1-C6-alkyl;
Ar1 denotes phenyl, which is unsubstituted, mono-, di- or trisubstituted by Hal, $NO_2$, CN, $R^{3a}$, $OR^{4a}$, $CONR^{4a}R^{4b}$, $NR^{4a}COR^{3b}$, $SO_2R^{3a}$, $SOR^{3a}$, $NR^{4a}R^{4b}$, Ar2, Het2 and/or $(CH_2)_r$-A2;
Het1 denotes saturated, unsaturated or aromatic 5- or 6-membered heterocycle having 1 to 4 N, O and/or S atoms, wherein each heterocycle may independently be unsubstituted or mono-, di-, tri-, tetra- or pentasubstituted by Hal, $NO_2$, CN, $R^{3a}$, $OR^{4a}$, $CONR^{4a}R^{4b}$, $NR^{4a}COR^{3b}$, $SO_2R^{3a}$, $SOR^{3a}$, $NR^{4a}R^{4b}$, Ar2, Het2 and/or $(CH_2)_r$-A2;
Ar2 denotes phenyl, biphenyl or naphthyl, each independently from one another unsubstituted or mono-, di- or trisubstituted by Hal, CN, $R^{3a}$, $OR^{4a}$, $CONR^{4a}R^{4b}$, $NR^{4a}COR^{3b}$, $SO_2R^{3a}$, $SOR^{3a}$, $NR^{4a}R^{4b}$ and/or $(CH_2)_q$-A2;
Het2 denotes a saturated, unsaturated or aromatic 5- or 6-membered heterocycle having 1 to 4 N, O and/or S atoms, which is unsubstituted or mono- di- or trisubstituted by Hal, CN, $R^{3a}$, $OR^{4a}$, $CONHR^{3a}$, $NR^{3a}COR^{3b}$, $SO_2R^{3a}$, $SOR^{3a}NR^{4a}R^{4b}$ and/or $(CH_2)_q$-A2;
Cyc denotes a mono- or bicyclic, 4-, 5-, 6-, 7-, 8-, 9- or 10-membered hydrocarbon or heterocycle, each independently from one another unsubstituted or mono-, di-, tri-, tetra- or pentasubstituted by Hal, CN, $R^{3a}$, $OR^{3a}$, $CONR^{4a}R^{4b}$, $NR^{3a}COR^{3b}$, $SO_2R^{3a}$, $SOR^{3a}$, $NR^{4a}R^{4b}$, Ar2, Het2 and/or $(CH_2)_r$-A2, wherein the monocyclic hydrocarbon system is aromatic and at least one ring of the bicyclic hydrocarbon or heterocycle is aromatic, and wherein the heterocyclic system contains 1, 2 or 3 N and/or O and/or S atoms;
n, p denote each, independently from one another, 1, 2, 3, 4, 5 or 6;
m, q, r denote each, independently from one another, 0, 1, 2, 3 or 4;
Hal denotes F, Cl, Br or I;
and derivatives, prodrugs, solvates, tautomers or stereoisomers thereof, as well as the physiologically acceptable salts of each of the foregoing, including mixtures thereof in all ratios.

Further specific embodiments of the present invention comprise compounds of formula (PI) wherein
$R^1$, $R^2$ denote each, independently from one another, H or C1-C4-alkyl (preferably methyl or ethyl) or $R^1$ and $R^2$ form together a residue according to formula (CE) (CE)

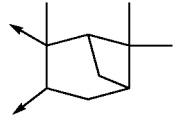

(CE)

and
X denotes phenyl, pyridinyl, pyrimidyl, pyrazinyl or triazinyl, each independently from one another unsubstituted or mono-, di-, tri-, tetra- or pentasubstituted by Hal, A1, CN, OH, $NR^{4a}R^{4b}$, Ar1, Het1, OA1, OAr1, OHet1, COA1, COAr1, COHet1, $CONR^{4a}R^{4b}$, $NR^{4a}COR^{3a}$, $NR^{4a}SO_2R^{3a}$, $SO_2R^{3a}$, $SOR^{3a}$, $NR^{4a}COOR^3$a $OCONR^{3a}R^{4a}$, $O-(CH_2)_q$-A1 and/or $(CH_2)_r$-A2;
Y denotes Cyc;
n, p denote each, independently from one another, 1, 2, 3 or 4; and
m denotes 1 or 2;
and derivatives, prodrugs, solvates, tautomers or stereoisomers thereof, as well as the physiologically acceptable salts of each of the foregoing, including mixtures thereof in all ratios.

In such an embodiment Cyc may for example denote phenyl, 1- or 2-naphthyl, 4- or 5-indanyl, 1-, 2-, 4-, 5- or 6-azulenyl, 1- or 2-tetrahydronaphthalin 5- or 6-yl, 2- or 3-furyl, 2-, 3-, 4-, 5-, 6- or 7-benzofuryl, 2-, 3-, 4-, 5-, 6- or 7-benzothiophenyl, benzodioxan-6- or 7-yl or 3,4-dihydro-1,5-benzodioxepin-6- or -7-yl, each independently from one another unsubstituted or mono-, di-, tri-, tetra- or pentasubstituted by Hal, CN, $R^{3a}$, $OR^{3a}$, $CONR^{4a}R^{4b}$, $NR^{3a}COR^{3b}$, $SO_2R^{3a}$, $SOR^{3a}$, $NR^{4a}R^{4b}$, Ar2, Het2 and/or $(CH_2)_r$-A2. In specific examples of such an embodiment Cyc is unsubstituted or mono-, di- or trisubstituted. Additionally, in case Cyc is substituted the substituents are preferably selected from a group comprising Hal, $R^{3a}$, $OR^{3a}$, Ar2, Het2. Thus, in such embodiments substituents of Cyc may e.g. be selected from a group consisting of F, Cl, Br, $OCH_3$, $OC_2H_5$, $CH_2OCH_3$, $CH_3$, $C_2H_5$, $CF_3$, $OCF_3$, phenyl, furyl, thienyl, pyrrolyl, imidazolyl, morpholinyl, piperazinyl, benzofuryl, benzodioxolyl and/or pyridyl or even more preferably selected from a group comprising F, Cl, Br, $OCH_3$, $CH_2OCH_3$, $CH_3$, $C_2H_5$, $CF_3$, $OCF_3$ and/or phenyl.

Another specific embodiment of the present invention comprises compounds of formula (PI) wherein:

LX denotes —CH$_2$—, O—CH$_2$—, O—CH$_2$—CH$_2$—, wherein in each case, independently from one another, 1 to 4 atoms may be replaced by Hal, A1, OR$^{4a}$, (CH$_2$)$_r$-A2, (CH$_2$)$_r$—Ar2 and/or (CH$_2$)$_r$-Het2, or cyclopropyl, cyclobutyl or cyclopentyl (wherein the cycloalkyl group is preferably attached to its adjacent groups LX and C=O via the same ring atom, as e.g. in Example 36);

LY denotes (CH$_2$)$_m$, wherein 1 to 4 H atoms may be replaced by Hal, R$^{3b}$, OR$^{4b}$;

Cyc denotes phenyl, which is unsubstituted, mono-, di- or trisubstituted by Hal, CN, R$^{3a}$, OR$^{3a}$, CONR$^{4a}$R$^{4b}$, NR$^{3a}$COR$^{3b}$, SO$_2$R$^{3a}$, SOR$^{3a}$, NR$^{4a}$R$^{4b}$, Ar2, Het2 and/or (CH$_2$)$_r$-A2; wherein in case of disubstitution substituents are in 2,4-, 2,5- or 3,4-position and in case of trisubstitution substituents are in 2,3,4-position;

or 1- or 2-naphthyl, 4- or 5-indanyl, 1-, 2-, 4-, 5- or 6-azulenyl, 1- or 2-tetrahydronaphthalin 5- or 6-yl, 2- or 3-furyl, 2-, 3-, 4-, 5-, 6- or 7-benzofuryl, 2-, 3-, 4-, 5-, 6- or 7-benzothiophenyl, benzodioxan-6- or 7-yl or 3,4-dihydro-1,5-benzodioxepin-6- or -7-yl, each independently from one another, unsubstituted, mono-, disubstituted or trisubstituted by Hal, CN, R$^{3a}$, OR$^{3a}$, CONR$^{4a}$R$^{3a}$NR$^{3a}$COR$^{3b}$, SO$_2$R$^{3a}$, SOR$^{3a}$, NR$^{4a}$R$^{3a}$, Ar2, Het2 and/or (CH$_2$)$_r$-A2;

and derivatives, prodrugs, solvates, tautomers or stereoisomers thereof, as well as the physiologically acceptable salts of each of the foregoing, including mixtures thereof in all ratios.

After all, a specific and preferred embodiment of the present invention comprises compounds of formula (PI) wherein:

R$^1$, R$^2$ denote H or C1-C4-alkyl (preferably methyl or ethyl) or R$^1$ and R$^2$ form together a residue according to formula (CE) as described above, particular preferably R$^1$ and R$^2$ denote H, methyl or ethyl and most preferably R$^1$ and R$^2$ denote H;

LX denotes —CH$_2$—, O—CH$_2$—, O—CH$_2$—CH$_2$—, wherein in each case, independently from one another, 1 to 4 atoms may be replaced by Hal (preferably F or Cl), A1, OR$^{4a}$, (CH$_2$)$_r$-A2, Ar2 and/or Het2, or cyclopropyl, cyclobutyl or cyclopentyl (wherein the adjacent groups LX and C=O are preferably attached to the same ring atom of the cycloalkyl, as e.g. in Example 36);

LY denotes —CH$_2$— or —CH$_2$—CH$_2$—, preferably CH$_2$;

X denotes phenyl, pyridinyl, pyrimidyl, pyrazinyl or triazinyl, each independently from one another unsubstituted or mono-, di-, tri-, tetra- or pentasubstituted (preferably mono-, di- or trisubstituted and most preferably mono- or disubstituted) by Hal, A1, CN, OH, NR$^{4a}$R$^{4b}$, Ar1, Het1, OA1, OAr1, OHet1, COA1, COAr1, COHet1, CONR$^{4a}$R$^{4b}$, NR$^{4a}$COR$^{3a}$, NR$^{4a}$SO$_2$R$^{3a}$, SO$_2$R$^{3a}$, SOR$^{3a}$NR$^{4a}$COOR$^{3a}$, OCONR$^{3a}$R$^{4a}$, O—(CH$_2$)$_q$-A1 and/or (CH$_2$)$_r$-A2;

Y denotes Cyc;

R$^{3a}$, R$^{3b}$ and R$^{3c}$ denote each, independently from one another, linear or branched C1-C4-alkyl, wherein 1 to 5 H atoms may be replaced by Hal, OH and/or OAlk, and particular preferably R$^{3a}$, R$^{3b}$ and R$^{3c}$ denote each, independently from one another, methyl, ethyl, propyl, isopropyl, CF$_3$, C$_2$F$_5$, CH$_2$OCH$_3$, CH$_2$OC$_2$H$_5$, CH$_2$OCH(CH$_3$)$_2$ or C$_2$H$_5$OCH$_3$;

A1 denotes C1-C6-alkyl (preferably C1-C3-alkyl) or C3-C6-cycloalkyl (preferably cyclopropyl, cyclopentyl or cyclohexyl), each independently from each other, unsubstituted or mono- or disubstituted by Hal, CN, R$^{3a}$, OR$^{4a}$ and/or (CH$_2$)$_r$-A2, wherein 1 or 2 CH$_2$ groups of the C3-C6-cycloalcyl group may be replaced by O, C=O and/or N;

Alk denotes methyl, ethyl, n-propyl or isopropyl;

A2 denotes OR$^4$ and even more preferably OH, OCH$_3$, OCH$_2$CH$_3$, OCF$_3$, O—CH$_2$—CH$_2$—OH or O—CH$_2$—CH$_2$—OCH$_3$;

Ar1 denotes phenyl, which is unsubstituted, mono-, di- or trisubstituted by Hal, NO$_2$, CN, R$^{3a}$, OR$^{4a}$, CONR$^{4a}$R$^{4b}$, NR$^{4a}$COR$^{3b}$, SO$_2$R$^{3a}$, SOR$^{3a}$, NR$^{4a}$R$^{4b}$, Ar2, Het2 and/or (CH$_2$)$_r$-A2 and particular preferably A1 denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methyl-aminocarbonyl)phenyl, o-, m- or p-acetamidophenyl, o-, m- or p-methoxyphenyl, o-, m- or p-ethoxyphenyl, o-, m- or p-(N,N-dimethylamino)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-cyanophenyl 2,3-, 2,4-, 2,5-, 2,6-, 3,4- or 3,5-dimethylphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,4- or 2,5-dinitrophenyl, 2,5- or 3,4-dimethoxyphenyl, Het1 denotes a saturated, unsaturated or aromatic 5- or 6-membered heterocycle having 1 to 4 N, O and/or S atoms, which is unsubstituted or mono- di- or trisubstituted by Hal, CN, R$^{3a}$, OR$^{4a}$, CONHR$^{3a}$, NR$^{3a}$COR$^{3b}$, SO$_2$R$^{3a}$, SOR$^{3a}$NR$^{4a}$R$^{4b}$ and/or (CH$_2$)$_q$-A2, and particular preferably Het 1 denotes 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl or pyrazinyl, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl; and Cyc denotes phenyl, which is unsubstituted, mono-, di- or trisubstituted by Hal, CN, R$^{3a}$, OR$^{3a}$, CONR$^{4a}$R$^{4b}$, NR$^{3a}$COR$^{3b}$, SO$_2$R$^{3a}$, SOR$^{3a}$, NR$^{4a}$R$^{4b}$, Ar2, Het2 and/or (CH$_2$)$_r$-A2, wherein disubstitution is in 2,4-, 2,5- or 3,4-position and trisubstitution is in 2,3,4-position;

or
- 1- or 2-naphthyl, 2-, 3-, 4-, 5-, 6- or 7-benzofuryl or benzodioxan-6- or 7-yl, each independently from one another, unsubstituted, mono-, di- or trisubstituted by Hal, CN, $R^{3a}$, $OR^{3a}$, $CONR^{4a}R^{4b}$, $NR^{3a}COR^{3b}$, $SO_2R^{3a}$, $SOR^{3a}$, $NR^{4a}R^{4b}$, Ar2, Het2 and/or $(CH_2)_r$-A2;
- q, r denote each, independently from one another, 0, 1, 2, 3 or 4;

and derivatives, prodrugs, solvates, tautomers or stereoisomers thereof, as well as the physiologically acceptable salts of each of the foregoing, including mixtures thereof in all ratios.

In further particular preferred embodiments Cyc is unsubstituted or mono, di- or tri-substituted by Hal, R3a or OR3a.

In general, the residues included in formula (I) and formula (PI) may have following meaning:

In LX denotes preferably $CH_2$—, $O$—$(CH_2)_{1-4}$, $S$—$(CH_2)_{1-4}$, particular preferably $CH_2$—, $O$—$CH_2$—, $O$—$CH_2$—$CH_2$—, $S$—$CH_2$— or $S$—$CH_2$—$CH_2$— and most preferably $CH_2$—, $O$—$CH_2$— or $O$—$CH_2$—$CH_2$—. In such embodiments the maximum number of H atoms of LX, which may be replaced is 5. However, in particular preferred embodiments 1 or 2 H atoms are replaced. In case one or more H atoms of LX are replaced by $(CH_2)_r$—Ar1 and $(CH_2)_r$-Het r denotes preferably 0, 1 or 2 and most preferably 0 or 1. The groups that replace the H atoms are preferably selected from the group consisting of OH, methyl, ethyl, isopropyl, $CF_3$, $CF_2CF_3$, $OCH_3$, $OCH_2CH_3$, $OCH(CH_3)_2$, $O$—$(CH_2)_{1-6}$—OH, $O$—$(CH_2)_{1-6}$—$OCH_3$, $O$—$(CH_2)_{1-6}$—$OCH(CH_3)_2$, phenyl, tolyl, ethylphenyl, fluorophenyl, chlorophenyl, bromophenyl, aminophenyl, benzyl, methoxybenzyl, fluorobenzyl, aminobenzyl, furyl, thienyl, pyrrolyl, imidazolyl, pyrazolyl, pyrimidyl, morpholinyl and/or piperidinyl.

LY denotes preferably —$CH_2$—, —$CH_2$—$CH_2$— or —$CH_2$—$CH_2$—$CH_2$— wherein 1 to 4 H atoms may be replaced by Hal and/or 1 H atom may be replaced by Hal, $R^{3b}$ and/or $OR^{4b}$, and/or wherein 1 or 2 non-adjacent $CH_2$ groups may be replaced by O, SO and/or $SO_2$. However, the maximum number of H atoms, which may be replaced is LX is 5. Most preferably LY denotes —$CH_2$—, —$CH_2$—, —$CH_2$—$CH_2$—, —$CH_2$—$CH_2$—$CH_2$—, —$CH_2$—$CH_2$—$CH_2$—$CH_2$—, wherein 1 to 4 H atoms may be replaced by F or Cl and/or 1 or 2 H atoms may be replaced by OH, methyl, ethyl, isopropyl, $CF_3$, $CF_2CF_3$, $OCH_3$, $OCH_2CH_3$, $O$—$CH_2$—$CH_2$—OH and/or $O$—$CH_2$—$CH_2$—$OCH_3$ and/or wherein 1 $CH_2$ group of LY may be replaced by O.

$R^1$, $R^2$ denote preferably each, independently from one another H or methyl, ethyl, n-propyl or isopropyl or $R^1$ and $R^2$ form together a residue according to formula (CE) as described above.

$R^{3a}$, $R^{3b}$, $R^{3c}$ denote preferably each, independently from one another, linear or branched C1-, C2- or C3-alkyl, wherein 1 to 5 H atoms may be replaced by F, Cl, OH and OAlk, wherein Alk is preferably methyl or ethyl. Most preferably $R^{3a}$, $R^{3b}$, $R^{3c}$ denote each, independently from one another, methyl, ethyl, n-propyl or isopropyl, wherein 1, 2 or 3 H atoms are replaced by F, Cl, OH, $OCH_3$, $OC_2H_5$ or $OCH(CH_3)_2$.

$R^{4a}$ and $R^{4b}$ denote preferably each, independently from one another, preferably H, methyl, furthermore ethyl, propyl, isopropyl, butyl, isobutyl, sec-butyl, tert-butyl or pentyl, wherein 1, 2 or 3 H atoms are replaced by F, Cl, OH, $OCH_3$, $OC_2H_5$ or $OCH(CH_3)_2$.

In embodiments where A1 is linear or branched C1-C6-alkyl it denotes preferably methyl, furthermore ethyl, propyl, isopropyl, butyl, isobutyl, sec-butyl, tert-butyl, pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, each unsubstituted or mono-, di- or trisubstituted by Hal (preferably F or Cl), CN, $R^{3a}$, $OR^{4a}$, and/or $(CH_2)_r$-A2. Most preferably A1 is selected from a group consisting of methyl, furthermore ethyl, propyl, isopropyl, butyl, isobutyl, sec-butyl, tert-butyl, pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl and 1,1,2- or 1,2,2-trimethylpropyl.

In embodiments where A1 is a cyclic alkyl group (cycloalkyl) it preferably denotes cyclopropyl, cyclobutyl, cyclopentyl or cyclohexyl, each unsubstituted or mono-, di- or trisubstituted by Hal (preferably F or Cl), CN, $R^{3a}$, $OR^{4a}$ and/or $(CH_2)_r$-A2, wherein 1 or 2 $CH_2$ groups of the cycloalkyl ring may be replaced be O, C=O or N. Most preferably A1 denotes cyclopropyl, cyclopentyl or cyclohexyl, each unsubstituted or mono- or di- by $R^{3a}$ or Hal (preferably F or Cl), wherein 1 or 2 $CH_2$ groups of the cycloalkyl ring may be replaced be O, C=O or N. Thus, in case A1 is a cycloalkyl group it may e.g. denote: cyclopropyl, cyclopentyl, morpholinyl, piperidinyl, 2-oxopyrrolidinyl, 2-oxopiperidiyl or tetrahydropyranyl.

Ar1 can for example denote phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-(N,N-dimethyl-amino)phenyl, o-, m- or p-(N-ethylamino)phenyl, o-, m- or p-(N,N-diethylamino) phenyl, o-, m- or p-fluorophenyl, o-, m- or p-bromophenyl, o-, m- or p-chlorophenyl, o-, m- or p-(methylsulfonyl) phenyl, o-, m- or p-methylsulfanylphenyl, o-, m- or p-cyanophenyl, o-, m- or p-(3-oxomorpholin-4-yl)phenyl, o-, m- or p-(piperidinyl)phenyl, o-, m- or p-(morpholin-4-yl)phenyl, o-, m- or p-trifluoromethyl-phenyl or o-, m- or p-trichloromethyl-phenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Most preferably Ar1 denotes, phenyl which is unsubstituted, mono-, di or trisubstituted by F, Cl, Br, $OCH_3$, $CH_2OCH_3$, $CH_3$, $C_2H_5$, $CF_3$, phenyl, biphenyl, naphthyl, furyl, thienyl, pyrrolyl, imidazolyl, morpholinyl, piperazinyl, benzofuryl, benzodioxolyl and/or pyridyl.

Het1 can for example denote 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl or pyrazinyl, each unsubstituted or mono-, di-, tri-, tetra- or pentasubstituted (preferably unsubstituted or mono-, di- or trisubstituted) by Hal, $NO_2$, CN, $R^{3a}$, $OR^{4a}$, $CONR^{4a}R^{4b}$, $NR^{4a}COR^{3b}$, $SO_2R^{3a}$, $SOR^{3a}$, $NR^{4a}R^{4b}$, Ar2, Het2 and/or $(CH_2)_r$-A2. In such embodiments Het1 is most preferably unsubstituted or mono-, di or trisubstituted (most preferably monosubstituted), by F, Cl, Br, $OCH_3$, $CH_2OCH_3$, $CH_3$, $CF_3$, phenyl, biphenyl, naphthyl, furyl, thienyl, pyrrolyl, imidazolyl, morpholinyl, piperazinyl, benzofuryl, benzodioxolyl and/or pyridyl.

However, Het1 may also be partially or fully hydrogenated. Thus, Het1 can also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl or 1-, 2- or 3-piperazinyl, each unsubstituted or mono-, di-, tri-, tetra- or pentasubstituted (preferably unsubstituted, mono-, di- or trisubstituted) by Hal (preferably F or Cl), $NO_2$, CN, $R^{3a}$, $OR^{4a}$, $CONR^{4a}R^{4b}$, $NR^{4a}COR^{3b}SO_2R^{3a}$, $SOR^{3a}$, $NR^{4a}R^{4b}$, Ar2, Het2 and/or $(CH_2)_r$-A2. In these embodiments Het1 is preferably unsubstituted or mono-, di or trisubstituted (most preferably monosubstituted), by F, Cl, Br, $OCH_3$, $CH_2OCH_3$, $CH_3$, $CF_3$, phenyl, biphenyl, naphthyl, furyl, thienyl, pyrrolyl, imidazolyl, morpholinyl, piperazinyl, benzofuryl, benzodioxolyl and/or pyridyl.

Cyc denotes preferably phenyl, 1- or 2-naphthyl, 4- or 5-indanyl, 1-, 2-, 3-, 4-, 5-, 6- or 7-indolyl, 1-, 2-, 4-, 5- or 6-azulenyl, 1- or 2-tetrahydronaphthalin 5- or 6-yl, 2- or 3-furyl, 2-, 3-, 4-, 5-, 6- or 7-benzofuryl, 2,3-dihydrobenzofuran-2- or 3-yl, 2- or 3-thienyl, 2- or 3-benzothienyl, 2-, 3-, 4-, 5-, 6- or 7-benzothiophenyl, methylenedioxyphenyl, benzodioxan-6- or 7-yl or 3,4-dihydro-1,5-benzodioxepin-6- or -7-yl, each independently from one another unsubstituted, mono-, di- or trisubstituted by Hal (preferably F or Cl), CN, $R^{3a}$, $OR^{3a}$, $CONR^{4a}R^{4b}$, $NR^{3a}COR^{3b}$, $SO_2R^{3a}$, $SOR^{3a}$, $NR^{4a}R^{4b}$, Ar2, Het2 and/or $(CH_2)_r$-A2. Most preferably Cyc denotes phenyl, 1- or 2-naphthyl 2-, 3-, 4-, 5-, 6- or 7-benzofuryl 2,3-dihydrobenzofuran-2- or 3-yl, 2- or 3-thienyl, 2- or 3-benzothienyl or benzodioxan-6- or 7-yl, each independently from one another, unsubstituted, mono-, disubstituted or trisubstituted by $CH_3$, $C_2H_5$, $CH_2OCH_3$, $OCH_3$, F, Cl, or $CF_3$. In case Cyc denotes a disubstituted phenyl the substituents are preferably in 2,4-, 2,5- or 3,4-position, most preferably in 2,4- or 3,4-position. In case Cyc denotes a trisubstituted phenyl the substituents are preferably in 2,3,4-position.

In particular Cyc can denote o-, m- or p-tolyl, o-, m- or p-ethylphenyl, o-, m- or p-propylphenyl, o-, m- or p-isopropylphenyl, o-, m- or p-tert-butylphenyl, o-, m- or p-acetamidophenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-trifluoromethyl-phenyl, o-, m- or p-trichloromethyl-phenyl, o-, m- or p-(methylsulfonyl)phenyl, o-, m- or p-phenoxyphenyl, o-, m- or p-methoxymethyl-phenyl further preferably 2,4-, 2,5-, 2,6- or 3,4-dimethylphenyl, 2,4-, 2,5- or 3,4-difluorophenyl, 2,4-, 2,5- or 3,4-dichlorophenyl, 2,4-, 2,5- or 3,4-dibromophenyl, 2,5- or 3,4-dimethoxyphenyl, 2,3,4-, 2,3,5-, 2,3, 6-, 2,4,6- or 3,4,5-trichlorophenyl, 2,3,4-, 2,3,5-, 2,3,6-, 2,4,6- or 3,4,5-trifluorophenyl, 2,3,4-, 2,3,5-, 2,3,6-, 2,4,6- or 3,4,5-trimethylphenyl, 2,3,4-, 2,3,5-, 2,3,6-, 2,4,6- or 3,4,5-tris-trifluormethyl-phenyl, 2,3,4-, 2,3,5-, 2,3,6-, 2,4,6- or 3,4,5-tristrichlormethyl-phenyl, 2,3,4-, 2,3,5-, 2,3,6-, 2,4, 6- or 3,4,5-trimethoxymethyl-phenyl, 2,4,6-trimethoxyphenyl, p-iodophenyl, 2-fluoro-3-chlorophenyl, 2-fluoro-3-bromophenyl, 2,3-difluoro-4-bromophenyl, 3-bromo-3-methoxyphenyl, 2-chloro-3-methoxyphenyl, 2-fluoro-3-methoxy-phenyl, 2-chloro-3-acetamidophenyl, 2-fluoro-3-methoxyphenyl, 2-chloro-3-acetamidophenyl, 2,3-dimethyl-4-chlorophenyl, 2,3-dimethyl-4-fluorophenyl.

Cyc can also denote 1- or 2-naphthyl, 4- or 5-indanyl, 1-, 2-, 4-, 5- or 6-azulenyl, 1- or 2-tetrahydronaphthalin 5- or 6-yl, 2- or 3-furyl, 2-, 3-, 4-, 5-, 6- or 7-benzofuryl, 2-, 3-, 4-, 5-, 6- or 7-benzothiophenyl, methylenedioxyphenylbenzodioxan-6- or 7-yl or 3,4-dihydro-1,5-benzodioxepin-6- or -7-yl, each independently from one another unsubstituted or mono-, di- or trisubstituted by Hal, CN, $R^{3a}$, $OR^{3a}$, $CONHR^{3a}$, $NR^{3a}COR^{3b}$, $SO_2R^{3a}$, $SOR^{3a}$, $NH_2$, $NHR^{3a}$, $N(R^{3a})_2$, Ar2, Het 2 and/or $(CH_2)_q$—Z. Particularly preferred substituents of Cyc are selected from a group comprising Hal, CN, $R^{3a}$, $OR^{3a}$ X denotes preferably phenyl, pyridinyl, pyrimidyl or pyrazinyl. In case X is substituted substituents are preferably selected from a group consisting of F, Cl, methyl, ethyl, methoxy, ethoxy, CN, $CF_3$, $OCF_3$, A1, COA1, COAr1, COHet1, $NR^{4a}COR^{3a}$, $NR^{4a}SO_2R^{3a}$, $NR^{4a}CR^{3a}$ and OA1.

Ar2 denotes preferably phenyl, which is unsubstituted or mono- or disubstituted by Hal, CN, $R^{3a}$, $OR^{3a}$, $CONHR^{3a}$, $NH_2$, $NHR^{3a}$ and/or $N(R^{3a})_2$. Thus, Ar2 preferably denotes e.g. phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl) phenyl, o-, m- or p-acetamidophenyl, o-, m- or p-methoxyphenyl, o-, m- or p-ethoxyphenyl, o-, m- or p-(N,N-dimethylamino)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-cyanophenyl.

Het2 denotes preferably a saturated, unsaturated or aromatic 5- or 6-membered heterocycle having 1 to 4 N, O and/or S atoms, which is unsubstituted or mono- or disubstituted by Hal, CN, $R^{3a}$, $OR^{3a}$, $CONHR^{3a}$, $NH_2$, $NHR^{3a}$ and/or $N(R^{3a})_2$. Thus, Het2 may e.g. denote 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, imidazolyl, morpholinyl or piperazinyl.

Alk denotes preferably methyl, ethyl, propyl, isopropyl, butyl, isobutyl, sec-butyl or tert-butyl, pentyl or hexyl, most preferably methyl, ethyl, propyl or isopropyl.

A2 denotes preferably OH, methyl, ethyl, isopropyl, $CF_3$, $CF_2CF_3$, $OCH_3$, $OCH_2CH_3$, O—$CH_2$—$CH_2$—OH or O—$CH_2$—$CH_2$—$OCH_3$.

Hal denotes preferably F, Cl or Br, most preferably F or Cl.

n denotes preferably 1, 2, 3 or 4, more preferably n is 2, 3 or 4 and most preferably n is 2 or 3.

m denotes preferably 0, 1 or 2, more 1 or 2 and most preferably 1.

q and r independently from each other denote preferably 0, 1, 2, 3 or 4 and even more preferably 0, 1 or 2.

In the context of the present invention "C1-C6-alkyl" means an alkyl moiety having 1, 2, 3, 4, 5 or 6 carbon atoms and being straight-chain or branched. The term "C3-C6-cycloalkyl" refers to saturated cyclic hydrocarbon groups having 3, 4, 5 or 6 carbon atoms.

The term "unsubstituted" means that the corresponding radical, group or moiety has no substituents other than H; the term "substituted" means that the corresponding radical, group or moiety has one or more substituents. Where a radical has a plurality of substituents, i.e. at least two, and a selection of various substituents is specified, the substituents are selected independently of one another and do not need to be identical.

Amino refers to the group —NRR', wherein R and R' are each independently from one another H or linear or branched C1-C6-alkyl (particularly methyl, ethyl, propyl, isopropyl, butyl, isobutyl, sec-butyl or tert-butyl, pentyl, hexyl).

The group "CO" as e.g. included in the COR$^a$, is group, wherein C and O are connected via a double bond (C=O).

Preferably, the compounds of the present invention are selected from the group consisting of:

Compound No. 1: [(1R)-1-[[2-[(3,5-dichloro-2-pyridyl)oxy]acetyl]amino]-2-phenyl-ethyl]boronic acid;
Compound No. 2: [(1R)-2-phenyl-1-[[2-(2-pyridyloxy)acetyl]amino]ethyl]boronic acid;
Compound No. 3: [(1R)-1-[(2-phenoxyacetyl)amino]-2-phenyl-ethyl]boronic acid;
Compound No. 4: [(1R)-1-(3-phenoxypropanoylamino)-2-(p-tolyl)ethyl]boronic acid;
Compound No. 5: [(1R)-1-[3-(4-methoxyphenoxy)propanoylamino]-2-(p-tolyl)ethyl]-boronic acid;
Compound No. 6: [(1R)-2-(benzofuran-3-yl)-1-[(2-phenylacetyl)amino]-ethyl]boronic acid;
Compound No. 7: [(1R)-2-(benzofuran-3-yl)-1-[3-(4-methylphenoxy)propanoylamino]-ethyl]boronic acid;
Compound No. 8: [(1R)-2-(benzofuran-3-yl)-1-[[2-(3-pyridyl)acetyl]amino]ethyl]-boronic acid;
Compound No. 9: [(1R)-2-(benzofuran-3-yl)-1-[[2-(4-cyanophenyl)acetyl]amino]ethyl]-boronic acid;
Compound No. 10: [(1R)-2-(benzofuran-3-yl)-1-[[2-(4-methoxyphenyl)acetyl]amino]-ethyl]boronic acid;
Compound No. 11: [(1R)-2-(benzofuran-3-yl)-1-[[2-(3-pyridyloxy)acetyl]amino]ethyl]-boronic acid;
Compound No. 12: [(1R)-2-(benzofuran-3-yl)-1-[[2-(6-methoxy-2-pyridyl)acetyl]amino]-ethyl]boronic acid;
Compound No. 13: [(1R)-2-(benzofuran-3-yl)-1-[[2-(5-ethoxy-2-pyridyl)acetyl]amino]-ethyl]boronic acid;
Compound No. 14: [(1R)-1-[(2-phenylacetyl)amino]-2-(p-tolyl)ethyl]boronic acid;
Compound No. 15: [(1R)-2-(benzofuran-3-yl)-1-[[2-(3-methoxyphenyl)acetyl]amino]-ethyl]boronic acid;
Compound No. 16: [(1R)-1-[[(2R)-2-hydroxy-2-phenyl-acetyl]amino]-2-(p-tolyl)ethyl]-boronic acid;
Compound No. 17: [(1R)-1-[[(2S)-2-hydroxy-2-phenyl-acetyl]amino]-2-(p-tolyl)ethyl]-boronic acid;
Compound No. 18: [(1R)-2-(benzofuran-3-yl)-1-[(2-pyrazin-2-ylacetyl)amino]ethyl]-boronic acid;
Compound No. 19: [(1R)-2-(benzofuran-3-yl)-1-[[2-(4-pyridyl)acetyl]amino]ethyl]-boronic acid;
Compound No. 20: [(1R)-2-(benzofuran-3-yl)-1-[(2-pyrimidin-2-ylacetyl)amino]ethyl]-boronic acid;
Compound No. 21: [(1R)-1-[[2-(4-acetamidophenyl)acetyl]amino]-2-(p-tolyl)ethyl]-boronic acid;
Compound No. 22: [(1R)-2-(benzofuran-3-yl)-1-[[2-(3,4,5-trifluorophenyl)acetyl]amino]-ethyl]boronic acid;
Compound No. 23: [(1R)-2-(benzofuran-3-yl)-1-[(2,2-difluoro-2-phenyl-acetyl)amino]-ethyl]boronic acid;
Compound No. 24: [(1R)-2-(benzofuran-3-yl)-1-[[2-[2-(trifluoromethyl)phenyl]acetyl]-amino]ethyl]boronic acid;
Compound No. 25: [(1R)-2-(benzofuran-3-yl)-1-[[2-(2,6-dichlorophenyl)acetyl]-amino]-ethyl]boronic acid;
Compound No. 26: [(1R)-1-[[2-(4-acetamidophenyl)acetyl]amino]-2-(benzofuran-3-yl)ethyl]boronic acid;
Compound No. 27: [(1R)-2-(benzofuran-3-yl)-1-[[2-(2-methoxyphenyl)acetyl]amino]-ethyl]boronic acid;
Compound No. 28: [(1R)-2-(benzofuran-3-yl)-1-[[2-[2-(trifluoromethoxy)phenyl]acetyl]-amino]ethyl]boronic acid;
Compound No. 29: [(1R)-2-(2,4-dimethylphenyl)-1-[(2-phenylacetyl)amino]ethyl]-boronic acid;
Compound No. 30: [(1R)-2-(benzofuran-3-yl)-1-[[2-[4-(methoxymethyl)phenyl]acetyl]-amino]ethyl]boronic acid;
Compound No. 31: [(1R)-2-(benzofuran-3-yl)-1-[[2-[3-(3-hydroxypropoxy)phenyl]-acetyl]amino]ethyl]boronic acid;
Compound No. 32: [(1R)-1-[[2-(3-acetamidophenyl)acetyl]amino]-2-(benzofuran-3-yl)ethyl]boronic acid;
Compound No. 33: [(1R)-2-(benzofuran-3-yl)-1-[[(2S)-2-methoxy-2-phenyl-acetyl]amino]ethyl]boronic acid;
Compound No. 34: [(1R)-2-(benzofuran-3-yl)-1-[[(2R)-2-methoxy-2-phenyl-acetyl]amino]ethyl]boronic acid;
Compound No. 35: [(1R)-2-(2,4-dimethylphenyl)-1-[[2-(2,6-dimethylphenyl)acetyl]-amino]ethyl]boronic acid;
Compound No. 36: [(1R)-2-(2,4-dimethylphenyl)-1-[(1-phenylcyclopropanecarbonyl)-amino]ethyl]boronic acid;
Compound No. 37: [(1R)-2-(benzofuran-3-yl)-1-[[(2S)-2-phenylpropanoyl]amino]ethyl]-boronic acid;
Compound No. 38: [(1R)-1-[[2-(4-acetamidophenyl)acetyl]amino]-2-(2,4-dimethylphenyl)ethyl]boronic acid;
Compound No. 39: [(1R)-2-(benzofuran-3-yl)-1-[[2-[4-(2-hydroxyethoxy)phenyl]acetyl]-amino]ethyl]boronic acid;
Compound No. 40: [(1R)-2-(benzofuran-3-yl)-1-[[2-[4-(3-hydroxypropoxy)-phenyl]acetyl]amino]ethyl]boronic acid;
Compound No. 41: [(1R)-2-(benzofuran-3-yl)-1-[[2-[3-(2-hydroxyethoxy)phenyl]acetyl]-amino]ethyl]boronic acid;
Compound No. 42: [(1R)-1-[[2-(2,6-dimethoxyphenyl)acetyl]amino]-2-(2,4-dimethylphenyl)ethyl]boronic acid;
Compound No. 43: [(1R)-2-(2,4-dimethylphenyl)-1-[[2-[4-(2-oxopyrrolidin-1-yl)phenyl]-acetyl]amino]ethyl]boronic acid;
Compound No. 44: [(1R)-1-[[2-(4-dimethylaminophenyl)acetyl]amino]-2-(2,4-dimethylphenyl)ethyl]boronic acid;
Compound No. 45: [(1R)-2-(benzofuran-3-yl)-1-[[(2R)-2-phenylpropanoyl]amino]ethyl]-boronic acid;
Compound No. 46: [(1R)-2-(2,4-dimethylphenyl)-1-[[2-[4-(methanesulfonamido)-phenyl]acetyl]amino]ethyl]boronic acid;
Compound No. 47: [(1R)-2-(2,4-dimethylphenyl)-1-[[2-[4-[(2-methoxyacetyl)amino]-phenyl]acetyl]amino]ethyl]boronic acid;
Compound No. 48: [(1R)-2-(benzofuran-3-yl)-1-[[2-[2-(methoxymethyl)phenyl]acetyl]-amino]ethyl]boronic acid;

Compound No. 49: [(1R)-2-(benzofuran-3-yl)-1-[[2-[3-(methoxymethyl)phenyl]acetyl]-amino]ethyl]boronic acid;

Compound No. 50: [(1R)-2-(benzofuran-3-yl)-1-[[2-[2-(2-hydroxyethoxy)phenyl]acetyl]-amino]ethyl]boronic acid;

Compound No. 51: [(1R)-2-(benzofuran-3-yl)-1-[[2,2-difluoro-2-(4-methoxyphenyl)-acetyl]amino]ethyl]boronic acid;

Compound No. 52: [(1R)-2-(benzofuran-3-yl)-1-[[2-(3,4,5-trimethoxyphenyl)acetyl]-amino]ethyl]boronic acid;

Compound No. 53: [(1R)-2-(2,4-dimethylphenyl)-1-[[2-[4-[(2,2,2-trifluoroacetyl)amino]-phenyl]acetyl]amino]ethyl]boronic acid;

Compound No. 54: [(1R)-2-(benzofuran-3-yl)-1-[[2-(2-tetrahydropyran-4-yloxyphenyl)-acetyl]amino]ethyl]boronic acid;

Compound No. 55: [(1R)-2-(benzofuran-3-yl)-1-[[2-[2-(3-hydroxypropoxy)phenyl]-acetyl]amino]ethyl]boronic acid;

Compound No. 56: [(1S)-2-(benzofuran-3-yl)-1-[[(2S)-3-hydroxy-2-phenyl-propanoyl]-amino]ethyl]boronic acid;

Compound No. 57: [(1R)-2-(benzofuran-3-yl)-1-[[(2S)-3-hydroxy-2-phenyl-propanoyl]-amino]ethyl]boronic acid;

Compound No. 58: [(1R)-2-(benzofuran-3-yl)-1-[[2-(2,5-dimethoxyphenyl)acetyl]-amino]ethyl]boronic acid;

Compound No. 59: [(1R)-2-(benzofuran-3-yl)-1-[[(2R)-3-hydroxy-2-phenyl-propanoyl]-amino]ethyl]boronic acid;

Compound No. 60: [(1R)-2-(benzofuran-3-yl)-1-[[2-(2,3,4-trimethoxyphenyl)acetyl]-amino]ethyl]boronic acid;

Compound No. 61: [(1S)-2-(benzofuran-3-yl)-1-[[2-[2-(3-hydroxypropoxy)phenyl]-acetyl]amino]ethyl]boronic acid;

Compound No. 62: [(1S)-2-(benzofuran-3-yl)-1-[[(2R)-3-hydroxy-2-phenyl-propanoyl]-amino]ethyl]boronic acid;

Compound No. 63: [(1R)-2-(benzofuran-3-yl)-1-[[2-[2-(morpholine-4-carbonyl)phenyl]-acetyl]amino]ethyl]boronic acid;

Compound No. 64: [(1R)-2-(benzofuran-3-yl)-1-[[2-[4-(2-oxopyrrolidin-1-yl)phenyl]-acetyl]amino]ethyl]boronic acid;

Compound No. 65: [(1R)-2-(benzofuran-3-yl)-1-[[2-[2-(ethylcarbamoyl)phenyl]acetyl]-amino]ethyl]boronic acid;

Compound No. 66: [(1R)-2-(benzofuran-3-yl)-1-[[2-[2-(dimethylcarbamoyl)phenyl]-acetyl]amino]ethyl]boronic acid;

Compound No. 67: [(1R)-2-(benzofuran-3-yl)-1-[[2-(4-phenylphenyl)acetyl]amino]-ethyl]boronic acid;

Compound No. 68: [(1R)-2-(benzofuran-3-yl)-1-[(2,2-diphenylacetyl)amino]ethyl]-boronic acid;

Compound No. 69: [(1S)-2-(benzofuran-3-yl)-1-[[2-(4-phenylphenyl)acetyl]amino]-ethyl]boronic acid;

Compound No. 70: [(1R)-2-(benzofuran-3-yl)-1-[[(2R)-2-ethoxy-2-phenyl-acetyl]-amino]ethyl]boronic acid;

Compound No. 71: [(1R)-2-(benzofuran-3-yl)-1-[[3-(4-methoxyphenyl)-2-phenyl-propanoyl]amino]ethyl]boronic acid;

Compound No. 72: [(1R)-2-(benzofuran-3-yl)-1-[[2-[3-(ethoxycarbonylamino)phenyl]-acetyl]amino]ethyl]boronic acid;

Compound No. 73: [(1R)-2-(2-chlorobenzofuran-3-yl)-1-[(2-phenylacetyl)amino]ethyl]-boronic acid;

Compound No. 74: [(1R)-2-(2,3-dihydrobenzofuran-3-yl)-1-[(2-phenylacetyl)amino]-ethyl]boronic acid;

Compound No. 75: [(1R)-2-(7-methylbenzofuran-3-yl)-1-[(2-phenylacetyl)amino]-ethyl]boronic acid;

Compound No. 76: [(1R)-1-[[(2R)-2-methoxy-2-phenyl-acetyl]amino]-2-(7-methylbenzofuran-3-yl)ethyl]boronic acid;

Compound No. 77: [(1R)-2-(7-methyl-2,3-dihydrobenzofuran-3-yl)-1-[(2-phenylacetyl)amino]ethyl]boronic acid;

Compound No. 78: [(1R)-1-[[2-(2,5-dimethoxyphenyl)acetyl]amino]-2-(7-methylbenzofuran-3-yl)ethyl]boronic acid;

Compound No. 79: [(1R)-1-[[(2S)-3-hydroxy-2-phenyl-propanoyl]amino]-2-(7-methylbenzofuran-3-yl)ethyl]boronic acid;

Compound No. 80: [(1S)-1-[[(2S)-3-hydroxy-2-phenyl-propanoyl]amino]-2-(7-methylbenzofuran-3-yl)ethyl]boronic acid;

Compound No. 81: [(1S)-1-[[2-(4-methoxyphenyl)acetyl]amino]-2-(7-methylbenzofuran-3-yl)ethyl]boronic acid;

Compound No. 82: [(1R)-1-[[2-(4-methoxyphenyl)acetyl]amino]-2-(7-methylbenzofuran-3-yl)ethyl]boronic acid;

Compound No. 83: [(1R)-1-[[(2R)-3-hydroxy-2-phenyl-propanoyl]amino]-2-(7-methylbenzofuran-3-yl)ethyl]boronic acid;

Compound No. 84: [(1S)-1-[[(2R)-3-hydroxy-2-phenyl-propanoyl]amino]-2-(7-methylbenzofuran-3-yl)ethyl]boronic acid;

Compound No. 85: [(1R)-2-(7-chlorobenzofuran-3-yl)-1-[(2-phenylacetyl)amino]ethyl]boronic acid;

Compound No. 86: [(1R)-1-[3-(5-methoxy-2-pyridyl)propanoylamino]-2-(7-methyl-2,3-dihydrobenzofuran-3-yl)ethyl]boronic acid;

Compound No. 87: [(1S)-1-[3-(5-methoxy-2-pyridyl)propanoylamino]-2-(7-methyl-2,3-dihydrobenzofuran-3-yl)ethyl]boronic acid;

Compound No. 88: [(1R)-1-[[2-(4-methoxyphenyl)acetyl]amino]-2-[(3R)-7-methyl-2,3-dihydrobenzofuran-3-yl]ethyl]boronic acid;

Compound No. 89: [(1R)-1-[[2-(4-methoxyphenyl)acetyl]amino]-2-[(3S)-7-methyl-2,3-dihydrobenzofuran-3-yl]ethyl]boronic acid;

Compound No. 90: [(1R)-2-(benzofuran-3-yl)-1-[[2-(2-cyanophenyl)acetyl]amino]ethyl]boronic acid;

Compound No. 91: [(1R)-2-(benzofuran-3-yl)-1-[[2-[4-(1-hydroxy-1-methyl-ethyl)phenyl]acetyl]amino]ethyl]boronic acid;

Compound No. 92: [(1R)-2-(7-methoxybenzofuran-3-yl)-1-[(2-phenylacetyl)amino]ethyl]boronic acid;

Compound No. 93: [(1R)-1-[[(2R)-2-methoxy-2-phenyl-acetyl]amino]-2-(7-methyl-2,3-dihydrobenzofuran-3-yl)ethyl]boronic acid;

Compound No. 94: [(1R)-2-(6,7-dimethylbenzofuran-3-yl)-1-[(2-phenylacetyl)amino]ethyl]boronic acid;

Compound No. 95: [(1R)-2-(6,7-dimethylbenzofuran-3-yl)-1-[3-(5-methoxy-2-pyridyl) propanoylamino]ethyl]boronic acid;

Compound No. 96: [(1R)-2-(benzofuran-3-yl)-1-[[(2S)-2-[2-(dimethylcarbamoyl)phenyl]propanoyl]amino]ethyl]boronic acid;

Compound No. 97: [(1R)-2-(benzofuran-3-yl)-1-[[(2R)-2-[2-(dimethylcarbamoyl)phenyl]propanoyl]amino]ethyl]boronic acid;

Compound No. 98: [(1R)-2-(benzofuran-3-yl)-1-[[2-(2-phenylphenyl)acetyl]amino]ethyl]boronic acid;

Compound No. 99: [(1R)-2-[(3S)-2,3-dihydrobenzofuran-3-yl]-1-[[(2R)-2-[2-(dimethylcarbamoyl)phenyl]propanoyl]amino]ethyl]boronic acid;

Compound No. 100: [(1R)-1-[[2-[2-(dimethylcarbamoyl)phenyl]acetyl]amino]-2-(7-methyl-2,3-dihydrobenzofuran-3-yl)ethyl]boronic acid;

Compound No. 101: [(1R)-2-(6,7-dimethyl-2,3-dihydrobenzofuran-3-yl)-1-[(2-phenylacetyl)amino]ethyl]boronic acid;
Compound No. 102: [(1R)-2-(6,7-dimethyl-2,3-dihydrobenzofuran-3-yl)-1-[3-(5-methoxy-2-pyridyl)propanoylamino]ethyl]boronic acid;
Compound No. 103: [(1R)-1-[[2-(2-acetamidophenyl)acetyl]amino]-2-(benzofuran-3-yl)ethyl]boronic acid;
Compound No. 104: [(1R)-1-[[2-(2-cyanophenyl)acetyl]amino]-2-(7-methylbenzofuran-3-yl)ethyl]boronic acid;
Compound No. 105: [(1R)-1-[[2-(2-cyanophenyl)acetyl]amino]-2-[(3S)-2,3-dihydrobenzofuran-3-yl]ethyl]boronic acid;
Compound No. 106: [(1R)-2-[(3R)-2,3-dihydrobenzofuran-3-yl]-1-[[(2S)-2-[2-(dimethylcarbamoyl)phenyl]propanoyl]amino]ethyl]boronic acid;
Compound No. 107: [(1R)-2-[(3S)-2,3-dihydrobenzofuran-3-yl]-1-[[(2S)-2-[2-(dimethylcarbamoyl)phenyl]propanoyl]amino]ethyl]boronic acid;
Compound No. 108: [(1R)-2-(benzofuran-2-yl)-1-[[2-(4-methoxyphenyl)acetyl]amino]ethyl]boronic acid;
Compound No. 109: [(1R)-1-[[(2R)-2-ethoxy-2-phenyl-acetyl]amino]-2-(7-methyl-2,3-dihydrobenzofuran-3-yl)ethyl]boronic acid;
Compound No. 110: [(1R)-2-(benzofuran-2-yl)-1-[(2-phenylacetyl)amino]ethyl]boronic acid;
Compound No. 111: [(1R)-2-(2,3-dihydrobenzofuran-3-yl)-1-[[(2R)-2-ethoxy-2-phenyl-acetyl]amino]ethyl]boronic acid;
Compound No. 112: [2-(benzofuran-3-yl)-1-[[2-(2-pyridyl)acetyl]amino]ethyl]boronic acid;
Compound No. 113: [(1R)-2-(7-chlorobenzofuran-3-yl)-1-[[2-(5-ethoxy-2-pyridyl)acetyl]amino]ethyl]boronic acid;
Compound No. 114: [(1R)-2-[(3S)-2,3-dihydrobenzofuran-3-yl]-1-[[2-(4-methoxyphenyl)acetyl]amino]ethyl]boronic acid;
Compound No. 115: [(1R)-2-[(3R)-2,3-dihydrobenzofuran-3-yl]-1-[[2-(4-methoxyphenyl)acetyl]amino]ethyl]boronic acid;
Compound No. 116: [(1R)-2-(7-chlorobenzofuran-3-yl)-1-[[2-(2-cyanophenyl)acetyl]amino]ethyl]boronic acid;
Compound No. 117: [(1S)-2-[(3S)-2,3-dihydrobenzofuran-3-yl]-1-[[2-(4-methoxyphenyl)acetyl]amino]ethyl]boronic acid;
Compound No. 118: [(1S)-2-[(3R)-2,3-dihydrobenzofuran-3-yl]-1-[[2-(4-methoxyphenyl)acetyl]amino]ethyl]boronic acid;
Compound No. 119: [(1R)-2-(benzofuran-3-yl)-1-[[2-[3-(morpholine-4-carbonyl)-2-pyridyl]acetyl]amino]ethyl]boronic acid;
Compound No. 120: [(1R)-2-[(3S)-7-methoxy-2,3-dihydrobenzofuran-3-yl]-1-[[2-(4-methoxyphenyl)acetyl]amino]ethyl]boronic acid;
Compound No. 121: [2-(7-fluorobenzofuran-3-yl)-1-[(2-phenylacetyl)amino]ethyl]boronic acid;
Compound No. 122: [(1R)-2-[(3R)-2,3-dihydrobenzofuran-3-yl]-1-[[2-(4-methoxyphenyl)acetyl]amino]ethyl]boronic acid;
Compound No. 123: [(1R)-2-(benzofuran-3-yl)-1-[[2-(3-cyanophenyl)acetyl]amino]ethyl]boronic acid;
Compound No. 124: [(1R)-2-[(3S)-7-methyl-2,3-dihydrobenzofuran-3-yl]-1-[(2-phenylacetyl)amino]ethyl]boronic acid;
Compound No. 125: [(1R)-2-(7-fluorobenzofuran-3-yl)-1-[(2-phenylacetyl)amino]ethyl]boronic acid;
Compound No. 126: [(1R)-2-(6-chloro-7-methyl-benzofuran-3-yl)-1-[(2-phenylacetyl)amino]ethyl]boronic acid;
Compound No. 127: [(1R)-2-[(3R)-7-methyl-2,3-dihydrobenzofuran-3-yl]-1-[(2-phenylacetyl)amino]ethyl]boronic acid;
Compound No. 128: [(1R)-2-(4,7-dimethylbenzofuran-3-yl)-1-[(2-phenylacetyl)amino]ethyl]boronic acid;
Compound No. 129: [(1R)-2-(4,7-dimethylbenzofuran-3-yl)-1-[[2-(4-methoxyphenyl)acetyl]amino]ethyl]boronic acid;
Compound No. 130: [(1R)-1-[[2-(2-cyanophenyl)acetyl]amino]-2-[(3S)-7-methyl-2,3-dihydrobenzofuran-3-yl]ethyl]boronic acid;
Compound No. 131: [(1R)-2-[(3S)-2,3-dihydrobenzofuran-3-yl]-1-[[2-(5-ethoxy-2-pyridyl)acetyl]amino]ethyl]boronic acid;
Compound No. 132: [(1R)-2-[(3S)-7-chloro-2,3-dihydrobenzofuran-3-yl]-1-[(2-phenylacetyl)amino]ethyl]boronic acid;
Compound No. 133: [(1R)-2-[(3R)-7-chloro-2,3-dihydrobenzofuran-3-yl]-1-[(2-phenylacetyl)amino]ethyl]boronic acid;
Compound No. 134: [(1R)-2-[(3S)-7-chloro-2,3-dihydrobenzofuran-3-yl]-1-[[2-(2-cyanophenyl)acetyl]amino]ethyl]boronic acid;
Compound No. 135: [(1R)-2-[(3R)-7-chloro-2,3-dihydrobenzofuran-3-yl]-1-[[2-(2-cyanophenyl)acetyl]amino]ethyl]boronic acid;
Compound No. 136: [(1R)-2-[(3S)-2,3-dihydrobenzofuran-3-yl]-1-(3-phenoxypropanoylamino)ethyl]boronic acid;

and derivatives, prodrugs, solvates, tautomers or stereoisomers thereof, as well as the physiologically acceptable salts of each of the foregoing, including mixtures thereof in all ratios.

A preferred process for the synthesis of compounds of Formula (I) as defined above and pharmaceutically acceptable salts, tautomers and stereoisomers thereof, is characterised in that a compound of Formula (III)

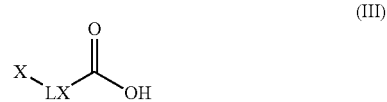

is coupled with a compound of Formula (VI)

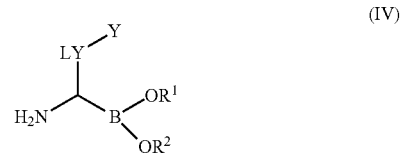

wherein all residues of formula (III) and formula (IV) are as defined above and wherein the obtained compound of Formula (Ib) is subsequently converted into a compound of Formula (Ia), by treatment with HCl, HBr, HI and/or TFA, in the presence or absence of an excess of a small molecular weight boronic acid (such as but not limited to i-BuB(OH)$_2$):

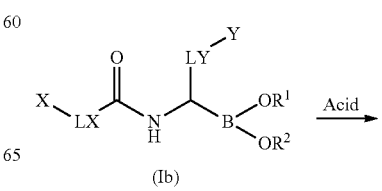

-continued

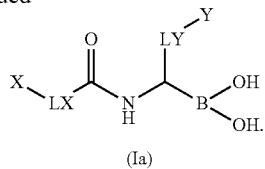

(Ia)

All residues of the compounds of formula (III) and formula (IV) are as defined above.

The following abbreviations refer to the abbreviations used below:

ACN (acetonitrile), AcOH (acetic acid), BINAP (2,2'-bis (disphenylphosphino)-1,1'-binaphthalene), dba (dibenzylidene acetone), tBu (tert-Butyl), tBuOK (potassium tert-butoxide), CDI (1,1'-Carbonyldiimidazole), DBU (1,8-dizabicyclo[5.4.0]undec-7-ene), DCC (dicyclohexylcarbodiimide), DCM (dichloromethane), DIAD (diisobutylazodicarboxylate), DIC (diisopropylcarbodiimide), DIEA (di-isopropyl ethylamine), DMA (dimethyl acetamide), DMAP (4-dimethylaminopyridine), DMSO (dimethyl sulfoxide), DMF (N, N-dimethylformamide), EDC.HCl (1-ethyl-3-(3-dimethylaminopropyl)carbodiimide hydrochloride), EtOAc (ethyl acetate), EtOH (ethanol), g (gram), cHex (cyclohexane), HATU (dimethylamino-([1,2,3]triazolo[4,5-b]pyridin-3-yloxy)-methylene]-dimethyl-ammonium hexafluorophosphate), HOBt (N-hydroxybenzotriazole), HPLC (high performance liquid chromatography), hr (hour), MHz (Megahertz), MeOH (methanol), min (minute), mL (milliliter), mmol (millimole), mM (millimolar), mp (melting point), MS (mass spectrometry), MW (microwave), NMM (N-methyl morpholine), NMR (Nuclear Magnetic Resonance), NBS (N-bromo succinimide), PBS (phosphate buffered saline), PMB (para-methoxybenzyl), PyBOP (benzotriazol-1-yl-oxytripyrrolidinophosphonium hexafluorophosphate), RT (room temperature), TBAF (tetra-butylammonium fluoride), TBTU (N,N,N',N'-tetramethyl-O-(benzotriazol-1-yl)uronium tetrafluoroborate), T3P (propane phosphonic acid anhydride), TEA (triethyl amine), TFA (trifluoroacetic acid), THF (tetrahydrofuran), PetEther (petroleum ether), TBME (tert-butyl methyl ether), TLC (thin layer chromatography), TMS (trimethylsilyl), TMSI (trimethylsilyl iodide), UV (ultraviolet).

Generally, compounds of Formula (I), wherein all residues are defined as above, can be obtained from a compound of Formula (III) as outlined in Scheme 1.

The first step consists of the reaction of a compound of Formula (III), wherein X and LX are defined as above, with a compound of Formula (IV), wherein $R^1$, $R^2$, LY and Y are defined as above. The reaction is performed using conditions and methods well known to those skilled in the art for the preparation of amides from a carboxylic acid with standard coupling agents, such as but not limited to HATU, TBTU, polymer-supported 1-alkyl-2-chloropyridinium salt (polymer-supported Mukaiyama's reagent), 1-methyl-2-chloropyridinium iodide (Mukaiyama's reagent), a carbodiimide (such as DCC, DIC, EDC) and HOBt, PyBOP® and other such reagents well known to those skilled in the art, preferably TBTU, in the presence or absence of bases such as TEA, DIEA, NMM, polymer-supported morpholine, preferably DIEA, in a suitable solvent such as DCM, THF or DMF, at a temperature between −10° C. and 50° C., preferably at 0° C., for a few hours, e.g. one hour to 24 h. Alternatively, the compounds of Formula (III) could be converted to carboxylic acid derivatives such as acyl halides or anhydrides, by methods well known to those skilled in the art, such as but not limited to treatment with $SOCl_2$, $POCl_3$, $PCl_5$, $(COCl)_2$, in the presence or absence of catalytic amounts of DMF, in the presence or absence of a suitable solvent such as toluene, DCM, THF, at a temperature rising from 20° C. to 100° C., preferably at 50° C., for a few hours, e.g. one hour to 24 h. Conversion of the carboxylic acid derivatives to compounds of Formula (I), can be achieved using conditions and methods well known to those skilled in the art for the preparation of amides from a carboxylic acid derivative (e.g. acyl chloride) with alkyl amines, in the presence of bases such as TEA, DIEA, NMM in a suitable solvent such as DCM, THF or DMF, at a temperature rising from 20° C. to 100° C., preferably at 50° C., for a few hours, e.g. one hour to 24 h.

In the process described above the reaction between the compound of Formula (III) and the compound of Formula (IV) is preferably performed in the presence of a coupling agent selected from HATU, TBTU, polymer-supported 1-alkyl-2-chloropyridinium salt (polymer-supported Mukaiyama's reagent), 1-methyl-2-chloropyridinium iodide (Mukaiyama's reagent) or a carbodiimide.

Compounds of Formula (Ia), wherein LX, X, LY and Y are defined as above and wherein $R^1$ and $R^2$ are H, can be prepared starting from compounds of Formula (Ib), using methods well known to those skilled in the art for the hydrolysis of boronic esters, such as but not limited to treatment with HCl, HBr, HI, TFA, in the presence or absence of an excess of a small molecular weight boronic acid, such as but not limited to i-BuB(OH)$_2$ (Scheme 2).

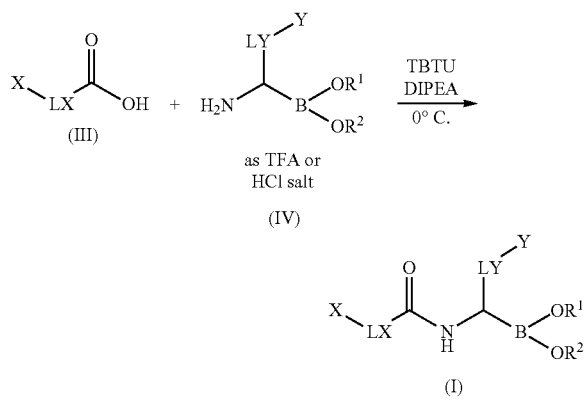

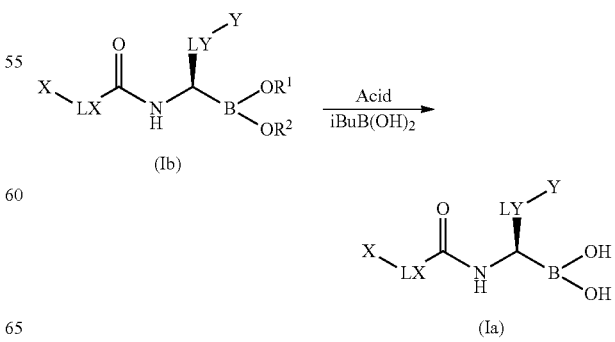

Compounds of Formula (III) or (IV) are either commercially available or can be prepared by methods well known to those skilled in the art.
In general, compounds of Formula (IV) are for example accessible by the following Scheme 3a:
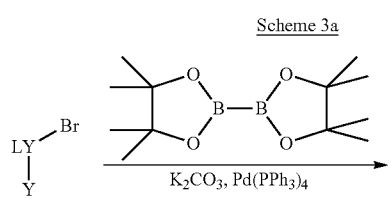
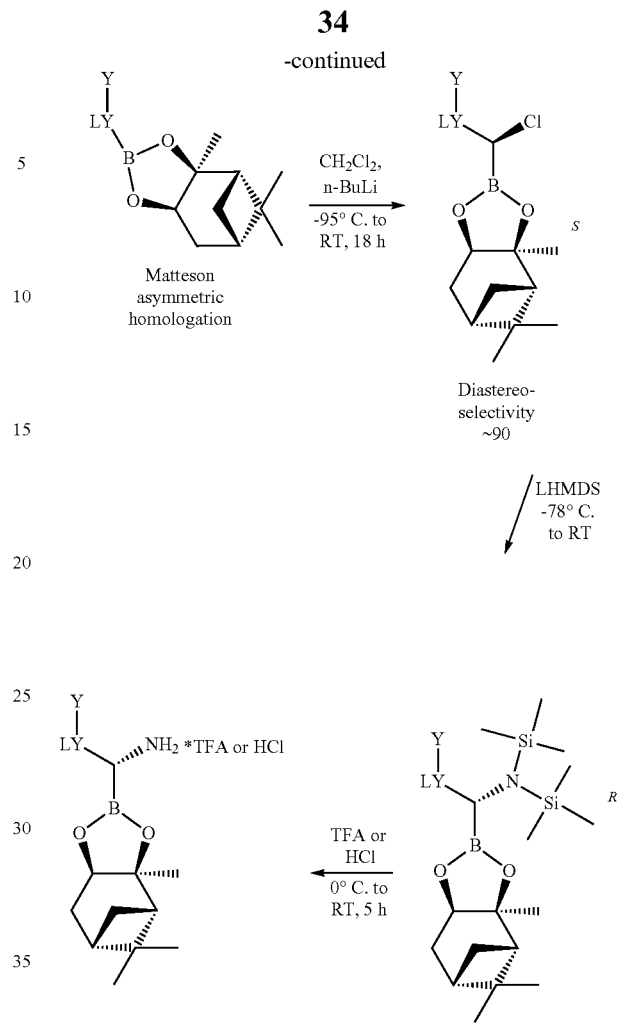
Compounds of formula (IV-1) wherein Y is a 2,3-dihydrobenzofuran-3-yl, are for example accessible by the following Scheme 3b:
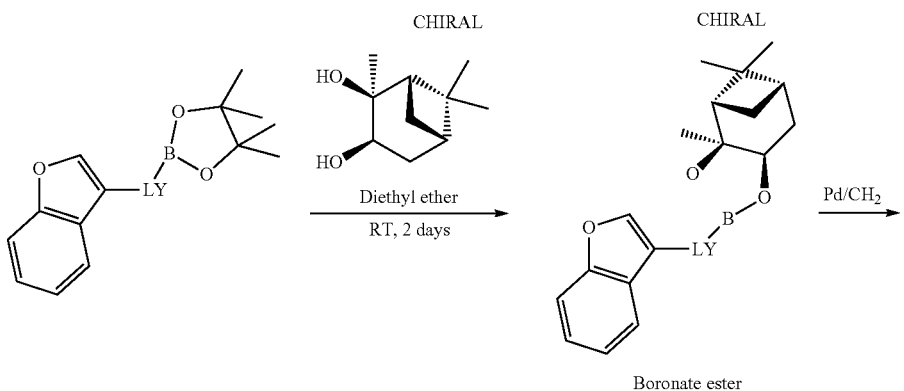

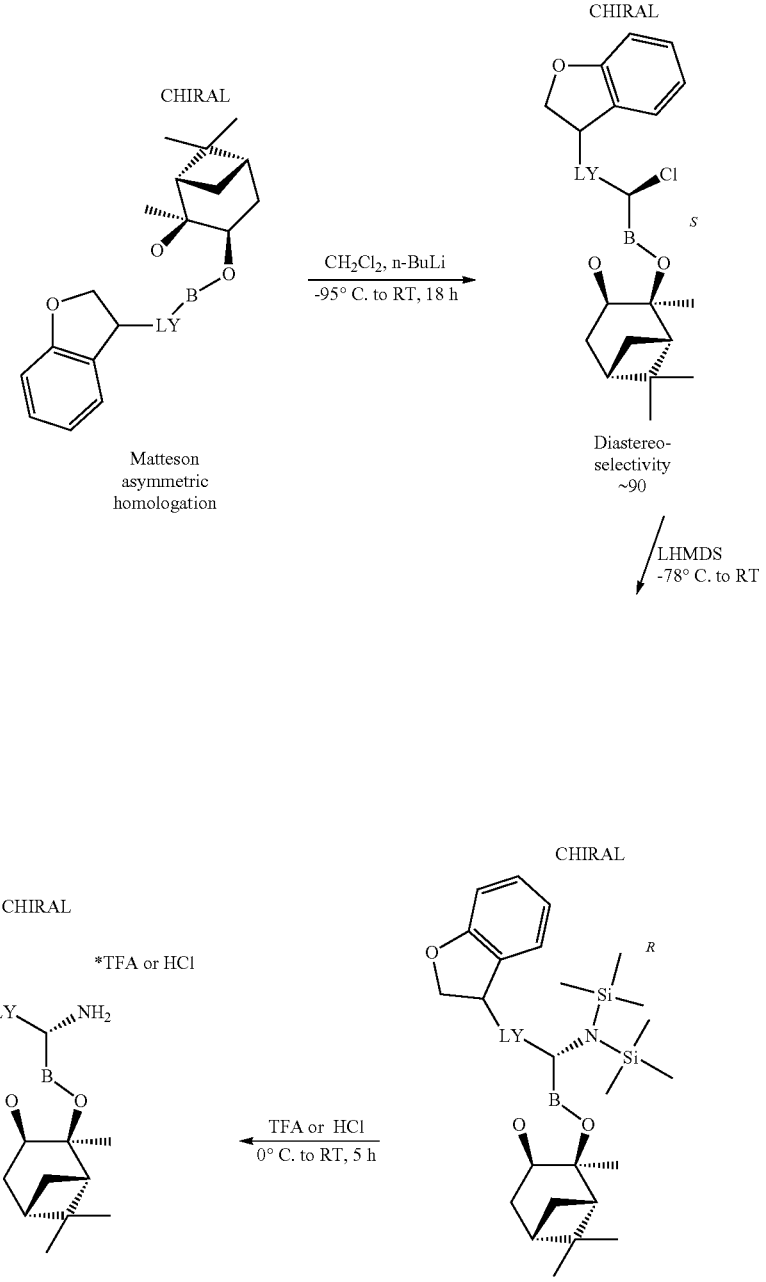
In this case typically both isomers at the 3 position of the 2,3-dihydrobenzofurane are formed.
Amino boronic acids of formula IV-1a or IV-1b containing stereochemically pure 2,3-dihydrobenzofurane are accessible by the following Scheme 4:

Scheme 4:
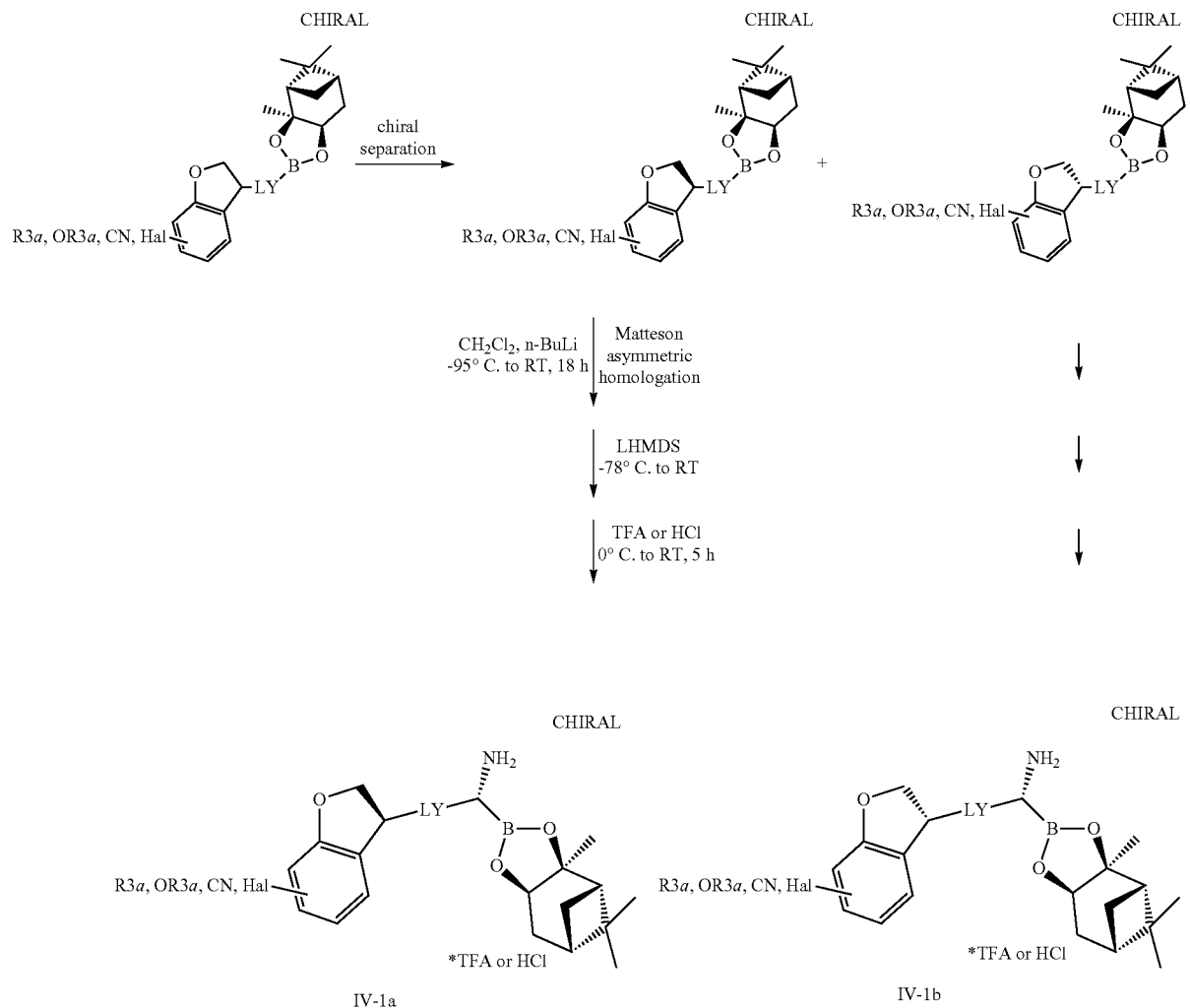
Compounds of formula I-1a and I-1b wherein Y is a 2,3-dihydrobenzofuran-3-yl are for example accessible by the following Scheme 5:
Scheme 5:
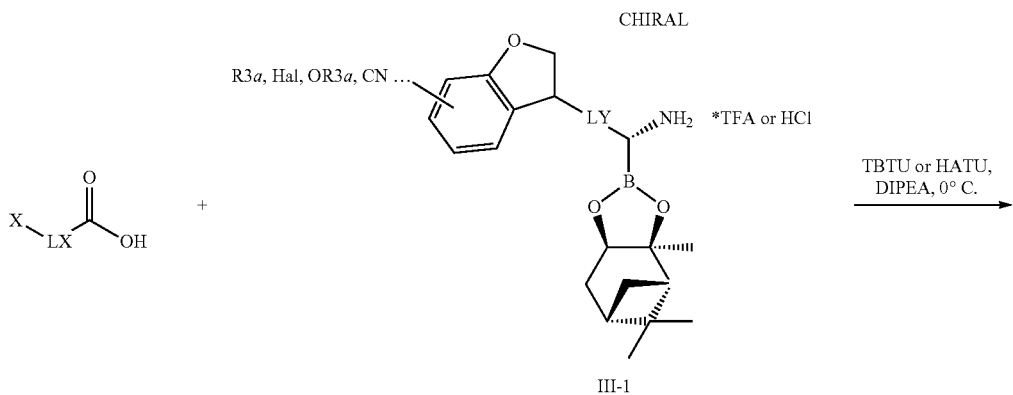

-continued

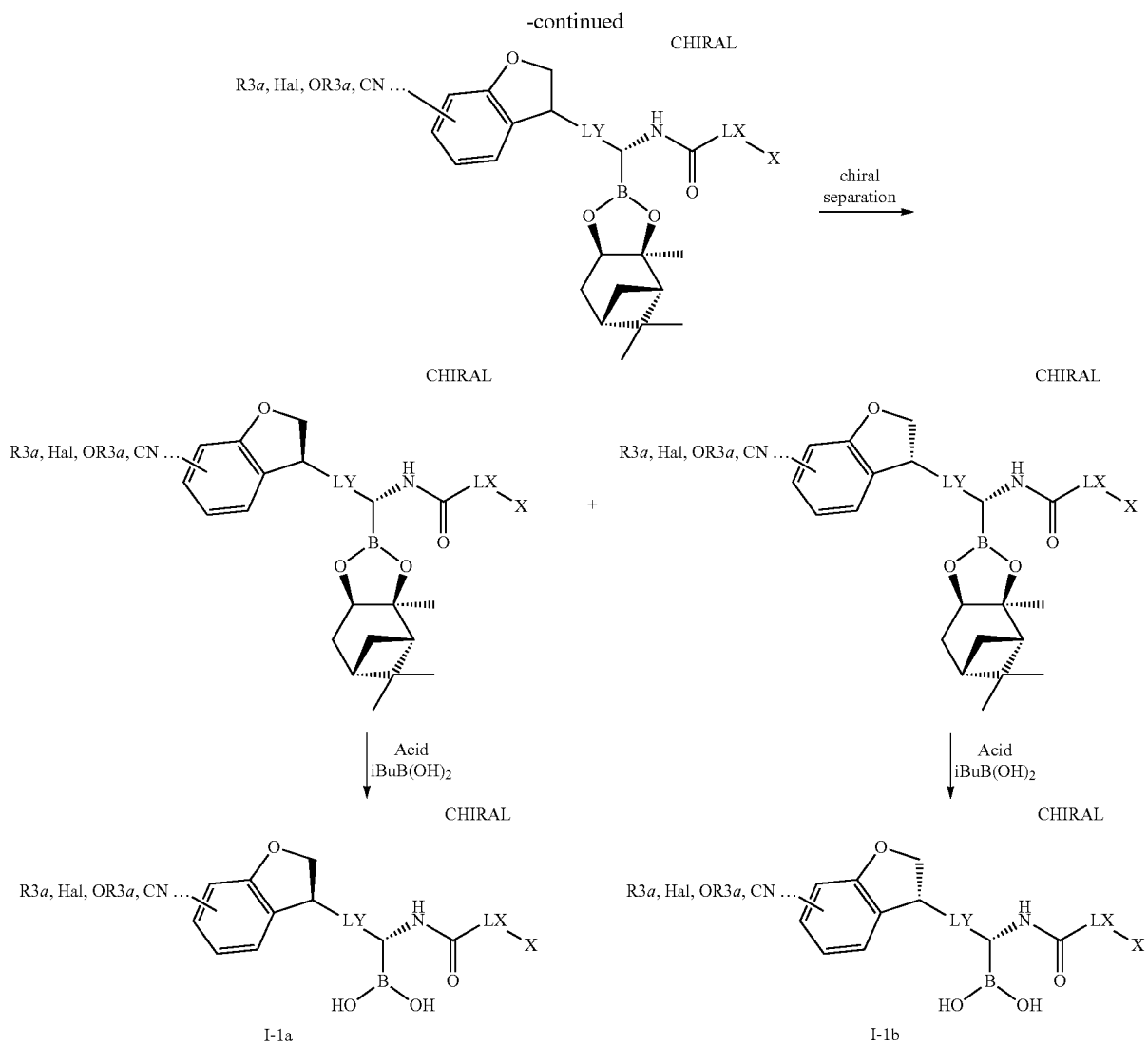

The chiral separation can be performed e.g. by chiral HLPC.

Compounds of Formula (III) are either commercially accessible of can be prepared by those skilled in the art using established procedures.

If the above set of general synthetic methods is not applicable to obtain compounds according to Formula (I) and/or necessary intermediates for the synthesis of compounds of Formula (I), suitable methods of preparation known by a person skilled in the art should be used.

In general, the synthesis pathways for any individual compounds of formula (I) will depend on the specific substituents of each molecule and upon the ready availability of Intermediates necessary; again such factors being appreciated by those of ordinary skill in the art. For all the protection and de-protection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

Compounds of this invention can be isolated in association with solvent molecules by crystallization from evaporation of an appropriate solvent. The pharmaceutically acceptable acid addition salts of the compounds of formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compounds of formula (I), which contain an acid center, with a suitable base. Both types of salts may be formed or interconverted using ion-exchange resin techniques.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of formula (I) can furthermore be obtained by liberating compounds of formula (I) from one of their functional derivatives by treatment with a solvolysing or hydrogenolysing agent.

Preferred starting materials for the solvolysis or hydrogenolysis are those which conform to formula (I), but contain corresponding protected amino and/or hydroxyl groups instead of one or more free amino and/or hydroxyl groups, preferably those which carry an amino-protecting group instead of an H atom bound to an N atom, in particular those which carry an R'—N group, in which R' denotes an amino-protecting group, instead of an HN group, and/or those which carry a hydroxyl-protecting group instead of the H atom of a hydroxyl group, for example those which conform to formula (I), but carry a —COOR" group, in which R" denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxy-carbonyl) and 2-iodoethoxycarbonyl; aralkoxycarbonyl, such as CBZ ("carbo-benz-oxy"), 4-methoxybenzyloxycarbonyl and FMOC; and aryl-sulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitro-benzoyl, p-toluenesulfonyl, tert-butyl and acetyl, where benzyl and tert-butyl are particularly preferred.

The term "solvates of the compounds" is taken to mean adductions of inert solvent molecules onto the compounds which form owing to their mutual attractive force. Solvates are, for example, mono- or dihydrates or alcoholates.

The compounds of formula (I) are liberated from their functional derivatives—depending on the protecting group used, for example, using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as THF or dioxane, amides, such as DMF, halogenated hydrocarbons, such as DCM, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid at a ratio of 9:1. The reaction temperatures for the cleavage are advantageously between about 0 and about 50° C., preferably between 15 and 30° C. (RT).

The BOC, OBut and Mtr groups can, for example, preferably be cleaved off using TFA in DCM or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, tri-fluoro-methylbenzene, chloroform or DCM; alcohols, such as methanol, ethanol, isopropanol, n-propanol, n-butanol or tert-butanol; ethers, such as diethyl ether, diisopropyl ether, tetrahydrofurane (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as EtOAc, or mixtures of the said solvents.

Esters can be saponified, for example, using LiOH, NaOH or KOH in water, water/THF, water/THF/ethanol or water/dioxane, at temperatures between 0 and 100° C. Furthermore, esters can be hydrolysed, for example, using acetic acid, TFA or HCL.

Free amino groups can furthermore be acylated in a conventional manner using an acyl chloride or anhydride or alkylated using an unsubstituted or substituted alkyl halide or reacted with CH$_3$—C(=NH)—OEt, advantageously in an inert solvent, such as DCM or THF and/or in the presence of a base, such as triethylamine or pyridine, at temperatures between −60° C. and +30° C.

Throughout the specification, the term leaving group preferably denotes Cl, Br, I or a reactively modified OH group, such as, for example, an activated ester, an imidazolide or alkylsulfonyloxy having 1 6 carbon atoms (preferably methylsulfonyloxy or trifluoromethylsulfonyloxy) or arylsulfonyloxy having 6 10 carbon atoms (preferably phenyl- or p tolylsulfonyloxy).

Radicals of this type for activation of the carboxyl group in typical acylation reactions are described in the literature (for example in the standard works, such as Houben-Weyl, Methoden der organischen Chemie [Methtods of Organic Chemistry], Georg-Thieme-Verlag, Stuttgart).

Activated esters are advantageously formed in situ, for example through addition of HOBt or N hydroxysuccinimide.

The term "pharmaceutically usable derivatives" is taken to mean, for example, the salts of the compounds of the formula I and so-called prodrug compounds.

The term "prodrug derivatives" is taken to mean compounds of the formula I which have been modified with, for example, alkyl or acyl groups, sugars or oligopeptides and which are rapidly cleaved in the organism to form the active compounds.

These also include biodegradable polymer derivatives of the compounds according to the invention, as described, for example, in Int. J. Pharm. 115, 61-67 (1995).

The present invention relates to a process for making the compounds according to Formula (I) and related Formulae.

The present invention relates to pharmaceutical compositions comprising at least one compound of formula (I) wherein all residues are as defined above, or its derivatives, prodrugs, solvates, tautomers or stereoisomers thereof as well as the physiologically acceptable salts of each of the foregoing, including mixtures thereof in all ratios, as active ingredient, together with a pharmaceutically acceptable carrier.

For the purpose of the present invention the term "pharmaceutical composition" refers to a composition or product comprising one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable carrier, excipient or vehicle. The pharmaceutical compositions of the present invention also encompass any composition that further comprises a second active ingredient or its derivatives, prodrugs, solvates, tautomers or stereoisomers thereof as well as the physiologically acceptable salts of each of the foregoing, including mixtures thereof in all ratios, wherein that second active ingredient is other than a compound of formula (I) wherein all residues are defined above.

The invention relates to compounds according to formula (I) or any specific embodiment described above and pharmaceutically usable salts, tautomers, solvates and stereoisomers thereof, including mixtures thereof in all ratios, for use in the treatment and/or prophylaxis (prevention) of an immunoregulatory abnormality or hematological malignancies.

For the purpose of the present invention immunoregulatory abnormality is an autoimmune or chronic inflammatory disease selected from the group consisting of systemic lupus erythematosus, chronic rheumatoid arthritis, inflammatory bowel disease, multiple sclerosis, amyotrophic lateral sclerosis (ALS), atherosclerosis, scleroderma, autoimmune hepatitis, Sjogren's syndrome, lupus nephritis, glomerulonephritis, Rheumatoid Arthritis, Psoriasis, Myasthenia Gravis, Immunoglobulin A nephropathy, Vasculitis, Transplant rejection, Myositis, Henoch-Schonlein Purpura and asthma.

The invention relates to compounds according to formula (I) or any specific embodiment described above and their derivatives, prodrugs, solvates, tautomers or stereoisomers thereof as well as the physiologically acceptable salts of each of the foregoing, including mixtures thereof in all ratios, for use in the prevention and/or treatment of medical conditions that are affected by inhibiting LMP7. The invention also relates to compounds according to formula (I) or any specific embodiment described above and its derivatives, prodrugs, solvates, tautomers or stereoisomers thereof as well as the physiologically acceptable salts of each of the foregoing, including mixtures thereof in all ratios, for use in the prevention and/or treatment of an immunoregulatory abnormality or hematological malignancies. In particular in such cases where the immunoregulatory abnormality selected from Amyotrophic Lateral Sclerosis, Sjogren's syndrome, systemic lupus erythematoses, lupus nephritis, glomerulonephritis, Rheumatoid Arthritis, Inflammatory bowel disease, ulcerative colitis, Crohn's diseases, multiple sclerosis, osteoarthritis, Atherosclerosis, Psoriasis, Myasthenia Gravis, Dermal fibrosis, renal fibrosis, cardiac fibrosis, Liver fibrosis, Lung fibrosis, Immunoglobulin A nephropathy, Vasculitis, Transplant rejection, Hematological malignancies and asthma.

The pharmaceutical preparations can be employed as medicaments in human and veterinary medicine.

The present invention further relates to a set (kit) consisting of separate packs of (a) an effective amount of a compound of formula (I) and/or pharmaceutically acceptable salts, tautomers and stereoisomers thereof, including mixtures thereof in all ratios, and (b) an effective amount of a further medicament active ingredient.

Pharmaceutical Salts and Other Forms

The said compounds of formula (I) can be used in their final non-salt forms. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of formula (I) are for the most part prepared by conventional methods. If the compound of formula (I) contains an acidic center, such as a carboxyl group, one of its suitable salts can be formed by reacting the compound with a suitable base to give the corresponding base-addition salt. Such bases are, for example, alkali metal hydroxides, including potassium hydroxide and sodium hydroxide; alkaline earth metal hydroxides, such as magnesium hydroxide and calcium hydroxide; and various organic bases, such as piperidine, diethanolamine, N-methyl-glucamine (meglumine), benzathine, choline, ethylenediamine, benethamine, diethylamine, piperazine, lysine, L-arginine, ammonia, triethanolamine, betaine, ethanolamine, morpholine and tromethamine. In the case of certain compounds of formula (I), which contain a basic center, acid-addition salts can be formed by treating these compounds with pharmaceutically acceptable organic and inorganic acids, for example hydrogen halides, such as hydrogen chloride or hydrogen bromide, other mineral acids and corresponding salts thereof, such as sulfate, nitrate or phosphate and the like, and alkyl- and monoaryl-sulfonates, such as methanesulfonate, ethanesulfonate, toluenesulfonate and benzene-sulfonate, and other organic acids and corresponding salts thereof, such as carbonate, acetate, trifluoro-acetate, tartrate, maleate, succinate, citrate, benzoate, salicylate, ascorbate and the like. Accordingly, pharmaceutically acceptable acid-addition salts of the compounds of formula (I) include the following: acetate, adipate, alginate, aspartate, benzoate, benzene-sulfonate (besylate), bisulfate, bisulfite, bromide, camphorate, camphor-sulfonate, caprate, caprylate, chloride, chlorobenzoate, citrate, cyclamate, cinnamate, digluconate, dihydrogen-phosphate, dinitrobenzoate, dodecyl-sulfate, ethanesulfonate, formate, glycolate, fumarate, galacterate (from mucic acid), galacturonate, glucoheptanoate, gluco-nate, glutamate, glycerophosphate, hemi-succinate, hemisulfate, heptanoate, hexanoate, hippurate, hydrochloride, hydrobromide, hydroiodide, 2-hydroxy-ethane-sulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmo-ate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of formula (I) include aluminum, ammonium, calcium, copper, iron (III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of formula (I) which are derived from pharmaceutically acceptable organic non-toxic bases include salts of primary, secondary and tertiary amines, substituted amines, also including naturally occurring substituted amines, cyclic amines, and basic ion exchange resins, for example arginine, betaine, caffeine, chloroprocaine, choline, N,N'-dibenzyl-ethylen-ediamine (benzathine), dicyclohexylamine, diethanol-amine, diethyl-amine, 2-diethyl-amino-ethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lido-caine, lysine, meglumine (N-methyl-D-glucamine), morpholine, piperazine, piperidine, polyamine resins, procaine, purines, theobromine, triethanol-amine, triethylamine, trimethylamine, tripropylamine and tris(hydroxy-methyl)-methylamine (tromethamine), but this is not intended to represent a restriction.

Compounds of formula (I) of the present invention which contain basic N2-containing groups can be quaternised using agents such as (C1-C4)-alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, do-decyl, lauryl, myristyl and stearyl chloride, bromide and iodide; and aryl-(C1-C4)alkyl halides, for example benzyl chloride and phenethyl bromide. Both water- and oil-soluble compounds of formula (I) can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of formula (I) are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of formula (I) are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ from the corresponding salt forms thereof with respect to certain physical properties, such as solubility in polar solvents; for the purposes of the invention, however, the salts otherwise correspond to the respective free acid forms thereof.

If a compound of formula (I) contains more than one group which is capable of forming pharmaceutically acceptable salts of this type, formula (I) also encompasses multiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of formula (I) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of formula (I) are chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the (R) and (S) forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of formula (I), and related formulae in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function or in combination with immunomodulating agents for example Fingolimod; cyclosporins, rapamycins or ascomycins, or their immunosuppressive analogs, e.g. cyclosporin A, cyclosporin G, FK-506, ABT-281, ASM981, rapamycin, 40-O-(2-hydroxy)ethyl-rapamycin etc.; corticosteroids; cyclophosphamide; azathioprene; methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodium; betamethasone valerate; budesonide; captopril; chlormethine chlorhydrate; cladribine; clobetasol propionate; cortisone acetate; cortivazol; cytarabine; daclizumab; dactinomycine; desonide; desoximetasone; dexamethasone; dexamethasone acetate; dexamethasone isonicotinate; dexamethasone metasulfobenzoate sodium; dexamethasone phosphate; dexamethasone tebutate; dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone, hydrocortisone acetate, hydrocortisone butyrate, hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethasone acetate; prednazoline, prednisolone; prednisolone acetate; prednisolone caproate; prednisolone metasulfobenzoate sodium; prednisolone phosphate sodium; prednisone; prednylidene; rifampicin; rifampicin sodium; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA41 g, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin and Fingolimod. These further medicaments, such as interferon beta, may be administered concomitantly or sequentially, e.g. by subcutaneous, intramuscular or oral routes.

These compositions can be used as medicaments in human and veterinary medicine.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acacia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting molds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of formula (I) and salts, solvates and physiologically functional derivatives thereof and the other active ingredients can also be administered in the form of liposome delivery systems, such as, for exam-pie, small unilamellar vesicles, large unilamellar vesicles and multilamellar vesicles. Liposomes can be formed from various phospholipids, such as, for example, cholesterol, stearylamine or phosphatidylcholines.

The compounds of formula (I) and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range of 20-500 microns, which is administered in the manner in which snuff is taken, i.e., by rapid inhalation via the nasal passages from a container containing the powder held close to the nose. Suitable formulations for administration as nasal spray or nose drops with a liquid as a carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of formula (I) and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range of 0.1 to 100 mg/kg of body weight of the recipient (mammal) per day and particularly typically in the range of 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a sphingosine 1-phosphate associated disorder, comprising administering to said subject an effective amount of a compound of formula (I). The present invention preferably relates to a method, wherein the sphingosine 1-phosphate associated disorder is an autoimmune disorder or condition associated with an overactive immune response.

The present invention furthermore relates to a method of treating a subject suffering from an immunoregulatory abnormality or hematological malignancy, comprising administering to said subject a compound of formula (I) in an amount that is effective for treating said immunoregulatory abnormality or hematological malignancies. The present invention preferably relates to a method wherein the immunoregulatory abnormality is an autoimmune or chronic inflammatory disease.

EXAMPLES $^1$HNMR:

Bruker 400 MHz

HPLC:

Method A

Method: A: 0.1% TFA in H$_2$O, B: 0.1% TFA in ACN: Flow 2.0 mL/min; Gradient: 0 min 5% B, 8.0 min: 100% B, 8.1 min: 100% B, 8.5 min: 5% B, 10.0 min: 5% B.

Column: XBridge C8 (50×4.6 mm, 3.5 μm).

Method B

Method: 10 min 5-100% Acetonitril 0.05% TFA.

Column: XBridge C8 (50×4.6 mm, 3.5 μm).

Method C

Method: 10 min; 2 mL/min; 215 nm; Puffer A 0.05% TFA/H$_2$O; Puffer B 0.04% TFA/ACN; 0.0-0.2 min 5% Puffer B; 0.2-8.5 min 5%-100% Puffer B; 8.5-10.0 min 99%-5% Puffer B Column: XBridge C8-3.5 μm 4.6×502 mm.

Intermediate 1a:

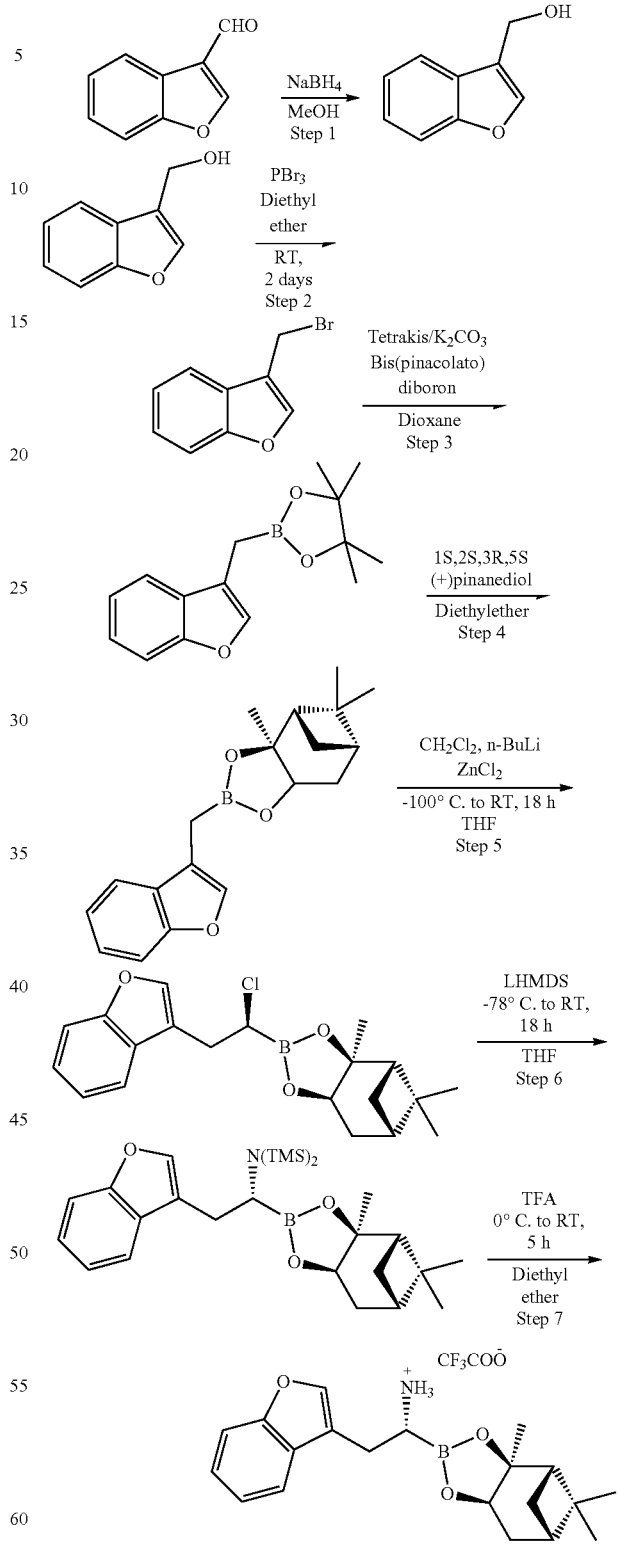

Step 1: benzofuran-3-ylmethanol

A solution of 1-Benzofuran-3-carbaldehyde (5 g, 34.2 mmol) in methanol (50 mL) was cooled with ice and sodium borohydride (1.9 g, 51.3 mmol) was added portionwise. The reaction mixture was stirred at room temperature for 1 h. The reaction mixture was concentrated and the residue was partitioned between saturated ammonium chloride and ethylacetate. The organic layer was separated, dried over sodium sulfate and concentrated. The crude product (5.0 g, colourless liquid, 98%) was taken as such for next step without purification.

$^1$H NMR (400 MHz, CDCl$_3$): δ 7.70-7.68 (m, 1H), 7.62 (s, 1H), 7.52-7.50 (m, 1H), 7.36-7.26 (m, 2H), 4.86 (s, 2H).

Step 2: 3-(bromomethyl)benzofuran

A cold (0° C.) solution of benzofuran-3-ylmethanol (5.0 g, 33.7 mmol) in diethyl ether (50 mL) was treated with phosphorus tribromide (1.1 mL, 11.2 mmol) and the reaction mixture was stirred at 0° C. for 30 min. The reaction mixture was then poured into ice and extracted with ether. The organic layer was dried over sodium sulfate and concentrated. The crude (7.1 g, yellow liquid, 100%) was taken as such for next step without purification.

$^1$H NMR (400 MHz, CDCl$_3$): δ 7.74-7.71 (m, 2H), 7.53 (s, 1H), 7.39-7.31 (m, 2H), 4.65 (s, 2H).

Step 3: 2-(benzofuran-3-ylmethyl)-4,4,5,5-tetramethyl-1,3,2-dioxaborolane

A solution of 3-(bromomethyl)benzofuran (7.1 g, 33.8 mmol) in degassed 1, 4-dioxane (70 ml) was treated with bis(pinacolato)diboron (10.3 g, 40.5 mmol), potassium carbonate (13.9 g, 101.0 mmol), tetrakis(triphenylphosphine) palladium(0) (1.9 g, 1.7 mmol) and the mixture heated at 100° C. for 12 h The contents of the flask were cooled to room temperature and filtered through a celite bed. Filtrate was concentrated and the crude was purified by flash column chromatography on silica gel, eluting with 2-5% of ethylacetate in petroleum ether to get the title compound (6.1 g, 69%) as yellow oil.

$^1$H NMR (400 MHz, CDCl$_3$) b 7.57-7.52 (m, 2H), 7.46-7.44 (m, 1H), 7.30-7.21 (m, 2H), 2.23 (s, 2H), 1.29 (s, 12H).

Step 4: 2-(benzofuran-3-ylmethyl)boronic acid (+)-pinanediol ester

A solution of 2-(benzofuran-3-ylmethyl)-4,4,5,5-tetramethyl-1,3,2-dioxaborolane (6.1 g, 23.6 mmol) in diethyl ether (60 ml) was treated with (1S, 2S, 3R, 5S)-(+)-pinanediol (6.0 g, 35.4 mmol). The reaction mixture was stirred at room temperature for 12 h then the mixture was washed with water twice, then with brine and dried over anhydrous sodium sulphate, then concentrated. The crude product was purified by flash column chromatography on silica gel, eluting with 5% of ethyl acetate in petroleum ether, to afford the title compound (6.3 g, 82%).

$^1$H NMR (400 MHz, CDCl$_3$): δ 7.58-7.56 (m, 1H), 7.55-7.53 (m, 1H), 7.46-7.44 (m, 1H), 7.28-7.23 (m, 2H), 4.33 (dd, J=1.88, 8.76 Hz, 1H), 2.34-2.32 (m, 1H), 2.28 (s, 2H), 2.22-2.21 (m, 1H), 2.08 (t, J=5.88 Hz, 1H), 1.42 (s, 3H), 1.29 (s, 3H), 1.13 (d, J=10.92 Hz, 1H), 0.85 (s, 3H). GCMS: m/z: 310.

Step 5: [(1S)-1-chloro-2-(benzofuran-3-ylmethyl) boronic acid (+)-pinanediol ester To a cooled (−100° C.) mixture of dichloromethane (6.3 ml, 60.9 mmol) and anhydrous tetrahydrofuran (36 ml) was added n-butyl lithium (1.6 M in hexanes, 14.0 ml, (22.3 mmol) over 20 min. After stirring for 20 min. at −100° C., a solution of 2-(benzofuran-3-ylmethyl)boronic acid (+)-pinanediol ester (6.3 g, 20.3 mmol) in anhydrous THF (22 ml) was added over 20 min. Then a solution of zinc chloride (0.5 M in THF, 36.5 mL, 18.2 mmol) was added at −100° C. over 30 min. The mixture was allowed to reach room temperature and stirred for 18 h and concentrated. To the resulting oil was added diethyl ether and saturated ammonium chloride. The organic layer was dried over anhydrous sodium sulphate and concentrated in vacuo. The residue (7.3 g, 99%) was taken as such for the next step.

$^1$H NMR (400 MHz, DMSO-d6): δ 7.60-7.57 (m, 2H), 7.49-7.47 (m, 1H), 7.31-7.25 (m, 2H), 4.36-4.34 (m, 1H), 3.31-3.29 (m, 1H), 3.24-3.22 (m, 1H), 2.35-2.31 (m, 1H), 2.14-2.12 (m, 1H), 2.06 (t, J=5.84 Hz, 1H), 1.90-1.86 (m, 2H), 1.42 (s, 3H), 1.04 (d, J=11.04 Hz, 1H), 0.85 (s, 3H). GCMS: m/z: 358.2.

Step 6: [(1R)-1-[bis(trimethylsilyl)amino]-2-(benzofuran-3-ylmethyl) boronic acid (+)-pinanediol ester To a cooled (−78° C.) solution of [(1S)-1-chloro-2-(benzofuran-3-ylmethyl)boronic acid (+)-pinanediol ester (7.3 g, 20.3 mmol) in 40 ml of anhydrous tetrahydrofuran was added lithium bis(trimethylsilyl)amide (1M in THF, 25.5 ml, 25.5 mmol). The mixture was allowed to room temperature, stirred for 18 h and concentrated to dryness. To the resulting residue was added hexane, and then the precipitated solid was filtered off. The filtrate was concentrated to give the required crude product (6.7 g, 68%) which was taken as such for the next step without purification.

$^1$H NMR (400 MHz, CDCl$_3$): δ 7.60-7.59 (m, 1H), 7.50-7.45 (m, 2H), 7.28-7.24 (m, 2H), 4.31 (dd, J=1.56, 8.70 Hz, 1H), 3.18-3.14 (m, 1H), 2.92-2.90 (m, 1H), 2.75-2.72 (m, 1H), 2.34-2.30 (m, 1H), 2.15-2.14 (m, 1H), 2.03 (t, J=5.68 Hz, 1H), 1.88-1.80 (m, 2H), 1.39 (s, 3H), 1.30 (s, 3H), 1.01 (d, J=10.88 Hz, 1H), 0.84 (s, 3H), 0.09 (s, 18H).

Step 7: [(1R)-1-amino-2-(benzofuran-3-ylmethyl) boronic acid (+)-pinanediol ester trifluroacetate A cooled (0° C.) solution of [(1R)-1-[bis(trimethylsilyl)amino]-2-(benzofuran-3-ylmethyl)boronic acid (+)-pinanediol ester (6.7 g, 13.9 mmol) in diethyl ether (30 ml) was treated with trifluoroacetic acid (3.2 ml, 41.7 mmol) dropwise. The reaction mixture was then stirred at RT for 3 h. Precipitation was seen. The reaction mixture was cooled to 0° C. and filtered. The filtered solid was washed with cold ether and dried under vacuum to afford the title compound (2.3 g, white solid, 36%).

$^1$H NMR (400 MHz, DMSO-d$_6$): δ 7.66 (s, 1H), 7.61-7.60 (m, 1H), 7.47-7.45 (m, 1H), 7.29-7.20 (m, 2H), 4.30-4.28 (m, 1H), 3.27-3.16 (m, 3H), 2.25-2.13 (m, 3H), 1.94 (t, J=5.56 Hz, 1H), 1.86-1.81 (m, 2H), 1.25 (s, 6H), 1.01 (d, J=8.00 Hz, 1H), 0.75 (s, 3H).

Intermediate 1b: 2-(7-Methyl-benzofuran-3-yl)-1-((1S,2S,6R,8S)-2,9,9-trimethyl-3,5-dioxa-4-boratricyclo[6.1.1.02,6]dec-4-yl)-ethylamine hydrochloride Step 1: 7-Methyl-benzofuran-3-carboxylic acid ethyl ester

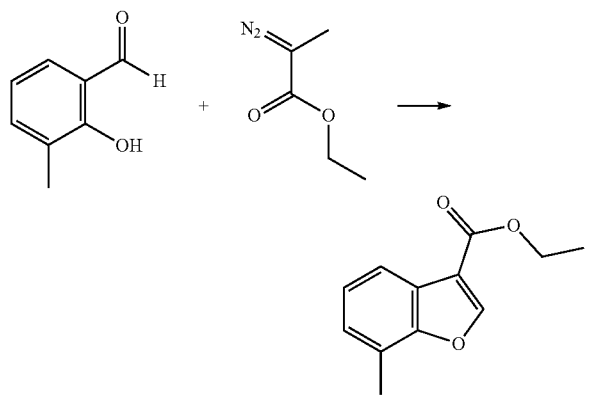

To a solution of 2-Hydroxy-3-methyl-benzaldehyde (20.00 g; 139.55 mmol; 1.00 eq.) in dichloromethane (120 mL) was added Tetrafluoroboric acid diethyl ether complex (1.88 ml; 13.96 mmol; 0.10 eq.). To the resulting dark red mixture, Ethyldiazoacetate (31.70 ml; 300.04 mmol; 2.15 eq.) in dichloromethane (80 mL) was added drop wise slowly at 25-30° C. (internal temperature) for about 50 min. (note: evolution of $N_2$ was observed). After 16 h, concentrated $H_2SO_4$ was added. The reaction mixture was stirred for 30 min. The reaction mixture was then neutralized with solid $NaHCO_3$, filtered through celite and the filtrate was concentrated to get a crude residue. The residue was purified by column chromatography using 2% ethyl acetate in petroleum ether to afford 7-Methyl-benzofuran-3-carboxylic acid ethyl ester (19.00 g; 86.83 mmol; 62.2%; yellow oil; Purified Product).

HPLC (Method A): RT 4.98 min, (HPLC purity 93%)

$^1$H NMR, 400 MHz, $CDCl_3$: 8.27 (s, 1H), 7.88-7.90 (m, 1H), 7.25-7.29 (m, 1H), 7.17 (d, J=7.32 Hz, 1H), 4.39-4.45 (m, 2H), 2.55 (s, 3H), 1.44 (t, J=7.16 Hz, 3H).

Step 2: (7-Methyl-benzofuran-3-yl)-methanol

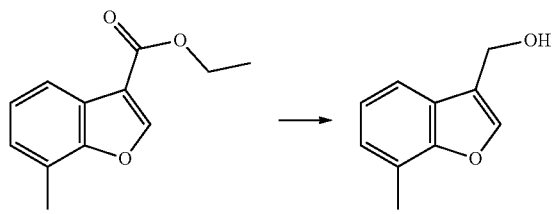

To a solution of 7-Methyl-benzofuran-3-carboxylic acid ethyl ester (19.00 g; 86.83 mmol; 1.00 eq.) in Dichloromethane (190.00 ml; 10.00 V) under nitrogen was added Diisobutyl Aluminium Hydride (1.0 M in Toluene) (191.03 ml; 191.03 mmol; 2.20 eq.) drop wise at −78° C. The reaction mixture was allowed to come to RT and stirred for 1 h. The reaction mixture was cooled with ice bath and quenched with an aqueous solution of 1.5N HCl. The resultant mixture (which had sticky solid mass suspended in solvent) was diluted with ethylacetate and filtered through celite. The celite bed was washed thoroughly with ethylacetate and dichloromethane. The filtrate was evaporated to get a crude residue. The solid which remained in the celite bed was taken and triturated with ethylacetate and filtered. The filtrate was mixed together with the crude residue and evaporated. The residue thus obtained was taken in ethylacetate and washed with an aqueous solution of 1.5 N HCl and brine. The organic layer was dried over anhydrous $Na_2SO_4$ and concentrated. The residue obtained was purified by flash column chromatography using 40-50% ethyl acetate in petroleum ether as eluent to get (7-Methyl-benzofuran-3-yl)-methanol (8.20 g; 48.40 mmol; 55.7%; light yellow oil; Purified Product).

HPLC (method A): RT 3.33 min., (HPLC purity 95.7%).

$^1$H NMR, 400 MHz, $CDCl_3$: 7.64 (s, 1H), 7.50-7.52 (m, 1H), 7.17-7.21 (m, 1H), 7.14 (d, J=7.20 Hz, 1H), 4.86-4.86 (m, 2H), 2.54 (s, 3H).

Step 3: 3-(bromomethyl)-7-methyl-benzofuran

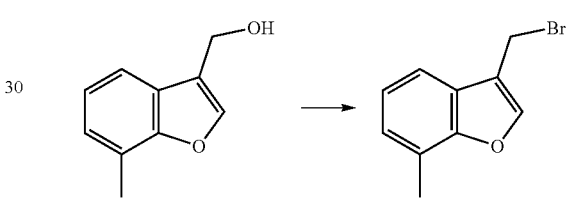

To an ice-cooled solution of (7-Methyl-benzofuran-3-yl)-methanol (8.20 g; 48.40 mmol; 1.00 eq.) in Diethyl ether (82.00 ml; 10.00 V) under nitrogen atmosphere was added phosphorus tribromide (1.53 ml; 16.12 mmol; 0.33 eq.) drop wise and the reaction mixture was stirred at ice cold condition for 30 minutes. The reaction mixture was poured into ice and extracted with diethyl ether. The organic layer was dried over anhydrous $Na_2SO_4$ and concentrated to afford 3-Bromomethyl-7-methyl-benzofuran (10.00 g; 44.43 mmol; 91.8%; colorless oil). The crude product was taken to next step without purification.

$^1$H NMR, 400 MHz, $CDCl_3$: 7.71 (s, 1H), 7.53-7.55 (m, 1H), 7.21-7.25 (m, 1H), 7.16 (d, J=7.32 Hz, 1H), 4.65 (s, 2H), 2.48 (s, 3H).

Step 4: 7-Methyl-3-(4,4,5,5-tetramethyl-[1,3,2]dioxaborolan-2-ylmethyl)-benzofuran

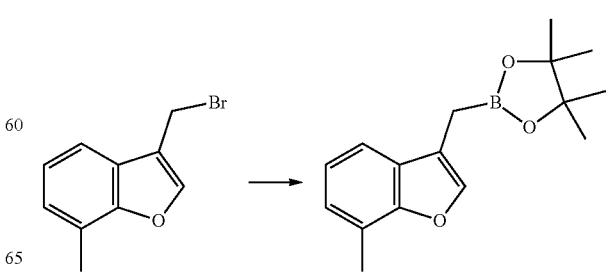

To a solution of 3-Bromomethyl-7-methyl-benzofuran (10.00 g; 44.43 mmol; 1.00 eq.) in degased Dioxane-1,4 (100.00 ml; 10.00 V) were added Bis(pinacolato)diboron (13.68 g; 53.31 mmol; 1.20 eq.), dried $K_2CO_3$ (18.61 g; 133.28 mmol; 3.00 eq.) and tetrakis(triphenylphosphine)palladium(0) (2.57 g; 2.22 mmol; 0.05 eq.). The reaction mixture was then heated at 100° C. under nitrogen atmosphere for 16 h. The reaction mixture was diluted with dichloromethane and filtered through celite. The filtrate was concentrated. The residue was dissolved in ethyl acetate and washed with brine. The organic layer was dried over anhydrous $Na_2SO_4$ and concentrated. The crude was purified by column chromatography using 2% ethyl acetate in petroleum ether to get 7-Methyl-3-(4,4,5,5-tetramethyl-[1,3,2]dioxaborolan-2-ylmethyl)-benzofuran (5.00 g; 18.37 mmol; 41.4%; colorless liquid; Purified Product).

$^1$H NMR, 400 MHz, DMSO-d6: 7.65 (s, 1H), 7.33-7.35 (m, 1H), 7.07-7.13 (m, 2H), 2.43 (s, 3H), 2.13 (s, 2H), 1.16 (s, 12H).

Step 5: Trimethyl-4-(7-methyl-benzofuran-3-ylmethyl)-3,5-dioxa-4-bora-tricyclo [6.1.1.02,6]decane

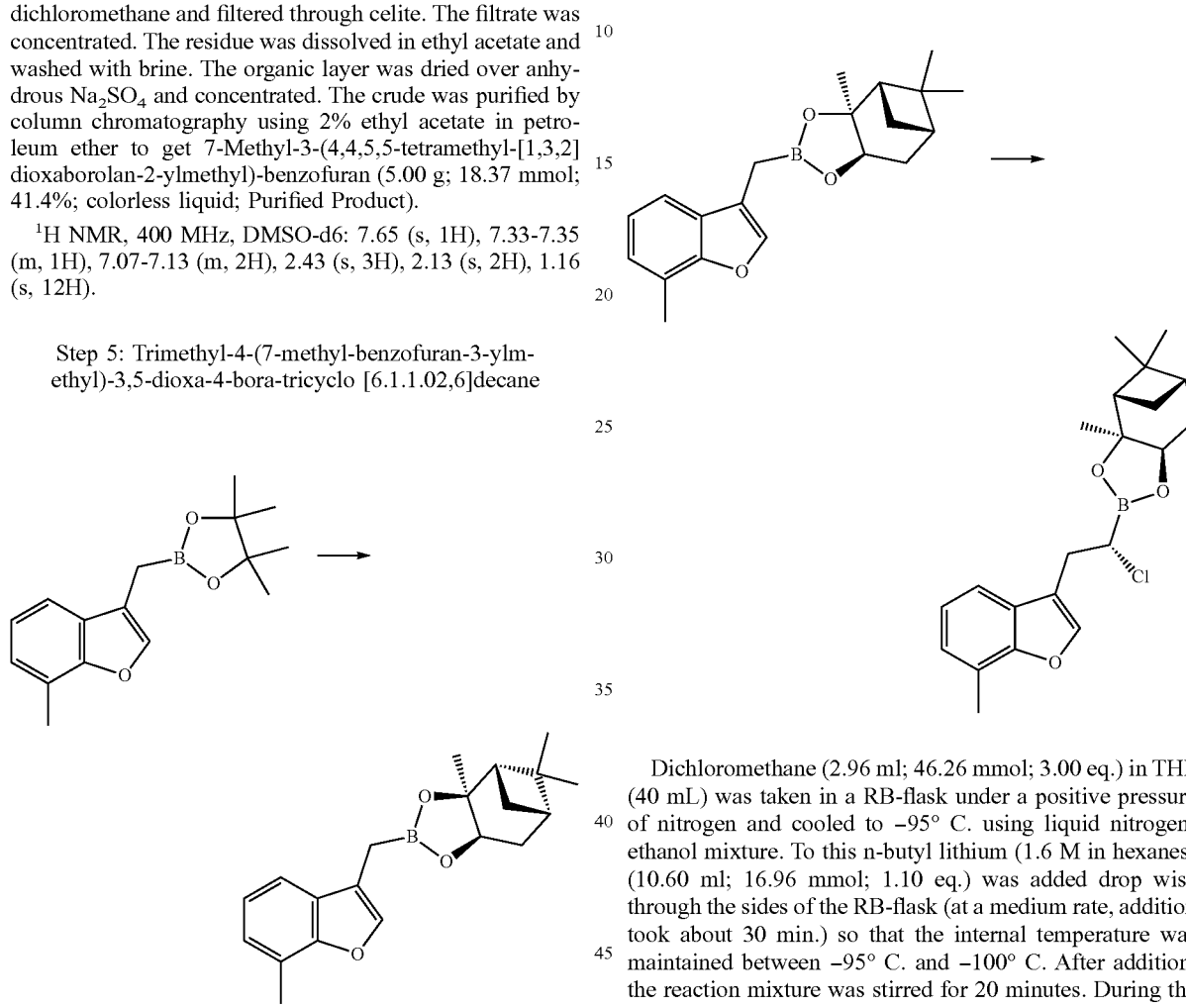

To an ice-cooled solution of 7-Methyl-3-(4,4,5,5-tetramethyl-[1,3,2]dioxaborolan-2-ylmethyl)-benzofuran (5.00 g; 18.37 mmol; 1.00 eq.) in $Et_2O$ (50.00 ml; 10.00 V) under nitrogen atmosphere was added 1S, 2S, 3R, 5S-(+)-2,3-pinane diol (4.69 g; 27.56 mmol; 1.50 eq.) and the reaction mixture was stirred at RT for 14 h. TLC analysis showed completion of reaction. The reaction mixture was washed with brine. The organic layer was dried over anhydrous $Na_2SO_4$ and concentrated. The crude was purified by flash column chromatography using 2% ethyl acetate in petroleum ether to get (1 S,2S,6R,8S)-2,9,9-Trimethyl-4-(7-methyl-benzofuran-3-ylmethyl)-3,5-dioxa-4-bora-tricyclo [6.1.1.02,6] decane (5.00 g; 13.00 mmol; 70.7%; colorless liquid; Purified Product).

GCMS: m/z: 324.2

$^1$H NMR, 400 MHz, $CDCl_3$: 7.53-7.55 (m, 1H), 7.39-7.40 (m, 1H), 7.12-7.27 (m, 1H), 7.06-7.08 (m, 1H), 4.31-4.34 (m, 1H), 2.53 (s, 3H), 2.30-2.37 (m, 1H), 2.26 (s, 2H), 2.18-2.23 (m, 1H), 2.07 (t, J=5.76 Hz, 1H), 1.84-1.93 (m, 2H), 1.42 (s, 3H), 1.29 (s, 3H), 1.12-1.15 (m, 1H), 0.85 (s, 3H).

Step 6: (1S,2S,6R,8S)-4-[1-Chloro-2-(7-methyl-benzofuran-3-yl)-ethyl]-2,9,9-trimethyl-3,5-dioxa-4-bora-tricyclo[6.1.1.02,6]decane Dichloromethane (2.96 ml; 46.26 mmol; 3.00 eq.) in THF (40 mL) was taken in a RB-flask under a positive pressure of nitrogen and cooled to −95° C. using liquid nitrogen-ethanol mixture. To this n-butyl lithium (1.6 M in hexanes) (10.60 ml; 16.96 mmol; 1.10 eq.) was added drop wise through the sides of the RB-flask (at a medium rate, addition took about 30 min.) so that the internal temperature was maintained between −95° C. and −100° C. After addition, the reaction mixture was stirred for 20 minutes. During the course of the reaction a white precipitate was formed (the internal temperature was maintained between −95° C. and −100° C.). Then a solution of (1S,2S,6R,8S)-2,9,9-Trimethyl-4-(7-methyl-benzofuran-3-ylmethyl)-3,5-dioxa-4-bora-tricyclo[6.1.1.02,6]decane (5.00 g; 15.42 mmol; 1.00 eq.) in THF (20 mL) was added drop wise through the sides of the RB-flask (about 25 min) so that the internal temperature was maintained between −95° C. and −100° C. After addition, immediately zinc chloride (0.5 M in THF) (27.76 ml; 13.88 mmol; 0.90 eq.) was added drop wise through the sides of the RB-flask (at a medium rate, addition took about 45 min.) so that the internal temperature was maintained between −95° C. and −100° C. The reaction mixture was then slowly allowed to attain RT and stirred at RT for 16 h. The reaction mixture was concentrated (temperature of the bath 30° C.). The residue was partitioned between diethyl ether and saturated $NH_4Cl$ solution. The organic layer was separated, dried over anhydrous $Na_2SO_4$ and concentrated (temperature of bath 30° C.) to afford (1S,2S,6R,8S)-4-[1-Chloro-2-(7-methyl-benzofuran-3-yl)-ethyl]-2,9,9-trimethyl-3,5-dioxa-4-bora-tricyclo[6.1.1.02,6]decane (5.90 g; 15.83 mmol; 102.7%; brown liquid; Crude Product).

¹H NMR, 400 MHz, CDCl₃: 7.57 (s, 1H), 7.42-7.44 (m, 1H), 7.27 (s, 1H), 7.09-7.18 (m, 1H), 4.34-4.36 (m, 1H), 3.74-3.76 (m, 1H), 3.28-3.30 (m, 1H), 3.20-3.22 (m, 1H), 2.52 (s, 3H), 2.32-2.34 (m, 1H), 2.07 (t, J=5.88 Hz, 1H), 1.85-1.91 (m, 2H), 1.42 (s, 3H), 1.29 (s, 3H), 1.06-1.09 (m, 1H), 0.85 (s, 3H).

Step 7: ((1S,2S,6R,8S)-4-[1-(1,1,1,3,3,3-Hexamethyl-disilazan-2-yl)-2-(7-methyl-benzofuran-3-yl)-ethyl]-2,9,9-trimethyl-3,5-dioxa-4-bora-tricyclo [6.1.1.02,6]decane

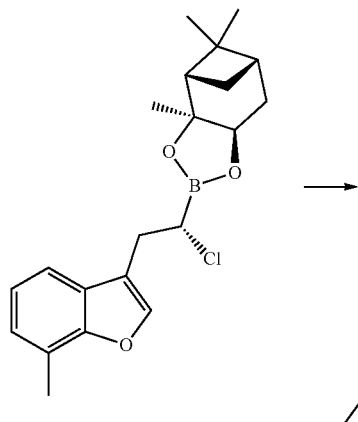

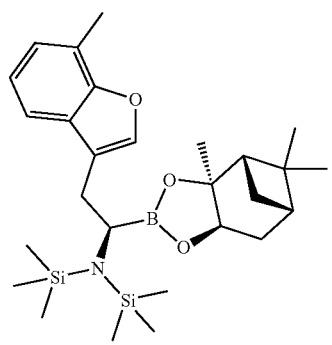

A solution of (1S,2S,6R,8S)-4-[1-Chloro-2-(7-methyl-benzofuran-3-yl)-ethyl]-2,9,9-trimethyl-3,5-dioxa-4-bora-tricyclo[6.1.1.02,6]decane (5.90 g; 15.83 mmol; 1.00 eq.) in THF (40.00 ml; 6.78 V) under a positive pressure of nitrogen atmosphere was cooled to −78° C. To this a solution of lithium (bistrimethylsilyl)amide (1.0 M in THF) (17.41 ml; 17.41 mmol; 1.10 eq.) was added drop wise over a period of 30 minutes. The reaction mixture was allowed to attain RT and stirred at RT for 18 h. The reaction mixture was evaporated at 30° C. The residue was triturated with n-hexane and the solid formed was filtered. The filtrate was concentrated at 30° C. to get (1S,2S,6R,8S)-4-[1-(1,1,1,3,3,3-Hexamethyl-disilazan-2-yl)-2-(7-methyl-benzofuran-3-yl)-ethyl]-2,9,9-trimethyl-3,5-dioxa-4-bora-tricyclo [6.1.1.02,6]decane (6.00 g; 12.06 mmol; 76.2%; brown dark oil; Crude Product).

The crude product was taken to next step without purification. The product was confirmed by ¹H-NMR and was unstable in LCMS conditions.

¹H NMR, 400 MHz, CDCl₃: 7.50 (s, 1H), 7.41-7.43 (m, 1H), 7.12-7.16 (m, 1H), 7.06-7.08 (m, 1H), 4.29-4.32 (m, 1H), 3.17-3.09 (m, 1H), 2.70-2.89 (m, 1H), 2.52-2.70 (m, 1H), 2.52 (s, 3H), 2.28-2.31 (m, 1H), 2.14-2.14 (m, 1H), 2.03 (t, J=5.68 Hz, 1H), 1.78-1.89 (m, 2H), 1.39 (s, 3H), 1.31 (s, 3H), 1.01-1.04 (m, 1H), 0.90-0.92 (m, 2H), 0.88 (s, 3H), 0.12 (s, 18H).

Step 8: 2-(7-Methyl-benzofuran-3-yl)-1-((1 S,2S, 6R,8S)-2,9,9-trimethyl-3,5-dioxa-4-bora-tricyclo [6.1.1.02,6]dec-4-yl)-ethylamine hydrochloride

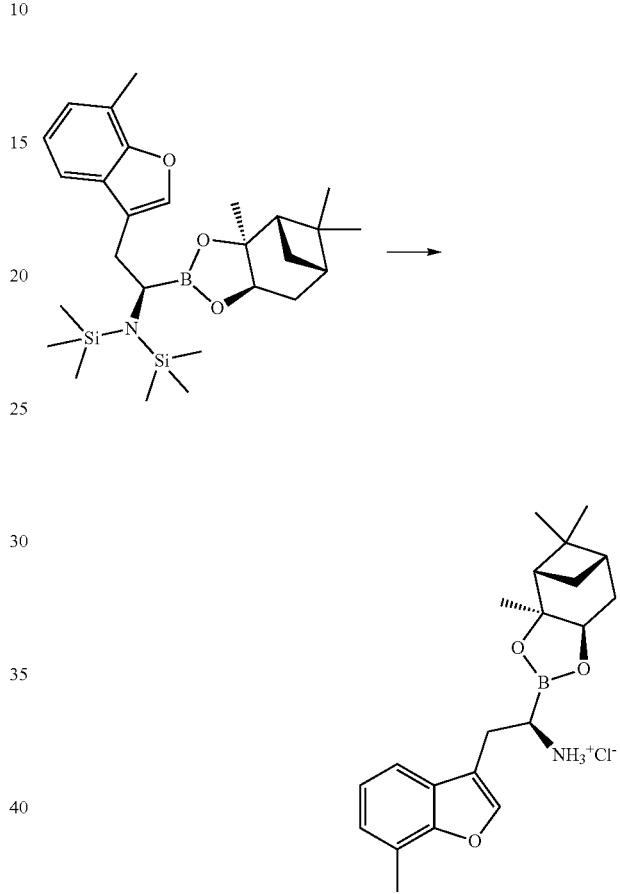

A stirred solution of (1S,2S,6R,8S)-4-[1-(1,1,1,3,3,3-Hexamethyl-disilazan-2-yl)-2-(7-methyl-benzofuran-3-yl)-ethyl]-2,9,9-trimethyl-3,5-dioxa-4-bora-tricyclo[6.1.1.02,6] decane (6.00 g; 12.06 mmol; 1.00 eq.) in Diethyl ether (60.00 ml; 10.00 V) under nitrogen atmosphere was cooled to −10° C. To this 2M solution of Hydrochloric acid in diethyl ether (15.07 ml; 30.14 mmol; 2.50 eq.) was added drop wise. The reaction mixture was stirred at RT for 2 h. The reaction mixture was evaporated at 30° C. To the residue diethyl ether (20 mL) was added and the solid formed was filtered off, washed with cold diethyl ether and dried under vacuum to get 2-(7-Methyl-benzofuran-3-yl)-1-((1 S,2S,6R, 8S)-2,9,9-trimethyl-3,5-dioxa-4-bora-tricyclo[6.1.1.02,6] dec-4-yl)-ethylamine hydrochloride (3.50 g; 8.98 mmol; 74.5%; brown orange solid; Crude Product).

¹H NMR, 400 MHz, DMSO-d6: 8.09 (s, 3H), 7.83 (s, 1H), 7.52-7.53 (m, 1H), 7.12-7.19 (m, 2H), 4.39 (dd, J=1.84, 8.62 Hz, 1H), 3.07-3.13 (m, 1H), 3.03-3.07 (m, 2H), 2.43 (s, 4H), 2.28-2.30 (m, 1H), 2.07-2.08 (m, 1H), 1.92 (t, J=5.68 Hz, 1H), 1.82-1.84 (m, 1H), 1.71-1.75 (m, 1H), 1.19-1.25 (m, 8H), 1.00-1.08 (m, 1H), 0.78 (s, 3H).

Intermediate 1c: (R)-2-(2,3-Dihydro-benzofuran-3-yl)-1-((1S,2S,6R,8S)-2,9,9-trimethyl-3,5-dioxa-4-bora-tricyclo[6.1.1.02,6]dec-4-yl)-ethylamine hydrochloride Step 1: (1S,2S,6R,8S)-4-(2,3-Dihydro-benzofuran-3-ylmethyl)-2,9,9-trimethyl-3,5-dioxa-4-bora-tricyclo[6.1.1.02,6]decane

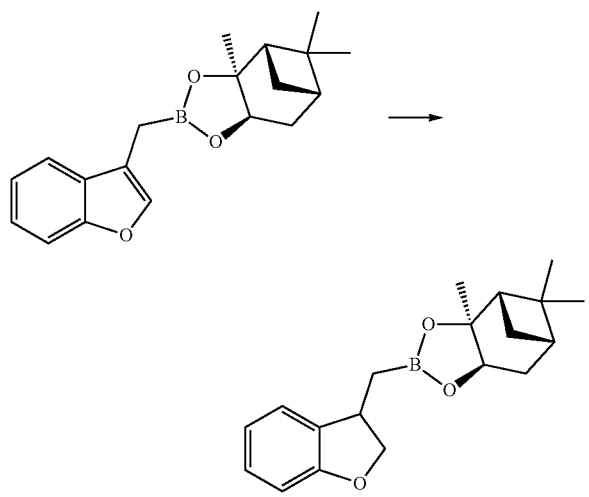

To a solution of (1S,2S,6R,8S)-4-Benzofuran-3-ylmethyl-2,9,9-trimethyl-3,5-dioxa-4-bora-tricyclo[6.1.1.02,6]decane (5.00 g; 10.72 mmol; 1.00 eq.) in methanol (100.00 ml; 20.00 V) in a tiny clave was added palladium on carbon (10 wt %) (2.28 g; 2.14 mmol; 0.20 eq.). The contents were hydrogenated under a H₂ pressure of 5 Kg/cm² for 3 h. TLC analysis revealed complete conversion. The reaction mixture was filtered through celite and the filtrate was evaporated. The crude was purified by Biotage-isolera column chromatography (C18 column; mobile phase: ACN/H₂O; 50:50 isocratic) to get a (1 S,2S,6R,8S)-4-(2,3-Dihydro-benzofuran-3-ylmethyl)-2,9,9-trimethyl-3,5-dioxa-4-bora-tricyclo [6.1.1.02,6]decane (4.10 g; 13.13 mmol; 122.5%; pale yellow liquid; Purified Product).

GCMS: m/z: 312.3.

Step 2: (1S,2S,6R,8S)-4-[1-Chloro-2-(7-methyl-benzofuran-3-yl)-ethyl]-2,9,9-trimethyl-3,5-dioxa-4-bora-tricyclo[6.1.1.02,6]decane

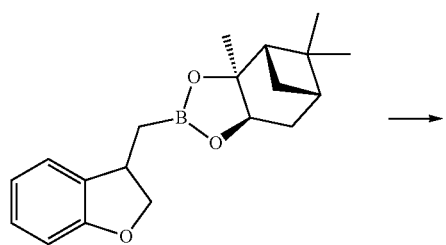

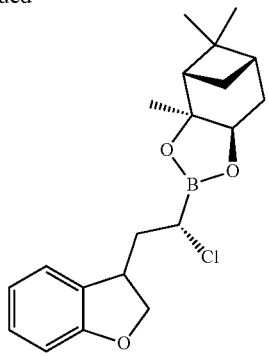

Dichloromethane (2.46 ml; 38.44 mmol; 3.00 eq.) in THF (40.00 ml; 10.00 V) was taken in a RB-flask under a positive pressure of nitrogen and cooled to −95° C. using liquid nitrogen-ethanol mixture. To this n-butyl lithium (1.6 M in THF) (8.81 ml; 14.09 mmol; 1.10 eq.) was added drop wise through the sides of the RB-flask (at a medium rate, addition took about 20 min.) so that the internal temperature was maintained between −95° C. and −100° C. After addition, the reaction mixture was stirred for 25 minutes.

During the course of the reaction a white precipitate was formed (the internal temperature was maintained between −95° C. and −100° C.). Then a solution of (1 S,2S,6R,8S)-4-(2,3-Dihydro-benzofuran-3-ylmethyl)-2,9,9-trimethyl-3,5-dioxa-4-bora-tricyclo[6.1.1.02,6]decane (4.00 g; 12.81 mmol; 1.00 eq.) in THF (15.00 ml; 3.75 V) was added drop wise through the sides of the RB-flask (about 25 min) so that the internal temperature was maintained between −95° C. and −100° C. After addition, immediately zinc chloride (0.5 M in THF) (25.62 ml; 12.81 mmol; 1.00 eq.) was added drop wise through the sides of the RB-flask (at a medium rate, addition took about 25 min.) so that the internal temperature was maintained between −95° C. and −100° C. The reaction mixture was then slowly allowed to attain RT and stirred at RT for 18 h. The reaction mixture was concentrated (temperature of the bath 30° C.). The residue was partitioned between diethyl ether and saturated NH₄Cl solution. The organic layer was dried over anhydrous Na₂SO₄ and concentrated (temperature of bath 30° C.) to afford (1 S,2S,6R, 8S)-4-[(S)-1-Chloro-2-(2,3-dihydro-benzofuran-3-yl)-ethyl]-2,9,9-trimethyl-3,5-dioxa-4-bora-tricyclo[6.1.1.02,6] decane (4.60 g; 12.75 mmol; 99.5%; yellow oil; Crude Product). The product was unstable in LCMS and HPLC conditions and was confirmed by ¹H NMR.

Chiral data could not be taken for the product. The product was assumed to be major S-isomer.

1H NMR, 400 MHz, CDCl₃: 7.29 (d, J=6.72 Hz, 1H), 7.21-7.10 (m, 1H), 6.90-6.77 (m, 2H), 4.68-4.65 (m, 1H), 4.32-4.29 (m, 2H), 3.65-3.60 (m, 1H), 2.40-2.08 (m, 4H), 1.94-1.85 (m, 2H), 1.42 (s, 3H), 1.33 (s, 3H), 1.22 (s, 3H), 1.17-1.15 (m, 1H), 0.86 (s, 3H).

Step 3: (1S,2S,6R,8S)-4-[(R)-2-(2,3-Dihydro-benzo-furan-3-yl)-1-(1,1,1,3,3,3-hexamethyl-disilazan-2-yl)-ethyl]-2,9,9-trimethyl-3,5-dioxa-4-bora-tricyclo[6.1.1.0²,⁶]decane Step 4: (R)-2-(2,3-Dihydro-benzofuran-3-yl)-1-((1S,2S,6R,8S)-2,9,9-trimethyl-3,5-dioxa-4-bora-tricyclo[6.1.1.0²,⁶]dec-4-yl)-ethylamine hydrochloride

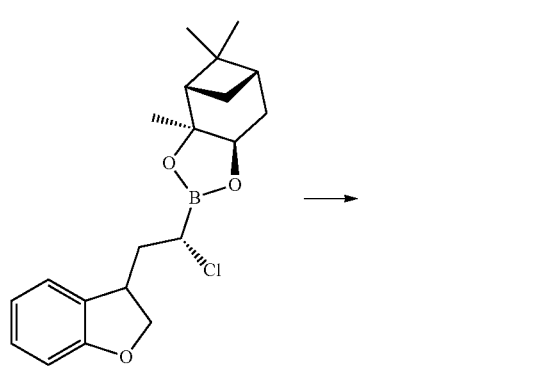

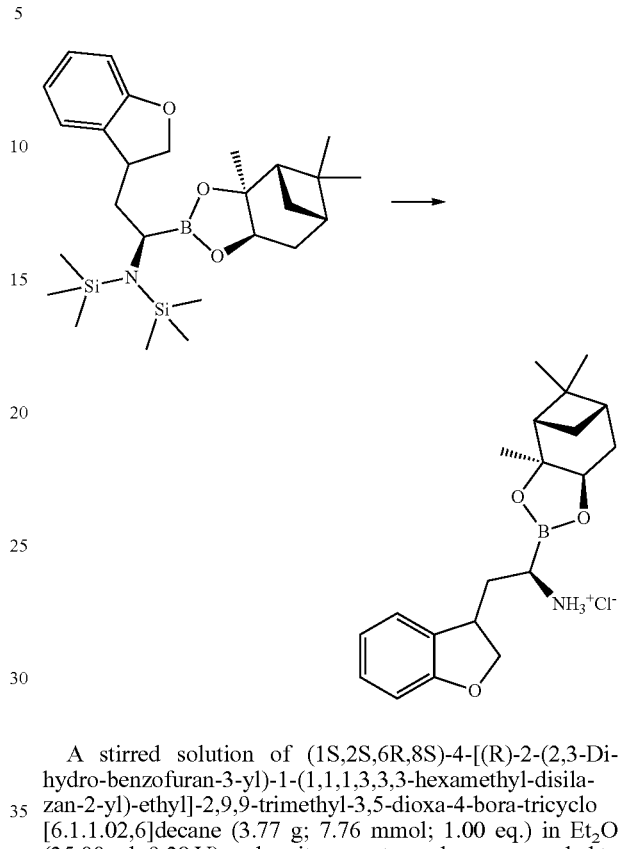

A stirred solution of (1S,2S,6R,8S)-4-[(R)-2-(2,3-Dihydro-benzofuran-3-yl)-1-(1,1,1,3,3,3-hexamethyl-disilazan-2-yl)-ethyl]-2,9,9-trimethyl-3,5-dioxa-4-bora-tricyclo[6.1.1.0²,⁶]decane (3.77 g; 7.76 mmol; 1.00 eq.) in Et₂O (35.00 ml; 9.28 V) under nitrogen atmosphere was cooled to −10° C. To this 2M solution of Hydrochloric acid in diethyl ether (9.70 ml; 19.41 mmol; 2.50 eq.) was added drop wise. The reaction mixture was stirred at RT for 2 h. The reaction mixture was evaporated to dryness under reduced pressure to get a solid. The solid formed was triturated with diethyl ether, filtered, washed with diethyl ether and dried under vacuum to get (R)-2-(2,3-Dihydro-benzofuran-3-yl)-1-((1 S,2S,6R,8S)-2,9,9-trimethyl-3,5-dioxa-4-bora-tricyclo[6.1.1.0²,⁶]dec-4-yl)-ethylamine hydrochloride (2.30 g; 5.25 mmol; 67.7%; pale brown solid; Purified Product).

Analysis showed the presence of isomers (~65.50%+20.75%) at the indicated (*) position.

LCMS: 4.73 min., 86.25% (max), 80.47% (220 nm), 342.20 (M+1).

1H NMR, 400 MHz, DMSO-d6: 8.11 (s, 3H), 7.23-7.19 (m, 1H), 7.13-7.10 (m, 1H), 6.85 (t, J=7.40 Hz, 1H), 6.77 (d, J=8.04 Hz, 1H), 4.61-4.57 (m, 1H), 4.48-4.45 (m, 1H), 4.25-4.22 (m, 1H), 3.68-3.62 (m, 1H), 2.90-2.85 (m, 1H), 2.34-2.32 (m, 1H), 2.19-2.17 (m, 1H), 2.02-1.99 (m, 2H), 1.89-1.77 (m, 3H), 1.39 (s, 3H), 1.25 (s, 3H), 1.17-1.14 (m, 1H), 0.82 (s, 3H).

A solution of (1S,2S,6R,8S)-4-[(S)-1-Chloro-2-(2,3-dihydro-benzofuran-3-yl)-ethyl]-2,9,9-trimethyl-3,5-dioxa-4-bora-tricyclo[6.1.1.0²,⁶]decane (4.60 g; 12.75 mmol; 1.00 eq.) in THF (45.00 ml; 9.78 V) under a positive pressure of nitrogen atmosphere was cooled to −78° C. To this a solution of Lithium(bistrimethylsilyl)amide (1.0 M in THF) (16.58 ml; 16.58 mmol; 1.30 eq.) was added drop wise over a period of 30 minutes. The reaction mixture was allowed to attain RT and stirred at RT for 18 h. The reaction mixture was evaporated at 30° C. The residue was triturated with hexane and the solid formed was filtered. The filtrate was allowed to stand for some time under vacuum and any solid if formed was filtered again. The filtrate was concentrated at 30° C. to get (1S,2S,6R,8S)-4-[(R)-2-(2,3-Dihydro-benzofuran-3-yl)-1-(1,1,1,3,3,3-hexamethyl-disilazan-2-yl)-ethyl]-2,9,9-trimethyl-3,5-dioxa-4-bora-tricyclo[6.1.1.0²,⁶]decane (3.77 g; 7.76 mmol; 60.9%; yellow oil; Crude Product). The crude product was taken to next step without purification. The product was confirmed by ¹H-NMR and was unstable in LCMS conditions. The major product formed is the R-isomer.

1H NMR, 400 MHz, CDCl₃: 7.22-7.10 (m, 2H), 6.90-6.79 (m, 2H), 4.62-4.59 (m, 1H), 4.33-4.27 (m, 1H), 2.34-2.20 (m, 2H), 2.07-2.05 (m, 1H), 1.94-1.84 (m, 2H), 1.40 (s, 3H), 1.30 (s, 3H), 1.15-1.13 (m, 1H), 0.86 (s, 3H), 0.10 (s, 18H).

Intermediate 2:

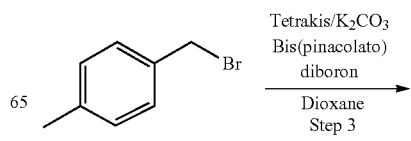

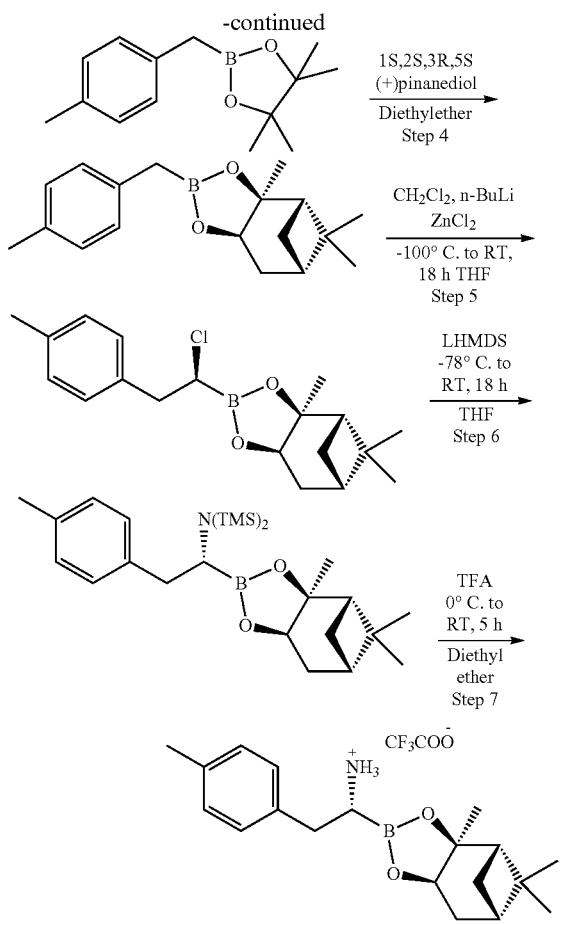

Step 1: 4,4,5,5-tetramethyl-2-(4-methylbenzyl)-1,3,2-dioxaborolane

A solution of 4-methylbenzylbromide (10.0 g, 53.5 mmol) in degassed 1, 4-dioxane (100 ml) was treated with bis(pinacolato)diboron (16.5 g, 64.2 mmol), potassium carbonate (22.6 g, 160.5 mmol), tetrakis(triphenylphosphine) palladium(0) (3.1 g, 2.7 mmol) and the mixture heated at 100° C. for 12 h The contents of the flask were cooled to room temperature and filtered through a celite bed. Filtrate was concentrated and the residue was dissolved in ethylacetate and washed with brine. The organic layer was dried over sodium sulfate and concentrated. The crude product was purified by Flash column chromatography on silica gel, eluting with 2% of ethylacetate in petroleum ether to get the title compound (9.3 g, 70%) as colourless liquid.

$^1$H NMR (400 MHz, CDCl$_3$) b 7.10-7.04 (m, 4H), 2.30 (s, 3H), 2.26 (s, 2H), 1.24 (s, 12H).

Step 2: 2-(4-methylbenzyl)boronic acid (+)-pinanediol ester

A solution of 4,4,5,5-tetramethyl-2-(4-methylbenzyl)-1,3,2-dioxaborolane (9.3 g, 37.6 mmol) in diethyl ether (90 ml) was treated with (1S, 2S, 3R, 5S)-(+)-pinanediol (9.7 g, 56.4 mmol). The reaction mixture was stirred at room temperature for 12 h then the mixture was washed with water twice, then with brine and dried over anhydrous sodium sulphate, then concentrated. The crude product was purified by flash column chromatography on silica gel, eluting with 3% of ethyl acetate in petroleum ether, to afford the title compound (11.0 g, colourless liquid, 93%).

$^1$H NMR (400 MHz, CDCl$_3$): δ 400 MHz, CDCl3: δ 7.08 (s, 4H), 4.28 (dd, J=1.88, 8.74 Hz, 1H), 2.34-2.28 (m, 6H), 2.21-2.17 (m, 1H), 2.06 (t, J=5.80 Hz, 1H), 1.91-1.81 (m, 2H), 1.39 (s, 3H), 1.29 (s, 3H), 1.07-0.91 (m, 1H), 0.84 (s, 3H). GCMS: m/z: 284.3.

Step 3: [(1S)-1-chloro-2-(4-methylbenzyl)boronic acid (+)-pinanediol ester

To a cooled (−100° C.) mixture of dichloromethane (4.0 ml, 62.3 mmol) and anhydrous tetrahydrofuran (40 ml) was added n-butyl lithium (1.6 M in hexanes, 14.3 ml, (22.8 mmol) over 20 min. After stirring for 20 min. at −100° C., a solution of 2-(4-methylbenzyl)boronic acid (+)-pinanediol ester (5.9 g, 20.7 mmol) in anhydrous THF (20 ml) was added over 20 min. Then a solution of zinc chloride (0.5 M in THF, 37.3 mL, 20.7 mmol) was added at −100° C. over 30 min. The mixture was allowed to reach room temperature and stirred for 18 h and concentrated. To the resulting oil was added diethyl ether and saturated ammonium chloride. The organic layer was dried over anhydrous sodium sulphate and concentrated in vacuo. The residue (6.5 g, pale yellow oil, 94%) was taken as such for the next step.

$^1$H NMR (400 MHz, CDCl$_3$): δ 7.18-7.08 (m, 5H), 4.37 (dd, J=1.32, 8.74 Hz, 1H), 3.77-3.75 (m, 1H), 3.67-3.63 (m, 1H), 3.19-3.17 (m, 1H), 3.10-3.08 (m, 1H), 2.36-2.31 (m, 5H), 2.09 (t, J=5.84 Hz, 1H), 1.93-1.86 (m, 4H), 1.39 (s, 3H), 1.30 (s, 3H), 1.13-1.10 (m, 1H), 0.84 (s, 3H). GCMS: m/z: 332.0.

Step 4: [(1R)-1-[bis(trimethylsilyl)amino]-2-(4-methylbenzyl) boronicacid (+)-pinanediol ester To a cooled (−78° C.) solution of [(1S)-1-chloro-2-(4-methylbenzyl) boronic acid (+)-pinanediol ester (6.5 g, 19.5 mmol) in 40 ml of anhydrous tetrahydrofuran was added lithium bis(trimethylsilyl)amide (1M in THF, 24.4 ml, 24.4 mmol). The mixture was allowed to attain room temperature, stirred for 18 h and concentrated to dryness. To the resulting residue was added hexane, and then the precipitated solid was filtered off. The filtrate was concentrated to give the required crude product (7.5 g, brown oil, 84%) which was taken as such for the next step without purification.

$^1$H NMR (400 MHz, CDCl$_3$): δ 7.15-7.11 (m, 2H), 7.08-7.05 (m, 2H), 4.28 (dd, J=1.88, 8.72 Hz, 1H), 3.02-2.99 (m, 1H), 2.80-2.78 (m, 1H), 2.64-2.61 (m, 1H), 2.33-2.30 (m, 5H), 2.29-2.29 (m, 1H), 2.01 (t, J=5.80 Hz, 1H), 2.00-1.81 (m, 2H), 1.38 (s, 3H), 1.29 (s, 3H), 0.98-0.96 (m, 1H), 0.84 (s, 3H), 0.09 (s, 18H).

Step 5: [(1R)-1-amino-2-(4-methylbenzyl)boronic acid (+)-pinanediol ester trifluroacetate A cooled (0° C.) solution of [(1R)-1-[bis(trimethylsilyl)amino]-2-(4-methylbenzyl)boronic acid (+)-pinanediol ester (7.5 g, 16.4 mmol) in diethyl ether (35 ml) was treated with trifluoroacetic acid (3.8 ml, 49.1 mmol) dropwise. The reaction mixture was then stirred at RT for 3 h. Precipitation was seen. The reaction mixture was cooled to 0° C. and filtered. The filtered solid was washed with cold ether and dried under vacuum to afford the title compound (2.8 g, white solid, 40%).

$^1$H NMR (400 MHz, CDCl$_3$): δ 7.75 (s, 3H), 7.17-7.11 (m, 4H), 4.32-4.30 (m, 1H), 3.18-3.11 (m, 2H), 3.09-2.97

(m, 1H), 2.32 (s, 3H), 2.27-2.15 (m, 3H), 1.97 (t, J=5.52 Hz, 1H), 1.97-1.95 (m, 1H), 1.89-1.89 (m, 1H), 1.37 (s, 3H), 1.28 (s, 3H), 1.09-1.08 (m, 1H), 0.84 (s, 3H).

By similar sequences the following compounds can be prepared:

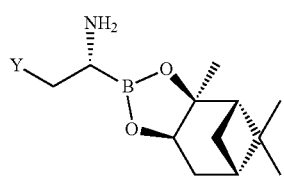

HCl or TFA SALT wherein the group Y denotes for example one of the following groups:

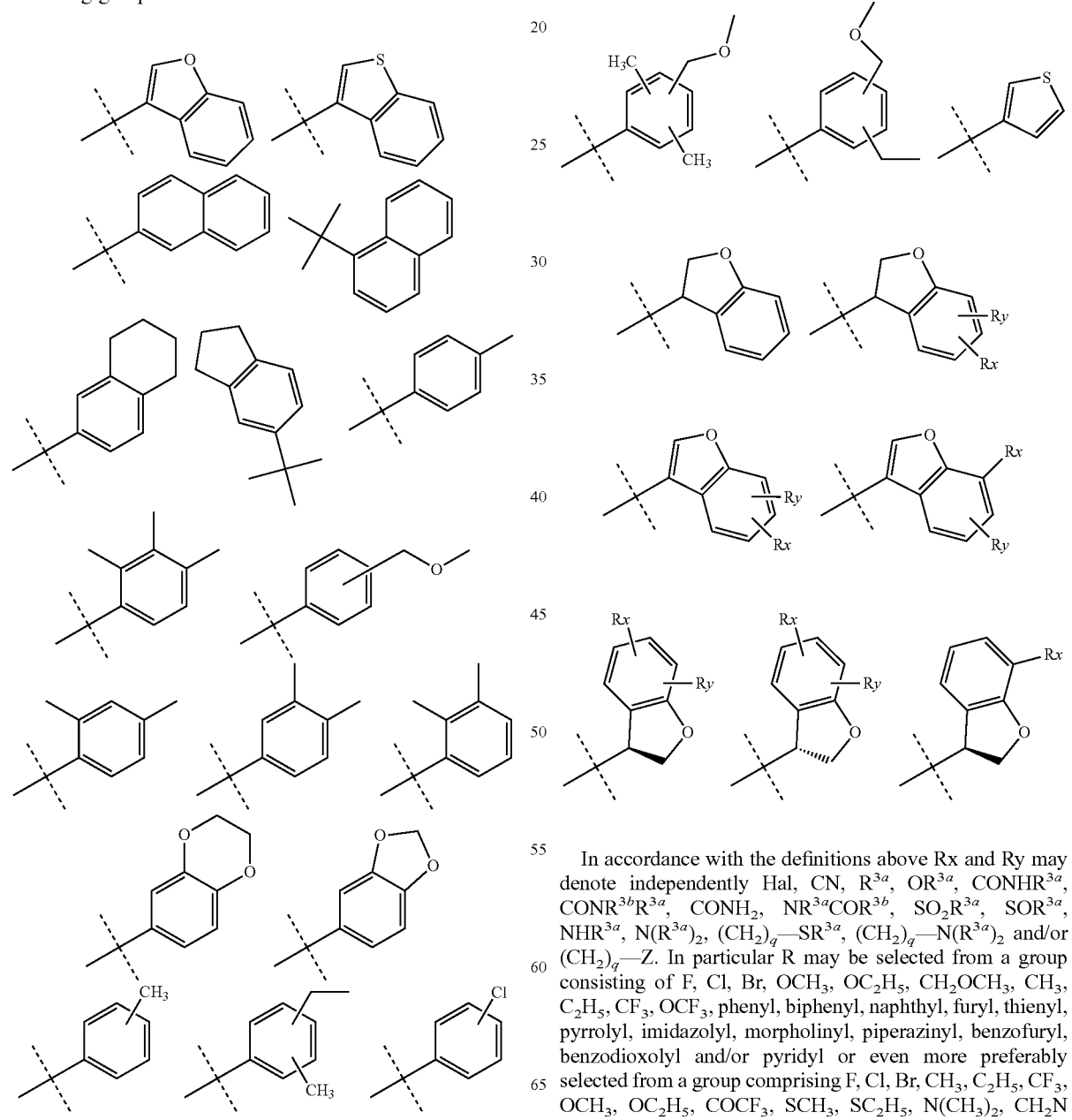

In accordance with the definitions above Rx and Ry may denote independently Hal, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_q—SR^{3a}$, $(CH_2)_q—N(R^{3a})_2$ and/or $(CH_2)_q—Z$. In particular R may be selected from a group consisting of F, Cl, Br, $OCH_3$, $OC_2H_5$, $CH_2OCH_3$, $CH_3$, $C_2H_5$, $CF_3$, $OCF_3$, phenyl, biphenyl, naphthyl, furyl, thienyl, pyrrolyl, imidazolyl, morpholinyl, piperazinyl, benzofuryl, benzodioxolyl and/or pyridyl or even more preferably selected from a group comprising F, Cl, Br, $CH_3$, $C_2H_5$, $CF_3$, $OCH_3$, $OC_2H_5$, $COCF_3$, $SCH_3$, $SC_2H_5$, $N(CH_3)_2$, $CH_2N(CH_3)_2$ and/or $N(C_2H_5)_2$.

Example 1: [(1R)-1-[[2-[(3,5-dichloro-2-pyridyl)oxy]acetyl]amino]-2-phenyl-ethyl]boronic acid (Compound No. 1)

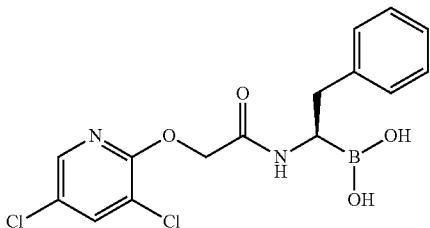

1H NMR (400 MHz, DMSO-d6) ppm=8.07-8.01 (m, 2H), 7.19-7.08 (m, 3H), 7.07-7.01 (m, 2H), 4.77-4.66 (m, 2H), 3.31 (dd, J=8.2, 5.2, 1H), 2.80 (dd, J=13.8, 5.2, 1H), 2.69 (dd, J=13.8, 8.2, 1H). MS (ESI+): 351.1 [M+H—H$_2$O]. HPLC (Method B): Rt. 3.0 min.

Example 2: [(1R)-2-phenyl-1-[[2-(2-pyridyloxy)acetyl]amino]ethyl]boronic acid (Compound No. 2)

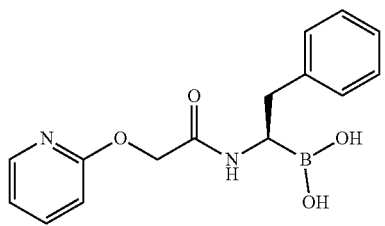

1H NMR (400 MHz, DMSO-d6) ppm=8.10 (ddd, J=5.1, 2.0, 0.8, 1H), 7.73 (ddd, J=8.4, 7.1, 2.0, 1H), 7.19-7.09 (m, 3H), 7.07-7.00 (m, 3H), 6.88-6.82 (m, 1H), 4.69 (d, J=14.9, 1H), 4.61 (d, J=14.9, 1H), 3.34 (dd, J=8.0, 5.4, 1H), 2.81 (dd, J=13.7, 5.5, 1H), 2.72 (dd, J=13.7, 8.0, 1H). MS (ESI+): 283.1 [M+H—H$_2$O]. HPLC (Method B): Rt. 3.75 min.

Example 3: [(1R)-1-[(2-phenoxyacetyl)amino]-2-phenyl-ethyl]boronic acid (Compound No. 3)

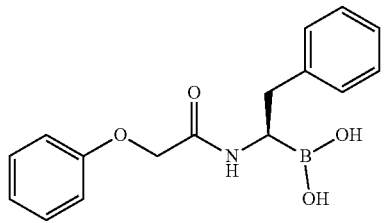

1H NMR (400 MHz, DMSO-d6) ppm=7.30-7.24 (m, 2H), 7.23-7.11 (m, 3H), 7.10-7.05 (m, 2H), 6.97 (tt, J=7.4, 1.1, 1H), 6.87-6.83 (m, 2H), 4.40 (d, J=14.8, 1H), 4.35 (d, J=14.8, 1H), 3.39 (dd, J=8.2, 5.4, 1H), 2.85 (dd, J=13.7, 5.4, 1H), 2.74 (dd, J=13.7, 8.3, 1H). MS (ESI+): 282.2 [M+H—H$_2$O]. HPLC (Method B): Rt. 4.48 min.

Example 4: [(1R)-1-(3-phenoxypropanoylamino)-2-(p-tolyl)ethyl]boronic acid (Compound No. 4)

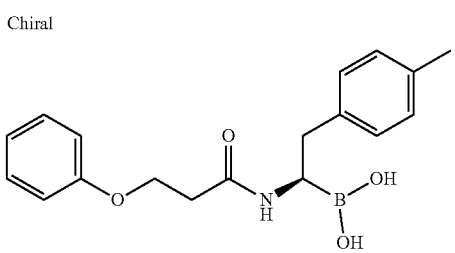 [SMILES: Cc1ccc(C[C@H](NC(=O)CCOc2ccccc2)B(O)O)cc1]

1H NMR (400 MHz, DMSO-d6) ppm=7.29-7.23 (m, 2H), 7.04-6.96 (m, 4H), 6.94-6.89 (m, 1H), 6.87-6.82 (m, 2H), 4.07 (t, J=6.1, 2H), 3.17 (dd, J=8.2, 5.5, 1H), 2.75 (dd, J=13.7, 5.5, 1H), 2.63 (dd, J=13.7, 8.3, 1H), 2.50-2.45 (m, 2H), 2.20 (s, 3H). MS (ESI+): 310.0 [M+H—H$_2$O]. HPLC (Method B): Rt. 4.56 min.

Example 5: [(1R)-1-[3-(4-methoxyphenoxy)propanoylamino]-2-(p-tolyl)ethyl]boronic acid (Compound No. 5)

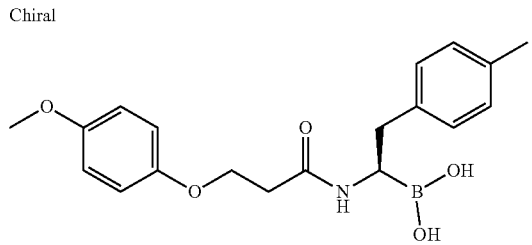

1H NMR (400 MHz, DMSO-d6) ppm=7.11-7.02 (m, 4H), 6.92-6.81 (m, 4H), 4.07 (t, J=6.1, 2H), 3.72 (s, 3H), 3.20 (dd, J=8.3, 5.5, 1H), 2.81 (dd, J=13.7, 5.5, 1H), 2.68 (dd, J=13.8, 8.4, 1H), 2.55-2.49 (m, 2H), 2.26 (s, 3H). MS (ESI+): 340.2 [M+H—H$_2$O]. HPLC (Method B): Rt. 4.58 min.

Example 6: [(1R)-2-(benzofuran-3-yl)-1-[(2-phenylacetyl)amino]ethyl]boronic acid (Compound No. 6)

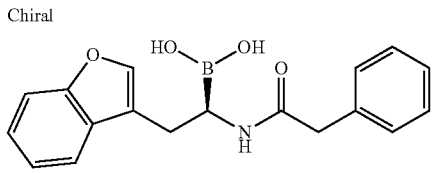 [SMILES: O=C(Cc1ccccc1)N[C@@H](Cc1coc2ccccc12)B(O)O]

MS (ESI+): 306.1 [M+H—H$_2$O]. HPLC (Method B): Rt. 4.66 min.

Example 7: [(1R)-2-(benzofuran-3-yl)-1-[3-(4-methylphenoxy)propanoylamino]-ethyl]boronic acid (Compound No. 7)

N—[(R)-2-Benzofuran-3-yl-1-((1 S,2S,6R,8S)-2,9,9-trimethyl-3,5-dioxa-4-boratricyclo[6.1.1.0²,⁶]dec-4-yl)-ethyl]-3-p-tolyloxy-propionamide

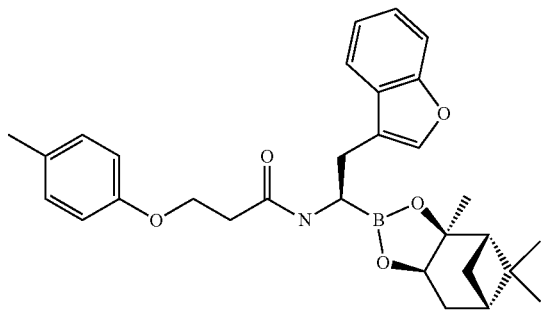

To a solution of 2-Benzofuran-3-yl-1-((1S,2S,6R,8S)-2,9,9-trimethyl-3,5-dioxa-4-bora-tricyclo[6.1.1.0²,⁶]dec-4-yl)-ethylamine trifluoroacetate (0.55 mmol; 0.25 g) in 12 mL DMF was added 3-p-tolyloxy-propionic acid (0.55 mmol; 0.1 g) at −10° C. under nitrogen atmosphere. Then N-Ethyl-diisopropyl-amine (1.65 mmol; 0.29 ml) and [(Benzotriazol-1-yloxy)-dimethylamino-methylene]-dimethyl-ammonium tetrafluoroborate (TBTU) (0.66 mmol; 0.21 g) were added. The pale brown solution was stirred for 3 h at −10° C. The reaction mixture was diluted with ethyl acetate and brine. The organic phase was washed with brine (5×10 mL). The organic layer was dried over sodium sulfate, filtered, concentrated in vacuo (bath temperature 30° C.) and purified by flash chromatography (silica gel, petroleum ether/ethyl acetate; gradient 0-30% ethyl acetate) to yield 0.25 g (78%) of the title compound as a white solid.

HPLC MS (Agilent-Waters Xbridge C8 (50×4.6 mm, 3.5 µm); 2.0 mL/min; 254 nm; buffer A: 0.1% TFA/H₂O, buffer B: 0.1% TFA/ACN; (0.0-8.0 min 5%-100% buffer B; 8.0-8.1 min 100% buffer B; 8.1-8.5 min 100%-5% buffer B; 8.5-10.0 min 5%-5% buffer B): (M+H) 502.2; Rt 6.21 min.

[(1R)-2-(benzofuran-3-yl)-1-[3-(4-methylphenoxy) propanoylamino]-ethyl]boronic acid (Compound No. 7)

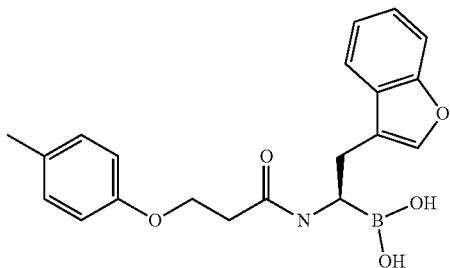

N—[(R)-2-Benzofuran-3-yl-1-((1 S,2S,6R,8S)-2,9,9-trimethyl-3,5-dioxa-4-bora tricyclo[6.1.1.0²,⁶]dec-4-yl)-ethyl]-3-p-tolyloxy-propionamide (0.43 mmol; 0.25 g) was dissolved in 10 ml n-pentane and 10 ml methanol and cooled to 0° C. Then isobutylboronic acid (1.72 mmol; 0.18 g) and 1.5 M Hydrochloric acid (3.75 mmol; 2.5 ml) were added and the reaction mixture was stirred 1 h at 0° C. and then over night at RT. The reaction mixture was washed with pentane (5×20 mL). The methanolic aqueous layer was evaporated (bath temperature 30° C.), the residue was basified with 1N NaOH and extracted with DCM (3×20 mL). The aqueous phase was acidified with 1.5 N HCl and extracted again with DCM (5×10 mL). The combined organic layers were dried over Na₂SO₄, filtered, reduced to dryness and lyophilisated to give 54 mg (31%) of the title compound as a white solid.

1H NMR (400 MHz, DMSO-d6) ppm=7.59-7.57 (m, 2H), 7.47 (d, J=8.12 Hz, 1H), 7.28-7.24 (m, 1H), 7.22-7.18 (m, 1H), 7.01 (d, J=8.28 Hz, 2H), 6.69-6.67 (m, 2H), 4.03 (t, J=6.04 Hz, 2H), 3.18-3.14 (m, 1H), 2.88-2.83 (m, 1H), 2.76-2.71 (m, 1H), 2.50-2.49 (m, 2H), 2.16 (s, 3H). MS (ESI+): 350.3 [M+H—H₂O]. HPLC (Method B): Rt. 3.98 min.

By similar sequences of coupling and deprotection all other examples are accessible. The required carboxylic acids are either commercially available or can be prepared by those skilled in the art using established procedures.

Example 8: [(1R)-2-(benzofuran-3-yl)-1-[[2-(3-pyridyl)acetyl]amino]ethyl]boronic acid (Compound No. 8)

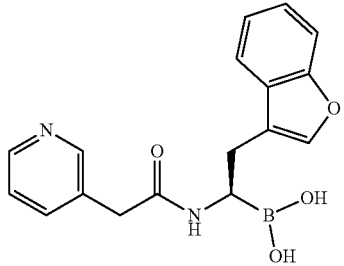

1H NMR (400 MHz, DMSO-d6) ppm=8.66-8.61 (m, 1H), 8.60-8.55 (m, 1H), 8.26-8.19 (m, 1H), 7.85 (dd, J=8.0, 5.6, 1H), 7.60-7.53 (m, 2H), 7.46 (d, J=8.1, 1H), 7.30-7.22 (m, 1H), 7.22-7.15 (m, 1H), 3.63 (s, 2H), 3.29 (dd, J=8.8, 5.5, 1H), 2.89 (dd, J=14.8, 5.4, 1H), 2.77 (dd, J=14.9, 8.8, 1H). MS (ESI+): 325.1 [M+H—H₂O]. HPLC (Method B): Rt. 3.1 min.

Example 9: [(1R)-2-(benzofuran-3-yl)-1-[[2-(4-cyanophenyl)acetyl]amino]ethyl]-boronic acid (Compound No. 9)

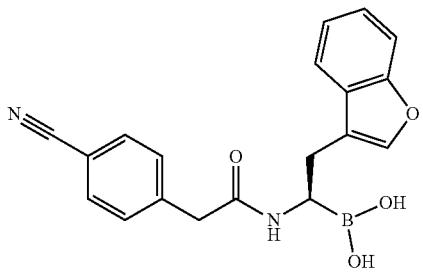

MS (ESI+): 331.1 [M+H—H₂O]. HPLC (Method B): Rt. 4.54 min.

Example 10: [(1R)-2-(benzofuran-3-yl)-1-[[2-(4-methoxyphenyl)acetyl]amino]ethyl]-boronic acid (Compound No. 10)

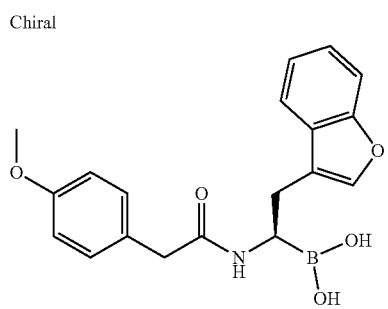 [SMILES: COc1ccc(CC(=O)N[C@@H](Cc2coc3ccccc23)B(O)O)cc1]

1H NMR (400 MHz, DMSO-d6) ppm=7.54 (d, J=7.6, 1H), 7.50-7.42 (m, 2H), 7.26 (t, J=7.3, 1H), 7.19 (t, J=7.4, 1H), 7.04 (d, J=8.5, 2H), 6.76 (d, J=8.5, 2H), 3.67 (s, 3H), 3.39-3.27 (m, 2H), 3.18-3.08 (m, 1H), 2.83 (dd, J=15.0, 5.5, 1H), 2.71 (dd, J=14.9, 8.4, 1H). MS (ESI+): 336.2 [M+H—H₂O]. HPLC (Method B): Rt. 4.63 min.

Example 11: [(1R)-2-(benzofuran-3-yl)-1-[[2-(3-pyridyloxy)acetyl]amino]ethyl]-boronic acid (Compound No. 11)

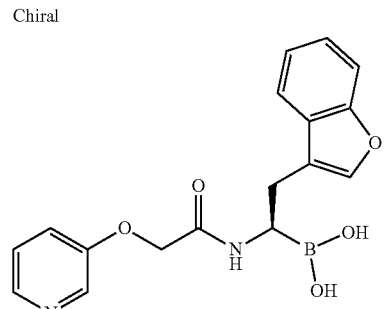

1H NMR (400 MHz, DMSO-d6) ppm=8.27-8.23 (m, 1H), 8.18 (dd, J=3.9, 2.0, 1H), 7.74 (d, J=7.1, 1H), 7.65 (d, J=7.3, 1H), 7.61 (s, 1H), 7.51 (d, J=8.2, 1H), 7.37-7.27 (m, 3H), 7.23 (t, J=7.0, 1H), 4.63-4.37 (m, 2H), 3.54-3.36 (m, 1H), 2.98 (dd, J=14.7, 5.1, 1H), 2.88 (dd, J=14.9, 8.5, 1H). MS (ESI+): 323.1 [M+H—H₂O]. HPLC (Method B): Rt. 3.4 min.

Example 12: [(1R)-2-(benzofuran-3-yl)-1-[[2-(6-methoxy-2-pyridyl)acetyl]amino]-ethyl]boronic acid (Compound No. 12)

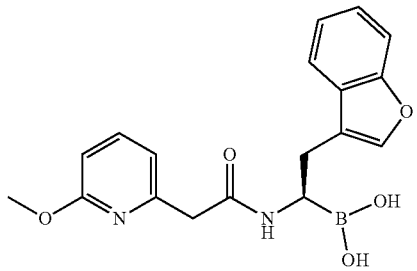

1H NMR (500 MHz, DMSO-d6) ppm=7.61-7.52 (m, 2H), 7.50-7.43 (m, 2H), 7.28-7.22 (m, 1H), 7.17 (t, J=7.3, 1H), 6.80 (d, J=7.2, 1H), 6.62 (d, J=8.3, 1H), 3.63 (s, 3H), 3.52-3.47 (m, 2H), 3.28 (dd, J=7.7, 5.6, 1H), 2.89 (dd, J=15.0, 5.3, 1H), 2.78 (dd, J=14.9, 7.9, 1H). MS (ESI+): 337.2 [M+H—H₂O]. HPLC (Method B): Rt. 4.38 min.

Example 13: [(1R)-2-(benzofuran-3-yl)-1-[[2-(5-ethoxy-2-pyridyl)acetyl]amino]-ethyl]boronic acid (Compound No. 13)

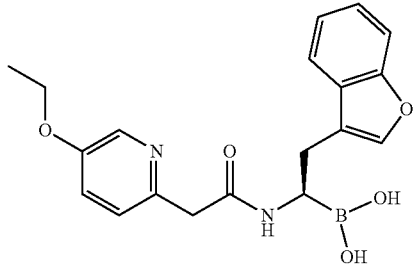

1H NMR (500 MHz, DMSO-d6) ppm=8.03 (d, J=2.9, 1H), 7.59-7.51 (m, 2H), 7.46 (d, J=8.2, 1H), 7.31-7.22 (m, 2H), 7.19 (t, J=7.4, 1H), 7.15 (d, J=8.6, 1H), 4.03 (q, J=7.0, 2H), 3.51 (s, 2H), 3.22 (dd, J=8.5, 5.5, 1H), 2.87 (dd, J=14.9, 5.2, 1H), 2.76 (dd, J=14.9, 8.7, 1H), 1.29 (t, J=7.0, 3H). MS (ESI+): 351.1 [M+H—H₂O]. HPLC (Method B): Rt. 3.9 min.

Example 14: [(1R)-1-[(2-phenylacetyl)amino]-2-(p-tolyl)ethyl]boronic acid (Compound No. 14)

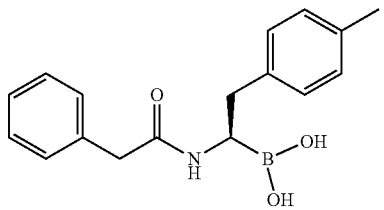

1H NMR (500 MHz, DMSO-d6) ppm=7.26-7.17 (m, 3H), 7.11 (d, J=6.8, 2H), 6.97 (d, J=7.9, 2H), 6.91 (d, J=7.9, 2H), 3.41-3.27 (m, 2H), 3.08 (dd, J=8.6, 5.5, 1H), 2.70 (dd, J=13.8, 5.4, 1H), 2.55 (dd, J=13.8, 8.7, 1H), 2.20 (s, 3H). MS (ESI+): 280.1 [M+H—H$_2$O]. HPLC (Method B): Rt. 4.58 min.

Example 15: [(1R)-2-(benzofuran-3-yl)-1-[[2-(3-methoxyphenyl)acetyl]amino]ethyl]-boronic acid (Compound No. 15)

Chiral

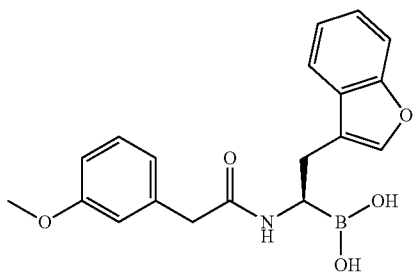

1H NMR (400 MHz, DMSO-d6) ppm=7.56-7.52 (m, 1H), 7.48-7.44 (m, 2H), 7.29-7.23 (m, 1H), 7.22-7.11 (m, 2H), 6.78-6.70 (m, 3H), 3.65 (s, 3H), 3.37 (s, 2H), 3.16 (dd, J=8.4, 5.5, 1H), 2.84 (dd, J=14.8, 5.4, 1H), 2.73 (dd, J=14.9, 8.4, 1H). MS (ESI+): 336.1 [M+H—H$_2$O]. HPLC (Method B): Rt. 4.68 min.

Example 16: [(1R)-1-[[(2R)-2-hydroxy-2-phenyl-acetyl]amino]-2-(p-tolyl)ethyl]-boronic acid (Compound No. 16)

Chiral

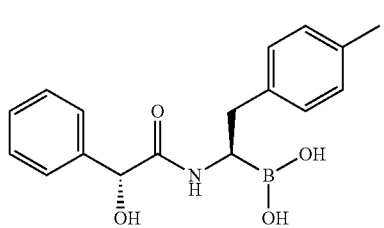

MS (ESI+): 296.1 [M+H—H$_2$O]. HPLC (Method B): Rt. 4.68 min.

Example 17: [(1R)-1-[[(2S)-2-hydroxy-2-phenyl-acetyl]amino]-2-(p-tolyl)ethyl]-boronic acid (Compound No. 17)

Chiral

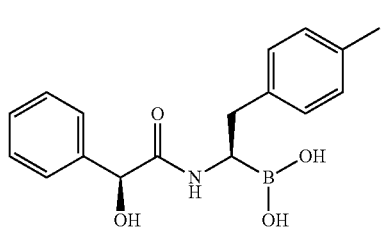

MS (ESI+): 296.1 [M+H—H$_2$O]. HPLC (Method B): Rt. 4.42 min.

Example 18: [(1R)-2-(benzofuran-3-yl)-1-[(2-pyrazin-2-ylacetyl)amino]ethyl]boronic acid (Compound No. 18)

Chiral

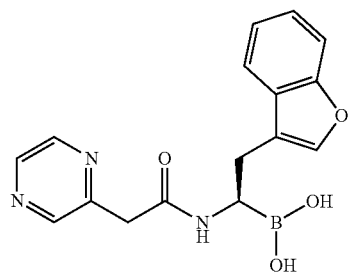

1H NMR (400 MHz, DMSO-d6) ppm=8.48-8.42 (m, 3H), 7.59-7.53 (m, 2H), 7.46 (d, J=8.1, 1H), 7.29-7.23 (m, 1H), 7.23-7.16 (m, 1H), 3.67-3.62 (m, 2H), 3.24 (dd, J=8.5, 5.5, 1H), 2.92-2.84 (m, 1H), 2.77 (dd, J=14.9, 8.7, 1H). MS (ESI+): 296.1 [M+H—H$_2$O]. HPLC (Method B): Rt. 4.42 min. MS (ESI+): 308.1 [M+H—H$_2$O]. HPLC (Method B): Rt. 3.62 min.

Example 19: [(1R)-2-(benzofuran-3-yl)-1-[[2-(4-pyridyl)acetyl]amino]ethyl]boronic acid (Compound No. 19)

Chiral

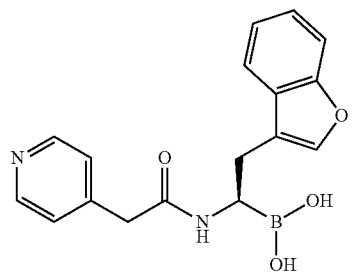

1H NMR (400 MHz, DMSO-d6) ppm=8.65-8.59 (m, 2H), 7.78-7.72 (m, 2H), 7.59-7.52 (m, 2H), 7.45 (d, J=8.1, 1H), 7.29-7.22 (m, 1H), 7.21-7.14 (m, 1H), 3.32 (dd, J=9.0, 5.4, 1H), 2.89 (dd, J=15.0, 5.5, 1H), 2.77 (dd, J=14.9, 9.1, 1H). MS (ESI+):325.1 [M+H—H$_2$O]. HPLC (Method B): Rt. 2.7 min.

Example 20: [(1R)-2-(benzofuran-3-yl)-1-[(2-pyrimidin-2-ylacetyl)amino]ethyl]-boronic acid (Compound No. 20)

Chiral

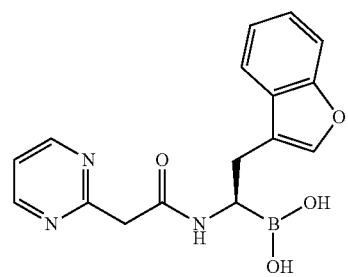

1H NMR (400 MHz, DMSO-d6) ppm=8.65 (d, J=5.0, 2H), 7.62-7.55 (m, 2H), 7.48-7.44 (m, 1H), 7.35 (t, J=5.0, 1H), 7.29-7.23 (m, 1H), 7.23-7.16 (m, 1H), 3.26 (dd, J=8.5, 5.4, 1H), 2.94-2.86 (m, 1H), 2.79 (dd, J=14.9, 8.5, 1H). MS (ESI+): 308.1 [M+H—H₂O]. HPLC (Method B): Rt. 3.61 min.

Example 21: [(1R)-1-[[2-(4-acetamidophenyl)acetyl]amino]-2-(p-tolyl)ethyl]boronic acid (Compound No. 21)

Chiral

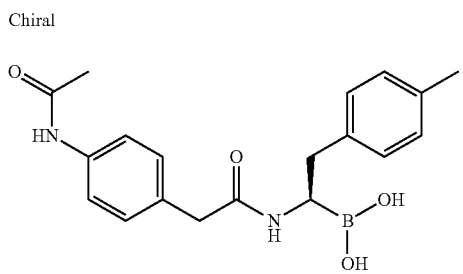 [SMILES: CC(=O)Nc1ccc(CC(=O)N[C@@H](Cc2ccc(C)cc2)B(O)O)cc1]

1H NMR (400 MHz, DMSO-d6) ppm=7.39-7.34 (m, 2H), 7.05-7.01 (m, 2H), 6.98-6.94 (m, 2H), 6.91-6.86 (m, 2H), 3.36-3.24 (m, 2H), 3.07 (dd, J=8.8, 5.4, 1H), 2.73-2.65 (m, 1H), 2.59-2.51 (m, 1H), 2.19 (s, 3H), 2.00 (s, 3H).). MS (ESI+): 337.2 [M+H—H₂O]. HPLC (Method B): Rt. 3.77 min.

Example 22: [(1R)-2-(benzofuran-3-yl)-1-[[2-(3,4,5-trifluorophenyl)acetyl]amino]-ethyl]boronic acid (Compound No. 22)

Chiral

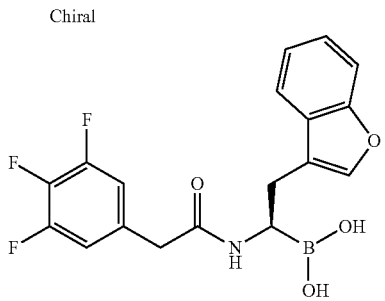 [SMILES: O=C(Cc1cc(F)c(F)c(F)c1)N[C@@H](Cc1coc2ccccc12)B(O)O]

1H NMR (400 MHz, DMSO-d6) ppm=7.62-7.57 (m, 1H), 7.55 (s, 1H), 7.52-7.47 (m, 1H), 7.33-7.26 (m, 1H), 7.26-7.19 (m, 1H), 7.08-6.99 (m, 2H), 3.40 (s, 2H), 3.32 (dd, J=8.9, 5.4, 1H), 2.96-2.87 (m, 1H), 2.80 (dd, J=14.9, 9.0, 1H). HPLC (Method B): Rt. 5.17 min.

Example 23: [(1R)-2-(benzofuran-3-yl)-1-[(2,2-difluoro-2-phenyl-acetyl)amino]-ethyl]boronic acid (Compound No. 23)

Chiral

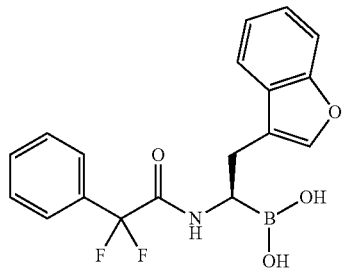

1H NMR (400 MHz, DMSO-d6) ppm=7.66-7.62 (m, 1H), 7.56-7.49 (m, 3H), 7.46-7.36 (m, 4H), 7.36-7.29 (m, 1H), 7.28-7.22 (m, 1H), 3.55 (dd, J=9.6, 5.2, 1H), 3.05-2.97 (m, 1H), 2.93 (dd, J=15.0, 9.6, 1H). MS (ESI+): 342.1 [M+H—H₂O]. HPLC (Method B): Rt. 5.41 min.

Example 24: [(1R)-2-(benzofuran-3-yl)-1-[[2-[2-(trifluoromethyl)phenyl]acetyl]-amino]ethyl]boronic acid (Compound No. 24)

Chiral

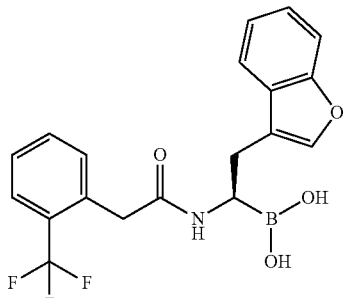

1H NMR (400 MHz, DMSO-d6) ppm=7.71-7.67 (m, 1H), 7.65-7.61 (m, 1H), 7.59 (s, 1H), 7.56-7.51 (m, 2H), 7.50-7.44 (m, 1H), 7.36-7.30 (m, 2H), 7.27 (td, J=7.4, 1.1, 1H), 3.67 (s, 2H), 3.30 (dd, J=8.6, 5.6, 1H), 2.93 (dd, J=15.1, 5.4, 1H), 2.81 (dd, J=15.0, 8.6, 1H). MS (ESI+): 374.1 [M+H—H₂O]. HPLC (Method B): Rt. 5.16 min.

Example 25: [(1R)-2-(benzofuran-3-yl)-1-[[2-(2,6-dichlorophenyl)acetyl]amino]-ethyl]boronic acid (Compound No. 25)

Chiral

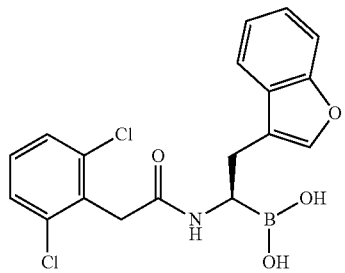

1H NMR (400 MHz, DMSO-d6) ppm=7.68-7.61 (m, 2H), 7.55-7.50 (m, 1H), 7.45-7.39 (m, 2H), 7.36-7.24 (m, 3H), 3.89-3.75 (m, 2H), 3.35 (dd, J=8.3, 5.5, 1H), 2.95 (dd, J=14.6, 5.5, 1H), 2.83 (dd, J=15.0, 8.3, 1H). MS (ESI+): 374.0 [M+H—H₂O]. HPLC (Method B): Rt. 5.14 min.

Example 26: [(1R)-1-[[2-(4-acetamidophenyl)acetyl]amino]-2-(benzofuran-3-yl)ethyl]boronic acid (Compound No. 26)

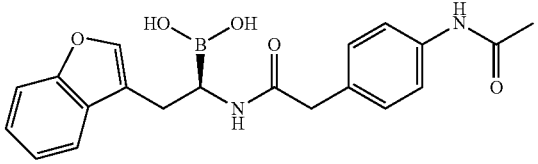

2-(4-Acetylamino-phenyl)-N—[(R)-2-benzofuran-3-yl-1-((1 S,2S,6R,8S)-2,9,9-trimethyl-3,5-dioxa-4-bora-tricyclo[6.1.1.02,6]dec-4-yl)-ethyl]-acetamide

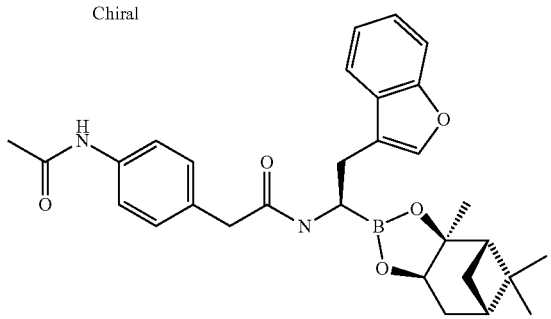

To a solution of (R)-2-Benzofuran-3-yl-1-((1S,2S,6R,8S)-2,9,9-trimethyl-3,5-dioxa-4-bora-tricyclo[6.1.1.02,6]dec-4-yl)-ethyl-aminehydrochloride (0.61 mmol; 0.25 g) in 10 mL DMF was added (4-Acetylamino-phenyl)-acetic acid (0.67 mmol; 0.13 g) at −10° C. under nitrogen atmosphere. Then N-Ethyl-diisopropyl-amine (1.83 mmol; 0.32 ml) and [(Benzotriazol-1-yloxy)-dimethylamino-methylene]-dimethyl-ammonium tetrafluoroborate (TBTU) (0.73 mmol; 0.23 g) were added. The solution was stirred for 3 h at −10° C. The reaction mixture was diluted with ethyl acetate and brine. The organic phase was washed with brine (5×10 mL). The organic layer was dried over sodium sulfate, filtered, concentrated in vacuo (bath temperature 30° C.) and purified by flash chromatography (silica gel, petroleum ether/ethyl acetate; gradient 0-100% ethyl acetate) to yield 0.27 g (78%) of the title compound as a brown gum.

HPLC MS (Agilent-Waters Xbridge C8 (50×4.6 mm, 3.5 μm); 2.0 mL/min; 254 nm; buffer A: 0.1% TFA/H₂O, buffer B: 0.1% TFA/ACN; (0.0-8.0 min 5%-100% buffer B; 8.0-8.1 min 100% buffer B; 8.1-8.5 min 100%-5% buffer B; 8.5-10.0 min 5%-5% buffer B): (M+H) 515.0; Rt 5.10 min.

[(1R)-1-[[2-(4-acetamidophenyl)acetyl]amino]-2-(benzofuran-3-yl)ethyl]boronic acid (Compound No. 26)

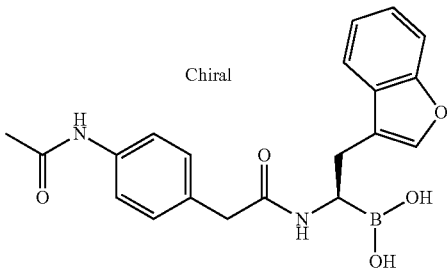 [SMILES: CC(=O)Nc1ccc(CC(=O)N[C@@H](Cc2coc3ccccc23)B(O)O)cc1]

2-(4-Acetylamino-phenyl)-N—[(R)-2-benzofuran-3-yl-1-((1 S,2S,6R,8S)-2,9,9-trimethyl-3,5-dioxa-4-bora-tricyclo [6.1.1.02,6]dec-4-yl)-ethyl]-acetamide. (0.48 mmol; 0.27 g) was dissolved in 15 ml n-pentane and 15 ml methanol and cooled to 0° C. Then isobutylboronic acid (1.92 mmol; 0.2 g) and 1.5 M Hydrochloric acid (2.25 mmol; 1.5 ml) were added and the reaction mixture was stirred 1 h at 0° C. and then over night at RT. The reaction mixture was washed with pentane (5×20 mL). The methanolic aqueous layer was evaporated (bath temperature 30° C.), the residue was basified with 1N NaOH and extracted with DCM (3×20 mL). The aqueous phase was acidified with 1.5 N HCl and extracted again with DCM (5×10 mL). The combined organic layers were dried over Na₂SO₄, filtered, reduced to dryness and lyophilisated to give 50 mg (24%) of the title compound as an Off-white solid.

1H NMR (400 MHz, DMSO-d6) ppm=7.53 (d, J=7.48 Hz, 1H), 7.48-7.45 (m, 2H), 7.34-7.36 (m, 2H), 7.28-7.24 (m, 1H), 7.21-7.17 (m, 1H), 7.05 (d, J=8.52 Hz, 2H), 3.35 (s, 2H), 3.13-3.09 (m, 1H), 2.85-2.80 (m, 1H), 2.73-2.67 (m, 1H), 1.99 (s, 3H). MS (ESI+): 363.0 [M+H—H₂O]. HPLC (Method B): Rt. 2.67 min.

Example 27: [(1R)-2-(benzofuran-3-yl)-1-[[2-(2-methoxyphenyl)acetyl]amino]ethyl]-boronic acid (Compound No. 27)

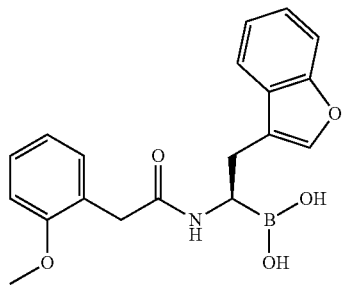

1H NMR (400 MHz, DMSO-d6) ppm=7.58-7.54 (m, 1H), 7.51-7.45 (m, 2H), 7.31-7.23 (m, 1H), 7.23-7.16 (m, 2H), 7.09-7.02 (m, 1H), 6.90 (d, J=8.2, 1H), 6.85-6.79 (m, 1H), 3.63 (s, 3H), 3.42-3.32 (m, 2H), 3.26-3.16 (m, 1H), 2.86 (dd, J=15.0, 5.6, 1H), 2.74 (dd, J=15.0, 8.1, 1H). MS (ESI+): 336.0 [M+H—H₂O]. HPLC (Method B): Rt. 4.73 min.

Example 28: [(1R)-2-(benzofuran-3-yl)-1-[[2-[2-(trifluoromethoxy)phenyl]acetyl]-amino]ethyl]boronic acid (Compound No. 28)

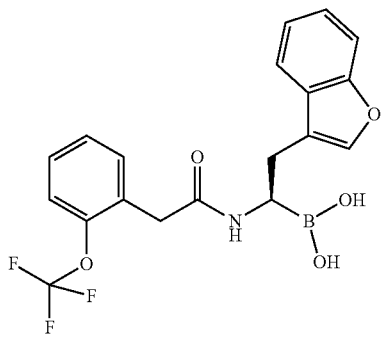

1H NMR (400 MHz, DMSO-d6) ppm=7.60-7.55 (m, 1H), 7.54 (s, 1H), 7.50-7.44 (m, 1H), 7.36-7.30 (m, 1H), 7.29-7.18 (m, 5H), 3.47 (s, 2H), 3.27 (dd, J=8.3, 5.6, 1H), 2.88 (dd, J=14.8, 5.7, 1H), 2.76 (dd, J=14.9, 8.3, 1H). MS (ESI+): 390.0 [M+H—H$_2$O]. HPLC (Method B): Rt. 5.32 min.

Example 29: [(1R)-2-(2,4-dimethylphenyl)-1-[(2-phenylacetyl)amino]ethyl]boronic acid (Compound No. 29)

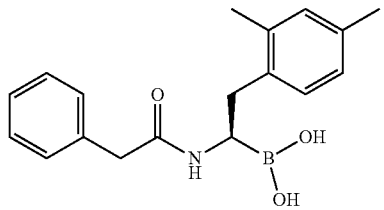

1H NMR (500 MHz, DMSO-d6) ppm=7.30-7.17 (m, 3H), 7.14-7.10 (m, 2H), 6.87-6.83 (m, 2H), 6.80-6.77 (m, 1H), 3.39-3.31 (m, 2H), 3.07-3.02 (m, 1H), 2.71 (dd, J=14.1, 5.8, 1H), 2.56 (dd, J=14.1, 9.3, 1H), 2.17 (s, 3H), 2.12 (s, 3H). MS (ESI+): 294.1 [M+H—H$_2$O]. HPLC (Method B): Rt. 4.8 min.

Example 30: [(1R)-2-(benzofuran-3-yl)-1-[[2-[4-(methoxymethyl)phenyl]acetyl]-amino]ethyl]boronic acid Compound No. 30)

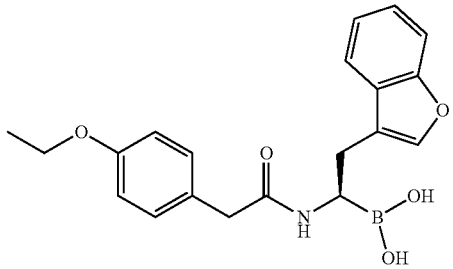

1H NMR (400 MHz, DMSO-d6) ppm=8.91-8.74 (m, 1H), 7.60-7.55 (m, 1H), 7.50-7.42 (m, 2H), 7.29-7.23 (m, 1H), 7.21-7.10 (m, 5H), 4.28-4.23 (m, 2H), 3.54 (s, 2H), 3.22-3.18 (m, 3H), 2.83-2.76 (m, 1H), 2.75-2.65 (m, 1H), 2.58-2.50 (m, 1H). MS (ESI+): 350.1 [M+H—H$_2$O]. HPLC (Method B): Rt. 4.54 min.

Example 31: [(1R)-2-(benzofuran-3-yl)-1-[[2-[3-(3-hydroxypropoxy)phenyl]acetyl]-amino]ethyl]boronic acid (Compound No. 31)

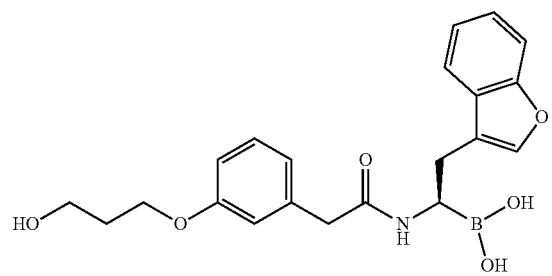

1H NMR (500 MHz, DMSO-d6) ppm=8.91-8.71 (m, 1H), 7.57-7.51 (m, 1H), 7.49-7.40 (m, 2H), 7.27-7.22 (m, 1H), 7.19-7.13 (m, 1H), 7.13-7.07 (m, 1H), 6.81-6.77 (m, 1H), 6.78-6.71 (m, 2H), 4.51-4.45 (m, 1H), 3.95-3.89 (m, 2H), 3.53-3.46 (m, 4H), 2.82-2.75 (m, 1H), 2.73-2.67 (m, 1H), 2.56-2.50 (m, 1H), 1.81-1.75 (m, 2H). MS (ESI+): 380.1 [M+H—H$_2$O]. HPLC (Method B): Rt. 4.3 min.

Example 32: [(1R)-1-[[2-(3-acetamidophenyl)acetyl]amino]-2-(benzofuran-3-yl)ethyl]boronic acid (Compound No. 32)

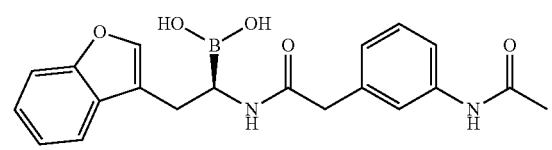

(3-Nitro-phenyl)-acetic acid methyl ester

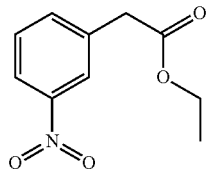

To a stirred solution of (3-Nitro-phenyl)-acetic acid (0.50 g; 2.76 mmol) in dry Methanol (30.00 ml) cooled to 0° C., thionyl Chloride (0.31 ml; 4.14 mmol) was added slowly. The reaction mixture was heated for 3 h. After removal of the solvent, the crude was basified with 10% sodium bicarbonate solution and extracted with dichloromethane (2×40 ml) washed with brine solution. The organic layer was dried over anhydrous sodium sulphate and evaporated under vacuum to get (3-Nitro-phenyl)-acetic acid methyl ester 0.50 g (92.4%) as a brown oil.

HPLC MS (Agilent-Waters Xbridge C8 (50×4.6 mm, 3.5 µm); 1.0 mL/min; 254 nm; buffer A: 10 mM NH$_4$HCO$_3$/H$_2$O, buffer B: ACN; (0.0-8.0 min 5%-100% buffer B; 8.0-8.1 min 100% buffer B; 8.1-8.5 min 100%-5% buffer B; 8.5-10.0 min 5%-5% buffer B): (M–H) 194.0; Rt 5.03 min.

(3-Amino-phenyl)-acetic acid methyl ester

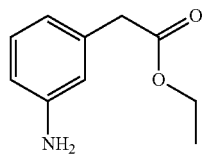

To a solution of (3-Nitro-phenyl)-acetic acid methyl ester (0.50 g; 2.55 mmol) in methanol (30.0 mL) was added palladium on carbon (10% w/w) (0.20 g; 0.19 mmol) portion wise under nitrogen atmosphere. The reaction mixture was hydrogenated under hydrogen atmosphere (bladder pressure) at RT for 16 h. The reaction mixture was filtered through celite, washed with methanol (75 mL) and the filtrate was concentrated to afford (3-Amino-phenyl)-acetic acid methyl ester 0.40 g (91%) as a brown solid.

HPLC MS (Agilent-Waters Xbridge C8 (50×4.6 mm, 3.5 µm); 2.0 mL/min; 220 nm; buffer A: 0.1% TFA/H$_2$O, buffer B: 0.1% TFA/ACN; (0.0-8.0 min 5%-100% buffer B; 8.0-8.1 min 100% buffer B; 8.1-8.5 min 100%-5% buffer B; 8.5-10.0 min 5%-5% buffer B): (M+H) 166.0; Rt. 1.39 min.

(3-Acetylamino-phenyl)-acetic acid methyl ester

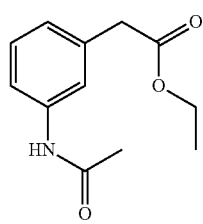 [SMILES: CCOC(=O)Cc1cccc(NC(C)=O)c1]

To a solution of (3-Amino-phenyl)-acetic acid methyl ester (0.40 g; 2.34 mmol) in DCM (20.00 ml), pyridine (0.57 ml; 7.01 mmol) was added. The solution was cooled to 0° C. and acetyl chloride (0.19 ml; 2.57 mmol) was added. The reaction mixture was stirred at RT for 4 h. To this reaction mixture 1.5N HCl solution (20 ml) was added and the organic layer was separated. The aqueous layer was extracted with DCM (2×25 ml). The combined organic layers were washed with saturated brine solution, dried over anhydrous sodium sulphate and evaporated to obtain (3-Acetylamino-phenyl)-acetic acid methyl ester 0.4 g (81%) as an oily liquid.

HPLC MS (Agilent-Waters Xbridge C8 (50×4.6 mm, 3.5 µm); 2.0 mL/min; 254 nm; buffer A: 0.1% TFA/H$_2$O, buffer B: 0.1% TFA/ACN; (0.0-8.0 min 5%-100% buffer B; 8.0-8.1 min 100% buffer B; 8.1-8.5 min 100%-5% buffer B; 8.5-10.0 min 5%-5% buffer B): (M+H) 208.0; Rt. 2.43 min.

(3-Acetylamino-phenyl)-acetic acid

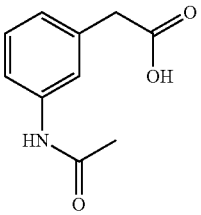

To a solution of (3-Acetylamino-phenyl)-acetic acid methyl ester (0.40 g; 1.90 mmol) in tetrahydrofuran (8.00 ml), Water (2.00 g) and LiOH (0.24 g; 5.69 mmol) was added. The reaction mixture was stirred at room temperature for 16 h. Solvents were evaporated off and the residue was acidified with 1.5N HCl (pH adjusted to 2) and extracted with dichloromethane (3×15 mL). The combined organic layers were dried over anhydrous Na$_2$SO$_4$ and concentrated to get (3-Acetylamino-phenyl)-acetic acid 0.30 g (79.9%) as a white solid.

HPLC MS (Agilent-Waters Xbridge C8 (50×4.6 mm, 3.5 µm); 2.0 mL/min; 254 nm; buffer A: 0.1% TFA/H$_2$O, buffer B: 0.1% TFA/ACN; (0.0-8.0 min 5%-100% buffer B; 8.0-8.1 min 100% buffer B; 8.1-8.5 min 100%-5% buffer B; 8.5-10.0 min 5%-5% buffer B): (M+H) 194.0; Rt. 1.79 min.

2-(3-Acetylamino-phenyl)-N—[(R)-2-benzofuran-3-yl-1-((1 S,2S,6R,8S)-2,9,9-trimethyl-3,5-dioxa-4-bora-tricyclo[6.1.1.0$^{2,6}$]dec-4-yl)-ethyl]-acetamide Chiral

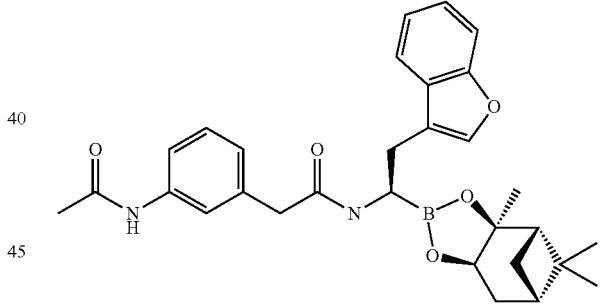

To a solution of (R)-2-Benzofuran-3-yl-1-((1S,2S,6R,8S)-2,9,9-trimethyl-3,5-dioxa-4-bora-tricyclo[6.1.1.0$^{2,6}$]dec-4-yl)-ethyl-aminehydrochloride (0.61 mmol; 0.25 g) in 10 mL DMF was added (3-Acetylamino-phenyl)-acetic acid (0.61 mmol; 0.12 g) at −10° C. under nitrogen atmosphere. Then N-Ethyl-diisopropyl-amine (1.83 mmol; 0.32 ml) and [(Benzotriazol-1-yloxy)-dimethylamino-methylene]-dimethyl-ammonium tetrafluoroborate (TBTU) (0.73 mmol; 0.23 g) were added. The solution was stirred for 3 h at −10° C. The reaction mixture was diluted with ethyl acetate and brine. The organic phase was washed with brine (5×10 mL). The organic layer was dried over sodium sulfate, filtered, concentrated in vacuo (bath temperature 30° C.) and purified by flash chromatography (silica gel, petroleum ether/ethyl acetate; gradient 0-100% ethyl acetate) to yield 0.3 g (81%) of the title compound as a brown gum.

HPLC MS (Agilent-Waters Xbridge C8 (50×4.6 mm, 3.5 µm); 254 nm; buffer A: 0.1% TFA/H$_2$O, buffer B: 0.1% TFA/ACN; (0.0-8.0 min 5%-100% buffer B; 8.0-8.1 min 100% buffer B; 8.1-8.5 min 100%-5% buffer B; 8.5-10.0 min 5%-5% buffer B): (M+H) 515.2; Rt. 5.22 min.

[(1R)-1-[[2-(3-acetamidophenyl)acetyl]amino]-2-(benzofuran-3-yl)ethyl]boronic acid (Compound No. 32)

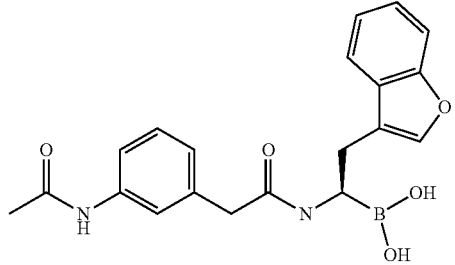

2-(3-Acetylamino-phenyl)-N—[(R)-2-benzofuran-3-yl-1-((1 S,2S,6R,8S)-2,9,9-trimethyl-3,5-dioxa-4-bora-tricyclo [6.1.1.02,6]dec-4-yl)-ethyl]-acetamide. (0.5 mmol; 0.3 g) was dissolved in 15 ml n-pentane and 15 ml methanol and cooled to 0° C. Then isobutylboronic acid (2.0 mmol; 0.21 g) and 1.5 M Hydrochloric acid (2.25 mmol; 1.5 ml) were added and the reaction mixture was stirred 1 h at 0° C. and then over night at RT. The reaction mixture was washed with pentane (5×20 mL). The methanolic aqueous layer was evaporated (bath temperature 30° C.), the residue was basified with 1N NaOH and extracted with DCM (3×20 mL). The aqueous phase was acidified with 1.5 N HCl and extracted again with DCM (5×10 mL). The combined organic layers were dried over Na$_2$SO$_4$, filtered, reduced to dryness and lyophilisated to give 80 mg (38%) of the title compound as an Off-white solid.

1H NMR (400 MHz, DMSO-d6) ppm=7.52 (d, J=7.48 Hz, 1H), 7.47-7.44 (m, 2H), 7.34-7.33 (m, 2H), 7.27-7.23 (m, 1H), 7.20-7.14 (m, 2H), 6.84 (d, J=7.68 Hz, 1H), 3.42 (s, 2H), 3.10-3.07 (m, 1H), 2.84-2.79 (m, 1H), 2.73-2.67 (m, 1H), 2.00 (s, 3H). MS (ESI+): 363.1 [M+H—H$_2$O]. HPLC (Method B): Rt. 2.82 min.

Example 33: [(1R)-2-(benzofuran-3-yl)-1-[[(2S)-2-methoxy-2-phenyl-acetyl]amino]-ethyl]boronic acid (Compound No. 33)

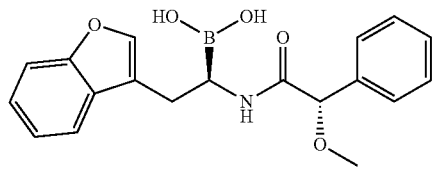

(S)—N—((R)-2-(benzofuran-3-yl)-1-((3aS,4S,6S, 7aR)-3a,5,5-trimethylhexahydro-4,6-methanobenzo [d][1,3,2]dioxaborol-2-yl)ethyl)-2-methoxy-2-phenylacetamide

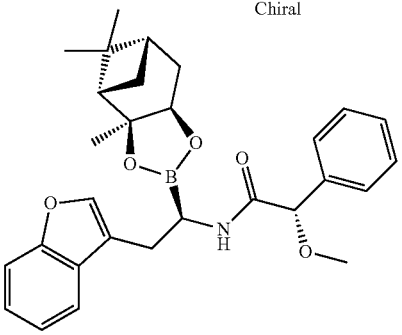 [SMILES: CO[C@H](C(=O)N[C@@H](Cc1coc2ccccc12)B1O[C@@H]2C[C@@H]3C[C@@H](C3(C)C)[C@]2(C)O1)c1ccccc1]

To a solution of (R)-2-Benzofuran-3-yl-1-((1S,2S,6R, 8S)-2,9,9-trimethyl-3,5-dioxa-4-bora-tricyclo[6.1.1.02,6] dec-4-yl)-ethyl-aminehydrochloride (0.85 mmol; 0.35 g) in 15 mL DMF was added (S)-Methoxy-phenyl-acetic acid (0.85 mmol; 0.14 g) at −10° C. under nitrogen atmosphere. Then N-Ethyl-diisopropyl-amine (2.56 mmol; 0.45 ml) and [(Benzotriazol-1-yloxy)-dimethylamino-methylene]-dimethyl-ammonium tetrafluoroborate (TBTU) (1.02 mmol; 0.33 g) were added. The solution was stirred for 3 h at −10° C. The reaction mixture was diluted with ethyl acetate and brine. The organic phase was washed with brine (5×20 mL). The organic layer was dried over sodium sulfate, filtered, concentrated in vacuo (bath temperature 30° C.) and purified by flash chromatography (silica gel, petroleum ether/ethyl acetate; gradient 0-50% ethyl acetate) to yield 0.3 g (53%) of the title compound as a pale green solid.

HPLC MS (Agilent-Waters Xbridge C8 (50×4.6 mm, 3.5 μm); 254 nm; buffer A: 0.1% TFA/H$_2$O, buffer B: 0.1% TFA/ACN; (0.0-8.0 min 5%-100% buffer B; 8.0-8.1 min 100% buffer B; 8.1-8.5 min 100%-5% buffer B; 8.5-10.0 min 5%-5% buffer B): (M+H) 488.0; Rt 6.24 min.

[(1R)-2-(benzofuran-3-yl)-1-[[(2S)-2-methoxy-2-phenyl-acetyl]amino]-ethyl]boronic acid (Compound No. 33)

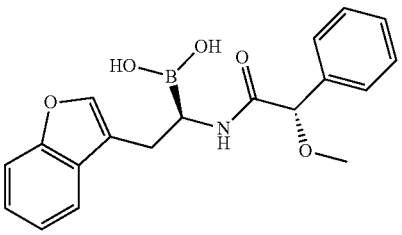

(S)—N—((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)-2-methoxy-2-phenylacetamide (0.33 mmol; 0.3 g) was dissolved in 12 ml n-pentane and 12 ml methanol and cooled to 0° C. Then isobutylboronic acid (1.3 mmol; 0.14 g) and 1.5 M Hydrochloric acid (2.40 mmol; 1.4 ml) were added and the reaction mixture was stirred 1 h at 0° C. and then over night at RT. The reaction mixture was washed with pentane (5×20 mL). The methanolic aqueous layer was evaporated (bath temperature 30° C.), the residue was basified with 1N NaOH and extracted with DCM (3×20 mL). The aqueous phase was acidified with 1.5 N HCl and extracted again with DCM (3×10 mL). The combined organic layers were dried over $Na_2SO_4$, filtered, reduced to dryness and lyophilisated to give 110 mg (86%) of the title compound as a pale pink solid.

1H NMR: (400 MHz, DMSO-d6) ppm=7.53 (d, J=7.40 Hz, 1H), 7.47-7.45 (m, 1H), 7.38 (s, 1H), 7.28-7.16 (m, 5H), 7.11-7.09 (m, 2H), 4.51 (s, 1H), 3.43-3.40 (m, 1H), 3.15 (s, 3H), 2.87-2.82 (m, 2H). MS (ESI+): 336.0 [M+H—$H_2O$]. HPLC (Method B): Rt. 3.93 min.

Example 34: [(1R)-2-(benzofuran-3-yl)-1-[[(2R)-2-methoxy-2-phenyl-acetyl]amino]-ethyl]boronic acid (Compound No. 34)

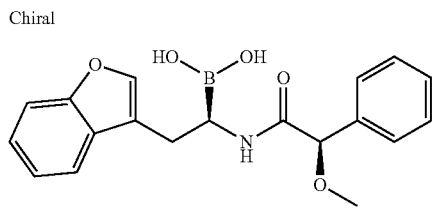 [SMILES: CO[C@@H](C(=O)N[C@@H](Cc1coc2ccccc12)B(O)O)c1ccccc1]

(R)—N—((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)-2-methoxy-2-phenylacetamide

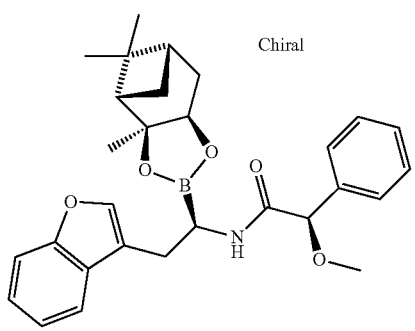

To a solution of (R)-2-Benzofuran-3-yl-1-((1S,2S,6R,8S)-2,9,9-trimethyl-3,5-dioxa-4-bora-tricyclo[6.1.1.02,6]dec-4-yl)-ethyl-aminehydrochloride (0.85 mmol; 0.35 g) in 10 mL DMF was added (R)-Methoxy-phenyl-acetic acid (0.85 mmol; 0.14 g) at −10° C. under nitrogen atmosphere. Then N-Ethyl-diisopropyl-amine (2.56 mmol; 0.45 ml) and [(Benzotriazol-1-yloxy)-dimethylamino-methylene]-dimethyl-ammonium tetrafluoroborate (TBTU) (1.02 mmol; 0.33 g) were added. The solution was stirred for 3 h at −10° C. The reaction mixture was diluted with ethyl acetate and brine. The organic phase was washed with brine (5×20 mL). The organic layer was dried over sodium sulfate, filtered, concentrated in vacuo (bath temperature 30° C.) and purified by flash chromatography (silica gel, petroleum ether/ethyl acetate; gradient 0-50% ethyl acetate) to yield 0.35 g (58%) of the title compound as a brown gum.

HPLC MS (Agilent-Waters Xbridge C8 (50×4.6 mm, 3.5 μm); 254 nm; buffer A: 0.1% TFA/$H_2O$, buffer B: 0.1% TFA/ACN; (0.0-8.0 min 5%-100% buffer B; 8.0-8.1 min 100% buffer B; 8.1-8.5 min 100%-5% buffer B; 8.5-10.0 min 5%-5% buffer B): (M+H) 488.0; Rt. 6.24 min.

(R)-(1-(2-(3-acetamidophenyl)acetamido)-2-(benzofuran-3-yl)ethyl)boronic acid

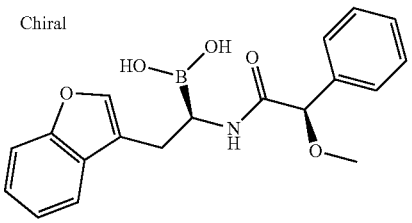 [SMILES: CO[C@@H](C(=O)N[C@@H](Cc1coc2ccccc12)B(O)O)c1ccccc1]

(R)—N—((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)-2-methoxy-2-phenylacetamide (0.5 mmol; 0.35 g) was dissolved in 15 ml n-pentane and 15 ml methanol and cooled to 0° C. Then isobutylboronic acid (2.0 mmol; 0.21 g) and 1.5 M Hydrochloric acid (2.40 mmol; 1.5 ml) were added and the reaction mixture was stirred 1 h at 0° C. and then over night at RT. The reaction mixture was washed with pentane (5×20 mL). The methanolic aqueous layer was evaporated (bath temperature 30° C.), the residue was basified with 1N NaOH and extracted with DCM (3×20 mL). The aqueous phase was acidified with 1.5 N HCl and extracted again with DCM (3×10 mL). The combined organic layers were dried over $Na_2SO_4$, filtered, reduced to dryness and lyophilisated to give 50 mg (24%) of the title compound as an Off-white solid.

1H NMR: (400 MHz, DMSO-d6) ppm=7.58-7.56 (m, 1H), 7.47-7.45 (m, 2H), 7.28-7.21 (m, 7H), 4.53 (s, 1H), 3.39-3.35 (m, 1H), 3.12 (s, 3H), 2.93-2.88 (m, 1H), 2.84-2.79 (m, 1H).). MS (ESI+): 336.0 [M+H—$H_2O$]. HPLC (Method B): Rt. 3.89 min.

Example 35: [(1R)-2-(2,4-dimethylphenyl)-1-[[2-(2,6-dimethylphenyl)acetyl]amino]-ethyl]boronic acid (Compound No. 35)

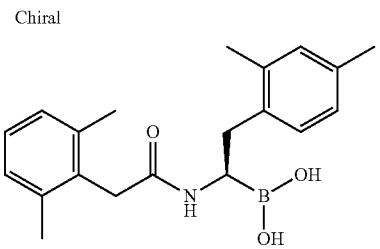 [SMILES: Cc1ccc(C[C@H](NC(=O)Cc2c(C)cccc2C)B(O)O)c(C)c1]

1H NMR (400 MHz, DMSO-d6) ppm=7.02-6.97 (m, 1H), 6.96-6.91 (m, 2H), 6.87-6.82 (m, 2H), 6.82-6.78 (m, 1H), 3.41 (s, 2H), 3.04 (dd, J=9.4, 5.5, 1H), 2.70 (dd, J=14.1, 5.7, 1H), 2.58-2.51 (m, 1H), 2.17 (s, 3H), 2.13-2.07 (m, 9H). MS (ESI+): 320.2 [M+H—$H_2O$]. HPLC (Method B): Rt. 5.24 min.

Example 36: [(1R)-2-(2,4-dimethylphenyl)-1-[(1-phenylcyclopropanecarbonyl)-amino]ethyl]boronic acid (Compound No. 36)

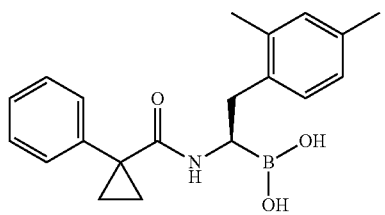

1H NMR (400 MHz, DMSO-d6) ppm=7.29-7.16 (m, 5H), 6.85-6.81 (m, 1H), 6.77-6.72 (m, 1H), 6.68 (d, J=7.7, 1H), 2.90 (dd, J=9.2, 5.2, 1H), 2.66 (dd, J=14.0, 5.3, 1H), 2.49-2.41 (m, 1H), 2.15 (s, 3H), 2.06 (s, 3H), 1.37-1.24 (m, 2H), 1.00-0.90 (m, 2H). MS (ESI+): 336.0 [M+H—H$_2$O]. HPLC (Method B): Rt. 3.89 min. MS (ESI+): 320.2 [M+H—H$_2$O]. HPLC (Method B): Rt. 5.17 min.

Example 37: [(1R)-2-(benzofuran-3-yl)-1-[[(2S)-2-phenylpropanoyl]amino]ethyl]-boronic acid (Compound No. 37)

(S)—N—((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)-2-phenylpropanamide

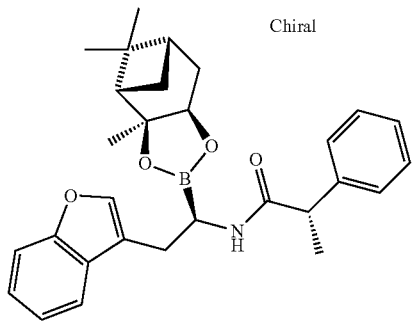

To a solution of (R)-2-Benzofuran-3-yl-1-((1S,2S,6R,8S)-2,9,9-trimethyl-3,5-dioxa-4-bora-tricyclo[6.1.1.02,6]dec-4-yl)-ethyl-aminehydrochloride (0.61 mmol; 0.25 g) in 10 mL DMF was added (S)-2-Phenyl-propionic acid (0.61 mmol; 0.09 g) at −10° C. under nitrogen atmosphere. Then N-Ethyl-diisopropyl-amine (1.83 mmol; 0.32 ml) and [(Benzotriazol-1-yloxy)-dimethylamino-methylene]-dimethylammonium tetrafluoroborate (TBTU) (0.73 mmol; 0.23 g) were added. The solution was stirred for 3 h at −10° C. The reaction mixture was diluted with ethyl acetate and brine. The organic phase was washed with brine (5×20 mL). The organic layer was dried over sodium sulfate, filtered, concentrated in vacuo (bath temperature 30° C.) and purified by flash chromatography (silica gel, petroleum ether/ethyl acetate; gradient 0-40% ethyl acetate) to yield 0.3 g (80%) of the title compound as a colorless gum.

HPLC MS (Agilent-Waters Xbridge C8 (50×4.6 mm, 3.5 µm); 254 nm; buffer A: 0.1% TFA/H$_2$O, buffer B: 0.1% TFA/ACN; (0.0-8.0 min 5%-100% buffer B; 8.0-8.1 min 100% buffer B; 8.1-8.5 min 100%-5% buffer B; 8.5-10.0 min 5%-5% buffer B): (M+H) 472.2; Rt. 6.12 min.

[(1R)-2-(benzofuran-3-yl)-1-[[(2S)-2-phenylpropanoyl]amino]ethyl]-boronic acid (Compound No. 37)

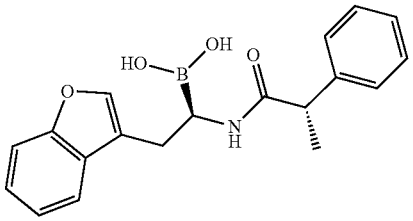

(S)—N—((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)-2-phenylpropanamide (0.49 mmol; 0.3 g) was dissolved in 15 ml n-pentane and 15 ml methanol and cooled to 0° C. Then isobutylboronic acid (1.95 mmol; 0.21 g) and 1.5 M Hydrochloric acid (3.75 mmol; 2.5 ml) were added and the reaction mixture was stirred 1 h at 0° C. and then over night at RT. The reaction mixture was washed with pentane (5×20 mL). The methanolic aqueous layer was evaporated (bath temperature 30° C.), the residue was basified with 1N NaOH and extracted with DCM (3×20 mL). The aqueous phase was acidified with 1.5 N HCl and extracted again with DCM (3×10 mL). The combined organic layers were dried over Na$_2$SO$_4$, filtered, reduced to dryness and lyophilisated to give 56 mg (29%) of the title compound as a white solid.

1H NMR: (400 MHz, DMSO-d6) ppm=7.50-7.43 (m, 2H), 7.33-7.16 (m, 8H), 3.63-3.54 (m, 1H), 3.15-2.98 (m, 1H), 2.82-2.70 (m, 1H), 2.67-2.61 (m, 1H), 1.31-1.23 (m, 3H). MS (ESI+): 320.2 [M+H—H$_2$O]. HPLC (Method B): Rt. 3.65 min.

Example 38: (1R)-1-[[2-(4-acetamidophenyl)acetyl]amino]-2-(2,4-dimethylphenyl)-ethyl]boronic acid (Compound No. 38)

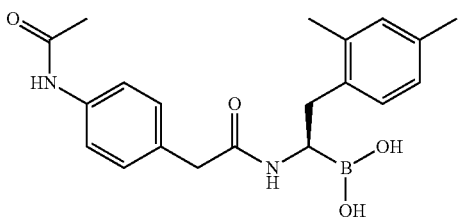

1H NMR (400 MHz, DMSO-d6) ppm=7.46-7.40 (m, 2H), 7.12-7.05 (m, 2H), 6.92-6.89 (m, 1H), 6.89-6.86 (m, 1H), 6.84-6.80 (m, 1H), 3.39-3.29 (m, 2H), 3.10 (dd, J=9.3, 5.7, 1H), 2.79-2.72 (m, 1H), 2.64-2.56 (m, 1H), 2.22 (s, 3H), 2.17 (s, 3H), 2.05 (s, 3H). MS (ESI+): 351.1 [M+H—H$_2$O]. HPLC (Method B): Rt. 4.0 min.

Example 39: [(1R)-2-(benzofuran-3-yl)-1-[[2-[4-(2-hydroxyethoxy)phenyl]acetyl]-amino]ethyl]boronic acid (Compound No. 39)

Chiral

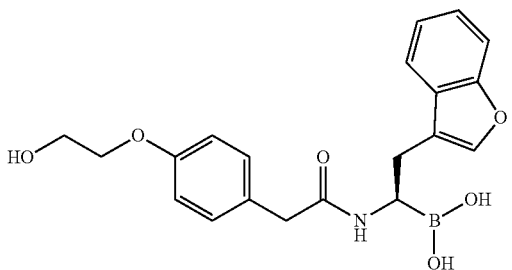

1H NMR (400 MHz, DMSO-d6) ppm=7.57-7.53 (m, 1H), 7.50-7.45 (m, 2H), 7.30-7.24 (m, 1H), 7.23-7.17 (m, 1H), 7.07-7.02 (m, 2H), 6.80-6.75 (m, 2H), 3.93-3.87 (m, 2H), 3.71-3.65 (m, 2H), 3.38-3.27 (m, 2H), 3.17 (dd, J=8.3, 5.6, 1H), 2.84 (dd, J=15.1, 5.3, 1H), 2.73 (dd, J=14.9, 8.3, 1H). MS (ESI+): 366.2 [M+H—H$_2$O]. HPLC (Method B): Rt. 3.97 min.

Example 40: [(1R)-2-(benzofuran-3-yl)-1-[[2-[4-(3-hydroxypropoxy)phenyl]acetyl]-amino]ethyl]boronic acid (Compound No. 40)

Chiral

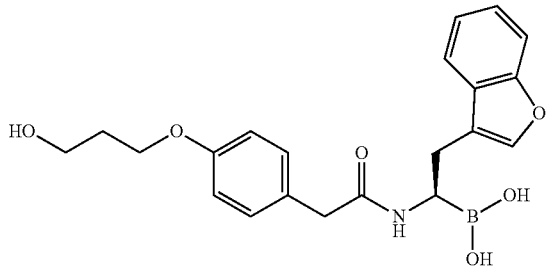

1H NMR (400 MHz, DMSO-d6) ppm=7.62-7.57 (m, 1H), 7.55-7.50 (m, 2H), 7.31 (td, J=8.2, 7.8, 1.4, 1H), 7.24 (td, J=7.4, 1.1, 1H), 7.12-7.06 (m, 2H), 6.84-6.78 (m, 2H), 3.99 (t, J=6.4, 2H), 3.56 (t, J=6.3, 2H), 3.39-3.30 (m, 2H), 3.23 (dd, J=8.2, 5.6, 1H), 2.89 (dd, J=15.1, 5.4, 1H), 2.78 (dd, J=14.9, 8.2, 1H), 1.86 (p, J=6.4, 2H). MS (ESI+): 380.1 [M+H—H$_2$O]. HPLC (Method B): Rt. 4.2 min.

Example 41: [(1R)-2-(benzofuran-3-yl)-1-[[2-[3-(2-hydroxyethoxy)phenyl]acetyl]-amino]ethyl]boronic acid (Compound No. 41)

Chiral

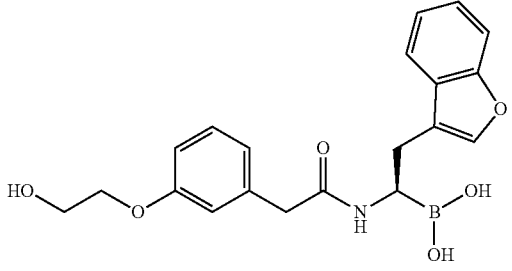

1H NMR (400 MHz, DMSO-d6) ppm=7.62-7.58 (m, 1H), 7.54-7.49 (m, 2H), 7.33-7.27 (m, 1H), 7.24 (td, J=7.4, 1.1, 1H), 7.21-7.15 (m, 1H), 6.83-6.74 (m, 3H), 3.95-3.90 (m, 2H), 3.73-3.68 (m, 2H), 3.39 (s, 2H), 3.25 (dd, J=8.1, 5.6, 1H), 2.95-2.84 (m, 1H), 2.79 (dd, J=14.9, 8.1, 1H). MS (ESI+): 366.1 [M+H—H$_2$O]. HPLC (Method B): Rt. 4.1 min.

Example 42: [(1R)-1-[[2-(2,6-dimethoxyphenyl)acetyl]amino]-2-(2,4-dimethylphenyl)ethyl]boronic acid (Compound No. 42)

Chiral

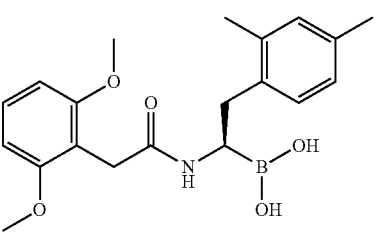

1H NMR (400 MHz, DMSO-d6) ppm=7.26 (t, J=8.4, 1H), 6.95-6.84 (m, 3H), 6.66 (d, J=8.4, 2H), 3.72 (s, 6H), 3.48-3.41 (m, 2H), 2.98 (dd, J=8.8, 5.4, 1H), 2.73 (dd, J=14.2, 5.5, 1H), 2.61-2.51 (m, 1H), 2.22 (s, 3H), 2.16 (s, 3H). MS (ESI+): 354.1 [M+H—H$_2$O]. HPLC (Method B): Rt. 5.07 min.

Example 43: [(1R)-2-(2,4-dimethylphenyl)-1-[[2-[4-(2-oxopyrrolidin-1-yl)phenyl]-acetyl]amino]ethyl]boronic acid (Compound No. 43)

Chiral

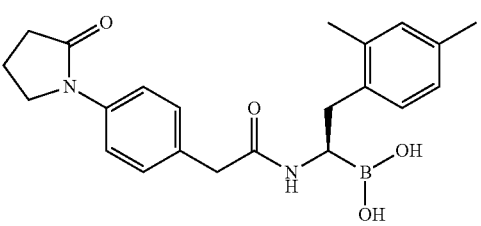

1H NMR (400 MHz, DMSO-d6) ppm=7.62-7.47 (m, 2H), 7.33-7.13 (m, 2H), 7.06-6.81 (m, 3H), 3.88-3.79 (m, 2H), 3.44-3.34 (m, 2H), 3.09 (dd, J=9.4, 5.7, 1H), 2.76 (dd, J=14.1, 5.7, 1H), 2.65-2.57 (m, 1H), 2.55-2.48 (m, 2H), 2.26-2.15 (m, 6H), 2.13-2.06 (m, 2H). MS (ESI+): 377.2 [M+H—H$_2$O]. HPLC (Method B): Rt. 4.35 min.

Example 44: [(1R)-1-[[2-(4-dimethylaminophenyl)acetyl]amino]-2-(2,4-dimethylphenyl)ethyl]boronic acid (Compound No. 44)

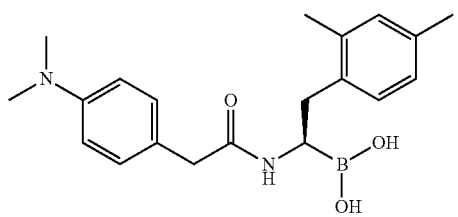

1H NMR (500 MHz, DMSO-d6) ppm=6.98-6.93 (m, 2H), 6.87-6.85 (m, 1H), 6.84-6.77 (m, 2H), 6.65-6.60 (m, 2H), 3.33-3.23 (m, 2H), 2.90-2.83 (m, 1H), 2.78 (s, 6H), 2.67 (dd, J=14.2, 5.4, 1H), 2.49-2.45 (m, 1H), 2.15 (s, 3H), 2.10 (s, 3H). MS (ESI+): 337.1 [M+H—H$_2$O]. HPLC (Method B): Rt. 3.56 min.

Example 45: [(1R)-2-(benzofuran-3-yl)-1-[[(2R)-2-phenylpropanoyl]amino]ethyl]-boronic acid (Compound No. 45)

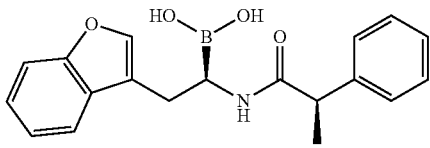

(R)—N—((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)-2-phenylpropanamide

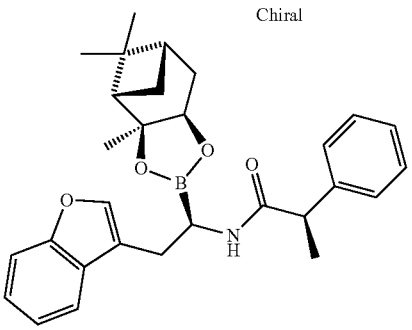

To a solution of (R)-2-Benzofuran-3-yl-1-((1S,2S,6R,8S)-2,9,9-trimethyl-3,5-dioxa-4-bora-tricyclo[6.1.1.0²,⁶]dec-4-yl)-ethyl-aminehydrochloride (0.85 mmol; 0.35 g) in 10 mL DMF was added (R)-2-Phenyl-propionic acid (0.61 mmol; 0.09 g) at −10° C. under nitrogen atmosphere. Then N-Ethyl-diisopropyl-amine (2.56 mmol; 0.45 ml) and [(Benzotriazol-1-yloxy)-dimethylamino-methylene]-dimethylammonium tetrafluoroborate (TBTU) (1.02 mmol; 0.33 g) were added. The solution was stirred for 3 h at −10° C. The reaction mixture was diluted with ethyl acetate and brine. The organic phase was washed with brine (5×20 mL). The organic layer was dried over sodium sulfate, filtered, concentrated in vacuo (bath temperature 30° C.) and purified by flash chromatography (silica gel, petroleum ether/ethyl acetate; gradient 0-40% ethyl acetate) to yield 0.28 g (41%) of the title compound as a pale brown gum.

HPLC MS (Agilent-Waters Xbridge C8 (50×4.6 mm, 3.5 μm); 254 nm; buffer A: 0.1% TFA/H$_2$O, buffer B: 0.1% TFA/ACN; (0.0-8.0 min 5%-100% buffer B; 8.0-8.1 min 100% buffer B; 8.1-8.5 min 100%-5% buffer B; 8.5-10.0 min 5%-5% buffer B): (M+H) 472.0; Rt 6.12 min.

((R)-2-(benzofuran-3-yl)-1-((S)-2-phenylpropanamido)ethyl) boronic acid

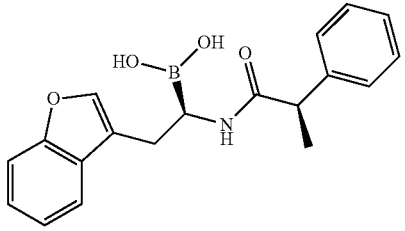

(R)—N—((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)-2-phenylpropanamide (0.49 mmol; 0.28 g) was dissolved in 15 ml n-pentane and 15 ml methanol and cooled to 0° C. Then isobutylboronic acid (1.64 mmol; 0.17 g) and 1.5 M Hydrochloric acid (2.25 mmol; 1.5 ml) were added and the reaction mixture was stirred 1 h at 0° C. and then over night at RT. The reaction mixture was washed with pentane (5×20 mL). The methanolic aqueous layer was evaporated (bath temperature 30° C.), the residue was basified with 1N NaOH and extracted with DCM (3×20 mL). The aqueous phase was acidified with 1.5 N HCl and extracted again with DCM (3×10 mL). The combined organic layers were dried over Na$_2$SO$_4$, filtered, reduced to dryness and lyophilisated to give 20 mg (14%) of the title compound as an Off-white solid.

1H NMR: (400 MHz, DMSO-d6) ppm=7.48-7.46 (m, 1H), 7.43-7.41 (m, 1H), 7.25-7.13 (m, 8H), 3.61-3.56 (m, 1H), 3.13 (t, J=6.8 Hz, 1H), 2.79-2.65 (m, 2H), 1.27 (d, J=7.2 Hz, 3H). MS (ESI+): 320.0 [M+H—H$_2$O]. HPLC (Method B): Rt. 3.7 min.

Example 46: [(1R)-2-(2,4-dimethylphenyl)-1-[[2-[4-(methanesulfonamido)phenyl]-acetyl]amino]ethyl] boronic acid (Compound No. 46)

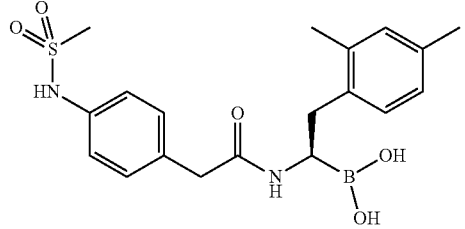

1H NMR (400 MHz, DMSO-d6) ppm=7.15-7.08 (m, 4H), 6.92-6.87 (m, 2H), 6.83 (d, J=8.2, 1H), 3.40-3.30 (m, 2H), 3.13 (dd, J=9.2, 5.7, 1H), 2.95 (s, 3H), 2.76 (dd, J=14.1, 5.6, 1H), 2.62 (dd, J=14.1, 9.3, 1H), 2.22 (s, 3H), 2.17 (s, 3H). MS (ESI+): 387.0 [M+H—$H_2O$]. HPLC (Method B): Rt. 4.25 min.

Example 47: [(1R)-2-(2,4-dimethylphenyl)-1-[[2-[4-[(2-methoxyacetyl)amino]-phenyl]acetyl]amino]ethyl]boronic acid (Compound No. 47)

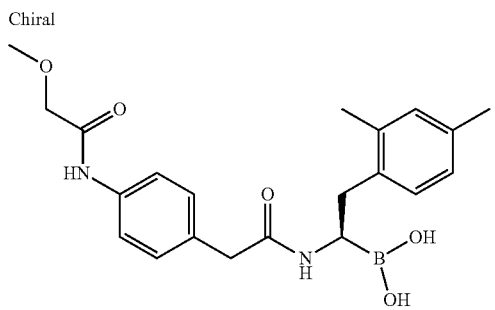

1H NMR (400 MHz, DMSO-d6) ppm=7.53-7.48 (m, 2H), 7.15-7.08 (m, 2H), 6.93-6.90 (m, 1H), 6.88 (d, J=7.6, 1H), 6.86-6.81 (m, 1H), 4.00 (s, 2H), 3.42-3.32 (m, 5H), 3.10 (dd, J=9.4, 5.6, 1H), 2.79-2.72 (m, 1H), 2.61 (dd, J=14.1, 9.4, 1H), 2.22 (s, 3H), 2.17 (s, 3H). MS (ESI+): 381.1 [M+H—$H_2O$]. HPLC (Method B): Rt. 4.21 min.

Example 48: [(1R)-2-(benzofuran-3-yl)-1-[[2-[2-(methoxymethyl)phenyl]acetyl]-amino]ethyl]boronic acid (Compound No. 48)

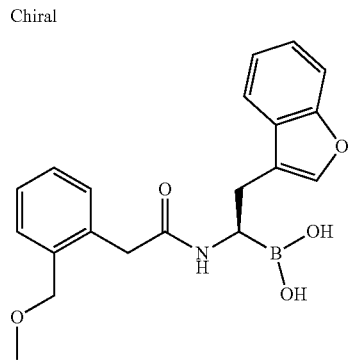 [SMILES: COCc1ccccc1CC(=O)N[C@@H](Cc1coc2ccccc12)B(O)O]

1H NMR (400 MHz, DMSO-d6) ppm=7.64-7.59 (m, 1H), 7.54-7.49 (m, 2H), 7.34-7.28 (m, 2H), 7.28-7.13 (m, 4H), 4.41-4.32 (m, 2H), 3.50 (s, 2H), 3.27 (dd, J=8.2, 5.5, 1H), 3.21 (s, 3H), 2.90 (dd, J=14.5, 5.8, 1H), 2.79 (dd, J=14.9, 8.3, 1H). MS (ESI+): 350.2 [M+H—$H_2O$]. HPLC (Method B): Rt. 4.73 min.

Example 49: [(1R)-2-(benzofuran-3-yl)-1-[[2-[3-(methoxymethyl)phenyl]acetyl]-amino]ethyl]boronic acid (Compound No. 49)

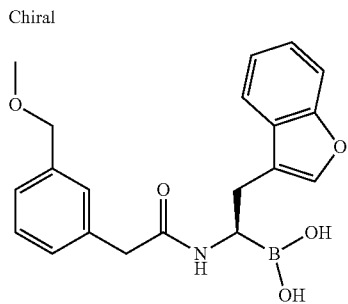 [SMILES: COCc1cccc(CC(=O)N[C@@H](Cc2coc3ccccc23)B(O)O)c1]

1H NMR (400 MHz, DMSO-d6) ppm=7.63-7.59 (m, 1H), 7.55-7.50 (m, 2H), 7.35-7.30 (m, 1H), 7.30-7.23 (m, 2H), 7.21-7.17 (m, 1H), 7.17-7.10 (m, 2H), 4.35 (s, 2H), 3.51-3.42 (m, 2H), 3.28 (s, 3H), 3.21 (dd, J=8.5, 5.6, 1H), 2.94-2.86 (m, 1H), 2.78 (dd, J=15.0, 8.7, 1H). MS (ESI+): 350.2 [M+H—$H_2O$]. HPLC (Method B): Rt. 4.6 min.

Example 50: [(1R)-2-(benzofuran-3-yl)-1-[[2-[2-(2-hydroxyethoxy)phenyl]acetyl]-amino]ethyl]boronic acid (Compound No. 50)

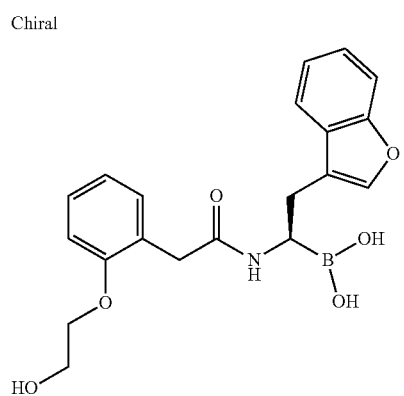 [SMILES: O=C(Cc1ccccc1OCCO)N[C@@H](Cc1coc2ccccc12)B(O)O]

1H NMR (400 MHz, DMSO-d6) ppm=7.64-7.59 (m, 1H), 7.54-7.49 (m, 2H), 7.30 (td, J=8.2, 7.7, 1.4, 1H), 7.27-7.19 (m, 2H), 7.12 (dd, J=7.4, 1.7, 1H), 6.94 (d, J=8.1, 1H), 6.86 (td, J=7.4, 1.0, 1H), 3.93 (t, J=4.8, 2H), 3.66 (t, J=4.8, 2H), 3.46 (s, 2H), 3.23 (dd, J=7.9, 5.8, 1H), 2.89 (dd, J=15.0, 5.8, 1H), 2.79 (dd, J=14.9, 7.9, 1H). MS (ESI+): 366.1 [M+H—$H_2O$]. HPLC (Method B): Rt. 4.4 min.

Example 51: [(1R)-2-(benzofuran-3-yl)-1-[[2,2-difluoro-2-(4-methoxyphenyl)acetyl]-amino]ethyl]boronic acid (Compound No. 51)

N—((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)-2,2-difluoro-2-(4-methoxyphenyl)acetamide

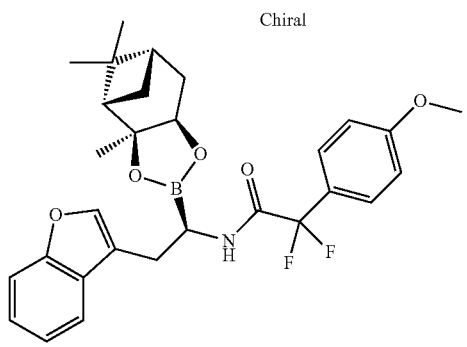 [SMILES: COc1ccc(C(F)(F)C(=O)N[C@@H](Cc2coc3ccccc23)B2O[C@@H]3C[C@@H]4C[C@@H](C4(C)C)[C@]3(C)O2)cc1]

To a solution of (R)-2-Benzofuran-3-yl-1-((1S,2S,6R,8S)-2,9,9-trimethyl-3,5-dioxa-4-bora-tricyclo[6.1.1.02,6]dec-4-yl)-ethyl-aminehydrochloride (1.22 mmol; 0.5 g) in 10 mL DMF was added Difluoro-(4-methoxy-phenyl)-acetic acid (1.22 mmol; 0.25 g) at −10° C. under nitrogen atmosphere. Then N-Ethyl-diisopropyl-amine (3.66 mmol; 0.65 ml) and [(Benzotriazol-1-yloxy)-dimethylamino-methylene]-dimethyl-ammonium tetrafluoroborate (TBTU) (1.46 mmol; 0.47 g) were added. The solution was stirred for 3 h at −10° C. The reaction mixture was diluted with ethyl acetate and brine. The organic phase was washed with brine (5×20 mL). The organic layer was dried over sodium sulfate, filtered, concentrated in vacuo (bath temperature 30° C.) and purified by flash chromatography (silica gel, petroleum ether/ethyl acetate; gradient 0-20% ethyl acetate) to yield 0.6 g (66%) of the title compound as a colorless gum.

HPLC MS (Agilent-Waters Xbridge C8 (50×4.6 mm, 3.5 µm); 254 nm; buffer A: 0.1% TFA/H$_2$O, buffer B: 0.1% TFA/ACN; (0.0-8.0 min 5%-100% buffer B; 8.0-8.1 min 100% buffer B; 8.1-8.5 min 100%-5% buffer B; 8.5-10.0 min 5%-5% buffer B): (M+H) 524.3; Rt 6.41 min.

[(1R)-2-(benzofuran-3-yl)-1-[[2,2-difluoro-2-(4-methoxyphenyl)acetyl]-amino]ethyl]boronic acid (Compound No. 51)

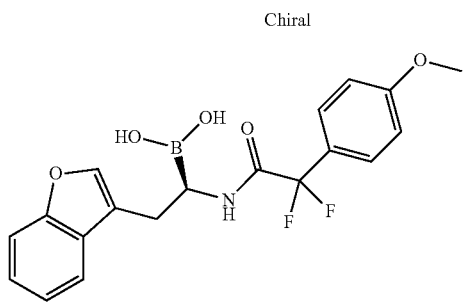 [SMILES: COc1ccc(C(F)(F)C(=O)N[C@@H](Cc2coc3ccccc23)B(O)O)cc1]

N—((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)-2,2-difluoro-2-(4-methoxyphenyl) acetamide (0.81 mmol; 0.6 g) was dissolved in 15 ml n-pentane and 15 ml methanol and cooled to 0° C. Then isobutylboronic acid (3.24 mmol; 0.34 g) and 1.5 M Hydrochloric acid (4.5 mmol; 3.0 ml) were added and the reaction mixture was stirred 1 h at 0° C. and then over night at RT. The reaction mixture was washed with pentane (5×20 mL). The methanolic aqueous layer was evaporated (bath temperature 30° C.), the residue was basified with 1N NaOH and extracted with DCM (3×20 mL). The aqueous phase was acidified with 1.5 N HCl and extracted again with DCM (3×20 mL). The combined organic layers were dried over Na$_2$SO$_4$, filtered, reduced to dryness and lyophilisated to give 200 mg (54%) of the title compound as an Off-white solid.

1H NMR: (400 MHz, DMSO-d6) ppm=7.56 (d, J=7.6 Hz, 1H), 7.46-7.44 (m, 2H), 7.27-7.16 (m, 4H), 6.85 (d, J=8.8 Hz, 2H), 3.71 (s, 3H), 3.49-3.45 (m, 1H), 2.95-2.82 (m, 2H). MS (ESI+): 372.3 [M+H—H$_2$O]. HPLC (Method B): Rt. 4.25 min.

Example 52: [(1R)-2-(benzofuran-3-yl)-1-[[2-(3,4,5-trimethoxyphenyl)acetyl]amino]-ethyl]boronic acid (Compound No. 52)

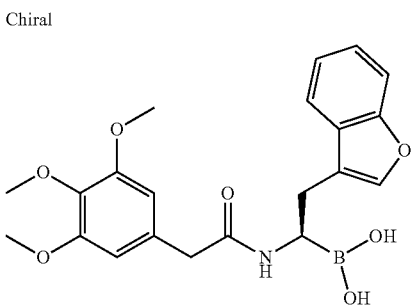 [SMILES: COc1cc(CC(=O)N[C@@H](Cc2coc3ccccc23)B(O)O)cc(OC)c1OC]

1H NMR (500 MHz, DMSO-d6) ppm=7.59 (d, J=7.6, 1H), 7.54-7.44 (m, 2H), 7.33-7.27 (m, 1H), 7.24 (t, J=7.2, 1H), 6.53 (s, 2H), 3.69 (s, 6H), 3.64 (s, 3H), 3.37 (s, 2H), 3.26 (dd, J=8.4, 5.4, 1H), 2.91 (dd, J=15.0, 5.2, 1H), 2.80 (dd, J=15.0, 8.5, 1H). MS (ESI+): 396.1 [M+H—H$_2$O]. HPLC (Method B): Rt. 4.46 min.

Example 53: [(1R)-2-(2,4-dimethylphenyl)-1-[[2-[4-[(2,2,2-trifluoroacetyl)amino]-phenyl]acetyl]amino]ethyl]boronic acid (Compound No. 53)

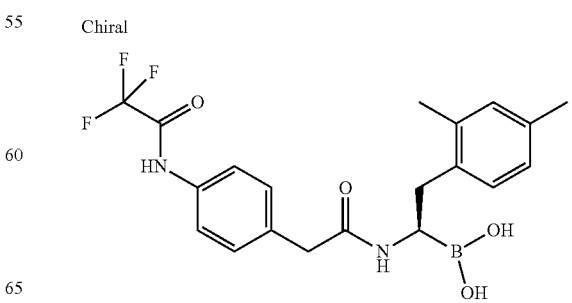

1H NMR (400 MHz, DMSO-d6) ppm=7.55-7.48 (m, 2H), 7.22-7.15 (m, 2H), 6.93-6.89 (m, 1H), 6.87 (d, J=7.6, 1H), 6.84-6.79 (m, 1H), 3.47-3.35 (m, 2H), 3.11 (dd, J=9.7, 5.5, 1H), 2.80-2.73 (m, 1H), 2.65-2.58 (m, 1H), 2.21 (s, 3H), 2.17 (s, 3H). MS (ESI+): 405.1 [M+H—H$_2$O]. HPLC (Method B): Rt. 5.02 min.

Example 54: [(1R)-2-(benzofuran-3-yl)-1-[[2-(2-tetrahydropyran-4-yloxyphenyl)-acetyl]amino]ethyl]boronic acid (Compound No. 54)

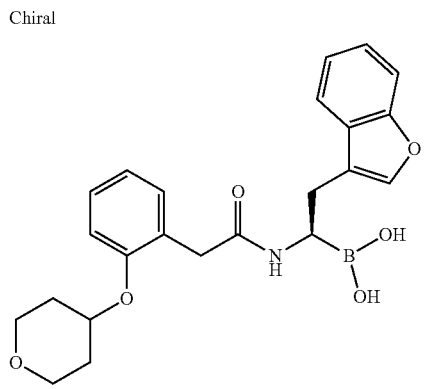 [SMILES: O=C(Cc1ccccc1OC1CCOCC1)N[C@@H](Cc1coc2ccccc12)B(O)O]

1H NMR (400 MHz, DMSO-d6) ppm=7.63-7.57 (m, 1H), 7.52 (d, J=8.2, 1H), 7.47 (s, 1H), 7.36-7.27 (m, 1H), 7.28-7.19 (m, 2H), 7.14 (dd, J=7.5, 1.7, 1H), 6.98 (d, J=8.1, 1H), 6.91-6.84 (m, 1H), 4.53-4.43 (m, 1H), 3.77-3.66 (m, 2H), 3.51-3.35 (m, 4H), 3.25 (dd, J=7.7, 5.7, 1H), 2.96-2.86 (m, 1H), 2.79 (dd, J=15.0, 7.8, 1H), 1.87-1.74 (m, 2H), 1.56-1.42 (m, 2H). MS (ESI+): 406.2 [M+H—H$_2$O]. HPLC (Method B): Rt. 4.81 min.

Example 55: [(1R)-2-(benzofuran-3-yl)-1-[[2-[2-(3-hydroxypropoxy)phenyl]acetyl]-amino]ethyl]boronic acid (Compound No. 55)

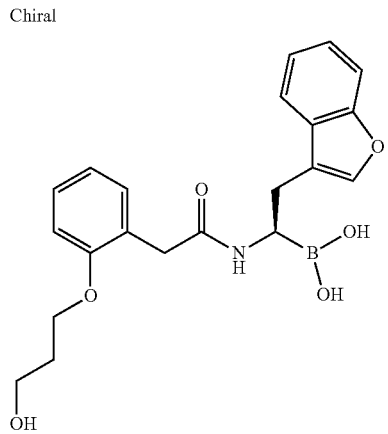 [SMILES: O=C(Cc1ccccc1OCCCO)N[C@@H](Cc1coc2ccccc12)B(O)O]

1H NMR (400 MHz, DMSO-d6) ppm=7.63-7.59 (m, 1H), 7.55-7.47 (m, 2H), 7.32 (td, J=8.2, 7.8, 1.4, 1H), 7.29-7.20 (m, 2H), 7.11 (dd, J=7.5, 1.7, 1H), 6.94 (d, J=8.2, 1H), 6.89-6.83 (m, 1H), 3.94 (t, J=6.2, 2H), 3.51 (t, J=6.2, 2H), 3.43 (s, 2H), 3.23 (dd, J=7.8, 5.8, 1H), 2.90 (dd, J=15.0, 5.7, 1H), 2.79 (dd, J=14.9, 7.8, 1H), 1.77 (p, J=6.2, 2H). MS (ESI+): 380.1 [M+H—H$_2$O]. HPLC (Method B): Rt. 4.46 min.

Example 56: [(1S)-2-(benzofuran-3-yl)-1-[[(2S)-3-hydroxy-2-phenyl-propanoyl]-amino]ethyl]boronic acid (Compound No. 56)

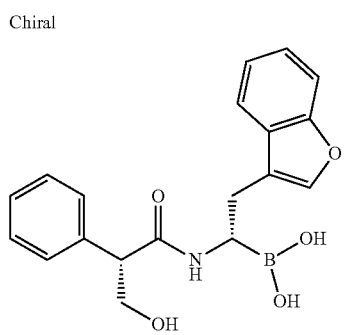 [SMILES: O=C(N[C@H](Cc1coc2ccccc12)B(O)O)[C@H](CO)c1ccccc1]

1H NMR (400 MHz, DMSO-d6) ppm=7.54 (d, J=7.6, 1H), 7.45 (d, J=8.2, 1H), 7.40 (s, 1H), 7.29-7.21 (m, 6H), 7.21-7.15 (m, 1H), 3.87 (dd, J=9.8, 8.1, 1H), 3.64-3.51 (m, 2H), 3.14-3.07 (m, 1H), 2.84 (dd, J=14.9, 5.6, 1H), 2.71 (dd, J=14.9, 8.2, 1H). MS (ESI+): 336.1 [M+H—H$_2$O]. HPLC (Method B): Rt. 4.4 min.

Example 57: [(1R)-2-(benzofuran-3-yl)-1-[[(2S)-3-hydroxy-2-phenyl-propanoyl]-amino]ethyl]boronic acid (Compound No. 57)

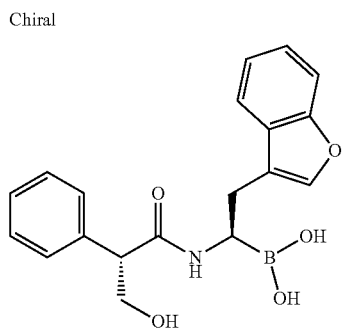 [SMILES: O=C(N[C@@H](Cc1coc2ccccc12)B(O)O)[C@H](CO)c1ccccc1]

1H NMR (400 MHz, DMSO-d6) ppm=7.50-7.40 (m, 2H), 7.29-7.19 (m, 7H), 7.16-7.11 (m, 1H), 3.90 (dd, J=10.2, 8.6, 1H), 3.61 (dd, J=8.6, 5.7, 1H), 3.54 (dd, J=10.2, 5.7, 1H), 3.23 (dd, J=7.7, 5.6, 1H), 2.80 (dd, J=15.2, 5.4, 1H), 2.72 (dd, J=14.9, 7.8, 1H).). MS (ESI+): 354.1 [M+H—H$_2$O]. HPLC (Method B): Rt. 4.41 min.

Example 58: [(1R)-2-(benzofuran-3-yl)-1-[[2-(2,5-dimethoxyphenyl)acetyl]amino]-ethyl]boronic acid (Compound No. 58)

Chiral

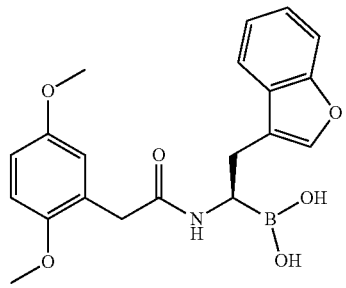

1H NMR (400 MHz, DMSO-d6) ppm=7.63-7.57 (m, 1H), 7.55-7.49 (m, 2H), 7.35-7.28 (m, 1H), 7.25 (td, J=7.5, 1.0, 1H), 6.88 (d, J=8.8, 1H), 6.80 (dd, J=8.9, 3.1, 1H), 6.76 (d, J=3.1, 1H), 3.67 (s, 3H), 3.63 (s, 3H), 3.46-3.36 (m, 2H), 3.23 (dd, J=8.0, 5.5, 1H), 2.95-2.87 (m, 1H), 2.78 (dd, J=15.1, 8.1, 1H). MS (ESI+): 366.1 [M+H—H$_2$O]. HPLC (Method B): Rt. 4.81 min.

Example 59: [(1R)-2-(benzofuran-3-yl)-1-[[(2R)-3-hydroxy-2-phenyl-propanoyl]-amino]ethyl]boronic acid (Compound No. 59)

Chiral

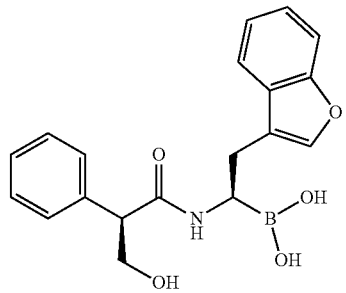

1H NMR (500 MHz, DMSO-d6) ppm=7.57-7.53 (m, 1H), 7.48-7.44 (m, 1H), 7.42 (s, 1H), 7.29-7.15 (m, 7H), 3.90-3.85 (m, 1H), 3.60 (dd, J=8.3, 5.8, 1H), 3.55 (dd, J=10.0, 5.8, 1H), 3.15 (dd, J=7.8, 5.7, 1H), 2.85 (dd, J=14.9, 5.6, 1H), 2.73 (dd, J=14.8, 7.9, 1H). MS (ESI+): 336.2 [M+H—H$_2$O]. HPLC (Method B): Rt. 4.36 min.

Example 60: [(1R)-2-(benzofuran-3-yl)-1-[[2-(2,3,4-trimethoxyphenyl)acetyl]amino]-ethyl]boronic acid (Compound No. 60)

Chiral

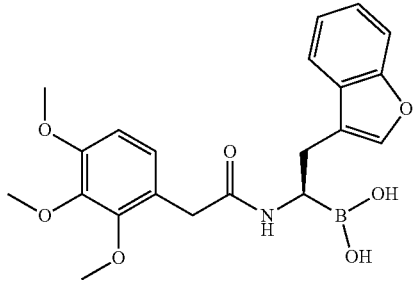

1H NMR (400 MHz, DMSO-d6) ppm=7.68-7.53 (m, 2H), 7.49 (d, J=8.0, 1H), 7.35-7.15 (m, 2H), 6.80 (d, J=8.6, 1H), 6.66 (d, J=8.6, 1H), 3.73 (s, 3H), 3.67 (s, 3H), 3.64 (s, 3H), 3.34 (s, 2H), 3.25-3.14 (m, 1H), 2.95-2.69 (m, 2H). MS (ESI+): 396.1 [M+H—H$_2$O]. HPLC (Method B): Rt. 4.7 min.

Example 61: [(1S)-2-(benzofuran-3-yl)-1-[[2-[2-(3-hydroxypropoxy)phenyl]acetyl]-amino]ethyl]boronic acid (Compound No. 61)

Chiral

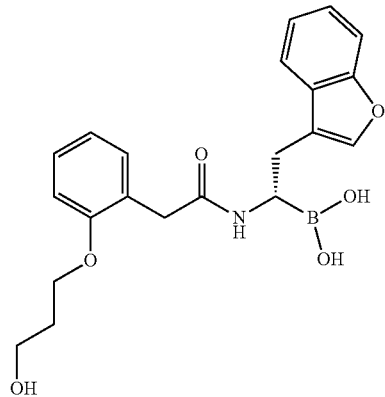

1H NMR (400 MHz, DMSO-d6) ppm=7.63-7.59 (m, 1H), 7.55-7.47 (m, 2H), 7.32 (td, J=8.2, 7.8, 1.4, 1H), 7.29-7.20 (m, 2H), 7.11 (dd, J=7.5, 1.7, 1H), 6.94 (d, J=8.2, 1H), 6.89-6.83 (m, 1H), 3.94 (t, J=6.2, 2H), 3.51 (t, J=6.2, 2H), 3.43 (s, 2H), 3.23 (dd, J=7.8, 5.8, 1H), 2.90 (dd, J=15.0, 5.7, 1H), 2.79 (dd, J=14.9, 7.8, 1H), 1.77 (p, J=6.2, 2H). MS (ESI+): 380.1 [M+H—H$_2$O]. HPLC (Method B): Rt. 4.46 min.

Example 62: [(1S)-2-(benzofuran-3-yl)-1-[[(2R)-3-hydroxy-2-phenyl-propanoyl]-amino]ethyl]boronic acid (Compound No. 62)

Chiral

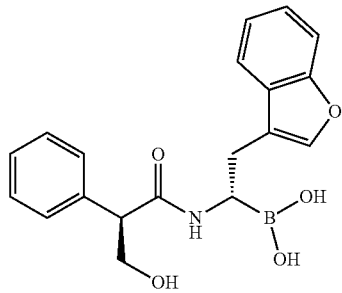

1H NMR (400 MHz, DMSO-d6) ppm=7.50-7.41 (m, 2H), 7.29-7.19 (m, 7H), 7.16-7.10 (m, 1H), 3.90 (dd, J=10.1, 8.5, 1H), 3.65-3.56 (m, 1H), 3.53 (dd, J=10.1, 5.7, 1H), 3.31-3.24 (m, 1H), 2.86-2.68 (m, 2H). MS (ESI+): 354.1 [M+H—H$_2$O].

Example 63: [(1R)-2-(benzofuran-3-yl)-1-[[2-[2-(morpholine-4-carbonyl)phenyl]-acetyl]amino]ethyl]boronic acid (Compound No. 63)

Chiral

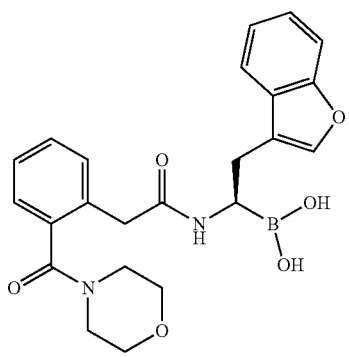

1H NMR (400 MHz, DMSO-d6) ppm=7.65-7.49 (m, 3H), 7.38-7.29 (m, 3H), 7.29-7.19 (m, 3H), 3.70-3.38 (m, 8H), 3.25 (dd, J=8.4, 5.4, 1H), 3.19-3.06 (m, 2H), 2.91 (dd, J=14.9, 5.5, 1H), 2.79 (dd, J=15.0, 8.6, 1H). MS (ESI+): 419.1 [M+H—H$_2$O]. HPLC (Method B): Rt 2.22 min.

Example 64: [(1R)-2-(benzofuran-3-yl)-1-[[2-[4-(2-oxopyrrolidin-1-yl)phenyl]acetyl]-amino]ethyl]boronic acid (Compound No. 64)

Chiral

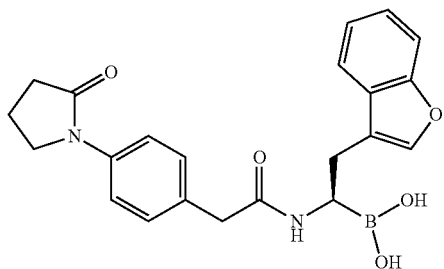

1H NMR (400 MHz, DMSO-d6) ppm=7.54 (d, J=7.6, 1H), 7.50 (s, 1H), 7.46 (d, J=8.2, 1H), 7.45-7.40 (m, 2H), 7.29-7.23 (m, 1H), 7.19 (t, J=7.4, 1H), 7.15-7.10 (m, 2H), 3.76 (t, J=7.0, 2H), 3.41-3.33 (m, 2H), 3.17 (dd, J=8.4, 5.7, 1H), 2.84 (dd, J=15.0, 5.6, 1H), 2.73 (dd, J=14.9, 8.5, 1H), 2.46 (t, J=8.1, 2H), 2.09-1.98 (m, 2H). MS (ESI+): 389.1 [M+H—H$_2$O]. HPLC (Method B): Rt 4.27 min.

Example 65: [(1R)-2-(benzofuran-3-yl)-1-[[2-[2-(ethylcarbamoyl)phenyl]acetyl]-amino]ethyl]boronic acid (Compound No. 65)

Chiral

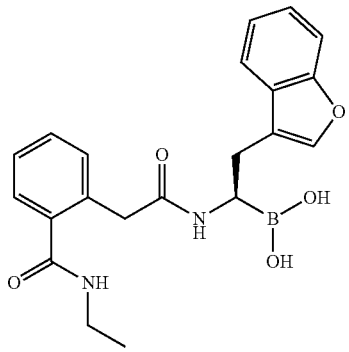

1H NMR (400 MHz, DMSO-d6) ppm=7.63-7.59 (m, 1H), 7.54-7.50 (m, 2H), 7.42 (dd, J=7.1, 2.0, 1H), 7.40-7.30 (m, 3H), 7.26 (td, J=7.4, 1.1, 1H), 7.20 (dd, J=7.2, 1.7, 1H), 3.59 (s, 2H), 3.29-3.20 (m, 3H), 2.91 (dd, J=14.9, 4.8, 1H), 2.79 (dd, J=14.9, 8.8, 1H), 1.10 (t, J=7.2, 3H). MS (ESI+): 377.1 [M+H—H$_2$O]. HPLC (Method B): Rt 4.42 min.

Example 66: [(1R)-2-(benzofuran-3-yl)-1-[[2-[2-(dimethylcarbamoyl)phenyl]acetyl]-amino]ethyl]boronic acid (Compound No. 66)

Chiral

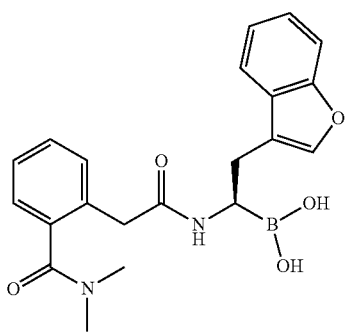

1H NMR (400 MHz, DMSO-d6) ppm=7.60-7.55 (m, 1H), 7.51 (s, 1H), 7.49-7.45 (m, 1H), 7.30-7.24 (m, 3H), 7.23-7.20 (m, 1H), 7.19-7.16 (m, 1H), 7.15-7.10 (m, 1H), 3.36 (s, 2H), 3.19 (dd, J=8.5, 5.5, 1H), 2.91 (s, 3H), 2.84 (dd, J=14.6, 5.7, 1H), 2.73 (dd, J=15.0, 8.5, 1H), 2.66 (s, 3H). MS (ESI+): 377.1 [M+H—H$_2$O]. HPLC (Method B): Rt 4.34 min.

Example 67: [(1R)-2-(benzofuran-3-yl)-1-[[2-(4-phenylphenyl)acetyl]amino]ethyl]-boronic acid (Compound No. 67)

Chiral

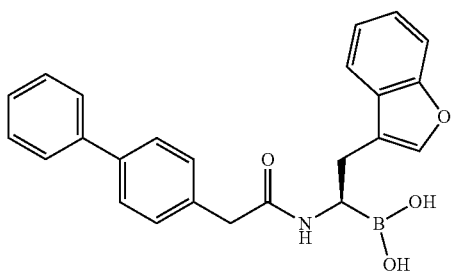

1H NMR (400 MHz, DMSO-d6) ppm=7.62-7.54 (m, 3H), 7.52-7.40 (m, 6H), 7.36-7.30 (m, 1H), 7.29-7.17 (m, 4H), 3.49-3.39 (m, 2H), 3.22 (dd, J=8.4, 5.6, 1H), 2.90-2.83 (m, 1H), 2.80-2.70 (m, 1H). MS (ESI+): 382.1 [M+H—H$_2$O]. HPLC (Method B): Rt 5.86 min.

Example 68: [(1R)-2-(benzofuran-3-yl)-1-[(2,2-diphenylacetyl)amino]ethyl]boronic acid (Compound No. 68)

Chiral

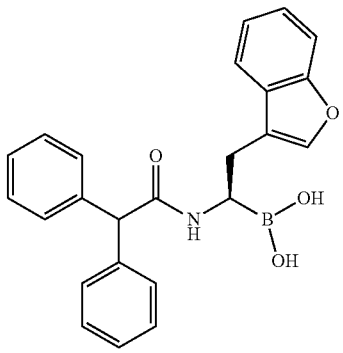

1H NMR (400 MHz, DMSO-d6/D2O) ppm=7.56-7.39 (m, 2H), 7.39-7.05 (m, 13H), 4.91 (s, 1H), 3.30 (dd, J=8.1, 5.6, 1H), 3.01-2.66 (m, 2H). MS (ESI+): 382.1 [M+H—H₂O]. HPLC (Method B): Rt 5.85 min.

Example 69: [(1S)-2-(benzofuran-3-yl)-1-[[2-(4-phenylphenyl)acetyl]amino]ethyl]-boronic acid (Compound No. 69)

Chiral

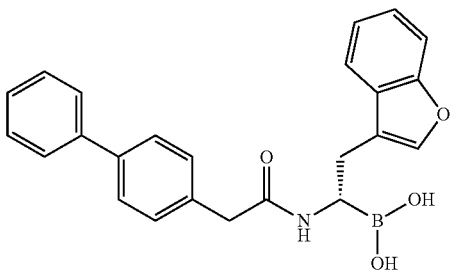

1H NMR (400 MHz, DMSO-d6/D2O) ppm=7.65-7.53 (m, 3H), 7.53-7.38 (m, 6H), 7.37-7.29 (m, 1H), 7.29-7.14 (m, 4H), 3.57-3.33 (m, 2H), 3.22 (dd, J=8.4, 5.7, 1H), 2.97-2.65 (m, 2H). MS (ESI+): 382.1 [M+H—H₂O]. HPLC (Method B): Rt 5.68 min.

Example 70: [(1R)-2-(benzofuran-3-yl)-1-[[(2R)-2-ethoxy-2-phenyl-acetyl]amino]-ethyl]boronic acid (Compound No. 70)

Ethyl-(R)-2-ethoxy-2-phenylacetate

Chiral

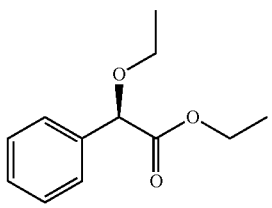

A stirred solution of (R)-Hydroxy-phenyl-acetic acid (1.00 g; 6.51 mmol) in iodo-ethane (27.25 ml; 325.34 mmol) was taken in pressure tube. Argentiooxysilver (3.02 g; 13.01 mmol) was added and the reaction mixture was stirred at RT for 20 h. The reaction mixture was passed through celite, washed with DCM (100 mL). The filtrate was washed with brine solution (1×50 mL). The organic layer was separated, dried over Na₂SO₄, filtered and concentrated in vacuum. The crude product was purified by flash chromatography (silica gel, petroleum ether/ethyl acetate; gradient 0-10% ethyl acetate) to yield 0.85 g (57%) of the title compound as a colorless liquid.

¹H NMR (400 MHz, DMSO-d6/D₂O): 7.39-7.33 (m, 5H), 4.96 (s, 1H), 4.15-4.02 (m, 2H), 3.57-3.50 (m, 1H), 3.46-3.38 (m, 1H), 1.16-1.10 (m, 6H). HPLC (Agilent-Waters Xbridge C8 (50×4.6 mm, 3.5 μm); 220 nm; buffer A: 0.1% TFA/H₂O, buffer B: 0.1% TFA/ACN; (0.0-8.0 min 5%-100% buffer B; 8.0-8.1 min 100% buffer B; 8.1-8.5 min 100%-5% buffer B; 8.5-10.0 min 5%-5% buffer B); (percent area) 98.56%; Rt 4.32 min.

(R)-2-ethoxy-2-phenylacetic acid

Chiral

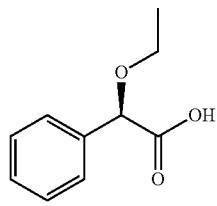

To a solution of Ethyl-(R)-2-ethoxy-2-phenylacetate (0.85 g; 3.97 mmol) in mixture of THF (24.00 ml), Water (6.00 ml) and Lithium Hydroxide Monohydrate (0.34 g; 7.93 mmol) at RT. The reaction mass was stirred at RT for 1 h. The reaction progress was confirmed by TLC. The reaction mass was evaporated completely under reduced pressure and extracted with dichloromethane (20 mL×3) to remove any impurities. The aqueous layer was acidified with an aqueous solution of 1.5 N hydrochloric acid and extracted with dichloromethane (10 mL×2). The organic layer thus obtained was dried over anhydrous Na₂SO₄ and concentrated to get the title compound 0.64 g (89%) as a pale brown gum.

¹H NMR (400 MHz, DMSO-d6/D₂O): 7.39-7.34 (m, 5H), 4.81 (s, 1H), 3.57-3.51 (m, 1H), 3.42-3.35 (m, 1H), 1.14 (t, J=7.0 Hz, 3H).

(R)—N—((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)-2-ethoxy-2-phenylacetamide Chiral

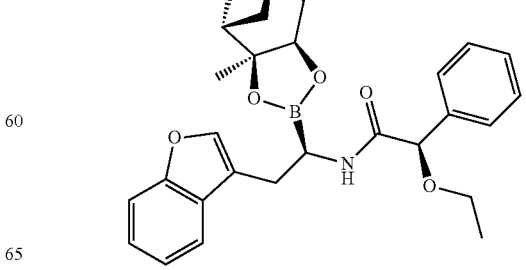

To a solution of (R)-2-Benzofuran-3-yl-1-((1S,2S,6R,8S)-2,9,9-trimethyl-3,5-dioxa-4-bora-tricyclo[6.1.1.02,6]dec-4-yl)-ethyl-aminehydrochloride (0.85 mmol; 0.35 g) in 10 mL DMF was added (R)-Ethoxy-phenyl-acetic acid (1.02 mmol; 0.18 g) at −10° C. under nitrogen atmosphere. Then N-Ethyl-diisopropyl-amine (2.56 mmol; 0.45 ml) and [(Benzotriazol-1-yloxy)-dimethylamino-methylene]-dimethyl-ammonium tetrafluoroborate (TBTU) (1.02 mmol; 0.33 g) were added. The solution was stirred for 3 h at −10° C. The reaction mixture was diluted with ethyl acetate and brine. The organic phase was washed with brine (5×20 mL). The organic layer was dried over sodium sulfate, filtered, concentrated in vacuo (bath temperature 30° C.) and purified by flash chromatography (silica gel, ethylacetate/methanol; gradient 0-0.5% methanol) to yield 0.45 g (78%) of the title compound as a brown gum.

HPLC MS (Agilent-Waters Xbridge C8 (50×4.6 mm, 3.5 μm); 254 nm; buffer A: 0.1% TFA/H₂O, buffer B: 0.1% TFA/ACN; (0.0-8.0 min 5%-100% buffer B; 8.0-8.1 min 100% buffer B; 8.1-8.5 min 100%-5% buffer B; 8.5-10.0 min 5%-5% buffer B): (M+H) 502.0; Rt 6.59 min.

[(1R)-2-(benzofuran-3-yl)-1-[[(2R)-2-ethoxy-2-phenyl-acetyl]amino]-ethyl]boronic acid (Compound No. 70)

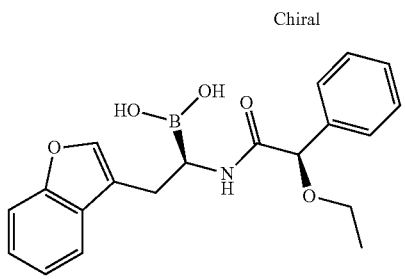 [SMILES: CCO[C@@H](C(=O)N[C@@H](Cc1coc2ccccc12)B(O)O)c1ccccc1]

(R)—N—((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)-2-ethoxy-2-phenylacetamide (0.67 mmol; 0.45 g) was dissolved in 15 ml n-pentane and 15 ml methanol and cooled to 0° C. Then isobutylboronic acid (2.67 mmol; 0.28 g) and 1.5 M Hydrochloric acid (3.0 mmol; 2.0 ml) were added and the reaction mixture was stirred 1 h at 0° C. and then over night at RT. The reaction mixture was washed with pentane (5×20 mL). The methanolic aqueous layer was evaporated (bath temperature 30° C.), the residue was basified with 1N NaOH and extracted with DCM (3×25 mL). The aqueous phase was acidified with 1.5 N HCl and extracted again with DCM (3×25 mL). The combined organic layers were dried over Na₂SO₄, filtered, reduced to dryness and lyophilisated to give 120 mg (47%) of the title compound as an Off-white solid.

1H NMR: (400 MHz, DMSO-d6) ppm=7.59-7.52 (m, 1H), 7.49-7.36 (m, 2H), 7.29-7.13 (m, 7H), 4.61 (s, 1H), 3.42-3.35 (m, 1H), 3.33-3.25 (m, 2H), 2.95-2.81 (m, 2H), 1.05-0.96 (m, 3H). MS (ESI+): 350.3 [M+H—H₂O]. HPLC (Method B): Rt 4.25 min.

Example 71: [(1R)-2-(benzofuran-3-yl)-1-[[3-(4-methoxyphenyl)-2-phenyl-propanoyl]amino]ethyl] boronic acid (Compound No. 71)

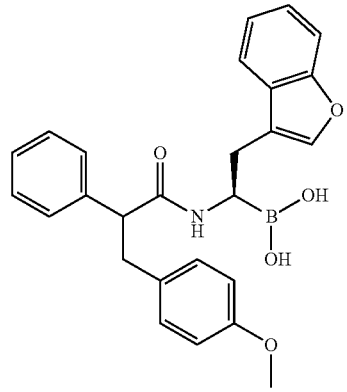

1H NMR (500 MHz, DMSO-d6/D2O) ppm=7.52-7.44 (m, 2H), 7.38-7.12 (m, 7H), 7.12-7.04 (m, 2H), 7.02 (d, J=9.4 Hz, 1H), 6.77, 6.75 (2x d, J=8.6 Hz, 2H, ratio 2:3, mixture of diastereomers), 3.76 (m, 1H), 3.68, 3.65 (2x s, 3H, ratio 2:3, mixture of diastereomers), 3.33-3.09 (m, 2H), 2.95-2.61 (m, 3H). MS (ESI+): 426.2 [M+H—H₂O]. HPLC (Method B): Rt 5.86 min.

Example 72: [(1R)-2-(benzofuran-3-yl)-1-[[2-[3-(ethoxycarbonylamino)phenyl]-acetyl]amino]ethyl] boronic acid (Compound No. 72)

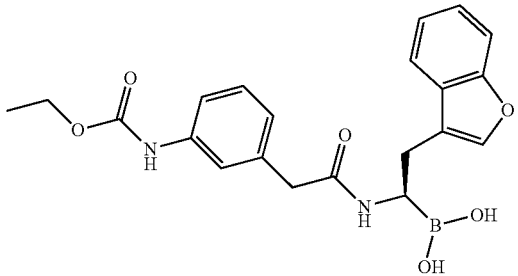

1H NMR (500 MHz, DMSO-d6/D2O) ppm=7.56-7.52 (m, 1H), 7.47 (s, 1H), 7.45 (d, J=8.2 Hz, 1H), 7.30-7.21 (m, 3H), 7.21-7.16 (m, 1H), 7.13 (t, J=7.8 Hz, 1H), 6.82-6.78 (m, 1H), 4.07 (q, J=7.1 Hz, 2H), 3.39-3.31 (m, 2H), 3.17 (dd, J=8.1, 5.8 Hz, 1H), 2.88-2.80 (m, 1H), 2.73 (dd, J=14.9, 8.2 Hz, 1H), 1.20 (t, J=7.1 Hz, 3H). MS (ESI+): 393.1 [M+H—H₂O]. HPLC (Method B): Rt 4.72 min.

Example 73: [(1R)-2-(2-chlorobenzofuran-3-yl)-1-[(2-phenylacetyl)amino]ethyl]-boronic acid (Compound No. 73)

Chiral

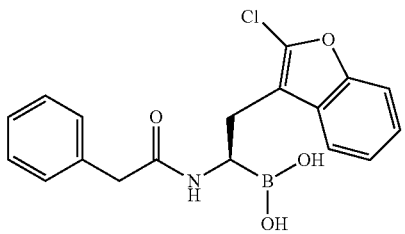

1H NMR (500 MHz, DMSO-d6/D2O) ppm=7.57-7.53 (m, 1H), 7.51-7.47 (m, 1H), 7.32-7.15 (m, 5H), 7.13-7.10 (m, 2H), 3.38-3.30 (m, 2H), 3.19 (dd, J=8.8, 5.6 Hz, 1H), 2.82 (dd, J=14.3, 5.5 Hz, 1H), 2.75 (dd, J=14.3, 8.9 Hz, 1H). MS (ESI+): 340.0 [M+H—H$_2$O]. HPLC (Method B): Rt 5.11 min.

Example 74 [(1R)-2-(2,3-dihydrobenzofuran-3-yl)-1-[(2-phenylacetyl)amino]-ethyl]boronic acid (Compound No. 74)

Chiral

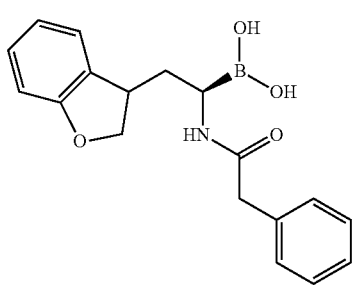

1H NMR (400 MHz, DMSO-d6): 7.17-7.28 (m, 5H), 7.03-7.14 (m, 2H), 6.76-6.81 (m, 1H), 6.67-6.69 (m, 1H), 4.39-4.45 (m, 1H), 4.00-4.11 (m, 1H), 3.45 (s, 2H), 3.24-3.32 (m, 1H), 2.80-2.85 (m, 1H), 1.76-1.85 (m, 1H), 1.52-1.60 (m, 1H). MS (ESI+): 308.2 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.20 min.

Example 75: [(1R)-2-(7-methylbenzofuran-3-yl)-1-[(2-phenylacetyl)amino]-ethyl]boronic acid (Compound No. 75)

Chiral

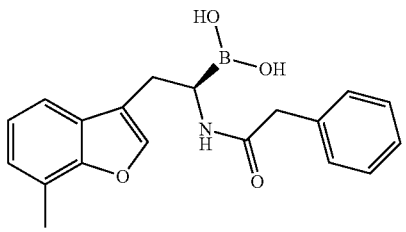

1H NMR: (400 MHz, DMSO-d6): 7.47 (s, 1H), 7.33 (d, J=5.8 Hz, 1H), 7.24-7.18 (m, 3H), 7.10-7.05 (m, 4H), 3.42 (s, 2H), 3.04-3.01 (m, 1H), 2.82-2.77 (m, 1H), 2.69-2.63 (m, 1H), 2.37 (s, 3H). MS (ESI+): 320.2 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.77 min.

Example 76: [(1R)-1-[[(2R)-2-methoxy-2-phenyl-acetyl]amino]-2-(7-methylbenzofuran-3-yl)ethyl] boronic acid (Compound No. 76)

Chiral

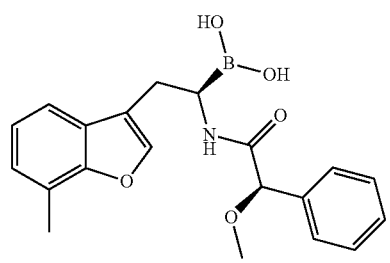

1H NMR: (400 MHz, DMSO-d6): 7.43-7.43 (m, 1H), 7.33-7.35 (m, 1H), 7.24-7.27 (m, 3H), 7.19-7.23 (m, 2H), 7.05-7.11 (m, 2H), 4.53 (s, 1H), 3.31-3.35 (m, 1H), 3.13 (s, 3H), 2.75-2.90 (m, 2H), 2.37 (s, 3H). MS (ESI+): 350.2 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 4.21 min.

Example 77: [(1R)-2-(7-methyl-2,3-dihydrobenzo-furan-3-yl)-1-[(2-phenylacetyl)-amino]ethyl]boronic acid (Compound No. 77)

Chiral

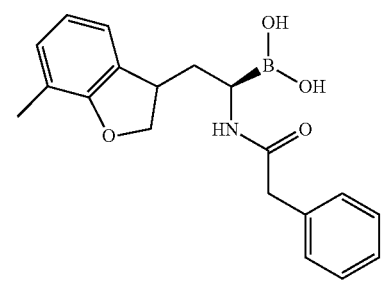

1H NMR: (400 MHz, DMSO-d6): 7.18-7.29 (m, 5H), 6.87-6.96 (m, 2H), 6.67-6.72 (m, 1H), 4.42-4.47 (m, 1H), 4.02-4.11 (m, 1H), 3.48 (s, 3H), 3.28-3.32 (m, 1H), 2.71-2.77 (m, 1H), 2.03 (s, 3H), 1.73-1.81 (m, 1H), 1.47-1.58 (m, 1H). MS (ESI+): 322.2 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.63 min.

Example 78: [(1R)-1-[[2-(2,5-dimethoxyphenyl) acetyl]amino]-2-(7-methylbenzofuran-3-yl)ethyl] boronic acid (Compound No. 78)

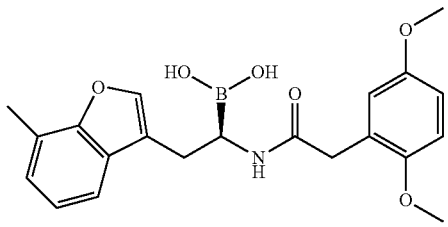 [SMILES: COc1ccc(OC)c(CC(=O)N[C@@H](Cc2coc3c(C)cccc23)B(O)O)c1]

400 MHz, DMSO-d6: 7.45 (s, 1H), 7.34 (d, J=6.8 Hz, 1H), 7.11-7.05 (m, 2H), 6.83 (t, J=5.8 Hz, 1H), 6.75 (dd, J=3.0, 8.9 Hz, 1H), 6.68 (d, J=3.0 Hz, 1H), 3.60 (s, 3H), 3.56 (s, 3H), 3.35 (d, J=1.8 Hz, 2H), 3.13-3.10 (m, 1H), 2.84-2.79 (m, 1H), 2.72-2.66 (m, 1H), 2.38 (s, 3H). MS (ESI+): 380.2 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.89 min.

Example 79: [(1R)-1-[[(2S)-3-hydroxy-2-phenyl-propanoyl]amino]-2-(7-methylbenzofuran-3-yl) ethyl]boronic acid (Compound No. 79)

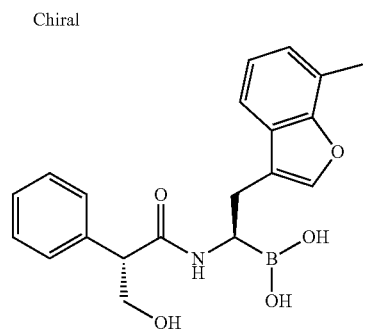 [SMILES: Cc1cccc2c(C[C@H](NC(=O)[C@H](CO)c3ccccc3)B(O)O)coc12]

1H NMR (500 MHz, DMSO-d6/D2O): 7.45 (s, 1H), 7.40-7.36 (m, 1H), 7.29-7.19 (m, 5H), 7.10-7.05 (m, 2H), 3.91-3.86 (m, 1H), 3.61-3.57 (m, 1H), 3.56-3.52 (m, 1H), 3.18 (dd, J=7.5, 5.8 Hz, 1H), 2.90-2.82 (m, 1H), 2.74 (dd, J=14.8, 7.6 Hz, 1H), 2.40 (s, 3H). MS (ESI+): 350.2 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 4.71 min.

Example 80: [(1S)-1-[[(2S)-3-hydroxy-2-phenyl-propanoyl]amino]-2-(7-methylbenzofuran-3-yl) ethyl]boronic acid (Compound No. 80)

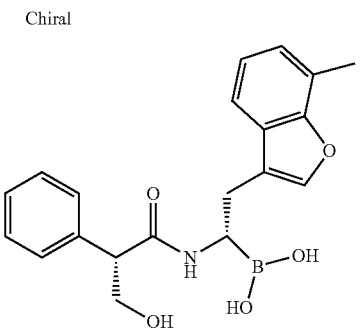 [SMILES: Cc1cccc2c(C[C@@H](NC(=O)[C@H](CO)c3ccccc3)B(O)O)coc12]

1H NMR (500 MHz, DMSO-d6/D2O): 7.31-7.19 (m, 7H), 7.06-7.00 (m, 2H), 3.89 (dd, J=10.2, 8.6 Hz, 1H), 3.60 (dd, J=8.6, 5.8 Hz, 1H), 3.52 (dd, J=10.2, 5.8 Hz, 1H), 3.28 (dd, J=7.5, 5.7 Hz, 1H), 2.79 (dd, J=14.9, 5.5 Hz, 1H), 2.72 (dd, J=14.8, 7.6 Hz, 1H), 2.38 (s, 3H). MS (ESI+): 350.2 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 4.75 min.

Example 81: [(1S)-1-[[2-(4-methoxyphenyl)acetyl] amino]-2-(7-methylbenzofuran-3-yl)ethyl]boronic acid (Compound No. 81)

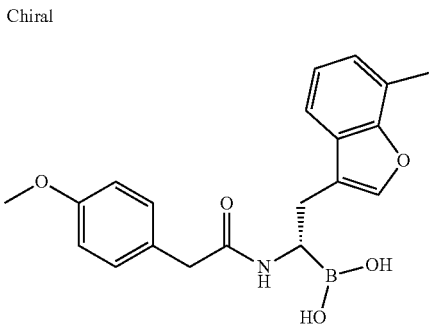

1H NMR (500 MHz, DMSO-d6/D2O): 7.48 (s, 1H), 7.37-7.32 (m, 1H), 7.11-7.02 (m, 4H), 6.79-6.73 (m, 2H), 3.67 (s, 3H), 3.35-3.27 (m, 2H), 3.15 (dd, J=8.4, 5.7 Hz, 1H), 2.85-2.79 (m, 1H), 2.71 (dd, J=14.8, 8.4 Hz, 1H), 2.40 (s, 3H). MS (ESI+): 350.2 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 5.02 min.

Example 82: [(1R)-1-[[2-(4-methoxyphenyl)acetyl]amino]-2-(7-methylbenzofuran-3-yl)ethyl]boronic acid (Compound No. 82)

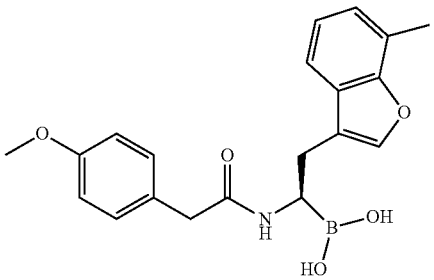

1H NMR (400 MHz, DMSO-d6/D2O) ppm=7.53 (s, 1H), 7.43-7.37 (m, 1H), 7.18-7.06 (m, 4H), 6.85-6.78 (m, 2H), 3.73 (s, 3H), 3.43-3.31 (m, 2H), 3.20 (dd, J=8.4, 5.6 Hz, 1H), 2.87 (dd, J=14.9, 5.6 Hz, 1H), 2.76 (dd, J=14.9, 8.5 Hz, 1H), 2.45 (s, 3H). MS (ESI+): 350.2 [M+H—H₂O]. HPLC Waters XBridge C8 3.5 μm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 5.02 min.

Example 83: [(1R)-1-[[(2R)-3-hydroxy-2-phenylpropanoyl]amino]-2-(7-methylbenzofuran-3-yl)ethyl]boronic acid (Compound No. 83)

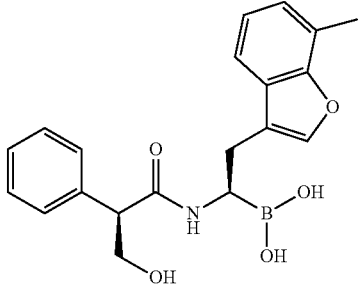

1H NMR (400 MHz, DMSO-d6/D2O) ppm=7.36-7.22 (m, 7H), 7.11-7.04 (m, 2H), 3.94 (dd, J=10.1, 8.5 Hz, 1H), 3.64 (dd, J=8.4, 5.7 Hz, 1H), 3.57 (dd, J=10.0, 5.7 Hz, 1H), 3.31 (dd, J=7.6, 5.7 Hz, 1H), 2.87-2.72 (m, 2H), 2.42 (s, 3H). MS (ESI+): 350.2 [M+H—H₂O]. HPLC Waters XBridge C8 3.5 μm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 4.75 min.

Example 84: [(1S)-1-[[(2R)-3-hydroxy-2-phenylpropanoyl]amino]-2-(7-methylbenzofuran-3-yl)ethyl]boronic acid (Compound No. 84)

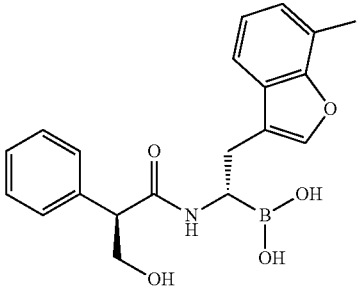

1H NMR (400 MHz, DMSO-d6/D2O) ppm=7.44 (s, 1H), 7.39-7.34 (m, 1H), 7.29-7.18 (m, 5H), 7.11-7.04 (m, 2H), 3.91-3.86 (m, 1H), 3.64-3.52 (m, 2H), 3.15 (dd, J=7.6, 5.8 Hz, 1H), 2.85 (dd, J=14.8, 5.7 Hz, 1H), 2.72 (dd, J=14.6, 7.7 Hz, 1H), 2.39 (s, 3H). MS (ESI+): 350.2 [M+H—H₂O]. HPLC Waters XBridge C8 3.5 μm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 4.70 min.

Example 85: [(1R)-2-(7-chlorobenzofuran-3-yl)-1-[(2-phenylacetyl)amino]ethyl]-boronic acid (Compound No. 85)

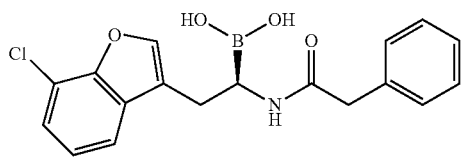

400 MHz, DMSO-d6: 7.58 (s, 1H), 7.52 (dd, J=0.9, 7.8 Hz, 1H), 7.34 (dd, J=0.7, 7.7 Hz, 1H), 7.22-7.17 (m, 4H), 7.09-7.07 (m, 2H), 3.42-3.34 (m, 2H), 3.13-3.10 (m, 1H), 2.85-2.80 (m, 1H), 2.74-2.67 (m, 1H). MS (ESI+): 340.6 [M+H—H₂O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.91 min.

Example 86: [(1R)-1-[3-(5-methoxy-2-pyridyl)propanoylamino]-2-(7-methyl-2,3-dihydrobenzofuran-3-yl)ethyl]boronic acid (Compound No. 86)

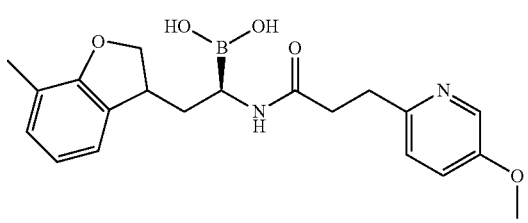

400 MHz, DMSO-d6: 8.03-8.02 (m, 1H), 7.23-7.18 (m, 2H), 6.87 (t, J=7.00 Hz, 1H), 6.70 (t, J=7.40 Hz, 1H), 4.35 (t, J=8.84 Hz, 1H), 4.06-4.04 (m, 1H), 3.60 (s, 3H), 3.03-3.01 (m, 1H), 2.93-2.87 (m, 2H), 2.85-2.80 (m, 1H), 2.51-2.49 (m, 2H), 2.05 (s, 3H), 1.72-1.65 (m, 1H), 1.47-1.39 (m, 1H) MS (ESI+): 390.0 [M+H]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 2.52 min.

Example 87: [(1S)-1-[3-(5-methoxy-2-pyridyl)propanoylamino]-2-(7-methyl-2,3-dihydrobenzofuran-3-yl)ethyl]boronic acid (Compound No. 87)

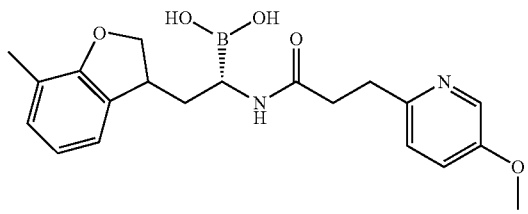

Chiral

400 MHz, DMSO-d6: 8.06-8.05 (m, 1H), 7.26-7.18 (m, 2H), 6.94 (d, J=7.28 Hz, 1H), 6.89 (d, J=7.44 Hz, 1H), 6.69 (t, J=7.44 Hz, 1H), 4.42 (t, J=8.84 Hz, 1H), 4.01-3.97 (m, 1H), 3.69 (s, 3H), 3.18-3.14 (m, 1H), 2.91-2.87 (m, 2H), 2.82-2.78 (m, 1H), 2.05 (s, 3H), 1.78-1.72 (m, 1H), 1.53-1.45 (m, 1H). MS (ESI+): 390.0 [M+H]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 2.52 min.

Example 88: [(1R)-1-[[2-(4-methoxyphenyl)acetyl]amino]-2-[(3R)-7-methyl-2,3-dihydrobenzofuran-3-yl]ethyl]boronic acid (Compound No. 88)

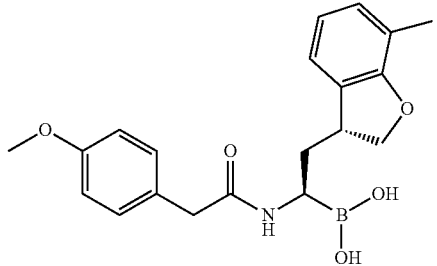

Chiral

1H NMR (400 MHz, DMSO-d6/D2O) d 7.21-7.15 (m, 2H), 6.96 (d, J=7.3 Hz, 1H), 6.89 (d, J=7.4 Hz, 1H), 6.86-6.80 (m, 2H), 6.69 (t, J=7.4 Hz, 1H), 4.46 (t, J=8.9 Hz, 1H), 4.06 (dd, J=8.9, 6.5 Hz, 1H), 3.68 (s, 3H), 3.41-3.33 (m, 2H), 3.33-3.25 (m, 1H), 2.96 (dd, J=8.6, 6.4 Hz, 1H), 2.06 (s, 3H), 1.91-1.81 (m, 1H), 1.63-1.53 (m, 1H). MS (ESI+): 352.2 [M+H—H2O]. HPLC Waters XBridge C8 3.5 μm; 4.6×50 mm; EliteLa Chrom 70173815; 8.1 min; 2 ml/min; 215 nm; buffer A: 0.05% TFA/H2O; buffer B: 0.04% TFA/ACN; 0.0-0.2 min 5% buffer B; 0.2-8.5 min 5%-100% buffer B; 8.5-10.0 min 99%-5% buffer B. Rt. 4.55 min.

Example 89: [(1R)-1-[[2-(4-methoxyphenyl)acetyl]amino]-2-[(3S)-7-methyl-2,3-dihydrobenzofuran-3-yl]ethyl]boronic acid (Compound No. 89)

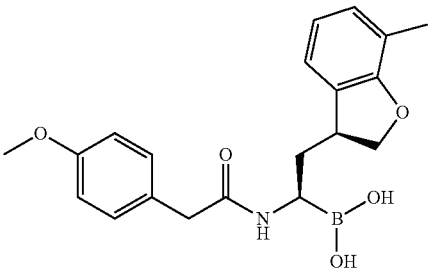

Chiral

1H NMR (400 MHz, DMSO-d6/D2O) 7.22-7.13 (m, 2H), 7.09-6.63 (m, 5H), 4.46-4.37 (m, 1H), 4.14-4.04 (m, 1H), 3.70-3.55 (m, 3H), 3.42-3.15 (m, 3H), 2.92-2.76 (m, 1H), 2.08-1.96 (m, 3H), 1.89-1.66 (m, 1H), 1.57-1.46 (m, 1H). MS (ESI+): 352.2 [M+H—H2O]. HPLC Waters XBridge C8 3.5 μm; 4.6×50 mm; EliteLa Chrom 70173815; 8.1 min; 2 ml/min; 215 nm; buffer A: 0.05% TFA/H2O; buffer B: 0.04% TFA/ACN; 0.0-0.2 min 5% buffer B; 0.2-8.5 min 5%-100% buffer B; 8.5-10.0 min 99%-5% buffer B. Rt. 4.75 min.

Example 90: [(1R)-2-(benzofuran-3-yl)-1-[[2-(2-cyanophenyl)acetyl]amino]ethyl]-boronic acid (Compound No. 90)

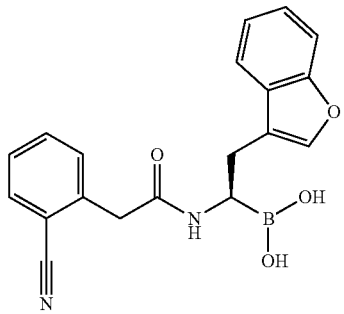

Chiral

1H NMR (500 MHz, DMSO-d6/D2O) ppm=7.73-7.68 (m, 1H), 7.61-7.56 (m, 2H), 7.56-7.51 (m, 1H), 7.47 (d, J=8.1 Hz, 1H), 7.39 (t, J=7.6 Hz, 1H), 7.31-7.24 (m, 2H), 7.21 (t, J=7.2 Hz, 1H), 3.67-3.57 (m, 2H), 3.29 (dd, J=8.2, 5.7 Hz, 1H), 2.89 (dd, J=14.9, 5.4 Hz, 1H), 2.78 (dd, J=14.9, 8.4 Hz, 1H). MS (ESI+): 331.2 [M+H—H2O]. HPLC Waters XBridge C8 3.5 μm; 4.6×50 mm; EliteLa Chrom 70173815; 8.1 min; 2 ml/min; 215 nm; buffer A: 0.05% TFA/H2O; buffer B: 0.04% TFA/ACN; 0.0-0.2 min 5% buffer B; 0.2-8.5 min 5%-100% buffer B; 8.5-10.0 min 99%-5% buffer B. Rt 4.61 min.

Example 91: [(1R)-2-(benzofuran-3-yl)-1-[[2-[4-(1-hydroxy-1-methyl-ethyl)phenyl]acetyl]amino]ethyl] boronic acid (Compound No. 91)

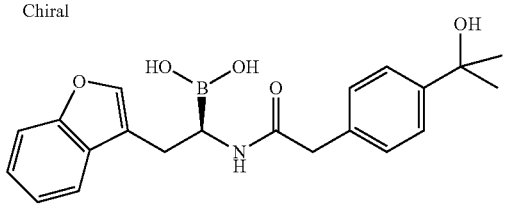 [SMILES: CC(C)(O)c1ccc(CC(=O)N[C@@H](Cc2coc3ccccc23)B(O)O)cc1]

1H NMR 400 MHz, DMSO-d6: 7.54 (d, J=7.7 Hz, 1H), 7.46-7.42 (m, 2H), 7.28-7.24 (m, 2H), 7.21-7.17 (m, 2H), 7.09-7.04 (m, 2H), 3.38 (s, 2H), 3.10-3.05 (m, 1H), 2.84-2.79 (m, 1H), 2.72-2.66 (m, 1H), 1.36 (s, 6H). MS (ESI+): 364.2 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.11 min.

Example 92: [(1R)-2-(7-methoxybenzofuran-3-yl)-1-[(2-phenylacetyl)amino]ethyl]-boronic acid (Compound No. 92)

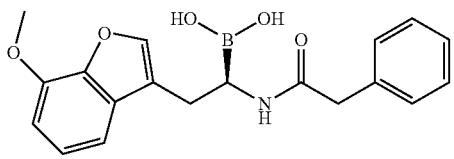

1H NMR 400 MHz, DMSO-d6: 7.43 (s, 1H), 7.24-7.18 (m, 3H), 7.14-7.10 (m, 4H), 6.87-6.85 (m, 1H), 3.85 (s, 3H), 3.39 (s, 2H), 3.11-3.08 (m, 1H), 2.82-2.77 (m, 1H), 2.71-2.65 (m, 1H). MS (ESI+): 336.2 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.29 min.

Example 93: [(1R)-1-[[(2R)-2-methoxy-2-phenyl-acetyl]amino]-2-(7-methyl-2,3-dihydrobenzofuran-3-yl)ethyl]boronic acid (Compound No. 93)

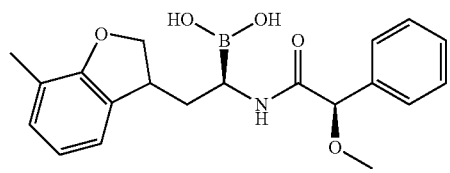 [SMILES: CO[C@@H](C(=O)N[C@@H](CC1COc2c(C)cccc21)B(O)O)c1ccccc1]

1H NMR 400 MHz, DMSO-d6: 7.35-7.26 (m, 5H), 6.96-6.85 (m, 2H), 6.71-6.67 (m, 1H), 4.62-4.59 (m, 1H), 4.46-4.40 (m, 1H), 4.05-4.02 (m, 1H), 3.25 (s, 3H), 3.24-3.23 (m, 1H), 3.13-3.09 (m, 1H), 2.04 (s, 3H), 1.89-1.79 (m, 1H), 1.66-1.57 (m, 1H). MS (ESI+): 352.0 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.95 min.

Example 94: [(1R)-2-(6,7-dimethyl benzofuran-3-yl)-1-[(2-phenylacetyl)amino]ethyl]boronic acid (Compound No. 94)

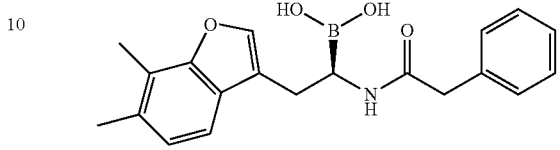

1H NMR (400 MHz): 7.42-7.42 (m, 1H), 7.18-7.25 (m, 4H), 7.12-7.14 (m, 2H), 6.98-7.00 (m, 1H), 3.37 (s, 2H), 3.17-3.20 (m, 1H), 2.78-2.83 (m, 1H), 2.66-2.72 (m, 1H), 2.28-2.30 (m, 6H). MS (ESI+): 334.0 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 4.02 min.

Example 95: [(1R)-2-(6,7-dimethylbenzofuran-3-yl)-1-[3-(5-methoxy-2-pyridyl)propanoylamino]ethyl]boronic acid (Compound No. 95)

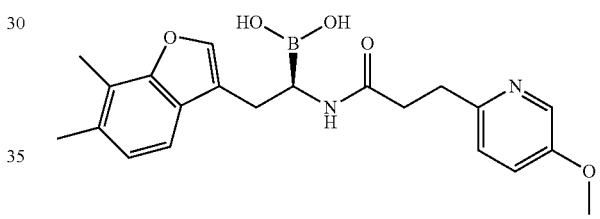

400 MHz, DMSO-d6: 8.06-8.00 (m, 1H), 7.40 (d, J=22.2 Hz, 1H), 7.31-7.12 (m, 3H), 7.01-6.98 (m, 1H), 6.98 (s, 3H), 2.95-2.63 (m, 6H), 2.50-2.49 (m, 1H), 2.29 (s, 3H), 2.26 (s, 3H). HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.55 min.

Example 96: [(1R)-2-(benzofuran-3-yl)-1-[[(2S)-2-[2-(dimethylcarbamoyl)phenyl]-propanoyl]amino]ethyl]boronic acid (Compound No. 96)

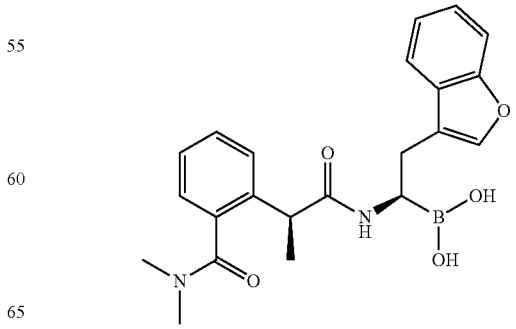

1H NMR (400 MHz, DMSO-d6/D2O) 7.57-7.05 (m, 9H), 3.54-3.43 (m, 1H), 3.07-2.42 (m, 9H), 1.24 (d, J=7.1 Hz, 3H). MS (ESI+): 391.2 [M+H—H₂O]. HPLC Waters XBridge C8 3.5 µm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 4.58 min.

Example 97: [(1R)-2-(benzofuran-3-yl)-1-[[(2R)-2-[2-(dimethylcarbamoyl)-phenyl]propanoyl]amino]ethyl]boronic acid (Compound No. 97)

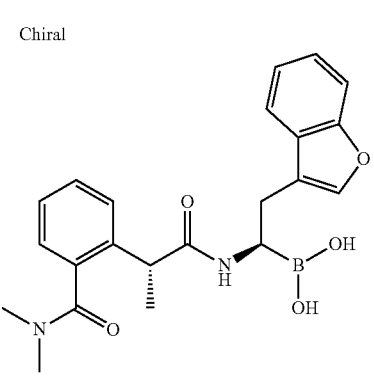 [SMILES: C[C@@H](C(=O)N[C@@H](Cc1coc2ccccc12)B(O)O)c1ccccc1C(=O)N(C)C]

1H NMR (400 MHz, DMSO-d6/D2O) 7.49 (d, J=7.8 Hz, 1H), 7.41 (d, J=8.2 Hz, 1H), 7.38-7.01 (m, 7H), 3.53-3.43 (m, 1H), 3.23-3.15 (m, 1H), 3.03-2.40 (m, 8H), 1.26 (d, J=7.0 Hz, 3H). MS (ESI+): 391.2 [M+H—H₂O]. HPLC Waters XBridge C8 3.5 µm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 4.64 min.

Example 98: [(1R)-2-(benzofuran-3-yl)-1-[[2-(2-phenylphenyl)acetyl]amino]-ethyl]boronic acid (Compound No. 98)

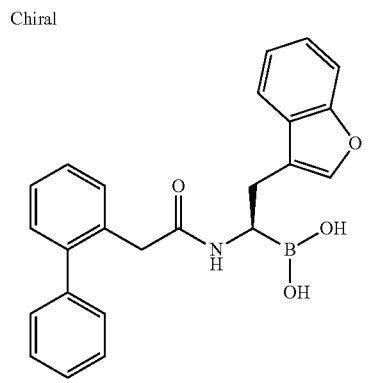 [SMILES: O=C(Cc1ccccc1-c1ccccc1)N[C@@H](Cc1coc2ccccc12)B(O)O]

1H NMR (400 MHz, DMSO-d6+4-5 drops D2O). 7.60 (d, J=7.2 Hz, 1H), 7.56 (s, 1H), 7.52 (d, J=8.2 Hz, 1H), 7.41-7.14 (m, 11H), 3.35 (s, 2H), 3.26 (dd, J=8.4, 5.6 Hz, 1H), 2.87 (dd, J=14.9, 5.1 Hz, 1H), 2.75 (dd, J=15.1, 8.5 Hz, 1H). MS (ESI+): 382.3[M+H—H₂O]. HPLC Waters XBridge C8 3.5 µm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 5.74 min.

Example 99: [(1R)-2-[(3S)-2,3-dihydrobenzofuran-3-yl]-1-[[(2R)-2-[2-(dimethylcarbamoyl)phenyl]propanoyl]amino]ethyl]boronic acid (Compound No. 99)

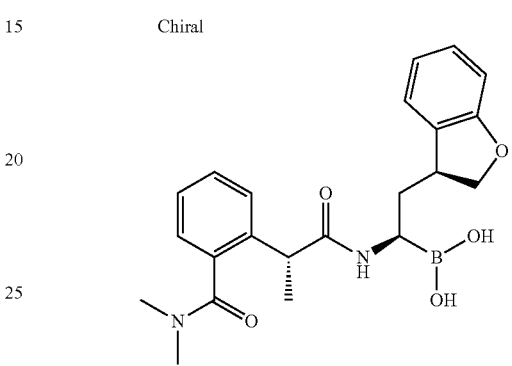

MS (ESI+): 393.2 [M+H—H₂O]. HPLC Waters XBridge C8 3.5 µm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 4.34 min.

Example 100: [(1R)-1-[[2-[2-(dimethylcarbamoyl)phenyl]acetyl]amino]-2-(7-methyl-2,3-dihydrobenzofuran-3-yl)ethyl]boronic acid (Compound No. 100)

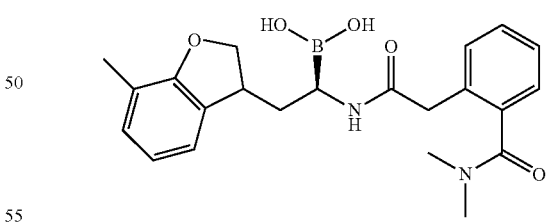

1H NMR 400 MHz, DMSO-d6: 7.33-7.25 (m, 3H), 7.16-7.14 (m, 1H), 6.98-6.88 (m, 1H), 6.73-6.72 (m, 1H), 4.49-4.41 (m, 1H), 4.12-4.10 (m, 1H), 3.43 (s, 2H), 3.28-3.26 (m, 1H), 2.95 (s, 2H), 2.94-2.92 (m, 2H), 2.73 (s, 3H), 2.05 (s, 3H), 1.85-1.76 (m, 1H), 1.61-1.52 (m, 1H). MS (ESI+): 393.2 [M+H—H₂O]. HPLC Column: XBridge C8, 3.5 µm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.25 min.

Example 101: [(1R)-2-(6,7-dimethyl-2,3-dihydrobenzofuran-3-yl)-1-[(2-phenylacetyl)-amino]ethyl]boronic acid (Compound No. 101)

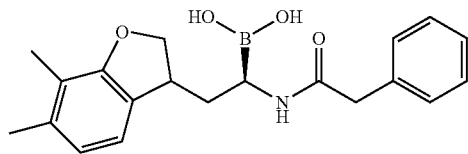 [SMILES: Cc1ccc2c(c1C)OCC2C[C@H](NC(=O)Cc1ccccc1)B(O)O]

1H-NMR (400 MHz, DMSO-d6): 7.27-7.24 (m, 4H), 7.22-7.17 (m, 1H), 6.85-6.78 (m, 1H), 6.61-6.57 (m, 1H), 4.44-4.39 (m, 1H), 4.12-4.02 (m, 1H), 3.42 (s, 2H), 3.27-3.24 (m, 1H), 2.98-2.94 (m, 1H), 2.11 (s, 3H), 1.97 (s, 3H), 1.83-1.74 (m, 1H), 1.60-1.43 (m, 1H). MS (ESI+): 336.2 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt 3.80 min.

Example 102: [(1R)-2-(6,7-dimethyl-2,3-dihydrobenzofuran-3-yl)-1-[3-(5-methoxy-2-pyridyl)propanoylamino]ethyl]boronic acid (Compound No. 102)

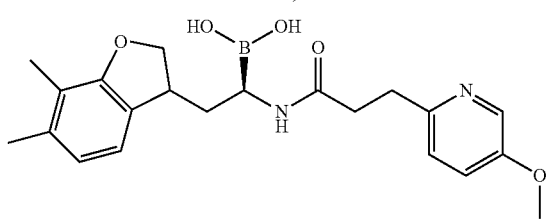

1H NMR 400 MHz, DMSO-d6: 8.09-8.06 (m, 1H), 7.26-7.16 (m, 2H), 6.86-6.75 (m, 1H), 6.59 (d, J=7.60 Hz, 1H), 4.43-4.35 (m, 1H), 4.08-3.99 (m, 1H), 3.72 (s, 3H), 3.16-3.14 (m, 1H), 2.95-2.86 (m, 3H), 2.50-2.48 (m, 2H), 2.12 (s, 3H), 1.98 (s, 3H), 1.78-1.70 (m, 1H), 1.53-1.43 (m, 1H). MS (ESI+): 398.3 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 2.80 min.

Example 103 [(1R)-1-[[2-(2-acetamidophenyl)acetyl]amino]-2-(benzofuran-3-yl)ethyl]boronic acid (Compound No. 103)

Chiral

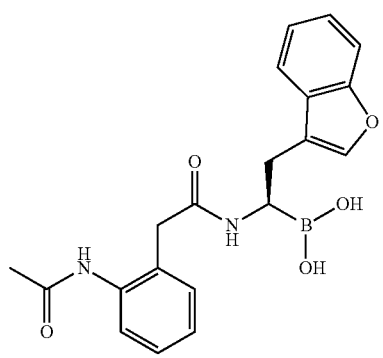

1H NMR (400 MHz, DMSO-d6/D2O) ppm=7.55 (d, J=7.6 Hz, 1H), 7.49-7.43 (m, 2H), 7.40 (d, J=8.0 Hz, 1H), 7.29-7.16 (m, 3H), 7.13 (d, J=7.5 Hz, 1H), 7.10-7.03 (m, 1H), 3.47-3.37 (m, 2H), 3.23-3.15 (m, 1H), 2.85 (dd, J=15.0 Hz, 5.6 Hz, 1H), 2.74 (dd, J=14.9 Hz, 8.6 Hz, 1H), 1.99 (s, 3H). MS (ESI+): 363.2 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt 4.12 min.

Example 104: [(1R)-1-[[2-(2-cyanophenyl)acetyl]amino]-2-(7-methylbenzofuran-3-yl)ethyl]boronic acid (Compound No. 104)

Chiral

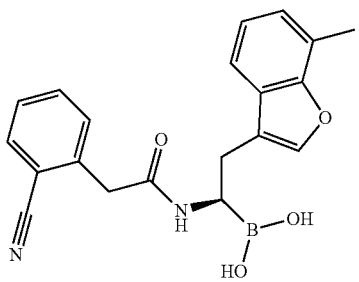

1H NMR (400 MHz, DMSO-d6/D2O) ppm=7.76 (dd, J=7.8, 1.4 Hz, 1H), 7.63 (s, 1H), 7.59 (td, J=7.7, 1.5 Hz, 1H), 7.48-7.42 (m, 2H), 7.33 (d, J=7.6 Hz, 1H), 7.18-7.11 (m, 2H), 3.67 (s, 2H), 3.32 (dd, J=8.3, 5.6 Hz, 1H), 2.92 (dd, J=15.1, 5.3 Hz, 1H), 2.82 (dd, J=14.8, 8.3 Hz, 1H), 2.45 (s, 3H). MS (ESI+): 345.2 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 4.93 min.

Example 105: [(1R)-1-[[2-(2-cyanophenyl)acetyl]amino]-2-[(3S)-2,3-dihydrobenzofuran-3-yl]ethyl]boronic acid (Compound No. 105)

Chiral

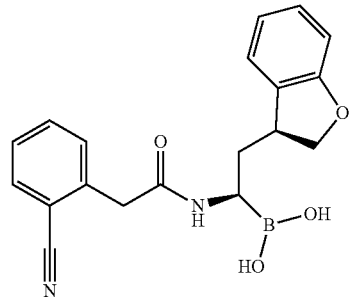

1H NMR (400 MHz, DMSO-d6/D2O) ppm=7.78 (dd, J=7.8, 1.4 Hz, 1H), 7.66 (td, J=7.7, 1.4 Hz, 1H), 7.50 (d, J=7.8 Hz, 1H), 7.46 (td, J=7.6, 1.2 Hz, 1H), 7.18 (d, J=7.3

Hz, 1H), 7.14-7.07 (m, 1H), 6.89-6.82 (m, 1H), 6.74 (d, J=7.9 Hz, 1H), 4.52 (t, J=8.9 Hz, 1H), 4.21 (dd, J=9.0, 6.7 Hz, 1H), 3.81-3.68 (m, 2H), 3.52-3.40 (m, 1H), 3.12 (dd, J=10.9, 4.3 Hz, 1H), 1.96-1.85 (m, 1H), 1.67-1.57 (m, 1H). MS (ESI+): 333.0 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 4.38 min.

Example 106: [(1R)-2-[(3R)-2,3-dihydrobenzofuran-3-yl]-1-[[(2S)-2-[2-(dimethylcarbamoyl)phenyl]propanoyl]amino]ethyl]boronic acid (Compound No. 106)

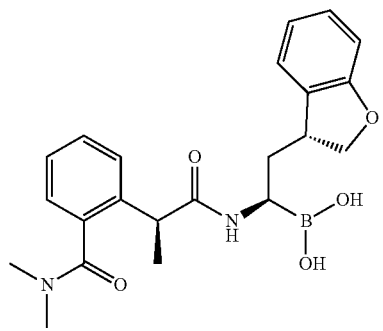

No NMR Data MS (ESI+): 392.2 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 4.37 min.

Example 107: [(1R)-2-[(3S)-2,3-dihydrobenzofuran-3-yl]-1-[[(2S)-2-[2-(dimethylcarbamoyl)phenyl]propanoyl]amino]ethyl]boronic acid (Compound No. 107)

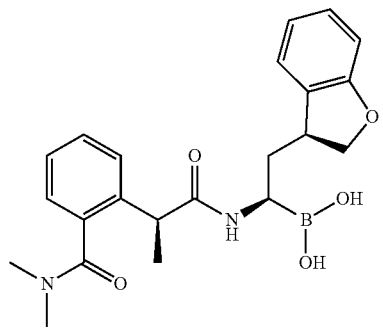

No NMR Data MS (ESI+): 393.2 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 3.55 min.

Example 108: [(1R)-2-(benzofuran-2-yl)-1-[[2-(4-methoxyphenyl)acetyl]-amino]ethyl]boronic acid (Compound No. 108)

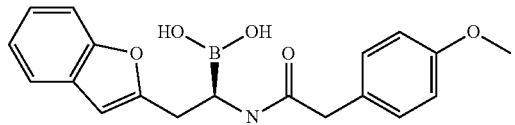

1H NMR 400 MHz, DMSO-d6: 7.48-7.45 (m, 1H), 7.37 (d, J=7.6 Hz, 1H), 7.21-7.14 (m, 2H), 7.04 (d, J=8.6 Hz, 2H), 6.72 (d, J=8.7 Hz, 2H), 6.42 (s, 1H), 3.64 (s, 3H), 3.45-3.37 (m, 2H), 3.04-3.00 (m, 1H), 2.93-2.88 (m, 1H), 2.79-2.73 (m, 1H). MS (ESI+): 336.2 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.55 min.

Example 109: [(1R)-1-[[(2R)-2-ethoxy-2-phenylacetyl]amino]-2-(7-methyl-2,3-dihydrobenzofuran-3-yl)ethyl]boronic acid (Compound No. 109)

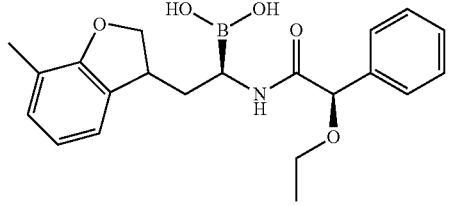 [SMILES: CCO[C@@H](C(=O)N[C@@H](CC1COc2c(C)cccc21)B(O)O)c1ccccc1]

1H NMR 400 MHz, DMSO-d6: 7.35-7.25 (m, 5H), 6.94-6.84 (m, 2H), 6.72-6.68 (m, 1H), 4.71-4.69 (m, 1H), 4.45-4.41 (m, 1H), 4.12-4.02 (m, 1H), 3.49-3.36 (m, 2H), 3.24-3.22 (m, 1H), 3.09-3.05 (m, 1H), 2.01 (s, 3H), 1.87-1.79 (m, 1H), 1.63-1.55 (m, 1H), 1.13-1.08 (m, 3H). MS (ESI+): 366.2 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 4.35 min.

Example 110: [(1R)-2-(benzofuran-2-yl)-1-[(2-phenylacetyl)amino]ethyl]boronic acid (Compound No. 110)

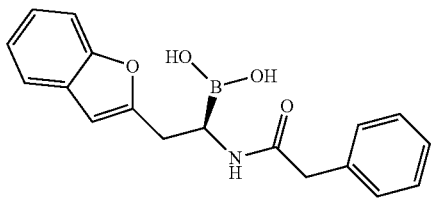

1H NMR (400 MHz), 7.44-7.47 (m, 1H), 7.36-7.38 (m, 1H), 7.10-7.21 (m, 7H), 6.40 (s, 1H), 3.41-3.49 (m, 2H), 3.03-3.06 (m, 1H), 2.87-2.92 (m, 1H), 2.73-2.79 (m, 1H). MS (ESI+): 323.3 [M+H—H₂O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.57 min.

Example 111: [(1R)-2-(2,3-dihydrobenzofuran-3-yl)-1-[[(2R)-2-ethoxy-2-phenyl-acetyl]amino]ethyl]boronic acid (Compound No. 111)

Chiral

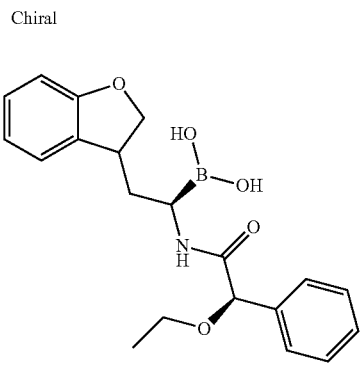 [SMILES: CCO[C@@H](C(=O)N[C@@H](CC1COc2ccccc21)B(O)O)c1ccccc1]

1H NMR (400 MHz) 7.24-7.36 (m, 5H), 7.01-7.12 (m, 2H), 6.76-6.81 (m, 1H), 6.64-6.69 (m, 1H), 4.70-4.71 (m, 1H), 4.34-4.42 (m, 1H), 3.99-4.09 (m, 1H), 3.21-3.48 (m, 2H), 3.21-3.21 (m, 1H), 3.04-3.09 (m, 1H), 1.81-1.85 (m, 1H), 1.55-1.57 (m, 1H), 1.07-1.12 (m, 3H). MS (ESI+): 369.2 [M+H—H₂O]. HPLC Column: XBridge C8, 3.5 μm, 4.6×50 mm; Solvent A: water+0.1% TFA; Solvent B: ACN+ 0.1% TFA; Flow: 2 ml/min; Gradient: 0 min: 5% B, 8 min: 100% B, 8.1 min: 100% B, 8.5 min: 5% B, 10 min 5% B. Rt. 4.04 min.

Example 112: [2-(benzofuran-3-yl)-1-[[2-(2-pyridyl)acetyl]amino]ethyl]boronic acid (Compound No.)

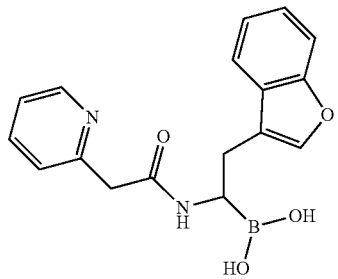 [SMILES: O=C(Cc1ccccn1)NC(Cc1coc2ccccc12)B(O)O]

1H NMR (500 MHz, DMSO-d6) δ 8.41-8.37 (m, 1H), 7.68 (td, J=7.7, 1.9 Hz, 1H), 7.61-7.58 (m, 1H), 7.57 (s, 1H), 7.50-7.46 (m, 1H), 7.30-7.18 (m, 4H), 3.62-3.55 (m, 2H), 3.28 (dd, J=8.6, 5.4 Hz, 1H), 2.93-2.87 (m, 1H), 2.79 (dd, J=14.9, 8.6 Hz, 1H). MS (ESI+): 307.1 [M+H—H₂O]. HPLC Waters XBridge C8 3.5 μm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 2.85 min.

Example 113: [(1R)-2-(7-chlorobenzofuran-3-yl)-1-[[2-(5-ethoxy-2-pyridyl)acetyl]amino]ethyl]boronic acid (Compound No. 113)

Chiral

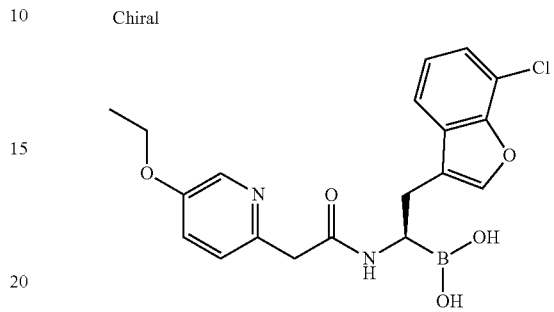

1H NMR (400 MHz, DMSO-d6/D2O) d 8.03 (d, J=2.9 Hz, 1H), 7.66 (s, 1H), 7.55 (dd, J=7.8, 1.1 Hz, 1H), 7.34 (dd, J=7.8, 1.0 Hz, 1H), 7.25-7.19 (m, 2H), 7.12 (d, J=8.6 Hz, 1H), 4.03 (q, J=6.9 Hz, 2H), 3.49 (s, 2H), 3.24 (dd, J=8.7, 5.4 Hz, 1H), 2.88 (dd, J=14.8, 5.1 Hz, 1H), 2.77 (dd, J=14.9, 8.7 Hz, 1H), 1.30 (t, J=7.0 Hz, 3H). MS (ESI+): 385.1 [M+H—H₂O]. HPLC Waters XBridge C8 3.5 μm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 2.56 min.

Example 114: [(1R)-2-[(3S)-2,3-dihydrobenzofuran-3-yl]-1-[[2-(4-methoxyphenyl)-acetyl]amino]ethyl]boronic acid (Compound No. 114)

Chiral

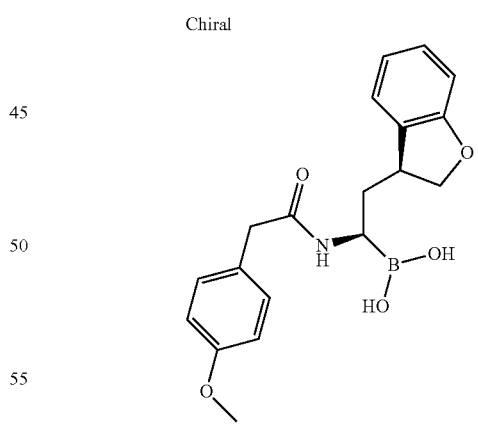

1H NMR (500 MHz, DMSO-d6/D2O) d 7.20-7.16 (m, 2H), 7.16-7.09 (m, 1H), 7.08-7.03 (m, 1H), 6.85-6.81 (m, 2H), 6.81-6.76 (m, 1H), 6.72-6.68 (m, 1H), 4.49-4.42 (m, 1H), 4.14-4.03 (m, 1H), 3.70-3.66 (m, 3H), 3.40-3.32 (m, 2H), 3.32-3.26 (m, 1H), 3.01-2.94 (m, 1H), 1.91-1.78 (m, 1H), 1.63-1.52 (m, 1H). MS (ESI+): 338.0 [M+H—H₂O]. HPLC Waters XBridge C8 3.5 μm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 2.91 min.

Example 115: [(1R)-2-[(3R)-2,3-dihydrobenzofuran-3-yl]-1-[[2-(4-methoxyphenyl)-acetyl]amino]ethyl] boronic acid (Compound No. 115)

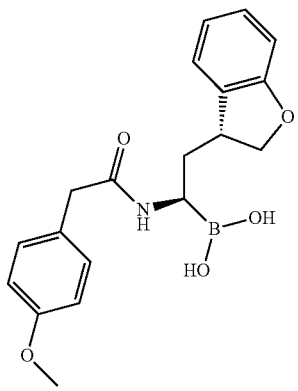

H NMR (500 MHz, DMSO-d6/D2O) d 7.20-7.16 (m, 2H), 7.16-7.09 (m, 1H), 7.08-7.03 (m, 1H), 6.85-6.81 (m, 2H), 6.81-6.76 (m, 1H), 6.72-6.68 (m, 1H), 4.49-4.42 (m, 1H), 4.14-4.03 (m, 1H), 3.70-3.66 (m, 3H), 3.40-3.32 (m, 2H), 3.32-3.26 (m, 1H), 3.01-2.94 (m, 1H), 1.91-1.78 (m, 1H), 1.63-1.52 (m, 1H). MS (ESI+): 338.0 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt 2.99 min.

Example 116: [(1R)-2-(7-chlorobenzofuran-3-yl)-1-[[2-(2-cyanophenyl)acetyl]amino]-ethyl]boronic acid (Compound No. 116)

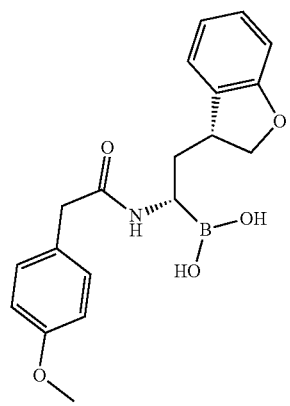

1H NMR (400 MHz, DMSO-d6/D2O) d 7.69-7.64 (m, 2H), 7.56-7.49 (m, 2H), 7.41-7.35 (m, 1H), 7.34 (d, J=7.5 Hz, 1H), 7.26-7.18 (m, 2H), 3.61 (s, 2H), 3.24 (dd, J=8.8, 5.5 Hz, 1H), 2.87 (dd, J=15.0, 5.5 Hz, 1H), 2.76 (dd, J=14.9, 8.9 Hz, 1H). MS (ESI+): 365.1 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 4.85 min.

Example 117: [(1S)-2-[(3S)-2,3-dihydrobenzofuran-3-yl]-1-[[2-(4-methoxyphenyl)-acetyl]amino]ethyl] boronic acid (Compound No. 117)

1H NMR (400 MHz, DMSO-d6/D2O) d 7.21-7.15 (m, 2H), 7.15-7.08 (m, 1H), 7.05 (t, J=7.8 Hz, 1H), 6.85-6.76 (m, 3H), 6.69 (d, J=8.0 Hz, 1H), 4.48-4.40 (m, 1H), 4.15-4.02 (m, 1H), 3.69-3.66 (m, 3H), 3.41-3.32 (m, 2H), 3.32-3.24 (m, 1H), 2.96 (dd, J=10.1, 5.0 Hz, 1H), 1.90-1.76 (m, 1H), 1.62-1.49 (m, 1H). MS (ESI+): 338.0[M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 4.21 min.

Example 118: [(1S)-2-[(3R)-2,3-dihydrobenzofuran-3-yl]-1-[[2-(4-methoxyphenyl)-acetyl]amino]ethyl] boronic acid (Compound No. 118)

1H NMR (400 MHz, DMSO-d6/D2O) d 7.19-7.15 (m, 2H), 7.13 (d, J=7.3 Hz, 1H), 7.08-7.02 (m, 1H), 6.85-6.76 (m, 3H), 6.69 (d, J=7.9 Hz, 1H), 4.45 (t, J=9.0 Hz, 1H), 4.03 (dd, J=9.0, 6.4 Hz, 1H), 3.67 (s, 3H), 3.44-3.35 (m, 2H), 3.33-3.24 (m, 1H), 2.86-2.79 (m, 1H), 1.88-1.77 (m, 1H), 1.61-1.51 (m, 1H). MS (ESI+): 338.0 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 4.11 min.

Example 119: [(1R)-2-(benzofuran-3-yl)-1-[[2-[3-(morpholine-4-carbonyl)-2-pyridyl]acetyl]amino]ethyl]boronic acid (Compound No. 119)

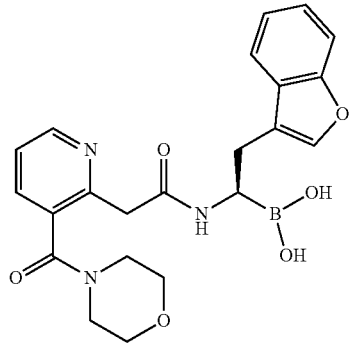

1H NMR (500 MHz, DMSO-d6/D2O) d 8.51 (dd, J=4.9, 1.7 Hz, 1H), 7.68 (dd, J=7.7, 1.7 Hz, 1H), 7.66-7.60 (m, 2H), 7.50 (d, J=8.1 Hz, 1H), 7.37 (dd, J=7.7, 4.9 Hz, 1H), 7.32-7.27 (m, 1H), 7.26-7.22 (m, 1H), 3.73-3.42 (m, 8H), 3.35-3.29 (m, 1H), 3.22-3.08 (m, 2H), 2.93 (dd, J=14.9, 5.2 Hz, 1H), 2.81 (dd, J=14.9, 8.4 Hz, 1H). MS (ESI+): 420.2 [M+H—H₂O]. HPLC Waters XBridge C8 3.5 µm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 3.36 min.

Example 120: [(1R)-2-[(3S)-7-methoxy-2,3-dihydrobenzofuran-3-yl]-1-[[2-(4-methoxyphenyl)acetyl]amino]ethyl]boronic acid (Compound No. 120)

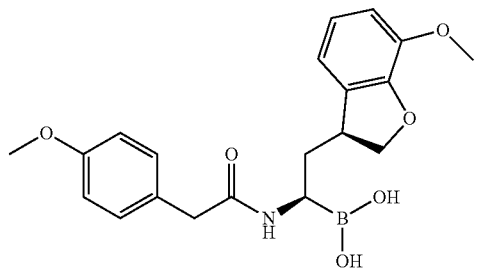

1H NMR (400 MHz, DMSO-d6/D2O) d 7.20-7.14 (m, 2H), 6.85-6.79 (m, 2H), 6.76 (d, J=4.4 Hz, 2H), 6.74-6.68 (m, 1H), 4.43 (t, J=8.9 Hz, 1H), 4.15-4.07 (m, 1H), 3.69 (s, 3H), 3.66 (s, 3H), 3.42-3.33 (m, 2H), 3.32-3.24 (m, 1H), 2.88 (dd, J=10.1, 4.9 Hz, 1H), 1.83-1.74 (m, 1H), 1.58-1.48 (m, 1H). MS (ESI+): 368.2 [M+H—H₂O]. HPLC Waters XBridge C8 3.5 µm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 4.22 min.

Example 121: [2-(7-fluorobenzofuran-3-yl)-1-[(2-phenylacetyl)amino]ethyl]boronic acid (Compound No. 121)

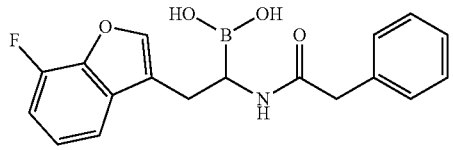 [SMILES: O=C(Cc1ccccc1)NC(Cc1coc2c(F)cccc12)B(O)O]

1H NMR 400 MHz, MeOD: 7.65 (s, 1H), 7.38-7.27 (m, 6H), 7.22-7.17 (m, 1H), 7.09-7.04 (m, 1H), 3.72 (s, 2H), 2.99-2.96 (m, 1H), 2.92-2.87 (m, 1H), 2.74-2.68 (m, 1H). MS (ESI+): 324.0 [M+H—H₂O]. HPLC Column: XBridge C8, 3.5 µm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.63 min.

Example 122: [(1R)-2-[(3R)-2,3-dihydrobenzofuran-3-yl]-1-[[2-(4-methoxyphenyl)-acetyl]amino]ethyl]boronic acid (Compound No. 122)

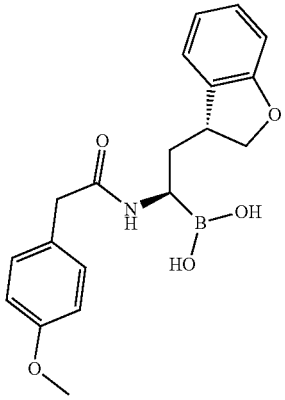

1H NMR (400 MHz, DMSO-d6/D2O) d 7.20-7.15 (m, 2H), 7.14 (d, J=7.3 Hz, 1H), 7.08-7.02 (m, 1H), 6.85-6.75 (m, 3H), 6.69 (d, J=7.9 Hz, 1H), 4.45 (t, J=8.9 Hz, 1H), 4.05-3.93 (m, 1H), 3.68-3.65 (m, 3H), 3.43-3.33 (m, 2H), 3.33-3.23 (m, 1H), 2.93-2.86 (m, 1H), 1.89-1.80 (m, 1H), 1.62-1.52 (m, 1H). MS (ESI+): 338.2 [M+H—H₂O]. HPLC Waters XBridge C8 3.5 µm; 4.6×50 mm; EliteLa Chrom 70173815; 8.1 min; 2 ml/min; 215 nm; buffer A: 0.05% TFA/H₂O; buffer B: 0.04% TFA/ACN; 0.0-0.2 min 5% buffer B; 0.2-8.5 min 5%-100% buffer B; 8.5-10.0 min 99%-5% buffer B. Rt. 4.07 min.

Example 123: [(1R)-2-(benzofuran-3-yl)-1-[[2-(3-cyanophenyl)acetyl]amino]ethyl]-boronic acid (Compound No. 123)

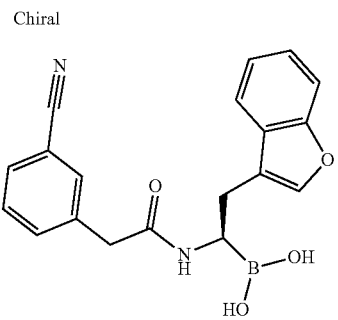 [SMILES: N#Cc1cccc(CC(=O)N[C@@H](Cc2coc3ccccc23)B(O)O)c1]

1H NMR (400 MHz, DMSO-d6/D2O) d 7.63-7.58 (m, 1H), 7.53 (d, J=7.7 Hz, 1H), 7.50-7.38 (m, 5H), 7.29-7.22 (m, 1H), 7.18 (t, J=7.5 Hz, 1H), 3.49-3.39 (m, 2H), 3.21 (dd, J=9.0, 5.4 Hz, 1H), 2.85 (dd, J=15.0, 5.4 Hz, 1H), 2.73 (dd, J=14.9, 9.0 Hz, 1H). MS (ESI+): 331.1 [M+H—H$_2$O]. HPLC Waters XBridge C8 3.5 μm; 4.6×500 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 4.46 min.

Example 124: [(1R)-2-[(3S)-7-methyl-2,3-dihydrobenzofuran-3-yl]-1-[(2-phenylacetyl)amino]ethyl]boronic acid (Compound No. 124

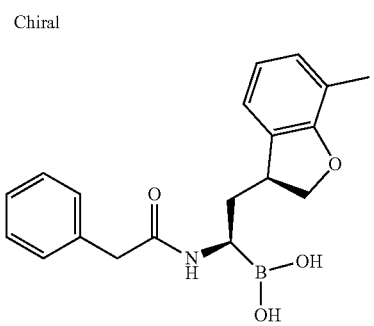 [SMILES: Cc1cccc2c1OC[C@H]2C[C@H](NC(=O)Cc1ccccc1)B(O)O]

1HNMR (400 MHz, CD3OD) 7.313 (m, 5H), 6.988 (d, 1H), 6.902 (d, 1H), 6.755 (t, 1H), 4.538 (t, 1H), 4.206 (m, 1H), 3.793 (s, 2H), 3.502 (m, 1H), 2.689 (m, 1H), 2.159 (s, 3H), 1.861 (m, 1H), 1.697 (m, 1H). MS (ESI+): 322.2 [M+H—H$_2$O]. HPLC A19/533 EliteLa Chrom 70173815; Waters XBridge C8 3.5 μm 4.6×50 mm—8.1 min; 2 mL/min; 215 nm; buffer A: 0.05% TFA/H$_2$O; buffer B: 0.04% TFA/ACN; 0.0-0.2 min 5% buffer B; 0.2-8.1 min 5%-100% buffer B; 8.1-10.0 min 100%-5% buffer B. Rt. 4.61 min.

Example 125: [(1R)-2-(7-fluorobenzofuran-3-yl)-1-[(2-phenylacetyl)amino]ethyl]-boronic acid (Compound No. 125)

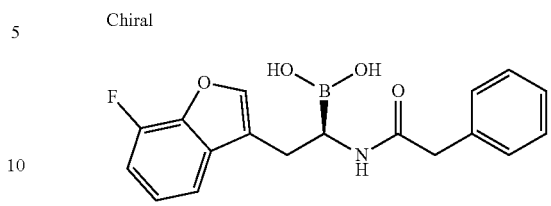

1H NMR (400 MHz, DMSO-d6/D2O) d 7.56 (s, 1H), 7.38 (d, J=7.7 Hz, 1H), 7.29-7.06 (m, 7H), 3.38 (s, 2H), 3.22-3.11 (m, 1H), 2.85 (dd, J=14.9, 5.1 Hz, 1H), 2.74 (dd, J=14.8, 8.7 Hz, 1H). MS (ESI+): 324.1 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 4.69 min.

Example 126: [(1R)-2-(6-chloro-7-methyl-benzofuran-3-yl)-1-[(2-phenylacetyl)-amino]ethyl]boronic acid (Compound No. 126)

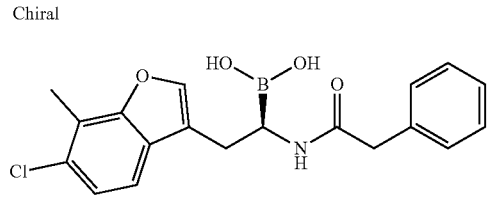 [SMILES: Cc1c(Cl)ccc2c(C[C@H](NC(=O)Cc3ccccc3)B(O)O)coc12]

1H NMR (500 MHz, DMSO-d6/D2O) d 7.53 (s, 1H), 7.38 (d, J=8.3 Hz, 1H), 7.24-7.17 (m, 4H), 7.13-7.09 (m, 2H), 3.42-3.32 (m, 2H), 3.18 (dd, J=8.5, 5.7 Hz, 1H), 2.85-2.79 (m, 1H), 2.71 (dd, J=14.8, 8.5 Hz, 1H), 2.42 (s, 3H). MS (ESI+): 354.0 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 5.26 min.

Example 127: [(1R)-2-[(3R)-7-methyl-2,3-dihydrobenzofuran-3-yl]-1-[(2-phenylacetyl)amino]ethyl] boronic acid (Compound No. 127)

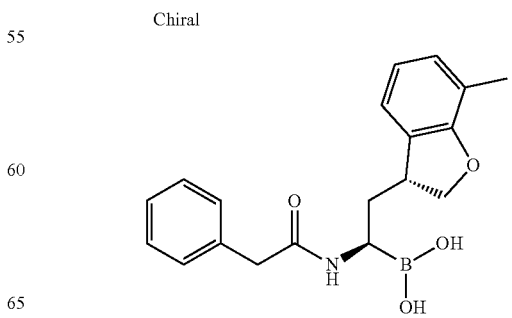

1H NMR (400 MHz, DMSO-d6/D2O) d 7.31-7.17 (m, 5H), 6.95 (d, J=7.3 Hz, 1H), 6.88 (d, J=7.5 Hz, 1H), 6.69 (t, J=7.4 Hz, 1H), 4.45 (t, J=8.9 Hz, 1H), 4.05 (dd, J=9.0, 6.4 Hz, 1H), 3.50-3.39 (m, 2H), 3.34-3.24 (m, 1H), 2.93 (dd, J=8.6, 6.5 Hz, 1H), 2.05 (s, 3H), 1.88-1.79 (m, 1H), 1.62-1.53 (m, 1H). MS (ESI+): 322.1 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 4.53 min.

Example 128: [(1R)-2-(4,7-dimethylbenzofuran-3-yl)-1-[(2-phenylacetyl)-amino]ethyl]boronic acid (Compound No. 128)

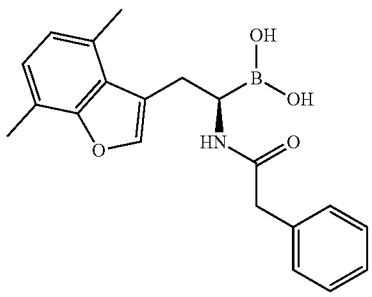

1H NMR (400 MHz): 7.42-7.40 (m, 1H), 7.26-7.20 (m, 3H), 7.17-7.15 (m, 2H), 6.94-6.92 (m, 1H), 6.84-6.82 (m, 1H), 3.44 (s, 2H), 3.01-2.96 (m, 2H), 2.83-2.76 (m, 1H), 2.47 (s, 3H), 2.33 (s, 3H). MS (ESI+): 334.0 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.96 min.

Example 129: [(1R)-2-(4,7-dimethylbenzofuran-3-yl)-1-[[2-(4-methoxyphenyl)-acetyl]amino]ethyl]boronic acid (Compound No. 129)

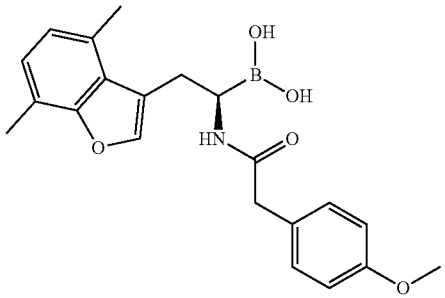

1H NMR (400 MHz): 7.50-7.48 (m, 1H), 7.26-7.24 (m, 2H), 6.96-6.85 (m, 4H), 3.80 (s, 3H), 3.69 (s, 2H), 3.10-3.04 (m, 1H), 2.94-2.91 (m, 1H), 2.83-2.77 (m, 1H), 2.58 (s, 3H), 2.43 (s, 3H). MS (ESI+): 364.2 [M+H—H$_2$O]. HPLC Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B. Rt. 3.98 min.

Example 130: [(1R)-1-[[2-(2-cyanophenyl)acetyl]amino]-2-[(3S)-7-methyl-2,3-dihydrobenzofuran-3-yl]ethyl]boronic acid (Compound No. 130)

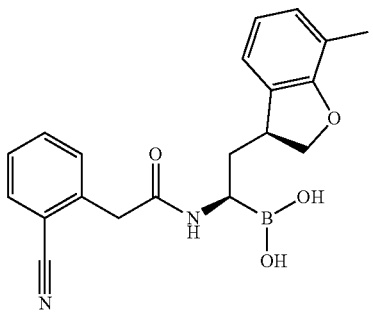

1HNMR (400 MHz, DMSO) 7.813 (d, 1H, J=8), 7.714 (t, 1H, J=7.6), 7.585 (m, 2H), 7.028 (d, 1H, J=7.2), 6.906 (d, 1H, J=7.6), 6.743 (t, 1H, J=7.2), 4.607 (t, 1H, J=8.8), 4.234 (m, 1H), 4.079 (s, 2H), 3.532 (m, 1H), 2.754 (m, 1H), 2.165 (s, 3H), 1.893 (m, 1H), 1.698 (m, 1H). MS (ESI+): 347.2 [M+H—H$_2$O]. HPLC Column: Shim-pack XR-ODS, 2.0*50 mm, 1.6 um; Mobile Phase A: Water/0.05% TFA, Mobile Phase B: ACN/0.05% TFA; Flow rate: 0.7 mL/min; Gradient: 5% B to 100% B in 2.1 min, hold 0.5 min; 220 nm. Rt. 1.27 min.

Example 131: [(1R)-2-[(3S)-2,3-dihydrobenzofuran-3-yl]-1-[[2-(5-ethoxy-2-pyridyl)acetyl]amino]ethyl]boronic acid (Compound No. 131)

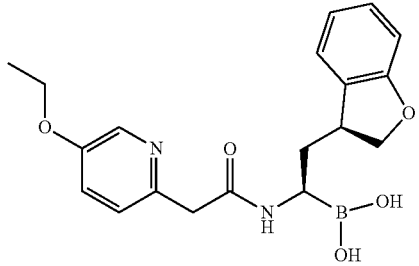

1H NMR (400 MHz, DMSO-d6/D2O) d 8.32 (d, J=2.9 Hz, 1H), 7.82 (dd, J=8.8, 2.9 Hz, 1H), 7.62 (d, J=8.8 Hz, 1H), 7.14 (d, J=7.3 Hz, 1H), 7.09-7.03 (m, 1H), 6.84-6.79 (m, 1H), 6.70 (d, J=7.9 Hz, 1H), 4.48 (t, J=8.9 Hz, 1H), 4.18-4.10 (m, 3H), 3.91-3.75 (m, 2H), 3.44-3.32 (m, 1H), 3.07 (dd, J=10.6, 4.5 Hz, 1H), 1.93-1.82 (m, 1H), 1.65-1.54 (m, 1H), 1.32 (t, J=6.9 Hz, 3H). MS (ESI+): 353.3 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 3.63 min.

Example 132: [(1R)-2-[(3S)-7-chloro-2,3-dihydrobenzofuran-3-yl]-1-[(2-phenylacetyl)amino]ethyl]boronic acid (Compound No. 132)

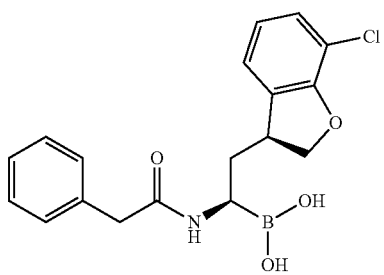

1H NMR (400 MHz, CD3OD, ppm): 7.364-7.319 (m, 5H), 7.103-7.084 (t, 2H), 6.823-6.785 (t, 1H) 4.697-4.653 (t, 1H), 4.338-4.300 (m, 1H), 3.775 (s, 2H), 3.660-3.560 (m, 1H), 2.710-2.620 (m, 1H), 1.920-1.820 (m, 1H), 1.740-1.650 (m, 1H). MS (ESI+): 342.3 [M+H—H₂O]. HPLC Column: Shim-pack XR-ODS, 2.0*50 mm, 1.6 um; Mobile Phase A: Water/0.05% TFA, Mobile Phase B: ACN/0.05% TFA; Flow rate: 0.7 mL/min; Gradient: 5% B to 100% B in 2.1 min, hold 0.5 min; 220 nm. Rt. 1.34 min.

Example 133: [(1R)-2-[(3R)-7-chloro-2,3-dihydrobenzofuran-3-yl]-1-[(2-phenylacetyl)amino]ethyl]boronic acid (Compound No. 133)

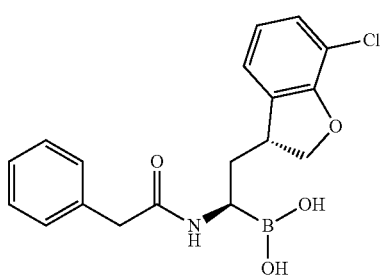

1H NMR (400 MHz, CD3OD, ppm) 7.55-7.26 (m, 5H), 7.15 (dt, J=7.4, 1.1 Hz, 1H), 7.09 (dt, J=8.1, 0.9 Hz, 1H), 6.80 (dd, J=8.1, 7.4 Hz, 1H), 4.68 (t, J=8.9 Hz, 1H), 4.30 (dd, J=8.9, 6.2 Hz, 1H), 3.77 (s, 2H), 3.57 (td, J=8.9, 4.4 Hz, 1H), 2.63 (dd, J=8.8, 6.9 Hz, 1H), 2.00-1.89 (m, 1H), 1.66 (ddd, J=13.2, 8.9, 6.8 Hz, 1H). MS (ESI+): 342.1 [M+H—H₂O]. HPLC Column: Shim-pack XR-ODS, 2.0*50 mm, 1.6 um; Mobile Phase A: Water/0.05% TFA, Mobile Phase B: ACN/0.05% TFA; Flow rate: 0.7 mL/min; Gradient: 5% B to 100% B in 2.1 min, hold 0.5 min; 220 nm. Rt. 1.30 min.

Example 134: [(1R)-2-[(3S)-7-chloro-2,3-dihydrobenzofuran-3-yl]-1-[[2-(2-cyanophenyl)acetyl]amino]ethyl]boronic acid (Compound No. 134)

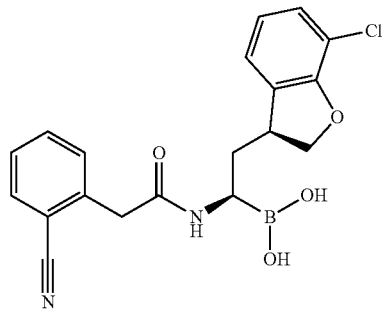

1H NMR (CD3OD, 400 MHz, ppm) 7.789-7.690 (m, 1H), 7.693-7.671 (m, 1H), 7.578-7.517 (m, 1H), 7.180-7.161 (d, 1H), 7.110-7.090 (d, 2H), 6.832-6.791 (t, 1H), 4.335-4.298 (m, 1H), 4.053 (s, 1H), 3.597-3.567 (m, 1H), 3.315-3.299 (m, 1H), 2.733-2.694 (t, 1H), 1.996-1.927 (m, 1H), 1.741-1.686 (m, 1H). MS (ESI+): 368.2 [M+H—H₂O]. HPLC Column: SPhenomenex Kinetext 2.6 um, 3.0*50 mm; Mobile Phase A: Water/0.1% FA, Mobile Phase B: ACN/0.1% FA; Flow rate: 1.5 mL/min; Gradient: 10% B to 100% B in 1.5 min, hold 1.0 min; 254 nm. Rt. 1.32 min.

Example 135: [(1R)-2-[(3R)-7-chloro-2,3-dihydrobenzofuran-3-yl]-1-[[2-(2-cyanophenyl)acetyl]amino]ethyl]boronic acid (Compound No. 135)

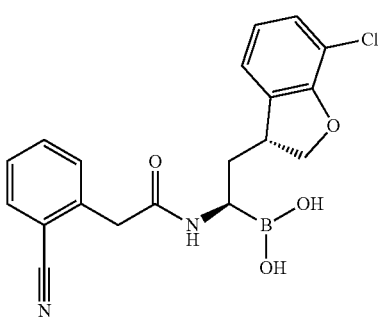

1H NMR (CD3OD, 400 MHz, ppm) 7.792-7.712 (m, 1H), 7.696-7.673 (m, 1H), 7.585-7.516 (m, 1H), 7.499-7.087 (m, 1H), 7.131-7.087 (m, 2H), 6.830-6.791 (m, 1H), 4.728-4.683 (m, 1H), 4.369-4.331 (m, 1H), 4.062 (m, 1H), 3.628 (t, 2H), 2.748-2.711 (m, 1H), 1.939-1.882 (m, 1H), 1.762-1.703 (m, 1H). MS (ESI+): 369.2 [M+H—H₂O]. HPLC Column: SPhenomenex Kinetext 2.6 um, 3.0*50 mm; Mobile Phase A: Water/0.1% FA, Mobile Phase B: ACN/0.1% FA; Flow rate: 1.5 mL/min; Gradient: 10% B to 100% B in 1.5 min, hold 1.0 min; 254 nm. Rt. 1.34 min.

Example 136: [(1R)-2-[(3S)-2,3-dihydrobenzofuran-3-yl]-1-(3-phenoxypropanoylamino)ethyl]boronic acid (Compound No. 136)

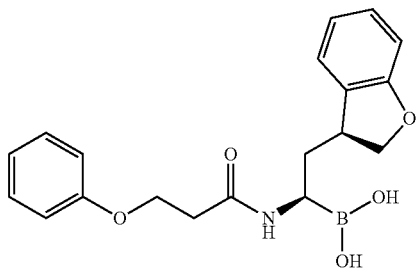

Chiral

1H NMR (400 MHz, DMSO-d6/D2O) d 7.24-7.16 (m, 2H), 7.11 (d, J=7.3 Hz, 1H), 7.06 (t, J=7.7 Hz, 1H), 6.88 (t, J=7.3 Hz, 1H), 6.85-6.78 (m, 3H), 6.70 (d, J=7.9 Hz, 1H), 4.48 (t, J=8.9 Hz, 1H), 4.20-4.10 (m, 3H), 3.47-3.36 (m, 1H), 3.06 (dd, J=10.6, 4.5 Hz, 1H), 2.65-2.51 (m, 2H), 1.90-1.81 (m, 1H), 1.61-1.52 (m, 1H). MS (ESI+): 338.2 [M+H—H$_2$O]. HPLC Waters XBridge C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer B. Rt. 4.60 min.

Example 137: Biological Activity

Determination of LMP7 Activity:

Measurement of LMP7 inhibition is performed in 384 well format based on fluorescence intensity assay.

Purified human immunoproteasome (0.25 nM) and serial diluted compounds in DMSO (range of concentrations from 30 μM to 15 μM) or controls are incubated for 20 minutes at 25° C. in assay buffer containing 50 mM Tris pH 7.4, 0.03% SDS, 1 mM EDTA and 1% DMSO. The reaction is initiated by the addition of the fluorogenic peptide substrate, Suc-LLVY-AMC (Bachem 1-1395), at a concentration of 40 μM. After 60 minutes of incubation at 37° C., fluorescence intensity is measured at $\lambda_{ex}$=350 nm and $\lambda_{em}$=450 nm with a fluorescence reader (Perkin Elmer Envision reader or equivalent).

The LMP7 activity of the compounds is summarized in Table 1.

Determination of Beta5 Activity:

Measurement of Beta5 inhibition is performed in 384 well format based on fluorescence intensity assay.

Purified human constitutive proteasome (1.25 nM) and serial diluted compounds in DMSO (range of concentrations from 30 μM to 15 μM) or controls are incubated for 20 minutes at 25° C. in assay buffer containing 50 mM Tris pH 7.4, 0.03% SDS, 1 mM EDTA and 1% DMSO. The reaction is initiated by the addition of the fluorogenic peptide substrate, Suc-LLVY-AMC (Bachem 1-1395), at a concentration of 40 μM. After 60 minutes of incubation at 37° C., fluorescence intensity is measured at $\lambda_{ex}$=350 nm and $\lambda_{em}$=450 nm with a fluorescence reader (Perkin Elmer Envision reader or equivalent).

Table 1 shows the Beta5 activity of compounds according to the invention and their selectivity to LMP7 versus Beta5.

TABLE 1

| Compound No. | LMP7 IC50 (M) | Beta5 IC50 (M) | Selectivity LMP7 vs Beta5 |
|---|---|---|---|
| 1 | **** | *** | ++ |
| 2 | *** | ** | ++ |
| 3 | **** | *** | ++ |
| 4 | **** | *** | ++ |
| 5 | **** | *** | ++ |
| 6 | **** | *** | +++++ |
| 7 | **** | **** | +++ |
| 8 | **** | *** | +++ |
| 9 | **** | *** | ++++ |
| 10 | **** | *** | ++++ |
| 11 | **** | *** | ++ |
| 12 | **** | *** | +++ |
| 13 | **** | *** | +++++ |
| 14 | *** | ** | +++ |
| 15 | **** | *** | ++++ |
| 16 | *** | ** | ++ |
| 17 | *** | * | ++ |
| 18 | **** | *** | ++ |
| 19 | **** | ** | +++ |
| 20 | **** | *** | ++ |
| 21 | **** | * | ++ |
| 22 | **** | *** | ++++ |
| 23 | **** | ** | +++++ |
| 24 | **** | ** | +++++ |
| 25 | **** | ** | ++++ |
| 26 | **** | *** | +++++ |
| 27 | **** | *** | ++++ |
| 28 | **** | ** | +++++ |
| 29 | *** | * | +++++ |
| 30 | **** | *** | ++++ |
| 31 | **** | *** | ++++ |
| 32 | **** | *** | ++++ |
| 33 | **** | ** | +++++ |
| 34 | **** | ** | +++++ |
| 35 | *** | ** | ++ |
| 36 | ** | * | + |
| 37 | **** | ** | +++++ |
| 38 | **** | ** | ++++ |
| 39 | **** | *** | +++++ |
| 40 | **** | *** | +++++ |
| 41 | **** | *** | +++++ |
| 42 | *** | * | ++ |
| 43 | **** | ** | +++++ |
| 44 | **** | * | +++++ |
| 45 | **** | ** | +++ |
| 46 | *** | * | ++++ |
| 47 | *** | * | +++++ |
| 48 | **** | ** | +++++ |
| 49 | **** | *** | +++++ |
| 50 | **** | ** | +++ |
| 51 | **** | ** | +++++ |
| 52 | **** | *** | ++ |
| 53 | **** | ** | ++ |
| 54 | **** | *** | +++++ |
| 55 | **** | ** | ++++ |
| 56 | *** | * | +++++ |
| 57 | **** | ** | +++++ |
| 58 | **** | *** | ++++ |
| 59 | **** | *** | ++++ |
| 60 | **** | *** | ++++ |
| 61 | *** | * | +++++ |
| 62 | **** | ** | +++++ |
| 63 | **** | ** | +++++ |
| 64 | **** | *** | +++ |
| 65 | **** | ** | ++++ |
| 66 | **** | ** | +++++ |
| 67 | **** | ** | ++ |
| 68 | **** | ** | +++++ |
| 69 | *** | ** | ++ |
| 70 | **** | * | +++++ |
| 71 | **** | ** | ++++ |
| 72 | **** | ** | +++ |
| 73 | *** | * | +++ |
| 74 | **** | ** | +++++ |
| 75 | **** | ** | +++++ |
| 76 | **** | ** | +++++ |
| 77 | **** | ** | +++++ |

TABLE 1-continued

| Compound No. | LMP7 IC50 (M) | Beta5 IC50 (M) | Selectivity LMP7 vs Beta5 |
|---|---|---|---|
| 78 | **** | ** | +++++ |
| 79 | **** | ** | +++++ |
| 80 | *** | * | +++++ |
| 81 | *** | * | +++++ |
| 82 | **** | ** | +++++ |
| 83 | **** | ** | +++++ |
| 84 | ** | * | ++ |
| 85 | **** | ** | +++++ |
| 86 | **** | * | +++++ |
| 87 | ** | * | + |
| 88 | *** | * | +++++ |
| 89 | **** | * | +++++ |
| 90 | **** | ** | +++++ |
| 91 | **** | *** | +++++ |
| 92 | **** | *** | +++++ |
| 93 | **** | * | +++++ |
| 94 | **** | ** | +++++ |
| 95 | **** | ** | +++++ |
| 96 | *** | * | +++++ |
| 97 | *** | * | +++++ |
| 98 | **** | ** | ++++ |
| 99 | *** | * | +++++ |
| 100 | *** | * | +++++ |
| 101 | **** | * | +++++ |
| 102 | *** | * | +++++ |
| 103 | ***** | ** | ++++ |
| 104 | **** | ** | +++++ |
| 105 | **** | ** | +++++ |
| 106 | **** | * | +++++ |
| 107 | ** | * | ++ |
| 108 | **** | ** | +++++ |
| 109 | **** | * | +++++ |
| 110 | *** | * | ++++ |
| 111 | **** | * | +++++ |
| 112 | **** | ** | +++++ |
| 113 | **** | ** | +++++ |
| 114 | **** | ** | +++++ |
| 115 | **** | * | +++++ |
| 116 | **** | ** | +++++ |
| 117 | *** | * | +++++ |
| 118 | *** | * | +++++ |
| 119 | **** | ** | +++++ |
| 120 | **** | ** | +++++ |
| 121 | **** | ** | +++++ |
| 122 | *** | * | +++++ |
| 123 | **** | ** | +++++ |
| 124 | **** | * | +++++ |
| 125 | **** | *** | +++++ |
| 126 | **** | ** | +++++ |
| 127 | ** | * | ++ |
| 128 | **** | * | +++++ |
| 129 | **** | ** | +++++ |
| 130 | **** | * | +++++ |
| 131 | **** | ** | +++++ |
| 132 | **** | ** | +++++ |
| 133 | ** | * | ++ |
| 134 | **** | ** | +++++ |
| 135 | *** | * | +++++ |
| 136 | **** | *** | +++++ |

\*: $IC_{50} > 5$ μM,
\*\*: $0.5$ μM $< IC_{50} < 5$ μM,
\*\*\*: $0.05$ μM $< IC_{50} < 0.5$ μM,
\*\*\*\*: $IC_{50} < 0.05$ μM,
+: Selectivity < 10,
++: $10 \leq$ Selectivity < 50,
+++: $50 \leq$ Selectivity < 70,
++++: $70 \leq$ Selectivity < 100,
+++++: Selectivity $\geq 100$,
n.d: not determined.

The following examples relate to medicaments:

Example A: Injection Vials

A solution of 100 g of an active ingredient of formula (I) and 5 g of disodium hydrogen phosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of formula (I) with 100 g of soya lecithin and 1400 g of cocoa butter is melted, poured into molds and allowed to cool. Each suppository contains 20 mg of active ingredient.

Example C: Solution

A solution is prepared from 1 g of an active ingredient of formula (I), 9.38 g of $NaH_2PO_4$ 2 $H_2O$, 28.48 g of $Na_2HPO_4$.12 $H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of an active ingredient of formula (I) are mixed with 99.5 g of Vaseline under aseptic conditions.

Example E: Tablets

A mixture of 1 kg of an active ingredient of formula (I), 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of an active ingredient of formula (I) are introduced into hard gelatine capsules in a conventional manner in such a way that each capsule contains 20 mg of the active ingredient.

Example H: Ampoules

A solution of 1 kg of an active ingredient of formula (I) in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula (I):

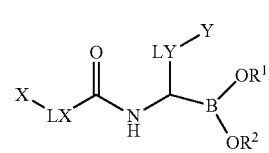

or a stereoisomer, tautomer or pharmaceutically acceptable salt thereof, wherein:
LX denotes —CH$_2$—, —O(CH$_2$)$_n$—, —S(CH$_2$)$_p$— or —(CH$_2$)$_p$S—, where 1, 2, 3, 4 or 5 H atoms may be independently replaced by Hal, N$_3$, R$^{3a}$, OR$^{4a}$, (CH$_2$)$_r$A2, (CH$_2$)$_r$Ar2 or (CH$_2$)$_r$Het2;

LY denotes —CH$_2$—;

X denotes an aromatic 6-membered carbocyclyl or aromatic 6-membered heterocyclyl, each optionally and independently substituted by 1, 2, 3, 4 or 5 substituents selected from Hal, A1, N$_3$, CN, OH, NR$^{4a}$R$^{4b}$, Ar1, Het1, OA1, OAr1, OHet1, C(O)A1, C(O)Ar1, C(O)Het1, C(O)NR$^{4a}$R$^{4b}$, NR$^{4a}$C(O)R$^{3a}$, NR$^{4a}$S(O)$_2$R$^{3a}$, S(O)$_2$R$^{3a}$, S(O)R$^{3a}$, NR$^{4a}$C(O)$_2$R$^{3a}$, OC(O)NR$^{3a}$R$^{4a}$, O(CH$_2$)$_q$A1, (CH$_2$)$_r$SR$^{3a}$, (CH$_2$)$_r$N(R$^{4a}$)$_2$ or (CH$_2$)$_r$A2;

Y denotes Cyc;

R$^1$ and R$^2$ each independently denote H or C1-C6 alkyl; or

R$^1$ and R$^2$, together with the oxygen atoms to which they are attached, form a residue according to formula (CE):

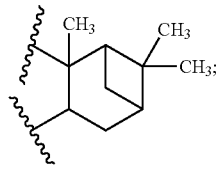

(CE)

R$^{3a}$ and R$^{3b}$ each independently denote linear or branched C1-C6 alkyl, where 1, 2, 3, 4 or 5 H atoms may be independently replaced by Hal, OH or OAlk;

R$^{4a}$ and R$^{4b}$ each independently denote H or R$^{3a}$; or

R$^{4a}$ and R$^{4b}$, together with the nitrogen atom to which they are attached, form a nitrogen-containing heterocyclyl comprising 3, 4, 5 or 6 carbon atoms;

A1 denotes linear or branched C1-C6 alkyl or C3-C6 cycloalkyl, each optionally and independently substituted by 1, 2, 3, 4 or 5 substituents selected from Hal, CN, R$^{3a}$, SR$^{3a}$, OR$^{4a}$ or (CH$_2$)$_r$A2, where 1, 2 or 3 CH$_2$ groups of C3-C6 cycloalkyl may be independently replaced by O, C(O) or N;

A2 denotes OR$^{4a}$;

Alk denotes linear or branched C1-C6 alkyl;

Ar1 denotes phenyl, optionally substituted by 1, 2 or 3 substituents selected from Hal, NO$_2$, CN, R$^{3a}$, OR$^{4a}$, C(O)NR$^{4a}$R$^{4b}$, NR$^{4a}$C(O)R$^{3b}$, S(O)$_2$R$^{3a}$, S(O)R$^{3a}$, NR$^{4a}$R$^{4b}$, Ar2, Het2 or (CH$_2$)$_r$A2;

Het1 denotes a saturated, unsaturated or aromatic 5- or 6-membered heterocyclyl comprising 1, 2, 3 or 4 heteroatoms independently selected from the group consisting of N, O and S, where each heterocyclyl may be optionally and independently substituted by 1, 2, 3, 4 or 5 substituents selected from Hal, NO$_2$, CN, R$^{3a}$, OR$^{4a}$, C(O)NR$^{4a}$R$^{4b}$, NR$^{4a}$C(O)R$^{3b}$, S(O)$_2$R$^{3a}$, S(O)R$^{3a}$, NR$^{4a}$R$^{4b}$, Ar2, Het2 or (CH$_2$)$_r$A2;

Ar2 denotes phenyl, biphenyl or naphthyl, each optionally and independently substituted by 1, 2 or 3 substituents selected from Hal, CN, R$^{3a}$, OR$^{4a}$, C(O)NR$^{4a}$R$^{4b}$, NR$^{4a}$C(O)R$^{3b}$, S(O)$_2$R$^{3a}$, S(O)R$^{3a}$, NR$^{4a}$R$^{4b}$ or (CH$_2$)$_q$A2;

Het2 denotes a saturated, unsaturated or aromatic 5- or 6-membered heterocyclyl comprising 1, 2, 3 or 4 heteroatoms independently selected from the group consisting of N, O and S, optionally substituted by 1, 2 or 3 substituents selected from Hal, CN, R$^{3a}$, OR$^{4a}$, C(O)NHR$^{3a}$, NR$^{3a}$C(O)R$^{3b}$, S(O)$_2$R$^{3a}$, S(O)R$^{3a}$, NR$^{4a}$R$^{4b}$ or (CH$_2$)$_q$A2;

Cyc denotes a monocyclic or bicyclic, 4-, 5-, 6-, 7-, 8-, 9- or 10-membered carbocyclyl or heterocyclyl, each optionally and independently substituted by 1, 2, 3, 4 or 5 substituents selected from Hal, CN, R$^{3a}$, OR$^{3a}$, C(O)NR$^{4a}$R$^{4b}$, NR$^{3a}$C(O)R$^{3b}$, S(O)$_2$R$^{3a}$, S(O)R$^{3a}$, NR$^{4a}$R$^{4b}$, Ar2, Het2, (CH$_2$)$_r$SR$^{3a}$, (CH$_2$)$_r$N(R$^{4a}$)$_2$ or (CH$_2$)$_r$A2, where the monocyclic carbocyclyl is aromatic and at least one ring of the bicyclic carbocyclyl or heterocyclyl is aromatic, and further where the heterocyclyl comprises 1, 2 or 3 heteroatoms independently selected from the group consisting of N, O and S;

n denotes 1, 2, 3, 4, 5 or 6;
p denotes 1, 2, 3, 4, 5 or 6;
q denotes 0, 1, 2, 3 or 4;
r denotes 0, 1, 2, 3 or 4; and
Hal denotes F, Cl, Br or I;
with the proviso that when LX denotes —O(CH$_2$)$_n$—, the oxygen atom of LX is bonded to X.

2. The compound according to claim 1, or a stereoisomer, tautomer or pharmaceutically acceptable salt thereof, wherein:

X denotes phenyl, pyridinyl, pyridazinyl, pyrimidinyl, pyrazinyl or triazinyl, each optionally and independently substituted by 1, 2, 3, 4 or 5 substituents selected from Hal, A1, N$_3$, CN, OH, NR$^{4a}$R$^{4b}$, Ar1, Het1, OA1, OAr1, OHet1, C(O)A1, C(O)Ar1, C(O)Het1, C(O)NR$^{4a}$R$^{4b}$, NR$^{4a}$C(O)R$^{3a}$, NR$^{4a}$S(O)$_2$R$^{3a}$, S(O)$_2$R$^{3a}$, S(O)R$^{3a}$, NR$^{4a}$C(O)$_2$R$^{3a}$, OC(O)NR$^{3a}$R$^{4a}$, O(CH$_2$)$_q$A1, (CH$_2$)$_r$SR$^{3a}$, (CH$_2$)$_r$N(R$^{4a}$)$_2$ or (CH$_2$)$_r$A2;

R$^1$ and R$^2$ each independently denote H or C1-C4 alkyl; or

R$^1$ and R$^2$, together with the oxygen atoms to which they are attached, form a residue according to formula (CE):

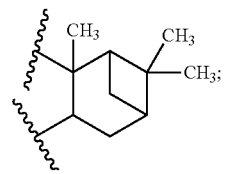

(CE)

n denotes 1, 2, 3 or 4;
p denotes 1, 2, 3 or 4;
q denotes 1, 2, 3 or 4; and
r denotes 1, 2, 3 or 4.

3. The compound according to claim 1, or a stereoisomer, tautomer or pharmaceutically acceptable salt thereof, wherein:

LX denotes —CH$_2$—, —OCH$_2$—, —O(CH$_2$)$_2$—, —SCH$_2$— or —S(CH$_2$)$_2$—, where 1, 2, 3 or 4 H atoms may be independently replaced by Hal, R$^{3a}$, OR$^{4a}$, (CH$_2$)$_r$A2, Ar2 or Het2; and Cyc denotes phenyl, optionally substituted by 1, 2 or 3 substituents selected from Hal, CN, R$^{3a}$, OR$^{3a}$, C(O)NR$^{4a}$R$^{4b}$, NR$^{3a}$C(O)R$^{3b}$, S(O)$_2$R$^{3a}$, S(O)R$^{3a}$, NR$^{4a}$R$^{4b}$, Ar2, Het2, (CH$_2$)$_r$SR$^{3a}$, (CH$_2$)$_r$N(R$^{4a}$)$_2$ or (CH$_2$)$_r$A2, where disubstitution occurs in a 2,4-, 2,5- or 3,4-pattern and trisubstitution occurs in a 2,3,4-pattern; or Cyc denotes 1-naphthalenyl, 2-naphthalenyl, 4-indanyl, 5-indanyl, 1-indolyl, 2-indolyl, 3-indolyl, 4-indolyl, 5-indolyl, 6-indolyl, 7-indolyl, 1-azulenyl, 2-azulenyl, 3-azulenyl, 4-azulenyl, 5-azulenyl, 6-azulenyl, 1-tetrahydronaphthalen-5-yl, 2-tetrahydronaphthalen-5-yl, 1-tetrahydronaphthalen-6-yl, 2-tetrahydronaphthalen-6-yl, 2-furanyl, 3-furanyl, 2-benzofuranyl, 3-benzofuranyl, 4-benzofuranyl, 5-benzofuranyl, 6-benzofuranyl, 7-benzofuranyl, 2,3-dihydrobenzofuran-2-yl, 2,3-dihydrobenzofuran-3-yl, 2-benzothiophenyl, 3-benzothiophenyl, 4-benzothiophenyl, 5-benzothiophenyl, 6-benzothiophenyl, 7-benzothiophenyl, methylenedioxyphenyl, 6-benzodioxanyl, 7-benzodioxanyl, 3,4-dihydro-1,5-benzodioxepin-6-yl or 3,4-dihydro-1,5-benzodioxepin-7-yl, each optionally and independently substituted by 1, 2 or 3 substituents selected from Hal, CN, $R^{3a}$, $OR^{3a}$, $C(O)NR^{4a}R^{4b}$, $NR^{3a}C(O)R^{3b}$, $S(O)_2R^{3a}$, $S(O)R^{3a}$, $NR^{4a}R^{4b}$, Ar2, Het2, $(CH_2)_rSR^{3a}$, $(CH_2)_rN(R^{4a})_2$ or $(CH_2)_rA2$.

4. The compound according to claim 1, or a stereoisomer, tautomer or pharmaceutically acceptable salt thereof, wherein:

LX denotes —$CH_2$—, —$OCH_2$—, —$O(CH_2)_2$—, —$SCH_2$— or —$S(CH_2)_2$—, where 1, 2, 3 or 4 H atoms may be independently replaced by Hal, $R^{3a}$, $OR^{4a}$, $(CH_2)_rA2$, phenyl, methylphenyl, ethylphenyl, fluorophenyl, chlorophenyl, bromophenyl, aminophenyl, furanyl, thiophenyl, pyrrolyl, imidazolyl, pyrazolyl, pyrimidinyl, morpholinyl or piperidinyl;

Cyc denotes 1-naphthalenyl, 2-naphthalenyl, 1-indolyl, 2-indolyl, 3-indolyl, 4-indolyl, 5-indolyl, 6-indolyl, 7-indolyl, 2-benzofuranyl, 3-benzofuranyl, 2,3-dihydrobenzofuran-2-yl, 2,3-dihydrobenzofuran-3-yl, 2-benzothiophenyl or 3-benzothiophenyl, each optionally and independently substituted by 1, 2 or 3 substituents selected from Hal, CN, $R^{3a}$, $OR^{3a}$, $C(O)NR^{4a}R^{4b}$, $NR^{3a}C(O)R^{3b}$, $S(O)_2R^{3a}$, $S(O)R^{3a}$, $NR^{4a}R^{4b}$, Ar2, Het2, $(CH_2)_rSR^{3a}$, $(CH_2)_rN(R^{4a})_2$ or $(CH_2)_rA2$;

q denotes 1, 2 or 3; and r denotes 1, 2 or 3.

5. The compound according to claim 1, or a stereoisomer, tautomer or pharmaceutically acceptable salt thereof, wherein:

LX denotes —$CH_2$—, —$OCH_2$—, —$O(CH_2)_2$—, —$SCH_2$— or —$S(CH_2)_2$—, where 1, 2, 3 or 4 H atoms may be independently replaced by Hal, $R^{3a}$, $OR^{4a}$ or $(CH_2)_rA2$;

X denotes phenyl, pyridinyl, pyridazinyl, pyrimidinyl, pyrazinyl or triazinyl, each optionally and independently substituted by 1, 2, 3, 4 or 5 substituents selected from Hal, A1, $N_3$, CN, OH, $NR^{4a}R^{4b}$, Ar1, Het1, OA1, OAr1, OHet1, C(O)A1, C(O)Ar1, C(O)Het1, $C(O)NR^{4a}R^{4b}$, $NR^{4a}C(O)R^{3a}$, $NR^{4a}S(O)_2R^{3a}$, $S(O)_2R^{3a}$, $S(O)R^{3a}$, $NR^{4a}C(O)_2R^{3a}$, $OC(O)NR^{3a}R^{4a}$, $O(CH_2)_qA1$ or $(CH_2)_rA2$;

$R^1$ and $R^2$ each independently denote H or C1-C4 alkyl; or $R^1$ and $R^2$, together with the oxygen atoms to which they are attached, form a residue according to formula (CE):

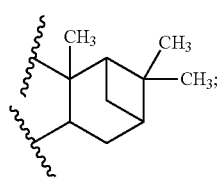

(CE)

$R^{3a}$ and $R^{3b}$ each independently denote linear or branched C1-C4 alkyl, where 1, 2, 3, 4 or 5 H atoms may be independently replaced by Hal, OH or OAlk;

A1 denotes linear or branched C1-C6 alkyl or C3-C6 cycloalkyl, each optionally and independently substituted by 1 or 2 substituents selected from Hal, CN, $R^{3a}$, $SR^{3a}$, $OR^{4a}$ or $(CH_2)_rA2$, where 1 or 2 $CH_2$ groups of C3-C6 cycloalkyl may be independently replaced by O, C(O) or N;

Alk denotes methyl, ethyl, n-propyl or isopropyl; and

Cyc denotes 1-naphthalenyl, 2-naphthalenyl, 1-indolyl, 2-indolyl, 3-indolyl, 4-indolyl, 5-indolyl, 6-indolyl, 7-indolyl, 2-benzofuranyl, 3-benzofuranyl, 2,3-dihydrobenzofuran-2-yl, 2,3-dihydrobenzofuran-3-yl, 2-benzothiophenyl or 3-benzothiophenyl, each optionally and independently substituted by 1, 2 or 3 substituents selected from Hal, CN, $R^{3a}$, $OR^{3a}$, $C(O)NR^{4a}R^{4b}$, $NR^{3a}C(O)R^{3b}$, $S(O)_2R^{3a}$, $S(O)R^{3a}$, $NR^{4a}R^{4b}$, Ar2, Het2, $(CH_2)_rSR^{3a}$, $(CH_2)_rN(R^{4a})_2$ or $(CH_2)_rA2$.

6. The compound according to claim 5, or a stereoisomer, tautomer or pharmaceutically acceptable salt thereof, wherein:

$R^{3a}$ and $R^{3b}$ each independently denote linear or branched C1-C3 alkyl, where 1, 2, 3, 4 or 5 H atoms may be independently replaced by F, Cl, OH or OAlk;

Cyc denotes 1-naphthalenyl, 2-naphthalenyl, 2-benzothiophenyl or 3-benzothiophenyl, each optionally and independently substituted by 1 or 2 substituents selected from Hal, CN, $R^{3a}$, $OR^{3a}$, $C(O)NR^{4a}R^{4b}NR^{3a}C(O)R^{3b}$, $S(O)_2R^{3a}$, $S(O)R^{3a}$, $NR^{4a}R^{4b}$, Ar2, Het2, $(CH_2)_rSR^{3a}$, $(CH_2)_rN(R^{4a})_2$ or $(CH_2)_rA2$; or Cyc denotes formula (Fa7) or formula (Fb7):

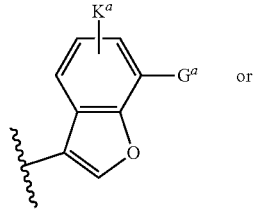

(Fa7)

or

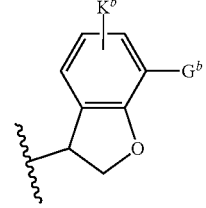

(Fb7)

wherein:

$G^a$ denotes F, Cl, Br, CN, $R^{3a}$, $OR^{3a}$, $C(O)NR^{3a}R^{3b}$, $C(O)NHR^{3a}$, $C(O)NH_2$, $NR^{3a}C(O)R^{3b}$, $S(O)_2R^{3a}$, $S(O)R^{3a}$, $NHR^{3a}$, $N(R^{3a})_2$, $(CH_2)_rSR^{3a}$, $(CH_2)_rN(R^{4a})_2$ or $(CH_2)_rA2$;

$G^b$ denotes H, F, Cl, Br, CN, $R^{3a}$, $OR^{3a}$, $C(O)NR^{3a}R^{3b}$, $C(O)NHR^{3a}$, $C(O)NH_2$, $NR^{3a}C(O)R^{3b}$, $S(O)_2R^{3a}$, $S(O)R^{3a}$, $NHR^{3a}$, $N(R^{3a})_2$, $(CH_2)_rSR^{3a}$, $(CH_2)_rN(R^{4a})_2$ or $(CH_2)_rA2$;

$K^a$ and $K^b$ each independently denote H, F, Cl, Br, CN, $R^{3a}$, $OR^{3a}$, $C(O)NR^{3a}R^{3b}$, $C(O)NHR^{3a}$, $C(O)NH_2$, $NR^{3a}C(O)R^{3b}$, $S(O)_2R^{3a}$, $S(O)R^{3a}$, $NHR^{3a}$, $N(R^{3a})_2$, $(CH_2)_rSR^{3a}$, $(CH_2)_rN(R^{4a})_2$ or $(CH_2)_rA2$;

Alk denotes methyl or ethyl; and r denotes 1 or 2.

7. The compound according to claim 6, or a stereoisomer, tautomer or pharmaceutically acceptable salt thereof, wherein:

Cyc denotes formula (Fa7) or (S)-formula (Fb7):

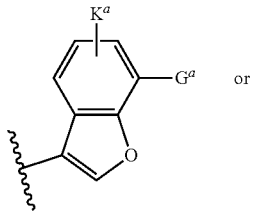

(Fa7)

or

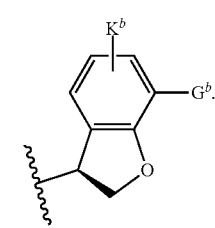

(S)-(Fb7)

8. The compound according to claim 6, a stereoisomer, tautomer or pharmaceutically acceptable salt thereof, wherein:

Cyc denotes 1-naphthalenyl or 2-naphthalenyl, each optionally and independently substituted by 1 or 2 substituents selected from F, Cl, $CH_3$, $CH_2CH_3$, $CF_3$, $OCH_3$, $OCH_2CH_3$, $SCH_3$, $SCH_2CH_3$, $CH_2OCH_3$, $N(CH_3)_2$, $CH_2N(CH_3)_2$ or $N(CH_2CH_3)_2$; or Cyc denotes formula (Fa7) or formula (Fb7):

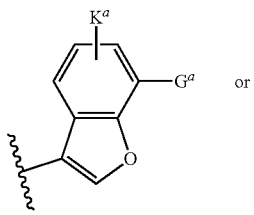

(Fa7)

or

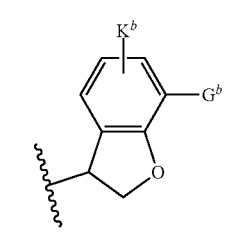

(Fb7)

wherein:
- $G^a$ denotes F, Cl, $CH_3$, $CH_2CH_3$, $CF_3$, $OCH_3$, $OCH_2CH_3$, $SCH_3$, $SCH_2CH_3$, $CH_2OCH_3$, $N(CH_3)_2$, $CH_2N(CH_3)_2$ or $N(CH_2CH_3)_2$;
- $G^b$ denotes H, F, Cl, $CH_3$, $CH_2CH_3$, $CF_3$, $OCH_3$, $OCH_2CH_3$, $SCH_3$, $SCH_2CH_3$, $CH_2OCH_3$, $N(CH_3)_2$, $CH_2N(CH_3)_2$ or $N(CH_2CH_3)_2$; and
- $K^a$ and $K^b$ each independently denote H, F, Cl, $CH_3$, $CH_2CH_3$, $CF_3$, $OCH_3$, $OCH_2CH_3$, $SCH_3$, $SCH_2CH_3$, $CH_2OCH_3$, $N(CH_3)_2$, $CH_2N(CH_3)_2$ or $N(CH_2CH_3)_2$.

9. The compound according to claim 1, wherein the compound is represented by formula (R)-(Ia):

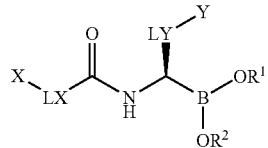

(R)-(Ia)

or a stereoisomer, tautomer or pharmaceutically acceptable salt thereof,
wherein:
- LX denotes —$CH_2$— or —$OCH_2$—, where 1, 2, 3 or 4 H atoms may be independently replaced by F or Cl or where 1 or 2 H atoms may be independently replaced by $CH_3$, $CH_2CH_3$, $CH(CH_3)_2$, $CF_3$, $CF_2CF_3$, $OCH_3$, $OCH_2CH_3$, $O(CH_2)_{20}H$ or $O(CH_2)_2OCH_3$;
- X denotes phenyl, pyridinyl, pyridazinyl, pyrazinyl or triazinyl, each optionally and independently substituted by 1, 2, 3, 4 or 5 substituents selected from Hal, A1, $N_3$, CN, OH, $NR^{4a}R^{4b}$, Ar1, Het1, OA1, OAr1, OHet1, C(O)A1, C(O)Ar1, C(O)Het1, C(O)$NR^{4a}R^{4b}$, $NR^{4a}C(O)R^{3a}$, $NR^{4a}S(O)_2R^{3a}$, $S(O)_2R^{3a}$, $S(O)R^{3a}$, $NR^{4a}C(O)_2R^{3a}$, $OC(O)NR^{3a}R^{4a}$, $O(CH_2)_qA1$ or $(CH_2)_rA2$;
- $R^1$ and $R^2$ each independently denote H or C1-C4 alkyl; or
- $R^1$ and $R^2$, together with the oxygen atoms to which they are attached, form a residue according to formula (CE):

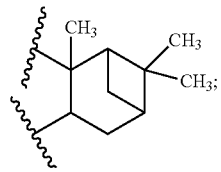

(CE)

- $R^{3a}$ and $R^{3b}$ each independently denote linear or branched C1-C3 alkyl, where 1, 2, 3, 4 or 5 H atoms may be independently replaced by F, Cl, OH or OAlk;
- A1 denotes ethyl, n-propyl, isopropyl, n-butyl, isobutyl, sec-butyl, tert-butyl, n-pentyl, 1-methylbutyl, 2-methylbutyl, isopentyl, 1,1-dimethylpropyl, 1,2-dimethylpropyl, neopentyl, 1-ethylpropyl, n-hexyl, 1-methylpentyl, 2-methylpentyl, 3-methylpentyl, isohexyl, 1,1-dimethylbutyl, 1,2-dimethylbutyl, 1,3-dimethylbutyl, 2,2-dimethylbutyl, 2,3-dimethylbutyl, neohexyl, 1-ethylbutyl, 2-ethylbutyl, 1-ethyl-1-methylpropyl or 1-ethyl-2-methylpropyl, each optionally and independently substituted by 1, 2, 3 or 4 substituents selected from Hal, CN, $R^{3a}$, $SR^{3a}$, $OR^3a$ or $(CH_2)_rA2$;
- A2 denotes OH, $OCH_3$, $OCH_2CH_3$, $OCF_3$, $O(CH_2)_{20}H$ or $O(CH_2)_2OCH_3$;
- Alk denotes methyl or ethyl;
- Ar1 denotes phenyl, 2-methylphenyl, 3-methylphenyl, 4-methylphenyl, 2-ethylphenyl, 3-ethylphenyl, 4-ethylphenyl, 2-n-propylphenyl, 3-n-propylphenyl, 4-n-propylphenyl, 2-isopropylphenyl, 3-isopropylphenyl, 4-isopropylphenyl, 2-tert-butylphenyl, 3-tert-butylphenyl, 4-tert-butylphenyl, 2-hydroxyphenyl, 3-hydroxyphenyl, 4-hydroxyphenyl, 2-nitrophenyl, 3-nitrophenyl, 4-nitrophenyl, 2-aminophenyl, 3-aminophenyl, 4-aminophenyl, 2-(N-methylamino)phenyl, 3-(N-methylamino)phenyl, 4-(N-methylamino)phenyl, 2-(N,N-dimethylamino)phenyl, 3-(N,N-dimethylamino)phenyl, 4-(N,N-dimethylamino)phenyl, 2-(N-methylaminocarbonyl)phenyl, 3-(N-methylaminocarbonyl)phenyl, 4-(N-methylaminocarbonyl)phenyl, 2-(acetamido)phenyl, 3-(acetamido)phenyl, 4-(acetamido)phenyl, 2-(N-ethylamino)phenyl, 3-(N-ethylamino)phenyl, 4-(N-ethylamino)phenyl, 2-(N,N-diethylamino)phenyl, 3-(N,N-diethylamino)phenyl, 4-(N,N-diethylamino)phenyl, 2-methoxyphenyl, 3-methoxyphenyl, 4-methoxyphenyl, 2-ethoxyphenyl, 3-ethoxyphenyl, 4-ethoxyphenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 2-(methylsulfonyl)phenyl, 3-(methylsulfonyl)phenyl, 4-(methylsulfonyl)phenyl, 2-cyanophenyl, 3-cyanophenyl, 4-cyanophenyl, 2-piperidinylphenyl, 3-piperidinylphenyl, 4-piperidinylphenyl, 2-(morpholin-4-yl)phenyl, 3-(morpholin-4-yl)phenyl, 4-(morpholin-4-yl)phenyl, 2,5-dimethylphenyl, 2,6-dimethylphenyl, 3,4-dimethylphenyl, 3,5-dimethylphenyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3-dibromophenyl, 2,4-dibromophenyl, 2,5-dibromophenyl, 2,6-dibromophenyl, 3,4-dibromophenyl, 3,5-dibromophenyl, 2,4-dinitrophenyl, 2,5-dinitrophenyl, 2,5-dimethoxyphenyl, 3,4-dimethoxyphenyl, 4-chloro-3-nitrophenyl, 3-amino-4-chlorophenyl, 2-amino-3-chlorophenyl, 2-amino-4-chlorophenyl, 2-amino-5-chlorophenyl, 2-amino-6-chlorophenyl, 4-(N,N-dimethylamino)-2-nitrophenyl, 4-(N,N-dimethylamino)-3-nitrophenyl, 2,3-diaminophenyl, 2,3,4-trichlorophenyl, 2,3,5-trichlorophenyl, 2,3,6-trichlorophenyl, 2,4,6-trichlorophenyl, 3,4,5-trichlorophenyl, 2,4,6-trimethoxyphenyl, 3,5-dichloro-2-hydroxyphenyl, 4-amino-3,6-dichlorophenyl, 3-chloro-4-fluorophenyl, 4-bromo-2-fluorophenyl, 4-bromo-2,5-difluorophenyl, 3-bromo-6-methoxyphenyl, 3-chloro-6-methoxyphenyl, 4-(acetamido)-3-chlorophenyl, 3-fluoro-4-methoxyphenyl, 3-amino-6-methylphenyl or 4-chloro-2,5-dimethylphenyl;

Het1 denotes 2-furanyl, 3-furanyl, 2-thiophenyl, 3-thiophenyl, 1-pyrrolyl, 2-pyrrolyl, 3-pyrrolyl, 1-imidazolyl, 2-imidazolyl, 4-imidazolyl, 5-imidazolyl, 1-pyrazolyl, 3-pyrazolyl, 4-pyrazolyl, 5-pyrazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,2,3-triazol-1-yl, 1,2,3-triazol-4-yl, 1,2,3-triazol-5-yl, 1,2,4-triazol-1-yl, 1,2,4-triazol-3-yl, 1,2,4-triazol-5-yl, 1-tetrazolyl, 5-tetrazolyl, 1,2,3-oxadiazol-4-yl, 1,2,3-oxadiazol-5-yl, 1,2,4-oxadiazol-3-yl, 1,2,4-oxadiazol-5-yl, 1,3,4-thiadiazol-2-yl, 1,3,4-thiadiazol-5-yl, 1,2,4-thiadiazol-3-yl, 1,2,4-thiadiazol-5-yl, 1,2,3-thiadiazol-4-yl, 1,2,3-thiadiazol-5-yl, 2,3-dihydro-2-furanyl, 2,3-dihydro-3-furanyl, 2,3-dihydro-4-furanyl, 2,3-dihydro-5-furanyl, 2,5-dihydro-2-furanyl, 2,5-dihydro-3-furanyl, 2,5-dihydro-4-furanyl, 2,5-dihydro-5-furanyl, 2-tetrahydrofuranyl, 3-tetrahydrofuranyl, 2-tetrahydrothiophenyl, 3-tetrahydrothiophenyl, 1,3-dioxolan-4-yl, 2,3-dihydro-1-pyrrolyl, 2,3-dihydro-2-pyrrolyl, 2,3-dihydro-3-pyrrolyl, 2,3-dihydro-4-pyrrolyl, 2,3-dihydro-5-pyrrolyl, 2,5-dihydro-1-pyrrolyl, 2,5-dihydro-2-pyrrolyl, 2,5-dihydro-3-pyrrolyl, 2,5-dihydro-4-pyrrolyl, 2,5-dihydro-5-pyrrolyl, 1-pyrrolidinyl, 2-pyrrolidinyl, 3-pyrrolidinyl, 1-tetrahydroimidazolyl, 2-tetrahydroimidazolyl, 4-tetrahydroimidazolyl, 1-tetrahydropyrazolyl, 3-tetrahydropyrazolyl, 4-tetrahydropyrazolyl, 2,3-dihydro-1-pyrazolyl, 2,3-dihydro-2-pyrazolyl, 2,3-dihydro-3-pyrazolyl, 2,3-dihydro-4-pyrazolyl, 2,3-dihydro-5-pyrazolyl, 2-pyridinyl, 3-pyridinyl, 4-pyridinyl, 2-pyrimidinyl, 4-pyrimidinyl, 5-pyrimidinyl, 6-pyrimidinyl, 3-pyridazinyl, 4-pyridazinyl, pyrazinyl, 1,4-dihydro-1-pyridinyl, 1,4-dihydro-2-pyridinyl, 1,4-dihydro-3-pyridinyl, 1,4-dihydro-4-pyridinyl, 1,2,3,4-tetrahydro-1-pyridinyl, 1,2,3,4-tetrahydro-2-pyridinyl, 1,2,3,4-tetrahydro-3-pyridinyl, 1,2,3,4-tetrahydro-4-pyridinyl, 1,2,3,4-tetrahydro-5-pyridinyl, 1,2,3,4-tetrahydro-6-pyridinyl, 1-piperidinyl, 2-piperidinyl, 3-piperidinyl, 4-piperidinyl, 2-tetrahydropyranyl, 3-tetrahydropyranyl, 4-tetrahydropyranyl, 2-morpholinyl, 3-morpholinyl, 4-morpholinyl, 1,4-dioxanyl, 1,3-dioxan-2-yl, 1,3-dioxan-4-yl, 1,3-dioxan-5-yl, 1-hexahydropyridazinyl, 3-hexahydropyridazinyl, 4-hexahydropyridazinyl, 1-hexahydropyrimidinyl, 2-hexahydropyrimidinyl, 4-hexahydropyrimidinyl, 5-hexahydropyrimidinyl, 1-piperazinyl, 2-piperazinyl or 3-piperazinyl, each optionally and independently substituted by 1 or 2 substituents selected from F, Cl, $CH_3$, $CH_2CH_3$, $CF_3$, $OCH_3$, $OCH_2CH_3$, $SCH_3$, $SCH_2CH_3$, $N(CH_3)_2$, $NHCH_3$, $CH_2N(CH_3)_2$ or $N(CH_2CH_3)_2$;

Cyc denotes 1-naphthalenyl or 2-naphthalenyl, each optionally and independently substituted by 1 or 2 substituents selected from Hal, CN, $R^{3a}$, $OR^{3a}$, $C(O)NHR^{4b}$, $NR^{3a}C(O)R^{3b}$, $S(O)_2R^{3a}$, $S(O)R^{3a}$, $NR^{4a}R^{4b}$, $(CH_2)_rSR^{3a}$, $(CH_2)_rN(R^{4a})_2$ or $(CH_2)_rA2$; or Cyc denotes formula (Fa7), formula (Fb7) or (S)-formula (Fb7):

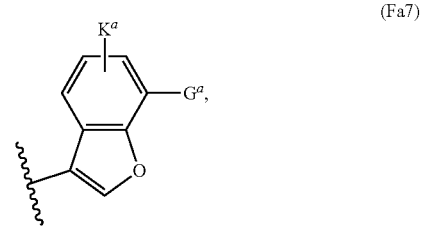

(Fa7)

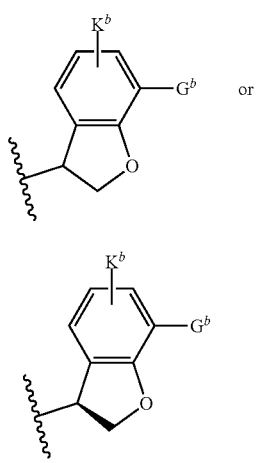

(Fb7)

or

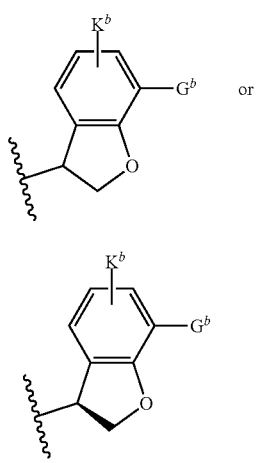

(S)-(Fb7)

wherein:
G$^a$ denotes F, Cl, Br, CN, R$^{3a}$, OR$^{3a}$, C(O)NR$^{3a}$R$^{3b}$, C(O)NHR$^{3a}$, C(O)NH$_2$, NR$^{3a}$C(O)R$^{3b}$, S(O)$_2$R$^{3a}$, S(O)R$^{3a}$, NHR$^{3a}$, N(R$^{3a}$)$_2$, (CH$_2$)$_r$SR$^{3a}$, (CH$_2$)$_r$N(R$^{4a}$)$_2$ or (CH$_2$)$_r$A2;
G$^b$ denotes H, F, Cl, Br, CN, R$^{3a}$, OR$^{3a}$, C(O)NR$^{3a}$R$^{3b}$, C(O)NHR$^{3a}$, C(O)NH$_2$, NR$^{3a}$C(O)R$^{3b}$, S(O)$_2$R$^{3a}$, S(O)R$^{3a}$, NHR$^{3a}$, N(R$^{3a}$)$_2$, (CH$_2$)$_r$SR$^{3a}$, (CH$_2$)$_r$N(R$^{4a}$)$_2$ or (CH$_2$)$_r$A2;
K$^a$ and K$^b$ each independently denote H, F, Cl, Br, CN, R$^{3a}$, OR$^{3a}$, C(O)NR$^{3a}$R$^{3b}$, C(O)NHR$^{3a}$, C(O)NH$_2$, NR$^{3a}$C(O)R$^{3b}$, S(O)$_2$R$^{3a}$, S(O)R$^{3a}$, NHR$^{3a}$, N(R$^{3a}$)$_2$, (CH$_2$)$_r$SR$^{3a}$, (CH$_2$)$_r$N(R$^{4a}$)$_2$ or (CH$_2$)$_r$A2; and
r denotes 1, 2, 3 or 4.

10. The compound according to claim 1, wherein the compound is represented by formula (R)-(Ia):

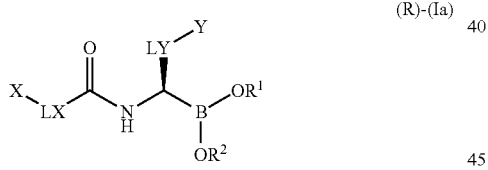

(R)-(Ia)

or a stereoisomer, tautomer or pharmaceutically acceptable salt thereof,
wherein:
LX denotes —CH$_2$— or —OCH$_2$—, where 1, 2, 3 or 4 H atoms may be independently replaced by F or Cl or where 1 or 2 H atoms may be independently replaced by OH, CH$_3$, CH$_2$CH$_3$, CH(CH$_3$)$_2$, CF$_3$, CF$_2$CF$_3$, OCH$_3$, OCH$_2$CH$_3$, O(CH$_2$)$_2$OH or O(CH$_2$)$_2$OCH$_3$;
X denotes phenyl, pyridinyl, pyridazinyl, pyrazinyl or triazinyl, each optionally and independently substituted by 1, 2 or 3 substituents selected from CH$_3$, CH$_2$CH$_3$, CH(CH$_3$)$_2$, CF$_3$, CF$_2$CF$_3$, CN, C(O)morpholinyl, C(O)piperazinyl, C(O)N(CH$_3$)$_2$, C(O)N(CH$_2$CH$_3$)$_2$, OH, OCH$_3$, OCH$_2$CH$_3$, O(CH$_2$)$_2$OH, O(CH$_2$)$_2$OCH$_3$ or CH$_2$OCH$_3$;
R$^1$ and R$^2$ each independently denote H or C1-C4 alkyl; or
R$^1$ and R$^2$, together with the oxygen atoms to which they are attached, form a residue according to formula (CE):

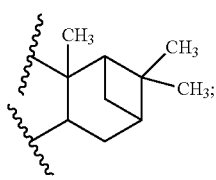

(CE)

R$^{3a}$ and R$^{3b}$ each independently denote linear or branched C1-C3 alkyl, where 1, 2, 3, 4 or 5 H atoms may be independently replaced by F, Cl, OH or OAlk;
A1 denotes ethyl, n-propyl, isopropyl, n-butyl, isobutyl, sec-butyl, tert-butyl, n-pentyl, 1-methylbutyl, 2-methylbutyl, isopentyl, 1,1-dimethylpropyl, 1,2-dimethylpropyl, neopentyl, 1-ethylpropyl, n-hexyl, 1-methylpentyl, 2-methylpentyl, 3-methylpentyl, isohexyl, 1,1-dimethylbutyl, 1,2-dimethylbutyl, 1,3-dimethylbutyl, 2,2-dimethylbutyl, 2,3-dimethylbutyl, neohexyl, 1-ethylbutyl, 2-ethylbutyl, 1-ethyl-1-methylpropyl or 1-ethyl-2-methylpropyl;
A2 denotes OH, OCH$_3$, OCH$_2$CH$_3$, OCF$_3$, O(CH$_2$)$_{20}$H or O(CH$_2$)$_2$OCH$_3$;
Alk denotes methyl or ethyl;
Cyc denotes 1-naphthalenyl or 2-naphthalenyl, each optionally and independently substituted by 1 or 2 substituents selected from Hal, CN, R$^{3a}$, OR$^{3a}$, C(O)NHR$^{4b}$, NR$^{3a}$C(O)R$^{3b}$, S(O)$_2$R$^{3a}$, S(O)R$^{3a}$, NR$^{4a}$R$^{4b}$, (CH$_2$)$_r$SR$^{3a}$ or (CH$_2$)$_r$N(R$^{4a}$)$_2$; or
Cyc denotes formula (Fa7) or (S)-formula (Fb7):

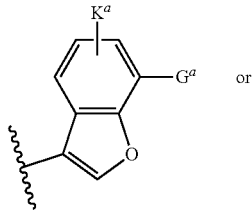

(Fa7)

or

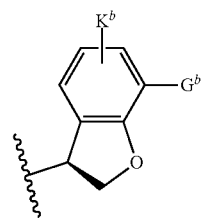

(S)-(Fb7)

wherein:
G$^a$ denotes F, Cl, CH$_3$, CH$_2$CH$_3$, CF$_3$, OCH$_3$, OCH$_2$CH$_3$, SCH$_3$, SCH$_2$CH$_3$, CH$_2$OCH$_3$, N(CH$_3$)$_2$, CH$_2$N(CH$_3$)$_2$ or N(CH$_2$CH$_3$)$_2$;
G$^b$ denotes H, F, Cl, CH$_3$, CH$_2$CH$_3$, CF$_3$, OCH$_3$, OCH$_2$CH$_3$, SCH$_3$, SCH$_2$CH$_3$, CH$_2$OCH$_3$, N(CH$_3$)$_2$, CH$_2$N(CH$_3$)$_2$ or N(CH$_2$CH$_3$)$_2$;
K$^a$ and K$^b$ each independently denote H, F, Cl, CH$_3$, CH$_2$CH$_3$, CF$_3$, OCH$_3$, OCH$_2$CH$_3$, SCH$_3$, SCH$_2$CH$_3$, CH$_2$OCH$_3$, N(CH$_3$)$_2$, CH$_2$N(CH$_3$)$_2$ or N(CH$_2$CH$_3$)$_2$; and
r denotes 1, 2, 3 or 4.

11. The compound according to claim 1, or a stereoisomer, tautomer or pharmaceutically acceptable salt thereof, wherein Cyc is optionally substituted by 1 or 2 substituents selected from Hal, $R^{3a}$ or $OR^{3a}$.

12. The compound according to claim 1, or a stereoisomer, tautomer or pharmaceutically acceptable salt thereof, wherein Cyc is optionally substituted by 1 or 2 substituents selected from F, Cl, $CH_3$, $CF_3$, $CH_2CH_3$, $CF_2CF_3$, $OCH_3$, $OCF_3$, $OCH_2CH_3$ or $OCF_2CF_3$.

13. A pharmaceutical composition comprising a pharmaceutically acceptable carrier and at least one compound according to claim 2, or a stereoisomer, tautomer or pharmaceutically acceptable salt thereof, as active ingredient.

14. The pharmaceutical composition according to claim 13, wherein the pharmaceutical composition further comprises a second active ingredient.

15. A kit consisting of separate packs of an effective amount of at least one compound according to claim 1, or a stereoisomer, tautomer or pharmaceutically acceptable salt thereof, and an effective amount of a second active ingredient.

16. A method for inhibiting large multifunctional protease 7 activity in a subject, comprising administering to a subject in need thereof a therapeutically effective amount of a compound according to claim 1, or a stereoisomer, tautomer or pharmaceutically acceptable salt thereof.

17. The method according to claim 16, wherein the subject has a medical condition that is affected by inhibiting large multifunctional protease 7 activity.

18. The method according to claim 17, wherein the medical condition that is affected by inhibiting large multifunctional protease 7 activity is selected from the group consisting of an immunoregulatory abnormality and a hematological malignancy.

19. The method according to claim 18, wherein the immunoregulatory abnormality is an autoimmune disease or chronic inflammatory disease selected from the group consisting of systemic lupus erythematosis, rheumatoid arthritis, inflammatory bowel disease, multiple sclerosis, amyotrophic lateral sclerosis, atherosclerosis, scleroderma, autoimmune hepatitis, Sjögren's syndrome, lupus nephritis, glomerulonephritis, psoriasis, myasthenia gravis, immunoglobulin A nephropathy, vasculitis, transplant rejection, myositis, Henoch-Schonlein purpura and asthma.

20. The method according to claim 18, wherein the hematological malignancy is a disease selected from the group consisting of multiple myeloma, chronic lymphoid leukemia, acute myeloid leukemia and mantle cell lymphoma.

21. A process for the preparation of a compound of formula (I):

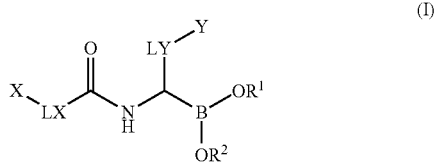

wherein the compound of formula (I) is represented by formula (Ia) and/or formula (Ib):

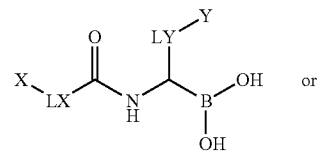

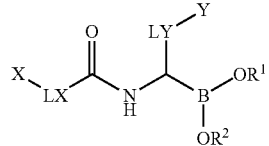

wherein:
LX denotes $-CH_2-$, $-O(CH_2)_n-$, $-S(CH_2)_p-$ or $-(CH_2)_pS-$, where 1, 2, 3, 4 or 5 H atoms may be independently replaced by Hal, $N_3$, $R^{3a}$, $OR^{4a}$, $(CH_2)_rA2$, $(CH_2)_rAr2$ or $(CH_2)_rHet2$;

LY denotes $-CH_2-$;

X denotes an aromatic 6-membered carbocyclyl or aromatic 6-membered heterocyclyl, each optionally and independently substituted by 1, 2, 3, 4 or 5 substituents selected from Hal, A1, $N_3$, CN, OH, $NR^{4a}R^{4b}$Ar1, Het1, OA1, OAr1, OHet1, C(O)A1, C(O)Ar1, C(O)Het1, $C(O)NR^{4a}R^{4b}$, $NR^{4a}C(O)R^{3a}$, $NR^{4a}S(O)_2R^{3a}$, $S(O)_2R^{3a}$, $S(O)R^{3a}$, $NR^{4a}C(O)_2R^{3a}$, $OC(O)NR^{3a}R^{4a}$, $O(CH_2)_qA1$, $(CH_2)_rSR^{3a}$, $(CH_2)_rN(R^{4a})_2$ or $(CH_2)_rA2$;

Y denotes Cyc;

$R^1$ and $R^2$ each independently denote C1-C6 alkyl; or $R^1$ and $R^2$, together with the oxygen atoms to which they are attached, form a residue according to formula (CE):

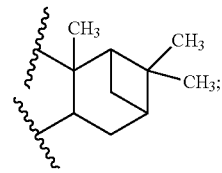

$R^{3a}$ and $R^{3b}$ each independently denote linear or branched C1-C6 alkyl, where 1, 2, 3, 4 or 5 H atoms may be independently replaced by Hal, OH or OAlk;

$R^{4a}$ and $R^{4b}$ each independently denote H or $R^{3a}$; or $R^{4a}$ and $R^{4b}$, together with the nitrogen atom to which they are attached, form a nitrogen-containing heterocyclyl comprising 3, 4, 5 or 6 carbon atoms;

A1 denotes linear or branched C1-C6 alkyl or C3-C6 cycloalkyl, each optionally and independently substituted by 1, 2, 3, 4 or 5 substituents selected from Hal, CN, $R^{3a}$, $SR^{3a}$, $OR^{4a}$ or $(CH_2)_rA2$, where 1, 2 or 3 $CH_2$ groups of C3-C6 cycloalkyl may be independently replaced by O, C(O) or N;

A2 denotes $OR^{4a}$;

Alk denotes linear or branched C1-C6 alkyl;

Ar1 denotes phenyl, optionally substituted by 1, 2 or 3 substituents selected from Hal, $NO_2$, CN, $R^{3a}OR^{4a}$, $C(O)NR^{4a}R^{4b}$, $NR^{4a}C(O)R^{3b}$, $S(O)_2R^{3a}$, $S(O)R^{3a}$, $NR^{4a}R^{4b}$, Ar2, Het2 or $(CH_2)_rA2$;

Het1 denotes a saturated, unsaturated or aromatic 5- or 6-membered heterocyclyl comprising 1, 2, 3 or 4 heteroatoms independently selected from the group consisting of N, O and S, where each heterocyclyl may be optionally and independently substituted by 1, 2, 3, 4 or 5 substituents selected from Hal, $NO_2$, CN, $R^{3a}$, $OR^{4a}$, $C(O)NR^{4a}R^{4b}$, $NR^{4a}C(O)R^{3b}$, $S(O)_2R^{3a}$, $S(O)R^{3a}$, $NR^{4a}R^{4b}$, Ar2, Het2 or $(CH_2)_rA2$;

Ar2 denotes phenyl, biphenyl or naphthyl, each optionally and independently substituted by 1, 2 or 3 substituents selected from Hal, CN, $R^{3a}$, $OR^{4a}$, $C(O)NR^{4a}R^{4b}$, $NR^{4a}C(O)R^{3b}$, $S(O)_2R^{3a}$, $S(O)R^{3a}$, $NR^{4a}R^{4b}$ or $(CH_2)_qA2$;

Het2 denotes a saturated, unsaturated or aromatic 5- or 6-membered heterocyclyl comprising 1, 2, 3 or 4 heteroatoms independently selected from the group consisting of N, O and S, optionally substituted by 1, 2 or 3 substituents selected from Hal, CN, $R^{3a}$, $OR^{4a}$, $C(O)NHR^{3a}$, $NR^{3a}C(O)R^{3b}$, $S(O)_2R^{3a}$, $S(O)R^{3a}$, $NR^{4a}R^{4b}$ or $(CH_2)_qA2$;

Cyc denotes a monocyclic or bicyclic, 4-, 5-, 6-, 7-, 8-, 9- or 10-membered carbocyclyl or heterocyclyl, each optionally and independently substituted by 1, 2, 3, 4 or 5 substituents selected from Hal, CN, $R^{3a}$, $OR^{3a}$, $C(O)NR^{4a}R^{4b}$, $NR^{3a}C(O)R^{3b}$, $S(O)_2R^{3a}$, $S(O)R^{3a}$, $NR^{4a}R^{4b}$, Ar2, Het2, $(CH_2)_rSR^{3a}$, $(CH_2)_rN(R^{4a})_2$ or $(CH_2)_rA2$, where the monocyclic carbocyclyl is aromatic and at least one ring of the bicyclic carbocyclyl or heterocyclyl is aromatic, and further where the heterocyclyl comprises 1, 2 or 3 heteroatoms independently selected from the group consisting of N, O and S;

n denotes 1, 2, 3, 4, 5 or 6;
p denotes 1, 2, 3, 4, 5 or 6;
q denotes 0, 1, 2, 3 or 4;
r denotes 0, 1, 2, 3 or 4; and
Hal denotes F, Cl, Br or I;
with the proviso that when LX denotes $-O(CH_2)_n-$, the oxygen atom of LX is bonded to X;

wherein the process comprises the following steps:
(i) reacting a compound of formula (III):

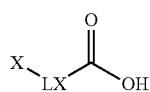

(III)

wherein:
LX denotes $-CH_2-$, $-O(CH_2)_n-$, $-S(CH_2)_p-$ or $-(CH_2)_pS-$, where 1, 2, 3, 4 or 5 H atoms may be independently replaced by Hal, $N_3$, $R^{3a}$, $OR^{4a}$, $(CH_2)_rA2$, $(CH_2)_rAr2$ or $(CH_2)_rHet2$;

X denotes an aromatic 6-membered carbocyclyl or aromatic 6-membered heterocyclyl, each optionally and independently substituted by 1, 2, 3, 4 or 5 substituents selected from Hal, A1, $N_3$, CN, OH, $NR^{4a}R^{4b}$, Ar1, Het1, OA1, OAr1, OHet1, C(O)A1, C(O)Ar1, C(O)Het1, $C(O)NR^{4a}R^{4b}$, $NR^{4a}C(O)R^{3a}$, $NR^{4a}S(O)_2R^{3a}$, $S(O)_2R^{3a}$, $S(O)R^{3a}$, $NR^{4a}C(O)_2R^{3a}$, $OC(O)NR^{3a}R^{4a}$, $O(CH_2)_qA1$, $(CH_2)_rSR^{3a}$, $(CH_2)_rN(R^{4a})_2$ or $(CH_2)_rA2$;

$R^{3a}$ and $R^{3b}$ each independently denote linear or branched C1-C6 alkyl, where 1, 2, 3, 4 or 5 H atoms may be independently replaced by Hal, OH or OAlk;

$R^{4a}$ and $R^{4b}$ each independently denote H or $R^{3a}$; or $R^{4a}$ and $R^{4b}$, together with the nitrogen atom to which they are attached, form a nitrogen-containing heterocyclyl comprising 3, 4, 5 or 6 carbon atoms;

A2 denotes $OR^{4a}$;
Alk denotes linear or branched C1-C6 alkyl;

Ar2 denotes phenyl, biphenyl or naphthyl, each optionally and independently substituted by 1, 2 or 3 substituents selected from Hal, CN, $R^{3a}$, $OR^{4a}$, $C(O)NR^{4a}R^{4b}$, $NR^{4a}C(O)R^{3b}$, $S(O)_2R^{3a}$, $S(O)R^{3a}$, $NR^{4a}R^{4b}$ or $(CH_2)_qA2$;

Het2 denotes a saturated, unsaturated or aromatic 5- or 6-membered heterocyclyl comprising 1, 2, 3 or 4 heteroatoms independently selected from the group consisting of N, O and S, optionally substituted by 1, 2 or 3 substituents selected from Hal, CN, $R^{3a}$, $OR^{4a}$, $C(O)NHR^{3a}$, $NR^{3a}C(O)R^{3b}$, $S(O)_2R^{3a}$, $S(O)R^{3a}$, $NR^{4a}R^{4b}$ or $(CH_2)_qA2$;

n denotes 1, 2, 3, 4, 5 or 6;
p denotes 1, 2, 3, 4, 5 or 6;
q denotes 0, 1, 2, 3 or 4;
r denotes 0, 1, 2, 3 or 4; and
Hal denotes F, Cl, Br or I;
with the proviso that when LX denotes $-O(CH_2)_n-$, the oxygen atom of LX is bonded to X;

with a compound of formula (IV):

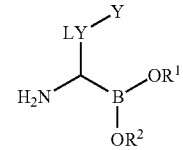

(IV)

wherein:
LY denotes $-CH_2-$;
Y denotes Cyc;
$R^1$ and $R^2$ each independently denote C1-C6 alkyl; or $R^1$ and $R^2$, together with the oxygen atoms to which they are attached, form a residue according to formula (CE):

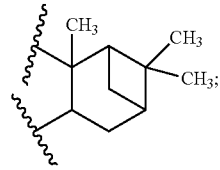

(CE)

$R^{3a}$ and $R^{3b}$ each independently denote linear or branched C1-C6 alkyl, where 1, 2, 3, 4 or 5 H atoms may be independently replaced by Hal, OH or OAlk;

$R^{4a}$ and $R^{4b}$ each independently denote H or $R^{3a}$; or $R^{4a}$ and $R^{4b}$, together with the nitrogen atom to which they are attached, form a nitrogen-containing heterocyclyl comprising 3, 4, 5 or 6 carbon atoms;

A2 denotes $OR^{4a}$;

Ar2 denotes phenyl, biphenyl or naphthyl, each optionally and independently substituted by 1, 2 or 3 substituents selected from Hal, CN, $R^{3a}$, $OR^{4a}$, $C(O)NR^{4a}R^{4b}$, $NR^{4a}C(O)R^{3b}$, $S(O)_2R^{3a}$, $S(O)R^{3a}$, $NR^{4a}R^{4b}$ or $(CH_2)_qA2$;

Het2 denotes a saturated, unsaturated or aromatic 5- or 6-membered heterocyclyl comprising 1, 2, 3 or 4 heteroatoms independently selected from the group consisting of N, O and S, optionally substituted by 1, 2 or 3 substituents selected from Hal, CN, $R^{3a}$, $OR^{4a}$, $C(O)NHR^{3a}$, $NR^{3a}C(O)R^{3b}$, $S(O)_2R^{3a}$, $S(O)R^{3a}$, $NR^{4a}R^{4b}$ or $(CH_2)_qA2$;

Cyc denotes a monocyclic or bicyclic, 4-, 5-, 6-, 7-, 8-, 9- or 10-membered carbocyclyl or heterocyclyl, each optionally and independently substituted by 1, 2, 3, 4 or 5 substituents selected from Hal, CN, $R^{3a}$, $OR^{3a}$, $C(O)NR^{4a}R^{4b}$, $NR^{3a}C(O)R^{3b}$, $S(O)_2R^{3a}$, $S(O)R^{3a}$, $NR^{4a}R^{4b}$, Ar2, Het2, $(CH_2)_rSR^{3a}$, $(CH_2)_rN(R^{4a})_2$ or $(CH_2)_rA2$, where the monocyclic carbocyclyl is aromatic and at least one ring of the bicyclic carbocyclyl or heterocyclyl is aromatic, and further where the heterocyclyl comprises 1, 2 or 3 heteroatoms independently selected from the group consisting of N, O and S;

q denotes 0, 1, 2, 3 or 4;

r denotes 0, 1, 2, 3 or 4; and

Hal denotes F, Cl, Br or I;

to provide a compound of formula (Ib):

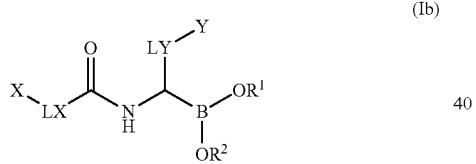

(Ib)

wherein:

LX denotes —$CH_2$—, —$O(CH_2)_n$—, —$S(CH_2)_p$— or —$(CH_2)_pS$—, where 1, 2, 3, 4 or 5 H atoms may be independently replaced by Hal, $N_3$, $R^{3a}$, $OR^{4a}$, $(CH_2)_rA2$, $(CH_2)_rAr2$ or $(CH_2)_rHet2$;

LY denotes —$CH_2$—;

X denotes an aromatic 6-membered carbocyclyl or aromatic 6-membered heterocyclyl, each optionally and independently substituted by 1, 2, 3, 4 or 5 substituents selected from Hal, A1, $N_3$, CN, OH, $NR^{4a}R^{4b}$, Ar1, Het1, OA1, OAr1, OHet1, C(O)A1, C(O)Ar1, C(O)Het1, $C(O)NR^{4a}R^{4b}$, $NR^{4a}C(O)R^{3a}$, $NR^{4a}S(O)_2R^{3a}$, $S(O)_2R^{3a}$, $S(O)R^{3a}$, $NR^{4a}C(O)_2R^{3a}$, $OC(O)NR^{3a}R^{4a}$, $O(CH_2)_qA1$, $(CH_2)_rSR^{3a}$, $(CH_2)_rN(R^{4a})_2$ or $(CH_2)_rA2$;

Y denotes Cyc;

$R^1$ and $R^2$ each independently denote C1-C6 alkyl; or $R^1$ and $R^2$, together with the oxygen atoms to which they are attached, form a residue according to formula (CE):

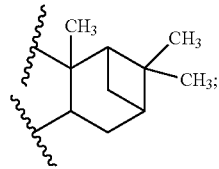

(CE)

$R^{3a}$ and $R^{3b}$ each independently denote linear or branched C1-C6 alkyl, where 1, 2, 3, 4 or 5 H atoms may be independently replaced by Hal, OH or OAlk;

$R^{4a}$ and $R^{4b}$ each independently denote H or $R^{3a}$; or $R^{4a}$ and $R^{4b}$, together with the nitrogen atom to which they are attached, form a nitrogen-containing heterocyclyl comprising 3, 4, 5 or 6 carbon atoms;

A1 denotes linear or branched C1-C6 alkyl or C3-C6 cycloalkyl, each optionally and independently substituted by 1, 2, 3, 4 or 5 substituents selected from Hal, CN, $R^{3a}$, $SR^{3a}$, $OR^{4a}$ or $(CH_2)_rA2$, where 1, 2 or 3 $CH_2$ groups of C3-C6 cycloalkyl may be independently replaced by O, C(O) or N;

A2 denotes $OR^{4a}$;

Alk denotes linear or branched C1-C6 alkyl;

Ar1 denotes phenyl, optionally substituted by 1, 2 or 3 substituents selected from Hal, $NO_2$, CN, $R^{3a}$, $OR^{4a}$, $C(O)NR^{4a}R^{4b}$, $NR^{4a}C(O)R^{3b}$, $S(O)_2R^{3a}$, $S(O)R^{3a}$, $NR^{4a}R^{4b}$, Ar2, Het2 or $(CH_2)_rA2$;

Het1 denotes a saturated, unsaturated or aromatic 5- or 6-membered heterocyclyl comprising 1, 2, 3 or 4 heteroatoms independently selected from the group consisting of N, O and S, where each heterocyclyl may be optionally and independently substituted by 1, 2, 3, 4 or 5 substituents selected from Hal, $NO_2$, CN, $R^{3a}$, $OR^{4a}$, $C(O)NR^{4a}R^{4b}$, $NR^{4a}C(O)R^{3b}$, $S(O)_2R^{3a}$, $S(O)R^{3a}$, $NR^{4a}R^{4b}$, Ar2, Het2 or $(CH_2)_rA2$;

Ar2 denotes phenyl, biphenyl or naphthyl, each optionally and independently substituted by 1, 2 or 3 substituents selected from Hal, CN, $R^{3a}$, $OR^{4a}$, $C(O)NR^{4a}R^{4b}$, $NR^{4a}C(O)R^{3b}$, $S(O)_2R^{3a}$, $S(O)R^{3a}$, $NR^{4a}R^{4b}$ or $(CH_2)_qA2$;

Het2 denotes a saturated, unsaturated or aromatic 5- or 6-membered heterocyclyl comprising 1, 2, 3 or 4 heteroatoms independently selected from the group consisting of N, O and S, optionally substituted by 1, 2 or 3 substituents selected from Hal, CN, $R^{3a}$, $OR^{4a}$, $C(O)NHR^{3a}$, $NR^{3a}C(O)R^{3b}$, $S(O)_2R^{3a}$, $S(O)R^{3a}$, $NR^{4a}R^{4b}$ or $(CH_2)_qA2$;

Cyc denotes a monocyclic or bicyclic, 4-, 5-, 6-, 7-, 8-, 9- or 10-membered carbocyclyl or heterocyclyl, each optionally and independently substituted by 1, 2, 3, 4 or 5 substituents selected from Hal, CN, $R^{3a}$, $OR^{3a}$, $C(O)NR^{4a}R^{4b}$, $NR^{3a}C(O)R^{3b}$, $S(O)_2R^{3a}$, $S(O)R^{3a}$, $NR^{4a}R^{4b}$, Ar2, Het2, $(CH_2)_rSR^{3a}$, $(CH_2)_rN(R^{4a})_2$ or $(CH_2)_rA2$, where the monocyclic carbocyclyl is aromatic and at least one ring of the bicyclic carbocyclyl or heterocyclyl is aromatic, and further where the heterocyclyl comprises 1, 2 or 3 heteroatoms independently selected from the group consisting of N, O and S;

n denotes 1, 2, 3, 4, 5 or 6;
p denotes 1, 2, 3, 4, 5 or 6;
q denotes 0, 1, 2, 3 or 4;
r denotes 0, 1, 2, 3 or 4; and
Hal denotes F, Cl, Br or I;
with the proviso that when LX denotes —O(CH$_2$)$_n$—, the oxygen atom of LX is bonded to X; and (ii) reacting the compound of formula (Ib) above with an acid selected from the group consisting of hydrochloric acid, hydrobromic acid, hydroiodic acid and trifluoroacetic acid, or a combination thereof, optionally in the presence of an excess of a small molecular weight boronic acid, to provide a compound of formula (Ia):

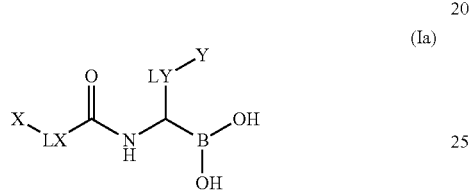

(Ia)

wherein:
LX denotes —CH$_2$—, —O(CH$_2$)$_n$—, —S(CH$_2$)$_p$— or —(CH$_2$)$_p$S—, where 1, 2, 3, 4 or 5 H atoms may be independently replaced by Hal, N$_3$, R$^{3a}$, OR$^{4a}$, (CH$_2$)$_r$A2, (CH$_2$)$_r$Ar2 or (CH$_2$)$_r$Het2;
LY denotes —CH$_2$—;
X denotes an aromatic 6-membered carbocyclyl or aromatic 6-membered heterocyclyl, each optionally and independently substituted by 1, 2, 3, 4 or 5 substituents selected from Hal, A1, N$_3$, CN, OH, NR$^{4a}$R$^{4b}$, Ar1, Het1, OA1, OAr1, OHet1, C(O)A1, C(O)Ar1, C(O)Het1, C(O)NR$^{4a}$R$^{4b}$, NR$^{4a}$C(O)R$^{3a}$, NR$^{4a}$S(O)$_2$R$^{3a}$, S(O)$_2$R$^{3a}$, S(O)R$^{3a}$, NR$^{4a}$C(O)$_2$R$^{3a}$, OC(O)NR$^{3a}$R$^{4a}$, O(CH$_2$)$_q$A1, (CH$_2$)$_r$SR$^{3a}$, (CH$_2$)$_r$N(R$^{4a}$)$_2$ or (CH$_2$)$_r$A2;
Y denotes Cyc;
R$^{3a}$ and R$^{3b}$ each independently denote linear or branched C1-C6 alkyl, where 1, 2, 3, 4 or 5 H atoms may be independently replaced by Hal, OH or OAlk;
R$^{4a}$ and R$^{4b}$ each independently denote H or R$^{3a}$; or
R$^{4a}$ and R$^{4b}$, together with the nitrogen atom to which they are attached, form a nitrogen-containing heterocyclyl comprising 3, 4, 5 or 6 carbon atoms;
A1 denotes linear or branched C1-C6 alkyl or C3-C6 cycloalkyl, each optionally and independently substituted by 1, 2, 3, 4 or 5 substituents selected from Hal, CN, R$^{3a}$, SR$^{3a}$, OR$^{4a}$ or (CH$_2$)$_r$A2, where 1, 2 or 3 CH$_2$ groups of C3-C6 cycloalkyl may be independently replaced by O, C(O) or N;
A2 denotes OR$^{4a}$;
Alk denotes linear or branched C1-C6 alkyl;
Ar1 denotes phenyl, optionally substituted by 1, 2 or 3 substituents selected from Hal, NO$_2$, CN, R$^{3a}$, OR$^{4a}$, C(O)NR$^{4a}$R$^{4b}$, NR$^{4a}$C(O)R$^{3b}$, S(O)$_2$R$^{3a}$, S(O)R$^{3a}$, NR$^{4a}$R$^{4b}$, Ar2, Het2 or (CH$_2$)$_r$A2;
Het1 denotes a saturated, unsaturated or aromatic 5- or 6-membered heterocyclyl comprising 1, 2, 3 or 4 heteroatoms independently selected from the group consisting of N, O and S, where each heterocyclyl may be optionally and independently substituted by 1, 2, 3, 4 or 5 substituents selected from Hal, NO$_2$, CN, R$^{3a}$, OR$^{4a}$, C(O)NR$^{4a}$R$^{4b}$, NR$^{4a}$C(O)R$^{3b}$, S(O)$_2$R$^{3a}$, S(O)R$^{3a}$, NR$^{4a}$R$^{4b}$, Ar2, Het2 or (CH$_2$)$_r$A2;
Ar2 denotes phenyl, biphenyl or naphthyl, each optionally and independently substituted by 1, 2 or 3 substituents selected from Hal, CN, R$^{3a}$, OR$^{4a}$, C(O)NR$^{4a}$R$^{4b}$, NR$^{4a}$C(O)R$^{3b}$, S(O)$_2$R$^{3a}$, S(O)R$^{3a}$, NR$^{4a}$R$^{4b}$ or (CH$_2$)$_q$A2;
Het2 denotes a saturated, unsaturated or aromatic 5- or 6-membered heterocyclyl comprising 1, 2, 3 or 4 heteroatoms independently selected from the group consisting of N, O and S, optionally substituted by 1, 2 or 3 substituents selected from Hal, CN, R$^{3a}$, OR$^{4a}$, C(O)NHR$^{3a}$, NR$^{3a}$C(O)R$^{3b}$, S(O)$_2$R$^{3a}$, S(O)R$^{3a}$, NR$^{4a}$R$^{4b}$ or (CH$_2$)$_q$A2;
Cyc denotes a monocyclic or bicyclic, 4-, 5-, 6-, 7-, 8-, 9- or 10-membered carbocyclyl or heterocyclyl, each optionally and independently substituted by 1, 2, 3, 4 or 5 substituents selected from Hal, CN, R$^{3a}$, OR$^{3a}$, C(O)NR$^{4a}$R$^{4b}$, NR$^{3a}$C(O)R$^{3b}$, S(O)$_2$R$^{3a}$, S(O)R$^{3a}$, NR$^{4a}$R$^{4b}$, Ar2, Het2, (CH$_2$)$_r$SR$^{3a}$, (CH$_2$)$_r$N(R$^{4a}$)$_2$ or (CH$_2$)$_r$A2, where the monocyclic carbocyclyl is aromatic and at least one ring of the bicyclic carbocyclyl or heterocyclyl is aromatic, and further where the heterocyclyl comprises 1, 2 or 3 heteroatoms independently selected from the group consisting of N, O and S;
n denotes 1, 2, 3, 4, 5 or 6;
p denotes 1, 2, 3, 4, 5 or 6;
q denotes 0, 1, 2, 3 or 4;
r denotes 0, 1, 2, 3 or 4; and
Hal denotes F, Cl, Br or I;
with the proviso that when LX denotes —O(CH$_2$)$_n$—, the oxygen atom of LX is bonded to X.

22. A compound selected from the group consisting of:
[(1R)-1-[[2-[(3,5-dichloro-2-pyridyl)oxy]acetyl]amino]-2-phenyl-ethyl]boronic acid;
[(1R)-2-phenyl-1-[[2-(2-pyridyloxy)acetyl]amino]ethyl]boronic acid;
[(1R)-1-[(2-phenoxyacetyl)amino]-2-phenyl-ethyl]boronic acid;
[(1R)-1-(3-phenoxypropanoylamino)-2-(p-tolyl)ethyl]boronic acid;
[(1R)-1-[3-(4-methoxyphenoxy)propanoylamino]-2-(p-tolyl)ethyl]-boronic acid;
[(1R)-2-(benzofuran-3-yl)-1-[(2-phenylacetyl)amino]-ethyl]boronic acid;
[(1R)-2-(benzofuran-3-yl)-1-[3-(4-methylphenoxy)propanoylamino]-ethyl]boronic acid;
[(1R)-2-(benzofuran-3-yl)-1-[[2-(3-pyridyl)acetyl]amino]ethyl]-boronic acid;
[(1R)-2-(benzofuran-3-yl)-1-[[2-(4-cyanophenyl)acetyl]amino]ethyl]-boronic acid;
[(1R)-2-(benzofuran-3-yl)-1-[[2-(4-methoxyphenyl)acetyl]amino]-ethyl]boronic acid;

[(1R)-2-(benzofuran-3-yl)-1-[[2-(3-pyridyloxy)acetyl]amino]ethyl]-boronic acid;
[(1R)-2-(benzofuran-3-yl)-1-[[2-(6-methoxy-2-pyridyl)acetyl]amino]-ethyl]boronic acid;
[(1R)-2-(benzofuran-3-yl)-1-[[2-(5-ethoxy-2-pyridyl)acetyl]amino]-ethyl]boronic acid;
[(1R)-1-[(2-phenylacetyl)amino]-2-(p-tolyl)ethyl]boronic acid;
[(1R)-2-(benzofuran-3-yl)-1-[[2-(3-methoxyphenyl)acetyl]amino]-ethyl]boronic acid;
[(1R)-1-[[(2R)-2-hydroxy-2-phenyl-acetyl]amino]-2-(p-tolyl)ethyl]-boronic acid;
[(1R)-1-[[(2S)-2-hydroxy-2-phenyl-acetyl]amino]-2-(p-tolyl)ethyl]-boronic acid;
[(1R)-2-(benzofuran-3-yl)-1-[(2-pyrazin-2-ylacetyl)amino]ethyl]-boronic acid;
[(1R)-2-(benzofuran-3-yl)-1-[[2-(4-pyridyl)acetyl]amino]ethyl]-boronic acid;
[(1R)-2-(benzofuran-3-yl)-1-[(2-pyrimidin-2-ylacetyl)amino]ethyl]-boronic acid;
[(1R)-1-[[2-(4-acetamidophenyl)acetyl]amino]-2-(p-tolyl)ethyl]-boronic acid;
[(1R)-2-(benzofuran-3-yl)-1-[[2-(3,4,5-trifluorophenyl)acetyl]amino]-ethyl]boronic acid;
[(1R)-2-(benzofuran-3-yl)-1-[(2,2-difluoro-2-phenyl-acetyl)amino]-ethyl]boronic acid;
[(1R)-2-(benzofuran-3-yl)-1-[[2-[2-(trifluoromethyl)phenyl]acetyl]amino]ethyl]-boronic acid;
[(1R)-2-(benzofuran-3-yl)-1-[[2-(2,6-dichlorophenyl)acetyl]-amino]-ethyl]boronic acid;
[(1R)-[[2-(4-acetamidophenyl)acetyl]amino]-2-(benzofuran-3-yl)ethyl]boronic acid;
[(1R)-2-(benzofuran-3-yl)-1-[[2-(2-methoxyphenyl)acetyl]amino]-ethyl]boronic acid;
[(1R)-2-(benzofuran-3-yl)-1-[[2-[2-(trifluoromethoxy)phenyl]acetyl]amino]-ethyl]boronic acid;
[(1R)-2-(2,4-dimethylphenyl)-1-[(2-phenylacetyl)amino]ethyl]-boronic acid;
[(1R)-2-(benzofuran-3-yl)-1-[[2-[4-(methoxymethyl)phenyl]acetyl]amino]ethyl]-boronic acid;
[(1R)-2-(benzofuran-3-yl)-1-[[2-[3-(3-hydroxypropoxy)phenyl]acetyl]amino]ethyl]-boronic acid;
[(1R)-1-[[2-(3-acetamidophenyl)acetyl]amino]-2-(benzofuran-3-yl)ethyl]boronic acid;
[(1R)-2-(benzofuran-3-yl)-1-[[(2S)-2-methoxy-2-phenyl-acetyl]amino]ethyl]boronic acid;
[(1R)-2-(benzofuran-3-yl)-1-[[(2R)-2-methoxy-2-phenyl-acetyl]amino]ethyl]boronic acid;
[(1R)-2-(2,4-dimethylphenyl)-1-[[2-(2,6-dimethylphenyl)acetyl]-amino]ethyl]boronic acid;
[(1R)-2-(2,4-dimethylphenyl)-1-[(1-phenylcyclopropanecarbonyl)amino]ethyl]-boronic acid;
[(1R)-2-(benzofuran-3-yl)-1-[[(2S)-2-phenylpropanoyl]amino]-ethyl]-boronic acid;
[(1R)-1-[[2-(4-acetamidophenyl)acetyl]amino]-2-(2,4-dimethylphenyl)ethyl]boronic acid;
[(1R)-2-(benzofuran-3-yl)-1-[[2-[4-(2-hydroxyethoxy)phenyl]acetyl]amino]ethyl]-boronic acid;
[(1R)-2-(benzofuran-3-yl)-1-[[2-[4-(3-hydroxypropoxy)-phenyl]acetyl]amino]ethyl]-boronic acid;
[(1R)-2-(benzofuran-3-yl)-1-[[2-[3-(2-hydroxyethoxy)phenyl]acetyl]amino]ethyl]-boronic acid;
[(1R)-1-[[2-(2,6-dimethoxyphenyl)acetyl]amino]-2-(2,4-dimethylphenyl)ethyl]-boronic acid;
[(1R)-2-(2,4-dimethylphenyl)-1-[[2-[4-(2-oxopyrrolidin-1-yl)phenyl]acetyl]-amino]ethyl]boronic acid;
[(1R)-1-[[2-(4-dimethylaminophenyl)acetyl]amino]-2-(2,4-dimethylphenyl)ethyl]-boronic acid;
[(1R)-2-(benzofuran-3-yl)-1-[[(2R)-2-phenylpropanoyl]amino]ethyl]-boronic acid;
[(1R)-2-(2,4-dimethylphenyl)-1-[[2-[4-(methanesulfonamido)phenyl]acetyl]-amino]ethyl]boronic acid;
[(1R)-2-(2,4-dimethylphenyl)-1-[[2-[4-[(2-methoxyacetyl)amino]phenyl]acetyl]-amino]ethyl]-boronic acid;
[(1R)-2-(benzofuran-3-yl)-1-[[2-[2-(methoxymethyl)phenyl]acetyl]amino]ethyl]-boronic acid;
[(1R)-2-(benzofuran-3-yl)-1-[[2-[3-(methoxymethyl)phenyl]acetyl]-amino]ethyl]-boronic acid;
[(1R)-2-(benzofuran-3-yl)-1-[[2-[2-(2-hydroxyethoxy)phenyl]acetyl]amino]ethyl]-boronic acid;
[(1R)-2-(benzofuran-3-yl)-1-[[2,2-di fluoro-2-(4-methoxyphenyl)acetyl]amino]ethyl]-boronic acid;
[(1R)-2-(benzofuran-3-yl)-1-[[2-(3,4,5-trimethoxyphenyl)acetyl]amino]ethyl]-boronic acid;
[(1R)-2-(2,4-dimethylphenyl)-1-[[2-[4-[(2,2,2-trifluoroacetyl)amino]phenyl]amino]ethyl]boronic acid;
[(1R)-2-(benzofuran-3-yl)-1-[[2-(2-tetrahydropyran-4-yloxyphenyl)acetyl]amino]-ethyl]-boronic acid;
[(1R)-2-(benzofuran-3-yl)-1-[[2-[2-(3-hydroxypropoxy)phenyl]-acetyl]amino]-ethyl]-boronic acid;
[(1S)-2-(benzofuran-3-yl)-1-[[(2S)-3-hydroxy-2-phenyl-propanoyl]-aminoethyl]-boronic acid;
[(1R)-2-(benzofuran-3-yl)-1-[[(2S)-3-hydroxy-2-phenyl-propanoyl]-amino]ethyl]-boronic acid;
[(1R)-2-(benzofuran-3-yl)-1-[[2-(2,5-dimethoxyphenyl)acetyl]-amino]ethyl]boronic acid;
[(1R)-2-(benzofuran-3-yl)-1-[[(2R)-3-hydroxy-2-phenyl-propanoyl]-amino]ethyl]-boronic acid;
[(1R)-2-(benzofuran-3-yl)-1-[[2-(2,3,4-trimethoxyphenyl)acetyl]amino]ethyl]-boronic acid;
[(1S)-2-(benzofuran-3-yl)-1-[[2-[2-(3-hydroxypropoxy)phenyl]acetyl]amino]ethyl]-boronic acid;
[(1S)-2-(benzofuran-3-yl)-1-[[(2R)-3-hydroxy-2-phenyl-propanoyl]amino]ethyl]-boronic acid;
[(1R)-2-(benzofuran-3-yl)-1-[[2-[2-(morpholine-4-carbonyl)phenyl]acetyl]amino]ethyl]boronic acid;
[(1R)-2-(benzofuran-3-yl)-1-[[2-[4-(2-oxopyrrolidin-1-yl)phenyl]-acetyl]amino]-ethyl]-boronic acid;
[(1R)-2-(benzofuran-3-yl)-1-[[2-[2-(ethylcarbamoyl)phenyl]acetyl]amino]ethyl]-boronic acid;
[(1R)-2-(benzofuran-3-yl)-1-[[2-[2-(dimethylcarbamoyl)phenyl]acetyl]amino]-ethyl]boronic acid;
[(1R)-2-(benzofuran-3-yl)-1-[[2-(4-phenylphenyl)acetyl]amino]ethyl]boronic acid;
[(1R)-2-(benzofuran-3-yl)-1-[(2,2-diphenylacetyl)amino]ethyl]boronic acid;
[(1 S)-2-(benzofuran-3-yl)-1-[[2-(4-phenylphenyl)acetyl]amino]ethyl]boronic acid;
[(1R)-2-(benzofuran-3-yl)-1-[[(2R)-2-ethoxy-2-phenyl-acetyl]amino]ethyl]boronic acid;
[(1R)-2-(benzofuran-3-yl)-1-[[3-(4-methoxyphenyl)-2-phenyl-propanoyl]amino]-ethyl]boronic acid;
[(1R)-2-(benzofuran-3-yl)-1-[[2-[3-(ethoxycarbonylamino)phenyl]-acetyl]amino]-ethyl]boronic acid;
[(1R)-2-(2-chlorobenzofuran-3-yl)-1-[(2-phenylacetyl)amino]ethyl]-boronic acid;
[(1R)-2-(2,3-dihydrobenzofuran-3-yl)-1-[(2-phenylacetyl)amino]-ethyl]boronic acid;
[(1R)-2-(7-methylbenzofuran-3-yl)-1-[(2-phenylacetyl)amino]-ethyl]boronic acid;
[(1R)-1-[[(2R)-2-methoxy-2-phenyl-acetyl]amino]-2-(7-methylbenzofuran-3-yl)ethyl]boronic acid;

[(1R)-2-(7-methyl-2,3-dihydrobenzofuran-3-yl)-1-[(2-phenylacetyl)amino]ethyl]boronic acid;
[(1R)-1-[[2-(2,5-dimethoxyphenyl)acetyl]amino]-2-(7-methylbenzofuran-3-yl)ethyl]boronic acid;
[(1R)-1-[[(2S)-3-hydroxy-2-phenyl-propanoyl]amino]-2-(7-methylbenzofuran-3-yl)ethyl]boronic acid;
[(1S)-1-[[(2S)-3-hydroxy-2-phenyl-propanoyl]amino]-2-(7-methylbenzofuran-3-yl)ethyl]boronic acid;
[(1S)-1-[[2-(4-methoxyphenyl)acetyl]amino]-2-(7-methylbenzofuran-3-yl)ethyl]boronic acid;
[(1R)-1-[[2-(4-methoxyphenyl)acetyl]amino]-2-(7-methylbenzofuran-3-yl)ethyl]boronic acid;
[(1R)-1-[[(2R)-3-hydroxy-2-phenyl-propanoyl]amino]-2-(7-methylbenzofuran-3-yl)ethyl]boronic acid;
[(1S)-1-[[(2R)-3-hydroxy-2-phenyl-propanoyl]amino]-2-(7-methylbenzofuran-3-yl)ethyl]boronic acid;
[(1R)-2-(7-chlorobenzofuran-3-yl)-1-[(2-phenylacetyl)amino]ethyl]boronic acid;
[(1R)-1-[3-(5-methoxy-2-pyridyl)propanoylamino]-2-(7-methyl-2,3-dihydrobenzofuran-3-yl)ethyl]boronic acid;
[(1S)-1-[3-(5-methoxy-2-pyridyl)propanoylamino]-2-(7-methyl-2,3-dihydrobenzofuran-3-yl)ethyl]boronic acid;
[(1R)-1-[[2-(4-methoxyphenyl)acetyl]amino]-2-[(3R)-7-methyl-2,3-dihydrobenzofuran-3-yl]ethyl]boronic acid;
[(1R)-1-[[2-(4-methoxyphenyl)acetyl]amino]-2-[(3S)-7-methyl-2,3-dihydrobenzofuran-3-yl]ethyl]boronic acid;
[(1R)-2-(benzofuran-3-yl)-1-[[2-(2-cyanophenyl)acetyl]amino]ethyl]boronic acid;
[(1R)-2-(benzofuran-3-yl)-1-[[2-[4-(1-hydroxy-1-methyl-ethyl)phenyl]acetyl]amino]-ethyl]boronic acid;
[(1R)-2-(7-methoxybenzofuran-3-yl)-1-[(2-phenylacetyl)amino]ethyl]boronic acid;
[(1R)-1-[[(2R)-2-methoxy-2-phenyl-acetyl]amino]-2-(7-methyl-2,3-dihydrobenzofuran-3-yl)ethyl]boronic acid;
[(1R)-2-(6,7-dimethylbenzofuran-3-yl)-1-[(2-phenylacetyl)amino]ethyl]boronic acid;
[(1R)-2-(6,7-dimethylbenzofuran-3-yl)-1-[3-(5-methoxy-2-pyridyl)propanoylamino]-ethyl]boronic acid;
[(1R)-2-(benzofuran-3-yl)-1-[[(2S)-2-[2-(dimethylcarbamoyl)phenyl]propanoyl]amino]ethyl]boronic acid;
[(1R)-2-(benzofuran-3-yl)-1-[[(2R)-2-[2-(dimethylcarbamoyl)phenyl]propanoyl]amino]-ethyl]boronic acid;
[(1R)-2-(benzofuran-3-yl)-1-[[2-(2-phenylphenyl)acetyl]amino]ethyl]boronic acid;
[(1R)-2-[(3S)-2,3-dihydrobenzofuran-3-yl]-1-[[(2R)-2-[2-(dimethylcarbamoyl)phenyl]-propanoyl]amino]ethyl]boronic acid;
[(1R)-1-[[2-[2-(dimethylcarbamoyephenyl]acetyl]amino]-2-(7-methyl-2,3-dihydrobenzofuran-3-yl)ethyl]boronic acid;
[(1R)-2-(6,7-dimethyl-2,3-dihydrobenzofuran-3-yl)-1-[(2-phenylacetyl)amino]ethyl]-boronic acid;
[(1R)-2-(6,7-dimethyl-2,3-dihydrobenzofuran-3-yl)-1-[3-(5-methoxy-2-pyridyl)-propanoylamino]ethyl]boronic acid;
[(1R)-1-[[2-(2-acetamidophenyl)acetyl]amino]-2-(benzofuran-3-yl)ethyl]boronic acid;
[(1R)-1-[[2-(2-cyanophenyl)acetyl]amino]-2-(7-methylbenzofuran-3-yl)ethyl]boronic acid;
[(1R)-1-[[2-(2-cyanophenyl)acetyl]amino]-2-[(3 S)-2,3-dihydrobenzofuran-3-yl]ethyl]-boronic acid;
[(1R)-2-[(3R)-2,3-dihydrobenzofuran-3-yl]-1-[[(2S)-2-[2-(dimethylcarbamoyephenyl]-propanoyl]amino]ethyl]boronic acid;
[(1R)-2-[(3 S)-2,3-dihydrobenzofuran-3-yl]-1-[[(2S)-2-[2-(dimethylcarbamoyephenyl]-propanoyl]amino]ethyl]boronic acid;
[(1R)-2-(benzofuran-2-yl)-14 [2-(4-methoxyphenyl)acetyl]amino]ethyl]boronic acid;
[(1R)-1-[[(2R)-2-ethoxy-2-phenyl-acetyl]amino]-2-(7-methyl-2,3-dihydrobenzofuran-3-yl)ethyl]boronic acid;
[(1R)-2-(benzofuran-2-yl)-1-[(2-phenylacetyl)amino]ethyl]boronic acid;
(1R)-2-(2,3-dihydrobenzofuran-3-yl)-1-[[(2R)-2-ethoxy-2-phenyl-acetyl]amino]ethyl]-boronic acid;
[2-(benzofuran-3-yl)-1-[[2-(2-pyridyl)acetyl]amino]ethyl]boronic acid;
[(1R)-2-(7-chlorobenzofuran-3-yl)-1-[[2-(5-ethoxy-2-pyridyl)acetyl]amino]ethyl]boronic acid;
[(1R)-2-[(3S)-2,3-dihydrobenzofuran-3-yl]-1-[[2-(4-methoxyphenyl)acetyl]amino]ethyl]-boronic acid;
[(1R)-2-[(3R)-2,3-dihydrobenzofuran-3-yl]-1-[[2-(4-methoxyphenyl)acetyl]amino]ethyl]-boronic acid;
[(1R)-2-(7-chlorobenzofuran-3-yl)-1-[[2-(2-cyanophenyl)acetyl]amino]ethyl]boronic acid;
[(1S)-2-[(3S)-2,3-dihydrobenzofuran-3-yl]-14 [2-(4-methoxyphenyl)acetyl]amino]ethyl]-boronic acid;
[(1S)-2-[(3R)-2,3-dihydrobenzofuran-3-yl]-1-[[2-(4-methoxyphenyl)acetyl]amino]ethyl]-boronic acid;
[(1R)-2-(benzofuran-3-yl)-1-[[2-[3-(morpholine-4-carbonyl)-2-pyridyl]acetyl]amino]-ethyl]boronic acid;
[(1R)-2-[(3S)-7-methoxy-2,3-dihydrobenzofuran-3-yl]-1-[[2-(4-methoxyphenyl)acetyl]-amino]ethyl]boronic acid;
[2-(7-fluorobenzofuran-3-yl)-1-[(2-phenylacetyl)amino]ethyl]boronic acid;
[(1R)-2-[(3R)-2,3-dihydrobenzofuran-3-yl]-1-[[2-(4-methoxyphenyl)acetyl]amino]ethyl]-boronic acid;
[(1R)-2-(benzofuran-3-yl)-1-[[2-(3-cyanophenyl)acetyl]amino]ethyl]boronic acid;
[(1R)-2-[(3 S)-7-methyl-2,3-dihydrobenzofuran-3-yl]-1-[(2-phenylacetyl)amino]ethyl]-boronic acid;
[(1R)-2-(7-fluorobenzofuran-3-yl)-1-[(2-phenylacetyl)amino]ethyl]boronic acid;
[(1R)-2-(6-chloro-7-methyl-benzofuran-3-yl)-1-[(2-phenylacetyl)amino]ethyl]boronic acid;
[(1R)-2-[(3R)-7-methyl-2,3-dihydrobenzofuran-3-yl]-1-[(2-phenylacetyl)amino]ethyl]-boronic acid;
[(1R)-2-(4,7-dimethylbenzofuran-3-yl)-1-[(2-phenylacetyl)amino]ethyl]boronic acid;
[(1R)-2-(4,7-dimethylbenzofuran-3-yl)-1-[[2-(4-methoxyphenyl)acetyl]amino]ethyl]boronic acid;
[(1R)-1-[[2-(2-cyanophenyl)acetyl]amino]-2-[(3S)-7-methyl-2,3-dihydrobenzofuran-3-yl]ethyl]boronic acid;
[(1R)-2-[(3 S)-2,3-dihydrobenzofuran-3-yl]-1-[[2-(5-ethoxy-2-pyridyl)acetyl]amino]-ethyl]boronic acid;
[(1R)-2-[(3S)-7-chloro-2,3-dihydrobenzofuran-3-yl]-1-[(2-phenylacetyl)amino]ethyl]-boronic acid;
[(1R)-2-[(3R)-7-chloro-2,3-dihydrobenzofuran-3-yl]-1-[(2-phenylacetyl)amino]ethyl]-boronic acid;
[(1R)-2-[(3S)-7-chloro-2,3-dihydrobenzofuran-3-yl]-1-[[2-(2-cyanophenyl)acetyl]-amino]ethyl]boronic acid;
[(1R)-2-[(3R)-7-chloro-2,3-dihydrobenzofuran-3-yl]-1-[[2-(2-cyanophenyl)acetyl]-amino]ethyl]boronic acid; and

[(1R)-2-[(3S)-2,3-dihydrobenzofuran-3-yl]-1-(3-phenoxypropanoylamino)ethyl]boronic acid, or a stereoisomer, tautomer or pharmaceutically acceptable salt thereof.

* * * * *

UNITED STATES PATENT AND TRADEMARK OFFICE
CERTIFICATE OF CORRECTION

PATENT NO. : 10,294,246 B2
APPLICATION NO. : 15/516424
DATED : May 21, 2019
INVENTOR(S) : Markus Klein et al.

It is certified that error appears in the above-identified patent and that said Letters Patent is hereby corrected as shown below:

In the Specification

Column 1,
Line 42, "a subunits" should read --α subunits--.
Line 43, "a subunits" should read --α subunits--.
Line 63, "3 subunits," should read --β subunits,--.

Column 18,
Line 22, "formula (CE) (CE)" should read --formula (CE)--.
Line 38, "$NR^{4a}COOR^3a$" should read --$NR^{4a}COOR^{3a}$--.

Column 31,

Lines 59-65, " 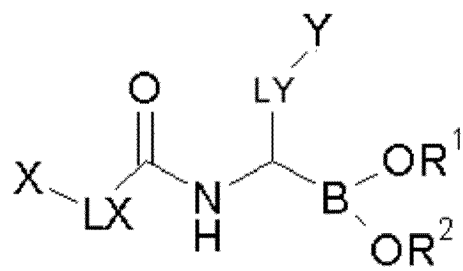 (I)   " should read

-- 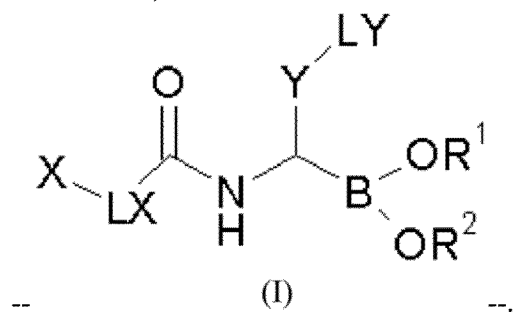 (I)   --.

Signed and Sealed this
Sixteenth Day of June, 2020

Andrei Iancu
*Director of the United States Patent and Trademark Office*

CERTIFICATE OF CORRECTION (continued)
U.S. Pat. No. 10,294,246 B2

Column 81,

Lines 55-66, " 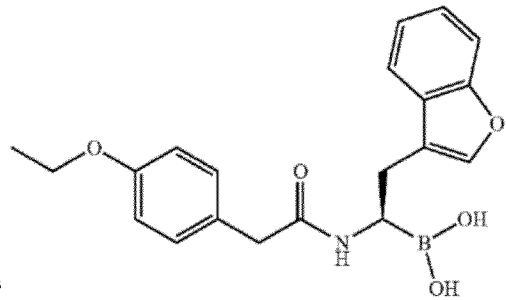 " should read

-- 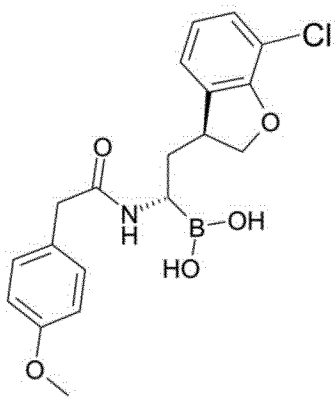 --.

Column 128,

Lines 7-24, " 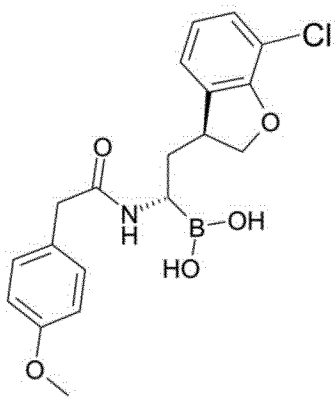 " should read -- 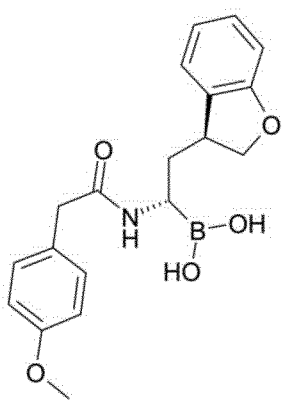 --.

CERTIFICATE OF CORRECTION (continued)
U.S. Pat. No. 10,294,246 B2

Column 131,

Lines 41-52, " 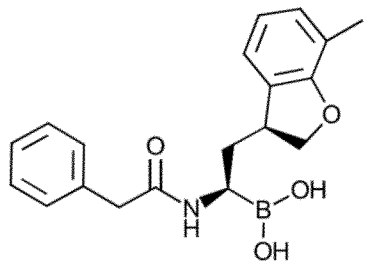 " should read -- 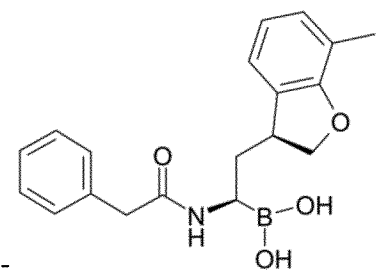 --.

In the Claims

Column 146,
Line 62, "O(CH$_2$)$_{20}$H" should read --O(CH$_2$)$_2$OH--.

Column 150,
Line 24, "O(CH2)20H" should read --O(CH$_2$)$_2$OH--.